US008835461B2

(12) United States Patent
Fujishita et al.

(10) Patent No.: US 8,835,461 B2
(45) Date of Patent: Sep. 16, 2014

(54) SUBSTITUTED 3-HYDROXY-4-PYRIDONE DERIVATIVE

(75) Inventors: Toshio Fujishita, Osaka (JP); Minako Mikamiyama, Osaka (JP); Makoto Kawai, Osaka (JP); Toshiyuki Akiyama, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 315 days.

(21) Appl. No.: 13/259,956

(22) PCT Filed: Mar. 23, 2010

(86) PCT No.: PCT/JP2010/054911
§ 371 (c)(1),
(2), (4) Date: Sep. 23, 2011

(87) PCT Pub. No.: WO2010/110231
PCT Pub. Date: Sep. 30, 2010

(65) Prior Publication Data
US 2012/0022255 A1 Jan. 26, 2012

(30) Foreign Application Priority Data

Mar. 26, 2009 (JP) .................................. 2009-075290

(51) Int. Cl.
| | |
|---|---|
| A61K 31/497 | (2006.01) |
| A61K 31/44 | (2006.01) |
| A61K 31/445 | (2006.01) |
| C07D 413/02 | (2006.01) |
| C07D 401/02 | (2006.01) |
| C07D 239/02 | (2006.01) |
| C07D 403/02 | (2006.01) |
| C07D 471/02 | (2006.01) |
| C07D 417/02 | (2006.01) |
| C07D 413/00 | (2006.01) |
| C07D 215/00 | (2006.01) |
| C07D 409/12 | (2006.01) |

(52) U.S. Cl.
USPC ........ 514/336; 514/252.1; 514/281; 514/306; 514/315; 544/131; 544/310; 544/316; 544/405; 546/113; 546/269.1; 546/152; 546/269.7; 546/272.1; 546/281.1; 546/282.4; 546/283.7; 546/296

(58) Field of Classification Search
USPC .................. 544/131, 310, 316, 405; 546/296, 546/281.1, 269.7, 272, 283.7, 113, 277.7, 546/152, 282.4, 269.1, 272.1; 514/252.1, 514/281, 306, 315, 336
See application file for complete search history.

(56) References Cited

U.S. PATENT DOCUMENTS

| 5,849,587 A | 12/1998 | Hanauske-Abel et al. |
| 7,550,463 B2 | 6/2009 | Yoshida |
| 2007/0249687 A1 | 10/2007 | Yoshida |

FOREIGN PATENT DOCUMENTS

| GB | 2 280 435 A | 2/1995 |
| JP | 11-514966 | 12/1999 |
| WO | WO 96/41639 A1 | 12/1996 |
| WO | WO 2006/030807 A1 | 3/2006 |

OTHER PUBLICATIONS

English-language International Search Report from the Japanese Patent Office for International Application No. PCT/JP2010/054911, mailing date Jun. 1, 2010.
English-language translation of the Written Opinion of the International Searching Authority for International Application No. PCT/JP2010/054911, mailed Jun. 1, 2010.
Hensens et al.; "Isolation and Structure of Flutimide, a Novel Endonuclease Inhibitor of Influenza Virus", Tetrahedron Letters, vol. 36, No. 12, pp. 2005-2008, (1995).
Singh; "Total Synthesis of Flutimide, a Novel Endonuclease Inhibitor of Influenza Virus", Tetrahedron Letters, vol. 36, No. 12, pp. 2009-2012, (1995).
Tomassini et al.; "Inhibition of CAP ($M^7$GpppXm)-Dependent Endonuclease of Influenza Virus by 4-Substituted 2,4-Dioxobutanoic Acid Compounds", Antimicrobial Agents and Chemotherapy, vol. 38, No. 12, pp. 2827-2837, (1994).
Hastings et al.; "Anti-Influenza Virus Activities of 4-Substituted 2,4-Dioxobutanoic Acid Inhibitors", Antimicrobial Agents and Chemotherapy, vol. 40, No. 5, pp. 1304-1307, (1996).
Parkes et al.; "Use of a Pharmacophore Model to Discover a New Class of Influenza Endonuclease Inhibitor", Journal of Medicinal Chemistry, vol. 46, No. 7, pp. 1153-1164, (2003).
Cianci et al.; "Identification of N-Hydroxamic Acid and N-Hydroxy-Imide Compounds That Inhibit the Influenza Virus Polymerase", Antiviral Chemistry & Chemotherapy, vol. 7, No. 6, pp. 353-360, (1996).
Singh et al.; "Synthesis of Natural Flutimide and Analogous Fully Substituted Pyrazine-2,6-Diones, Endonuclease Inhibitors of Influenza Virus", J. Org. Chem., vol. 66, No. 16, pp. 5504-5516, (2001).

*Primary Examiner* — James O. Wilson
*Assistant Examiner* — Ebenezer O Sackey
(74) *Attorney, Agent, or Firm* — Finnegan, Henderson, Farabow, Garrett & Dunner, L.L.P.

(57) ABSTRACT

This invention provides compounds having antiviral activities especially inhibiting activity for influenza virus, more preferably provides substituted 3-hydroxy-4-pyridone derivatives having cap-dependent endonuclease inhibitory activity.

12 Claims, No Drawings

SUBSTITUTED 3-HYDROXY-4-PYRIDONE DERIVATIVE

TECHNICAL FIELD

This invention relates to substituted 3-hydroxy-4-pyridone derivatives having cap-dependent endonuclease inhibitory activity, and pharmaceutical compositions including thereof.

BACKGROUND ART

Influenza is an acute respiratory infectious disease caused by infection with an influenza virus. In Japan, there is a report of a few millions of influenza-like patients every winter, and influenza is accompanied with high morbidity and mortality. Influenza is a particularly important disease in a high risk population such as baby and elderly, a complication rate with pneumonia is high in elderly, and death with influenza is occupied with elderly in many cases.

As anti-influenza drugs, Symmetrel (trade name: Amantadine) and Flumadine (trade name: Rimantadine) which inhibit the denucleation process of a virus, and Oseltamivir (trade name: Tamiflu) and Zanamivir (trade name: Relenza) which are neuraminidase inhibitors suppressing virus budding and release from a cell are known. However, since problems of apperances of resistant strains and side effects, and worldwide epidemic of a new-type influenza virus having high pathogenicity and mortality are feared, development of an anti-influenza drug having a novel mechanism has been desired.

Since a cap-dependent endonuclease which is an influenza virus-derived enzyme is essential for virus proliferation, and has the virus-specific enzymatic activity which is not possessed by a host, it is believed that the endonuclease is suitable for a target of an anti-influenza drug. The cap-dependent endonuclease has a host mRNA precursor as a substrate, and has the endonuclease activity of producing a fragment of 9 to 13 bases including a cap structure (not including the number of bases of the cap structure). This fragment functions as a primer of a virus RNA polymerase, and is used in synthsizing mRNA encoding a virus protein. That is, it is believed that a substance which inhibits the cap-dependent endonuclease inhibits synthesis of a virus protein by inhibiting synthesis of virus mRNA and, as a result, inhibits virus proliferation.

As the substance which inhibits the cap-dependent endonuclease, flutimide (Patent Document 1 and Non-Patent Documents 1 and 2) and 4-substituted 2,4-dioxobutanoic acid (Non-Patent Documents 3 to 5) are reported, but they have not yet led to clinical use as anti-influenza drugs. In addition, Patent Documents 2 describe compounds having a similar structure to that of this invention, however, the documents dose not describe cap-dependent endonuclease. Furthermore, these compounds in the prior art have a different structures from those of this inventive compounds.

PRIOR ART DOCUMENTS

Patent Documents

[Patent Document 1] GB No. 2280435 specification
[Patent Document 2] International Publication No. 2006/030807 pamphlet

Non-Patent Documents

[Non-Patent Document 1] Tetrahedron Lett 1995, 36(12), 2005
[Non-Patent Document 2] Tetrahedron Lett 1995, 36(12), 2009
[Non-Patent Document 3] Antimicrobial Agents And Chemotherapy, December 1994, p. 2827-2837
[Non-Patent Document 4] Antimicrobial Agents And Chemotherapy, May 1996, p. 1304-1307
[Non-Patent Document 5] J. Med. Chem. 2003, 46, 1153-1164

SUMMARY OF THE INVENTION

Problems to be Solved by the Invention

An object of the present invention is to provide compounds having antiviral activities especially inhibiting growth activity of influenza virus. More preferably, this invention provides compounds and medicament including thereof which inhibit increase of influenza virus by exhibiting cap-dependent endonuclease inhibitory activity.

Means for Solving the Problems

The present invention provides the following items.
(Item 1)
A compound shown by formula (I), or a pharmaceutically acceptable salt thereof or a solvate thereof:

[Formula 1]

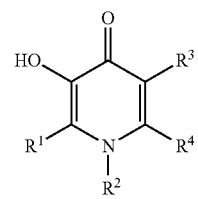

(I)

[wherein $R^1$ is selected from a substituent group consisting of 1) to 4) below:
1) hydrogen,
2) lower alkyl optionally substituted by substituent A,
3) lower alkenyl optionally substituted by substituent A, and
4) lower alkynyl optionally substituted by substituent A,
wherein substituent A is at least one group selected from a substituent group consisting of halogen, amino, and hydroxy;
$R^2$ is selected from a substituent group consisting of 1) to 5) below:
1) amino optionally substituted by substituent B,
wherein substituent B is at least one group selected from a substituent group consisting of alkyl, aryl, and aryl lower alkyl,
2) a group represented by $-(CX^1X^2)_m-Y-(CH_2)_n-Z$,
[wherein $X^1$ and $X^2$ are each independently hydrogen, hydroxy, hydroxy lower alkyl, lower alkyl, aryl, aryl lower alkyl, or monocyclic heterocycle,
Y is a single bond, S, $SO_2$, O, NH, NHCO, or CONH,
m and n are each independently an integer of 0 or more, with a proviso that each $X^1$ may be the same or different and each $X^2$ may be the same or different,
Z is selected from a substituent group consisting of a) to l) below:

[Formula 2]

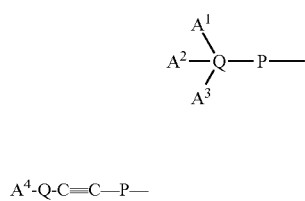

a)

$A^4\text{-}Q\text{-}C\equiv C\text{-}P\text{-}$ b) [Formula 3]

c) $A^5\text{-}Q\text{-}C=C\text{-}P\text{-}$, d) $A^6\text{-}Q\text{-}(CH_2)_{r1}\text{-}P\text{-}$, e) $A^7\text{-}Q\text{-}CO\text{-}P\text{-}$, f) $A^8\text{-}Q\text{-}(CH_2)_{r2}\text{-}O\text{-}CO\text{-}P\text{-}$, g) $A^9\text{-}Q\text{-}CO\text{-}(CH_2)_{r3}\text{-}O\text{-}CO\text{-}P\text{-}$, h) $A^{10}\text{-}Q\text{-}CO\text{-}NH\text{-}P\text{-}$, i) $A^{11}\text{-}Q\text{-}O\text{-}P\text{-}$, j) $A^{12}\text{-}Q\text{-}S\text{-}P\text{-}$, k) $A^{13}\text{-}Q\text{-}SO_2\text{-}P\text{-}$, and

[Formula 4]

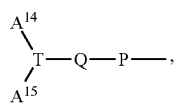

l)

(with a proviso that P is a single bond, monocyclic hydrocarbon, monocyclic heterocycle, condensed polycyclic hydrocarbon, or condensed polycyclic heterocycle, wherein when P is not a single bond, P may be substituted by at least one substituent selected from a group consisting of halogen, hydroxy, nitrile, amino, lower alkylamino, aminosulfonyl, aminocarbonyl, lower alkylcarbonyl, lower alkyl, halogeno lower alkyl, lower alkyloxy, oxo, and aryl, Q is monocyclic hydrocarbon, condensed polycyclic hydrocarbon, monocyclic heterocycle, polycyclic hydrocarbon, or condensed polycyclic heterocycle, T is monocyclic heterocycle, $A^1, A^2, A^3, A^4, A^5, A^6, A^7, A^8, A^9, A^{10}, A^{11}, A^{12}, A^{13}, A^{14}$ and $A^{15}$ are each independently selected from a substituent group consisting of hydrogen, lower alkyl, halogeno lower alkyl, lower alkyloxy lower alkyl, lower alkyloxy, lower alkyloxy lower alkyloxy, halogeno lower alkyloxy, halogeno lower alkylcarbonyl, aryl, aryloxy, lower alkyloxy aryl, aryl lower alkyloxy, lower alkylcarbonyl, aminocarbonyl, lower alkyl aminocarbonyl, cycloalkylaminocarbonyl, amino, lower alkylamino, lower alkylcarbonylamino, cycloalkyl lower alkylamino, aminosulfonyl, arylsulfonyl, lower alkylsulfonyl, lower alkylsulfonylamino, morpholinylcarbonyl, pyrroridinylcarbonyl, hydroxy, hydroxy lower alkyl, nitrile, oxo, arylaminocarbonyl and halogen;

r1, r2, and r3 are each independently an integer of 1 or more]

3) C4-C10 alkyl, 4) lower alkyloxy lower alkyl, and 5) a group shown below,

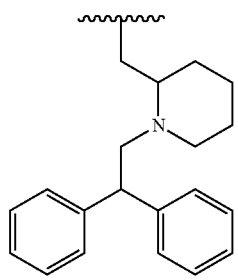

[Formula 5]

$R^3$ is selected from a group consisting of 1)-6) below:

1) hydroxy, 2) carboxy, 3) phenylaminocarbonyl optionally substituted by substituent C, 4) sulfonylaminocarbonyl optionally substituted by substituent C, 5) monocyclic heterocycle optionally substituted by substituent C, and 6) condensed polycyclic heterocycle optionally substituted by substituent C, wherein substituent C is at least one substituent selected from a group consisting of a) to e)

a) optionally substituted lower alkyl (with a proviso that the substituent is halogen), b) halogen, c) optionally substituted monocyclic hydrocarbon (with a proviso that the substituent is lower alkyl, and/or halogen), d) monocyclic heterocycle, and e) optionally substituted aryl lower alkyl (with a proviso that the substituent is lower alkyl, and/or halogen);

$R^4$ is selected from a group consisting of 1)-4) below:

1) hydrogen, 2) lower alkyl optionally substituted by substituent D, 3) lower alkenyl optionally substituted by substituent D, and 4) lower alkynyl optionally substituted by substituent D, wherein substituent D is at least one substituent selected from a group consisting of halogen, amino, and hydroxy].

(Item 2)

The compound according to item 1, or the pharmaceutically acceptable salt thereof or the solvate thereof, wherein $R^1$ is hydrogen or lower alkyl optionally substituted by substituent A.

(Item 3)

The compound according to item 1 or 2, or the pharmaceutically acceptable salt thereof or the solvate thereof, wherein $R^4$ is hydrogen, or lower alkyl optionally substituted by substituent D.

(Item 4)

The compound according to any one of items 1 to 3, or the pharmaceutically acceptable salt thereof or the solvate thereof, wherein $R^3$ is selected from a group consisting of 1)-4) below:

1) hydroxy, 2) carboxy, 3) phenylaminocarbonyl optionally substituted by substituent C, and 4) sulfonylaminocarbonyl substituted by substituent C, wherein substituent C is at least one substituent selected from a group consisting of a) to e) below:

a) lower alkyl optionally substituted (with a proviso that the substituent is halogen), b) halogen,
c) monocyclic hydrocarbon optionally substituted (with a proviso that the substituent is lower alkyl, and/or halogen),
d) monocyclic heterocycle, and
e) aryl lower alkyl optionally substituted (with a proviso that the substituent is lower alkyl, and/or halogen).

(Item 5)

The compound according to item 4, or the pharmaceutically acceptable salt thereof or the solvate thereof,
wherein $R^3$ is carboxy.

(Item 6)

The compound according to any one of items 1 to 3, or the pharmaceutically acceptable salt thereof or the solvate thereof,
wherein $R^3$ is selected from a group consisting of 5) and 6) below:
5) monocyclic heterocycle optionally substituted by substituent C,
6) condensed polycyclic heterocycle optionally substituted by substituent C, and
wherein the substituent C is at least one substituent selected from a group consisting of a) and b) below:
  a) lower alkyl optionally substituted (with a proviso that the substituent is halogen), and
  b) halogen.

(Item 7)

The compound according to any one of items 1 to 6, or the pharmaceutically acceptable salt thereof or the solvate thereof,
wherein $R^2$ is selected from a group consisting of 1) to 5) below;
1) amino optionally substituted by substituent B,
wherein the substituent B is at least one substituent selected from a group consisting of alkyl, aryl, and aryl lower alkyl;
2) a group represented by $—(CX^1X^2)_m—Y—(CH_2)_n—Z$,
[wherein $X^1$ and $X^2$ are each independently hydrogen, hydroxy, hydroxy lower alkyl, lower alkyl, aryl, aryl lower alkyl, or monocyclic heterocycle,
Y is a single bond, S, $SO_2$, O, NH, NHCO, or CONH,
m and n are each independently an integer of 0 or more, with a proviso that m of $X^1$s may be same or different, m of $X^2$s may be same or different,
Z is selected from a group consisting of a) to l) below:

[Formula 6]

a) $A^2—Q—P—$,
  $A^1$
  $A^3$ ($A^1$, $A^2$ and $A^3$ are each independently hydrogen, lower alkyl, halogeno lower alkyl, lower alkyloxy lower alkyl, lower alkyloxy, halogeno lower alkyloxy, halogeno lower alkylcarbonyl, aryl, aryloxy, aryl lower alkyloxy, lower alkylcarbonyl, aminocarbonyl, lower alkyl aminocarbonyl, cycloalkylaminocarbonyl, lower alkylamino, cycloalkyl lower alkylamino, arylsulfonyl, lower alkylsulfonyl, lower alkylsulfonylamino, morphollinylcarbonyl, pyrrolidinylcarbonyl, hydroxy, hydroxy lower alkyl, nitrile, oxo, arylaminocarbonyl, and halogen), b) [Formula 7]  $A^4$-Q-C≡C—P—

($A^4$ is hydrogen),
c) $A^5$-Q-C=C—P—  ($A^5$ is hydrogen, halogeno lower alkyl, or lower alkyloxy),
d) $A^6$-Q-$(CH_2)_{r1}$—P—  ($A^6$ is hydrogen, lower alkyl, aryl, nitrile, or halogen),
e) $A^7$-Q-CO—P—  ($A^7$ is hydrogen, or halogen),
f) $A^8$-Q-$(CH_2)_{r2}$—O—CO—P—  ($A^8$ is hydrogen, lower alkyl, halogeno lower alkyl, lower alkyloxy aryl, nitrile, or halogen),
g) $A^9$-Q-CO—$(CH_2)_{r3}$—O—CO—P—  ($A^9$ is hydrogen),
h) $A^{10}$-Q-CO—NH—P—  ($A^{10}$ is hydrogen),
i) $A^{11}$-Q-O—P—  ($A^{11}$ is hydrogen, or lower alkyl),
j) $A^{12}$-Q-S—P—  ($A^{12}$ is hydrogen, or hydroxy lower alkyl),
k) $A^{13}$-Q-$SO_2$—P—  ($A^{13}$ is hydrogen, or halogen), and

[Formula 8]

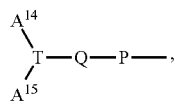

l)

($A^{14}$ and $A^{15}$ are each independently hydrogen, or oxo),
(with a proviso that P is a single bond, monocyclic hydrocarbon, monocyclic heterocycle, condensed polycyclic hydrocarbon, or condensed polycyclic heterocycle, wherein when P is not a single bond, P may be substituted by at least one substituent group consisting of halogen, hydroxy, nitrile, amino, lower alkylamino, aminosulfonyl, aminocarbonyl, loweralkylcarbonyl, lower alkyl, halogeno lower alkyl, lower alkyloxy, oxo, and phenyl;
Q is monocyclic hydrocarbon, condensed polycyclic hydrocarbon, monocyclic heterocycle, or condensed polycyclic heterocycle,
T is monocyclic heterocycle,
r1, r2, and r3 are each independently an integer of 1 or more);
3) C4-C10 alkyl;
4) lower alkyloxy lower alkyl; and
5) a group shown below:

[Formula 9]

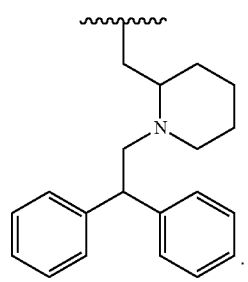

(Item 8)

The compound according to any one of items 1 to 7, or the pharmaceutically acceptable salt thereof or the solvate thereof,
$R^2$ is a substituent shown by 2) below;

$—(CX^1X^2)_m—Y—(CH_2)_n—Z$,   2)

[wherein $X^1$ and $X^2$ are each independently hydrogen, hydroxy, hydroxy lower alkyl, lower alkyl, aryl, aryl lower alkyl, or monocyclic heterocycle,
Y is a single bond, S, $SO_2$, O, or CONH, m and n are each independently an integer of 0 or more, with a proviso that m of $X^1$s may be same or different, m of $X^2$s may be same or different, Z is selected from a substituent group consisting of

[Formula 10]

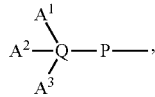

a)

(wherein $A^1$, $A^2$ and $A^3$ are each independently selected from a group consisting of hydrogen, lower alkyl, halogeno lower alkyl, lower alkyloxy, halogeno lower alkyloxy, halogeno lower alkylcarbonyl, aryl, aryloxy, lower alkylcarbonyl, aminocarbonyl, cycloalkyl aminocarbonyl, lower alkylcarbonylamino, lower alkylamino, cycloalkyl lower alkylamino, arylsulfonyl, lower alkylsulfonyl, lower alkylsulfonylamino, hydroxy, nitrile, aryl aminocarbonyl, and halogen, and a group shown below:

[Formula 11]

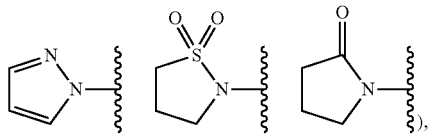

d) $A^6$-Q-$(CH_2)_{r1}$—P— ($A^6$ is hydrogen, nitrile, or halogen),
f) $A^8$-Q-$(CH_2)_{r2}$—O—CO—P— ($A^8$ is hydrogen, lower alkyl, halogeno lower alkyl, lower alkyloxy aryl, nitrile, or halogen),
h) $A^{10}$-Q-CO—NH—P— ($A^{10}$ is hydrogen),
i) $A^{11}$-Q-O—P— ($A^{11}$ is hydrogen), and
j) $A^{12}$-Q-S—P— ($A^{12}$ is hydroxy lower alkyl), (wherein P is a single bond, monocyclic hydrocarbon, monocyclic heterocycle, condensed polycyclic hydrocarbon, or condensed polycyclic heterocycle, wherein P is not a single bond, the cyclic group may be substituted by one or more substituent selected from a group consisting of halogen, hydroxy, nitrile, amino, lower alkylamino, aminosulfonyl, aminocarbonyl, lower alkylcarbonyl, lower alkyl, halogeno lower alkyl, lower alkyloxy, oxo, and aryl, Q is monocyclic hydrocarbon, condensed polycyclic hydrocarbon, monocyclic heterocycle, or condensed polycyclic heterocycle, and r1, r2, and r3 are each independently an integer of 1 or more)].

(Item 9)

The compound according to any one of items 1 to 8, or the pharmaceutically acceptable salt thereof or the solvate thereof, wherein $R^2$ is a group 2) shown below:

—$(CX^1X^2)_m$—Y—$(CH_2)_n$—Z,    2)

[wherein $X^1$ and $X^2$ are each independently hydrogen, hydroxymethyl, methyl, ethyl, or phenyl, Y is a single bond, or S, m and n are each independently an integer of 0 or more, with a proviso that m of $X^1$s may be same or different, m of $X^2$s may be same or different, Z is selected from a substituent group consisting of

[Formula 12]

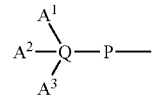

a)

($A^1$, $A^2$ and $A^3$ are each independently selected from a substituent group consisting of hydrogen, methyl, trifluoromethyl, methoxy, ethoxy, trifluoromethoxy, trifluoromethylcarbonyl, phenyl, phenoxy, methylcarbonyl, aminocarbonyl, cyclopropylaminocarbonyl, methylcarbonylamino, dimethylamino, cyclohexylmethylamino, phenylsulfonyl, methylsulfonyl, methylsulfonylamino, hydroxy, nitrile, phenylaminocarbonyl, fluoro, and chloro, and a group shown below:

[Formula 13]

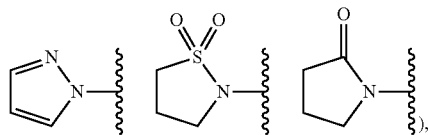

d) $A^6$-Q-$(CH_2)_{r1}$—P— ($A^6$ is hydrogen, nitrile, or chloro),
f) $A^8$-Q-$(CH_2)_{r2}$—O—CO—P— ($A^8$ is hydrogen, tert-butyl, trifluoromethyl, methoxyphenyl, nitrile, or fluoro),
h) $A^{10}$-Q-CO—NH—P— ($A^{10}$ is hydrogen),
i) $A^{11}$-Q-O—P— ($A^{11}$ is hydrogen), and
j) $A^{12}$-Q-S—P— ($A^{12}$ is hydroxy methyl), (with a proviso that P is a single bond or a group shown below:

[Formula 14]

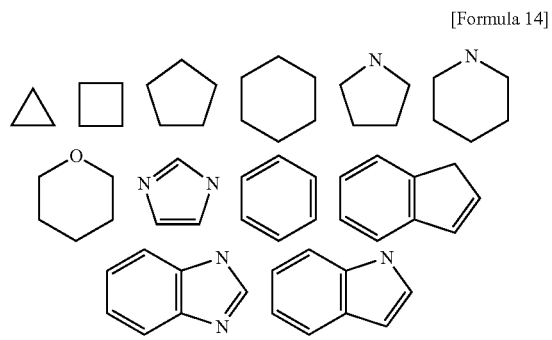

wherein when P is not a single bond, P may be substituted by hydroxy, lower alkyl, oxo, or phenyl (provided when the substituent is oxo, P is saturated monocyclic hydrocarbon, or saturated monocyclic heterocycle), Q is a group shown below:

[Formula 15]

and r1, r2, and r3 are each independently an integer of 1 or more)].

(Item 10)

The compound according to any one of items 1 to 9, or the pharmaceutically acceptable salt thereof or the solvate thereof, wherein $R^2$ is any one of formulae shown below:

[Formula 16]

(wherein $A^1$, $A^2$ and $A^3$ are selected from a group consisting of hydrogen, methyl, trifluoromethyl, methoxy, ethoxy, trifluoromethoxy, trifluoromethylcarbonyl, phenyl, phenoxy, methylcarbonyl, aminocarbonyl, cyclopropylaminocarbonyl, methylcarbonylamino, dimethylamino, methylsulfonyl, methylsulfonylamino, hydroxy, nitrile, fluoro, and chloro).

(Item 11)

A pharmaceutical composition comprising a compound according to any one of items 1 to 10, or a pharmaceutically acceptable salt thereof or a solvate thereof.

(Item 12)

A pharmaceutical composition according to item 11 which exhibits cap-dependent endonuclease inhibitory activity.

(Item 13)

A cap-dependent endonuclease inhibitory agent according to item 12 which is a therapeutic agent for influenza infectious disease.

(Item 14)

A method for treating influenza infectious disease characterized in administering the compound shown by formula (I) according to above item 1, or the pharmaceutically acceptable salt thereof or the solvate thereof.

(Item 15)

Use of the compound shown by formula (I) according to above item 1, or the pharmaceutically acceptable salt thereof or the solvate thereof, for manufacturing a therapeutic agent for influenza infectious disease.

(Item 16)

The compound shown by formula (I) according to above item 1, or the pharmaceutically acceptable salt thereof or the solvate thereof, for treating influenza infectious disease.

Effect of the Invention

The compounds of this invention, having inhibitory activities to cap-dependent endonuclease, are effective as therapeutic agents and/or preventive agents for influenza infectious disease.

MODE FOR CARRYING OUT THE INVENTION

The meanings of each term in this specification are explained below. Each term is used in a unified meaning, and then the term is used as same meaning when used alone or in combination with other terms.

"Lower alkyl" includes straight or branched alkyl having 1 to 15 carbons, preferably 1 to 10 carbons, more preferably 1 to 6 carbons, further preferably 1 to 4 carbons, and examples thereof include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, and n-decyl.

"C4-C10 alkyl" is alkyl with such a scope of carbons, and includes examples of the above "lower alkyl".

"Lower alkyl" in "aryl lower alkyl", "hydroxy lower alkyl", the "lower alkyl amino", the "lower alkylcarbonyl", the "halogeno lower alkyl", the "lower alkyloxy", the "lower alkyloxy lower alkyl", the "lower alkyloxy lower alkyloxy", the "halogeno lower alkyloxy", the "halogeno lower alkylcarbonyl", the "lower alkyloxyaryl", the "lower alkylaminocarbonyl", the "lower alkylcarbonylamino", the "cycloalkyl lower alkylamino", the "lower alkylsulfonyl", and the "lower alkylsulfonylamino" are the same as the above "lower alkyl".

"Lower alkenyl" includes straight or branched alkenyl having one or more double bonds at the arbitrary positions and having 2 to 15 carbons, preferably 2 to 10 carbons, more preferably 2 to 6 carbons, and further preferably 2 to 4 carbons. Specifically, examples thereof include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl.

"Lower alkynyl" includes straight or branched alkynyl having 2 to 10 carbons, preferably 2 to 8 carbons, and further preferably 3 to 6 carbons, having one or more triple bonds at the arbitrary positions. Specifically, examples thereof include ethynyl, propynyl, butynyl, pentynyl, hexynyl, heptynyl, octynyl, nonynyl and decynyl. These may further have a double bond at an arbitrary position.

"Halogen" includes a fluorine atom, a chlorine atom, a bromine atom, and an iodine atom.

"Halogen" in the "halogeno lower alkyl", the "halogeno lower alkyloxy", and the "halogeno lower alkylcarbonyl" are the same as the above "halogen". The arbitrary positions on the alkyl group of "lower alkyl", "lower alkyloxy", and "lower alkylcarbonyl" may be substituted by same or different one or a plurality of halogens, respectively.

The examples of "lower alkyloxy" are methoxy, ethoxy, propyloxy, isopropyloxy, tert-butyloxy, isobutyloxy, sec-butyloxy, pentyloxy, isopentyloxy and hexyloxy, and the like.

The examples of "lower alkylcarbonyl" are methylcarbonyl, ethylcarbonyl, propylcarbonyl, isopropylcarbonyl, tert-butylcarbonyl, isobutylcarbonyl, sec-butylcarbonyl, pentylcarbonyl, isopentylcarbonyl, hexylcarbonyl, and the like.

The examples of "halogeno lower alkyl" are monofluoromethyl, monochloromethyl, trifluoromethyl, trichloromethyl, 2,2,2-trifluoromethyl, 2,2,2-trichloromethyl, 1,2-dibromoethyl, and the like.

The examples of "halogeno lower alkyl" are monofluoromethoxy, monofluoroethoxy, trifluoromethoxy, trichloromethoxy, trifluoroethoxy, trichloroethoxy, and the like.

The examples of "halogeno lower alkylcarbonyl" are monofluoromethylcarbonyl, monochloromethylcarbonyl, trifluoromethylcarbonyl, trichloromethylcarbony, and the like.

The "aryl" includes phenyl, naphthyl, anthryl and phenanthryl, and the like. Preferable are phenyl and naphthyl, and further preferable is phenyl. The parts of "aryl" in the "aryl lower alkyl", and "lower alkyloxyaryl" are the same as the above "aryl".

The examples of "aryl lower alkyl" are benzyl, phenethyl, phenylpropyl, and the like.

The examples of "lower alkyloxy aryl" are methoxyphenyl, ethoxyphenyl, propyloxyphenyl, isopropyloxyphenyl, and the like.

The examples of "hydroxy lower alkyl" are hydroxymethyl, 1-hydroxyethyl, 2-hydroxyethyl, 1,2-dihydroxyethyl, and the like.

The examples of "lower alkylamino" are methylamino, dimethylamino, ethylamino, diethylamino, isopropylamino, N,N-diisopropylamino, N-methyl-N-ethylamino, N-isopropyl-N-ethylamino, and the like.

The examples of "lower alkyloxy lower alkyl" are methoxymethyl, methoxyethyl, ethoxymethyl, ethoxyethyl, methoxypropyl, methoxybutyl, ethoxypropyl, ethoxybutyl, and the like.

The examples of "lower alkyloxy lower alkyloxy" are methoxymethoxy, methoxyethoxy, ethoxymethoxy, ethoxyethoxy, methoxypropyloxy, methoxybutyloxy, ethoxypropyloxy, ethoxybutyloxy, and the like.

The examples of "lower alkylaminocarbonyl" are methylaminocarbonyl, ethylaminocarbonyl, propylaminocarbonyl, isopropylaminocarbonyl, tert-butylaminocarbonyl, isobutylaminocarbonyl, sec-butylaminocarbonyl, N,N-dimethylaminocarbonyl, N,N-diethylaminocarbonyl, N,N-diisopropylaminocarbonyl, and the like.

The examples of "lower alkylcarbonylamino" are methylcarbonylamino, ethylcarbonylamino, propylcarbonylamino, isopropylcarbonylamino, tert-butylcarbonylamino, isobutylcarbonylamino, sec-butylcarbonylamino, and the like.

The examples of "lower alkylsulfonyl" are methylsulfonyl, ethylsulfonyl, propylsulfonyl, isopropylsulfonyl, tert-butylsulfonyl, isobutylsulfonyl, sec-butylsulfonyl, and the like.

The examples of "lower alkylsulfonylamino" are methylsulfonylamino, ethylsulfonylamino, propylsulfonylamino, isopropylsulfonylamino, tert-butylsulfonylamino, isobutylsulfonylamino, sec-butylsulfonylamino, and the like.

"Monocyclic hydrocarbon" includes "carbocycle" having all the bond between two carbons are single bond having 3 to 10 carbons, preferably a 3 to 8 carbons, and more preferably 3 to 7 carbons, and includes "cycloalkyl" such as for example, cyclopropyl, cyclobutyl, cyclopenthyl, cyclohexyl, cycloheptyl, cycloocthyl, cyclononyl, and cyclodecyl, and the like. Or the "monocyclic hydrocarbon" includes aforementioned "carbocycle" having one or more double bonds at the arbitrary positions in the cyclic group, and specifically includes "cycloalkenyl" such as cyclopropenyl, cyclobutenyl, cyclopentenyl, cyclohexenyl, cycloheptynyl, cyclooctynyl cyclohexadienyl, phenyl, and the like.

"Monocyclic heterocycle" includes heterocycle having one or more same or different heteroatoms arbitrarily selected from O, S and N in the cyclic group, preferably 4 to 8-membered cyclic group, and more preferably 5 to 6-membered cyclic group, specifically, "aromatic heterocycle" such as pyrrolyl, imidazolyl, pyrazolyl, pyridyl, pyridazinyl, pyrimidinyl, pyrazinyl, triazolyl, triazinyl, tetrazolyl, furyl, thienyl, isooxazolyl, oxazolyl, oxadiazolyl, isothiazolyl, thiazolyl and thiadiazolyl, and the like; and "non-aromatic heterocycle" such as dioxanyl, thiiranyl, oxyranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, and tetrahydropyridazinyl, and the like.

"Condensed polycyclic hydrocarbon" includes condensed group composed of two or more cyclic groups selected from above "cycloalkyl", "cycloalkenyl", and "aryl", specifically, adamantyl, indanyl, indenyl, tetrahydronaphthyl, and fluorenyl, and the like.

"Condensed polycyclic heterocycle" includes a condensed group which is condensed by one or more cyclic groups selected from "monocyclic heterocycle" and "monocyclic hydrocarbon" to above "monocyclic heterocycle"; and includes a "condensed bicyclic heterocycle" such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzoisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyridyl, pyrazolopyridyl, thiazolopyridyl, pyrazolopyrimidinyl, pyrazolotriazinyl, pyridazolopyridyl, triazolopyridyl, imidazothiazolyl, pyrazinopyridazinyl, quinazolinyl, quinolyl, isoquinolyl, naphthyridinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxynyl, dihydrobenzoxezinyl, dihydrobenzodioxepinyl tetrahydrobenzoannulenyl, pyrorlopyridinyl, dihydroindenyl, and dihydrothienodioxynyl, and the like; and includes a "condensed tricyclic heterocycle" such as carbazolyl, acridinyl, xanthenyl, phenothiazinyl, phenoxathiinyl, phenoxazinyl, dibenzofuryl, imidazoquinolyl, and tetrahydrocarbazolyl, and the like.

"Cycloalkyl" in the "cycloalkyl lower alkylamino" is the same as the above exemplified "monocyclic hydrocarbon". The examples of "cycloalkyl lower alkylamino" are cyclopropylmethylamino, cyclopropylethylamino, cyclobutylmethylamino, cyclopenthylmethylamino, and cyclohexylmethylamino, and the like.

The cyclic group as P and/or Q in aforementioned item 9 forms 2 or more bonds with the adjacent groups at the arbitrary carbon atom and/or nitrogen atom in the cyclic group which can form chemically acceptable bonds. In addition, at the cyclic group as P and/or Q selected from substituents below, when nitrogen atom as shown by "—N—" dose not participate in forming the above bond, the nitrogen atom binds to hydrogen atom.

[Formula 17]

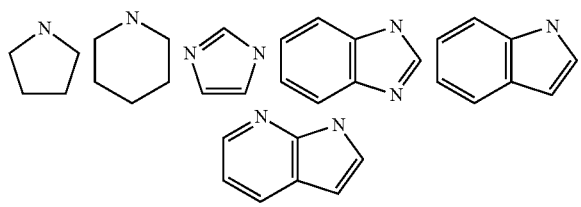

In this case, each cyclic group specifically represents below:

[Formula 18]

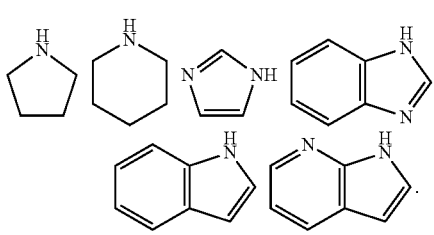

The examples of "lower alkyl substituted by substituent A" at $R^1$ are methyl, ethyl, propyl, isopropyl, tert-butyl, isobutyl, sec-butyl, hydroxymethyl, trifluoromethyl, aminomethyl, 1-aminoethyl, 2-aminoethyl, 1-hydroxyethyl, 2-hydroxyethyl, and the like, preferably, methyl, ethyl, propyl, tert-butyl, trifluoromethyl, and the like.

The examples of "lower alkenyl substituted by substituent A" at $R^1$ are ethylenyl, 1-propenyl, 2-propenyl, 3,3,3-trifluoropropenyl, 3-aminopropenyl, 3-hydroxypropenyl, and the like, preferably, ethylenyl, 1-propenyl, 2-propenyl, and the like.

The examples of "lower alkynyl substituted by substituent A" at $R^1$ are ethynyl, 1-propynyl, 2-propynyl, 3,3,3-trifluoropropynyl, 3-aminopropynyl, 3-hydroxypropynyl, and the like, preferably, ethynyl, 1-propynyl, 2-propynyl, 3,3,3-trifluoropropynyl, and the like.

The examples of "amino substituted by substituent B" at $R^2$ are methylamino, ethylamino, propylamino, isopropylamino, tert-butylamino, isobutylamino, sec-butylamino, phenylamino, benzylamino, phenethylamino, phenylpropylamino, N-phenyl-N-benzylamino, N-ethyl-N-benzylamino, N,N-dimethylamino, N,N-diethylamino, N,N-diisopropylamino, N,N-diphenylamino, N,N-dibenzylamino, and the like, preferably, methylamino, ethylamino, N-phenyl-N-benzylamino, N-ethyl-N-benzylamino, N,N-dimethylamino, N,N-diethylamino, and the like.

The examples of "phenylaminocarbonyl substituted by substituent C" at $R^3$ are phenylaminocarbonyl, 4-methylphenylaminocarbonyl, 3,5-dimethylphenylaminocarbonyl, 2,6-dimethylphenylaminocarbonyl, 4-trifluoromethylphenylaminocarbonyl, 4-fluorophenylaminocarbonyl, 3,5-difluorophenylaminocarbonyl, 2,6-difluorophenylaminocarbonyl, and the like, preferably, 2,6-difluorophenylaminocarbonyl.

The examples of "sulfonylaminocarbonyl substituted by substituent C" at $R^3$ are methylsulfonylaminocarbonyl, ethylsulfonylaminocarbonyl, propylsulfonylaminocarbonyl, butylsulfonylaminocarbonyl, tert-butylsulfonylaminocarbonyl, phenylsulfonylaminocarbonyl, 1,5-difluorophenylsulfonylaminocarbonyl, 2-methyl-4-fluorophenylsulfonylaminocarbonyl, 3-methyl-4-fluorophenylsulfonylaminocarbonyl, 2-methylphenylsulfonylaminocarbonyl, 4-methylphenylsulfonylaminocarbonyl, 3,4-difluorophenylsulfonylaminocarbonyl, 2,4-difluorophenylsulfonylaminocarbonyl, 3,5-difluorophenylsulfonylaminocarbonyl, 2,6-difluorophenylsulfonylaminocarbonyl, 2-chlorophenylsulfonylaminocarbonyl, 3-chlorophenylsulfonylaminocarbonyl, 4-chlorophenylsulfonylaminocarbonyl, 2-fluorophenylsulfonylaminocarbonyl, 3-fluorophenylsulfonylaminocarbonyl, 4-fluorophenylsulfonylaminocarbonyl, 2-fluoro-3-chlorophenylsulfonylaminocarbonyl, cyclopropylsulfonylaminocarbonyl, cyclobutylsulfonylaminocarbonyl, benzylsulfonylaminocarbonyl, phenethylsulfonylaminocarbonyl, 2-thiophenylsulfonylaminocarbonyl, trifluoromethylsulfonylaminocarbonyl, trichloromethylsulfonylaminocarbonyl, and the like.

"Monocyclic heterocycle" of "monocyclic heterocycle substituted by substituent C" at $R^3$ includes above "monocyclic heterocycle", preferably includes tetrazolyl, imidazolyl, triazolyl, pyridyl, pyrimidinyl, thiazolyl, pyrrolyl, indolyl, and the like. Herein, the preferable aspects of "substituent C" are methyl, ethyl, propyl, phenyl, fluoro, chloro, and the like.

"Condensed polycyclic heterocycle" of "condensed polycyclic heterocycle substituted by substituent C" at $R^3$ includes above "condensed polycyclic heterocycle", preferably, includes benzoimidazolyl, benzothiazolyl, indolyl, and the like. Herein the preferable aspects of "substituent C" are methyl, ethyl, propyl, phenyl, fluoro, chloro, and the like.

The examples of "lower alkyl substituted by substituent D" at $R^4$ are methyl, ethyl, propyl, isopropyl, tert-butyl, isobutyl, sec-butyl, hydroxymethyl, trifluoromethyl, trichloromethyl, aminomethyl, 1-aminoethyl, 2-aminoethyl, 1-hydroxyethyl, 2-hydroxyethyl, and the like, preferably, methyl, ethyl, propyl, tert-butyl, trifluoromethyl, and the like.

The examples of "lower alkenyl substituted by substituent D" at $R^4$ are ethylenyl, 1-propenyl, 2-propenyl, 3,3,3-trifluoropropenyl, 3-aminopropenyl, 3-hydroxypropenyl, and the like, preferably, ethylenyl, 1-propenyl, 2-propenyl, and the like.

The examples of "lower alkynyl substituted by substituent D" at $R^4$ are ethynyl, 1-propynyl, 2-propynyl, 3,3,3-trifluoropropynyl, 3-aminopropynyl, 3-hydroxypropynyl, and the like, preferably, ethynyl, 1-propynyl, 2-propynyl, 3,3,3-trifluoropropynyl, and the like.

The preferable aspects of $R^1$ are hydrogen, methyl, ethyl, propyl, isopropyl, tert-butyl, ethylenyl, ethynyl, preferably, hydrogen, methyl, ethyl, and further preferably, hydrogen.

The preferable aspects of "monocyclic carbocycle" defined as P in $R^2$ are

[Formula 19]

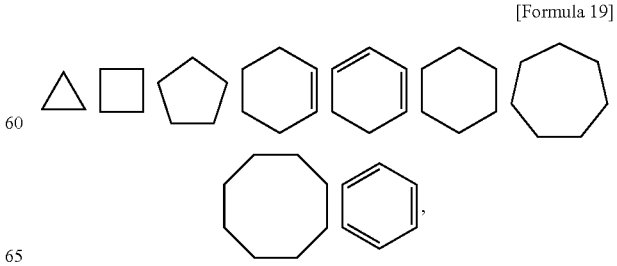

more preferably, P are

[Formula 20]

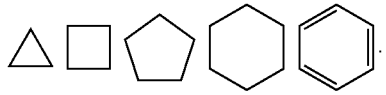

The preferable aspects of "monocyclic heterocycle" defined as P in $R^2$ are

[Formula 21]

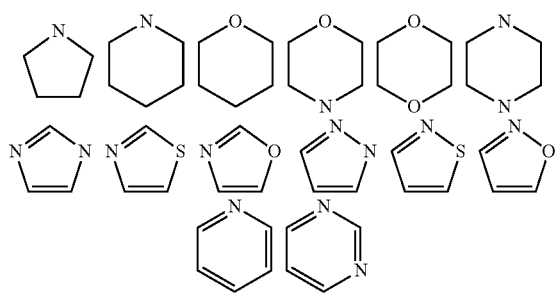

(wherein when the nitrogen atom described by "—N—" dose not bind to the adjacent group of P, the nitrogen atom binds to hydrogen atom), more preferably,

[Formula 22]

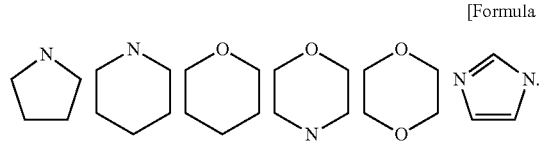

The preferable aspects of "condensed polycyclic hydrocarbon" defined as P in $R^2$ are

[Formula 23]

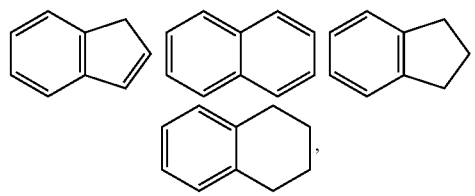

more preferably,

[Formula 24]

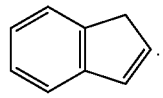

The preferable aspects of "condensed polycyclic hererocycle" defined as P in $R^2$ are

[Formula 25]

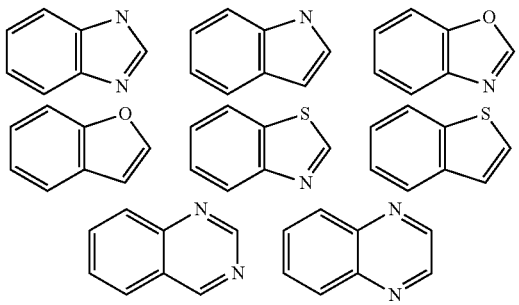

(wherein when the nitrogen atom described by "—N—" dose not bind to the adjacent group of P, the nitrogen atom binds to hydrogen atom), more preferably,

[Formula 26]

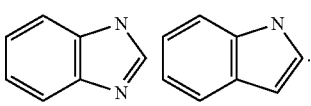

The preferable aspects of "monocyclic carbocycle" defined as Q in $R^2$ are

[Formula 27]

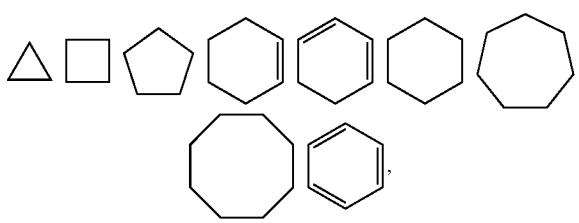

more preferably,

[Formula 28]

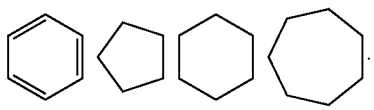

The preferable aspects of "monocyclic heterocycle" defined as Q in $R^2$ are

[Formula 29]

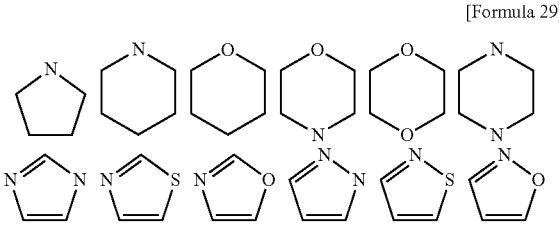

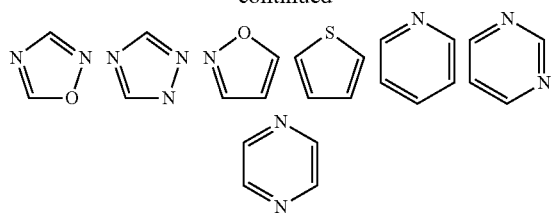

(wherein when the nitrogen atom described by "—N—" dose not bind to the adjacent group of P, the nitrogen atom binds to hydrogen atom), more preferably,

[Formula 30]

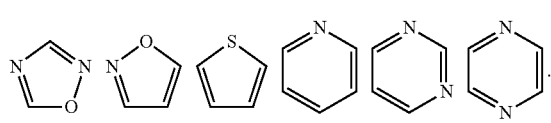

The preferable aspects of "condensed polycyclic hydrocarbon" defined as Q in $R^2$ are

[Formula 31]

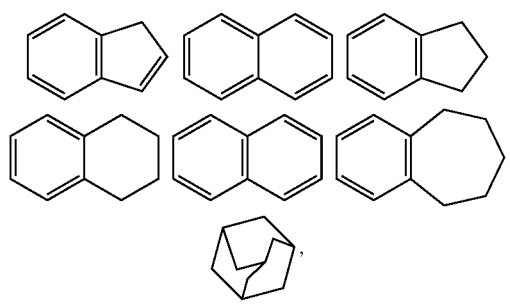

more preferably,

[Formula 32]

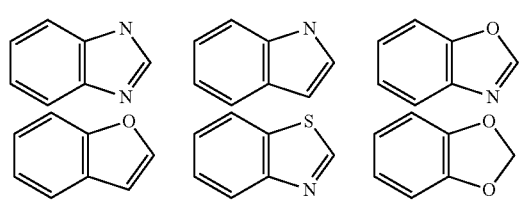

The preferable aspects of "condensed polycyclic heterocycle" defined as Q in $R^2$ are

[Formula 33]

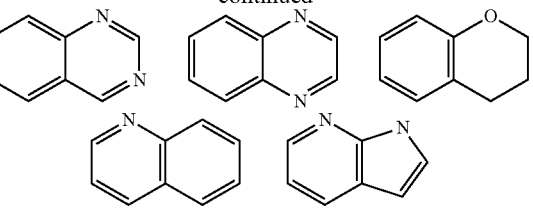

(wherein when the nitrogen atom described by "—N—" dose not bind to the adjacent group of P, the nitrogen atom binds to hydrogen atom), more preferably,

[Formula 34]

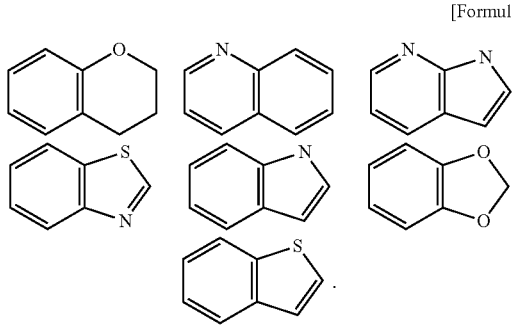

The preferable aspects of "monocyclic heterocycle" defined as T in $R^2$ are

[Formula 35]

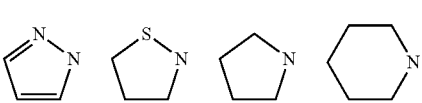

(wherein when the nitrogen atom described by "—N—" dose not bind to adjacent groups of P, the group binds to hydrogen atom).

The preferable aspects of $R^3$ are hydroxy, carboxy, 2,6-difluorophenylaminocarbonyl, methylsulfonylaminocarbonyl, butylsulfonylaminocarbonyl, phenylsulfonylaminocarbonyl, 1,5-difluorophenylsulfonylaminocarbonyl, 2-methyl-4-fluorophenylsulfonylaminocarbonyl, 3-methyl-4-fluorophenylsulfonylaminocarbonyl, 2-methylphenylsulfonylaminocarbonyl, 4-methylphenylsulfonylaminocarbonyl, 3,4-difluorophenylsulfonylaminocarbonyl, 2,4-difluorophenylsulfonylaminocarbonyl, 3,5-difluorophenylsulfonylaminocarbonyl, 2,6-difluorophenylsulfonylaminocarbonyl, 2-chlorophenylsulfonylaminocarbonyl, 3-chlorophenylsulfonylaminocarbonyl, 4-chlorophenylsulfonylaminocarbonyl, 2-fluorophenylsulfonylaminocarbonyl, 3-fluorophenylsulfonylaminocarbonyl, 4-fluorophenylsulfonylaminocarbonyl, 2-fluoro-3-chlorophenylsulfonylaminocarbonyl, cyclopropylsulfonylaminocarbonyl, cyclobutylsulfonylaminocarbonyl, benzylsulfonylaminocarbonyl, 2-thiophenylsulfonylaminocarbonyl, trifluoromethylsulfonylaminocarbonyl, more preferably hydroxy, and carboxy, and further more preferably, carboxy.

The preferable aspects of $R^4$ are hydrogen, methyl, ethyl, propyl, isoproptl, tert-butyl, ethylenyl, ethynyl, more preferably, hydrogen, methyl, ethyl, and further more preferably, hydrogen.

The "solvate" includes for example a solvate with organic solvent and hydrate, and the like. In the case of hydrate, the compound may coordinate arbitrary number of water molecules.

The compound of this invention includes "pharmaceutically acceptable salts".

For example, salts with alkali metal (Li, Na, or K, and the like), alkali earth metal (Mg or Ca, and the like), ammonium, organic base, and amino acid, or inorganic acid (hydrochloric acid, sulfuric acid, nitric acid, hydrobromic acid, phosphoric acid, or hydriodic acid, and the like), and organic acids (acetic acid, trifluoroacetic acid, citric acid, lactic acid, tartaric acid, oxalic acid, maleic acid, fumaric acid, mandelic acid, glutaric acid, malic acid, benzoic acid, phthalic acid, benzenesulfonic acid, p-toluene sulfonic acid, methane sulfonic acid, or ethanesulfonic acid, and the like). These salts can be formed by common methods.

In addition, the compounds of this invention are not limited to particular isomers, but include any possible isomers (keto-enol isomer, imine-enamine isomer, diastereo isomer, stereoisomer, and rotational isomer, and the like) and racemates.

One of the characteristic points of this invention is enhancing cap-dependent endonuclease inhibitory activity by applying a substituent except for hydrogen to $R^2$ in formula (I), preferably a substituent selected from a group consisting of 1) to 5) below:

1) amino optionally substituted by substituent B,
wherein the substituent B is at least one substituent selected from a group consisting of alkyl, aryl, and aryl lower alkyl;
2) a group shown by —$(CX^1X^2)_m$—Y—$(CH_2)_n$—Z
[wherein $X^1$ and $X^2$ are each independently hydrogen, hydroxy, hydroxy lower alkyl, lower alkyl, aryl, aryl lower alkyl, or monocyclic heterocycle,
Y is a single bond, S, $SO_2$, O, NH, NHCO, or CONH,
m and n are each independently an integer of 0 or more, with a proviso that m of $X^1$s may be same or different, m of $X^2$s may be same or different,
Z is selected from a group consisting of a) to l) below;

[Formula 36]

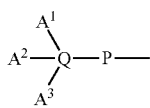

a)

b) [Formula 37]

A$^4$-Q-C≡C—P— c) A$^5$-Q-C≡C—P—
d) A$^6$-Q-(CH$_2$)$_{r1}$—P—
e) A$^7$-Q-CO—P—
f) A$^8$-Q-(CH$_2$)$_{r2}$—O—CO—P—
g) A$^9$-Q-CO—(CH$_2$)$_{r3}$—O—CO—P—
h) A$^{10}$-Q-CO—NH—P—
i) A$^{11}$-Q-O—P—
j) A$^{12}$-Q-S—P—
k) A$^{13}$-Q-SO$_2$—P—

[Formula 38]

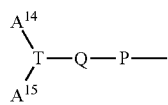

l)

T is monocyclic heterocycle,
(with a proviso that P is a single bond, monocyclic hydrocarbon, monocyclic heterocycle, condensed polycyclic hydrocarbon, or condensed polycyclic heterocycle, wherein when P is not a single bond, P may be substituted by at least one substituent selected from a group consisting of halogen, hydroxy, nitrile, amino, lower alkylamino, aminosulfonyl, aminocarbonyl, lower alkylcarbonyl, lower alkyl, halogeno lower alkyl, lower alkyloxy, oxo, and aryl,
Q is monocyclic hydrocarbon, monocyclic heterocycle, condensed polycyclic hydrocarbon, or condensed polycyclic heterocycle,
$A^1, A^2, A^3, A^4, A^5, A^6, A^7, A^8, A^9, A^{10}, A^{11}, A^{12}, A^{13}, A^{14}$ and $A^{15}$ are each independently selected from a substituent group consisting of hydrogen, lower alkyl, halogeno lower alkyl, lower alkyloxy lower alkyl, lower alkyloxy, lower alkyloxy lower alkyloxy, halogeno lower alkyloxy, halogeno lower alkylcarbonyl, aryl, aryloxy, lower alkyloxyaryl, aryl lower alkyloxy, lower alkylcarbonyl, aminocarbonyl, lower alkyl aminocarbonyl, cycloalkylaminocarbonyl, amino, lower alkylamino, lower alkylcarbonylamino, cycloalkyl lower alkylamino, aminosulfonyl, arylsulfonyl, lower alkylsulfonyl, lower alkylsulfonylamino, morphollinylcarbonyl, pyrroridinylcarbonyl, hydroxy, hydroxy lower alkyl, nitrile, oxo, aryl aminocarbonyl, and halogen;
r1, r2, and r3 are each independently an integer of 1 or more) 1,
3) C4-C10 alkyl,
4) lower alkyloxy lower alkyl, and
5) a group shown below,

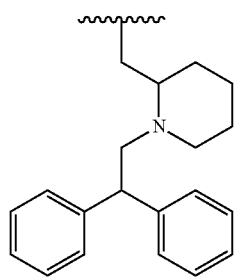

[Formula 39]

The preferable aspect of $R^2$ is above 2); a group shown by —$(CX^1X^2)_m$—Y—$(CH_2)_n$—Z [wherein $X^1$ and $X^2$ are each independently hydrogen, hydroxy, hydroxy lower alkyl, lower alkyl, aryl, aryl lower alkyl, or monocyclic heterocycle,
Y is a single bond, S, $SO_2$, O, or CONH,
m and n are each independently an integer of 0 or more, with a proviso that m of $X^1$s may be same or different, m of $X^2$s may be same or different,
Z is selected from a substituent group consisting of:

[Formula 40]

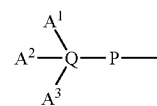

a)

(wherein $A^1$, $A^2$ and $A^3$ are each independently selected from a group consisting of hydrogen, lower alkyl, halogeno lower alkyl, lower alkyloxy, halogeno lower alkyloxy, halogeno lower alkylcarbonyl, aryl, aryloxy, lower alkylcarbonyl, aminocarbonyl, cycloalkyl aminocarbonyl, lower alkylcarbonylamino, lower alkylamino, cycloalkyl lower alkylamino, arylsulfonyl, lower alkylsulfonyl, lower alkylsulfonylamino, hydroxy, nitrile, aryl aminocarbonyl, and halogen, and a group shown below:

[Formula 41]

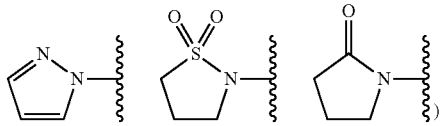

d) $A^6$-Q-$(CH_2)_{r1}$—P— ($A^6$ is hydrogen, nitrile, or halogen),
f) $A^8$-Q-$(CH_2)_{r2}$—O—CO—P— ($A^8$ is hydrogen, lower alkyl, halogeno lower alkyl, lower alkyloxy aryl, nitrile, or halogen),
h) $A^{10}$-Q-CO—NH—P— ($A^{10}$ is hydrogen),
i) $A^{11}$-Q-O—P— ($A^{11}$ is hydrogen), and
j) $A^{12}$-Q-S—P— ($A^{12}$ is hydroxy lower alkyl),
(wherein P is a single bond, monocyclic hydrocarbon, monocyclic heterocycle, condensed polycyclic hydrocarbon, or condensed polycyclic heterocycle,
wherein when P is not a single bond, P may be substituted by one or more substituent selected from a group consisting of halogen, hydroxy, nitrile, amino, lower alkylamino, aminosulfonyl, aminocarbonyl, lower alkylcarbonyl, lower alkyl, halogeno lower alkyl, lower alkyloxy, oxo, and aryl,
Q is monocyclic hydrocarbon, condensed polycyclic hydrocarbon, monocyclic heterocycle, or condensed polycyclic heterocycle, and
r1, r2, and r3 are each independently an integer of 1 or more)].
The more preferable aspect of $R^2$ is any one of a formula shown below:

[Formula 42]

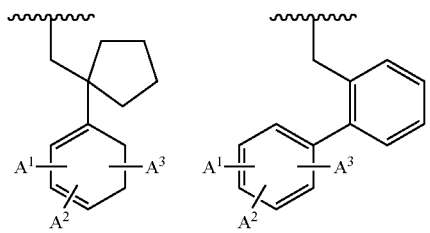

(wherein $A^1$, $A^2$, and $A^3$ is selected from a group consisting of hydrogen, methyl, trifluoromethyl, methoxy, ethoxy, trifluoromethoxy, trifluoromethylcarbonyl, phenyl, phenoxy, methylcarbonyl, aminocarbonyl, cyclopropylaminocarbonyl, methylcarbonylamino, dimethylamino, methylsulfonyl, methylsulfonylamino, hydroxy, nitrile, fluoro, and chloro).

Another characteristic point of this invention is enhancing cap-dependent endonuclease inhibitory activity by applying a substituent to $R^3$ in formula (I), preferably a substituent selected from a group consisting of 1) to 6) below:
1) hydroxy,
2) carboxy,
3) phenylaminocarbonyl optionally substituted by substituent C,
4) sulfonylaminocarbonyl optionally substituted by substituent C,
5) monocyclic heterocycle optionally substituted by substituent C, and
6) condensed polycyclic heterocycle optionally substituted by substituent C,
wherein substituent C is at least one substituent selected from a group consisting of a) to e):
a) optionally substituted lower alkyl (with a proviso that the substituent is halogen),
b) halogen,
c) optionally substituted monocyclic hydrocarbon (with a proviso that the substituent is lower alkyl, and/or halogen),
d) monocyclic heterocycle, and
e) optionally substituted aryl lower alkyl (with a proviso that the lower alkyl, and/or halogen);

The preferable aspect of $R^3$ is one substituent selected from a group consisting of 1) to 4) below:
1) hydroxy,
2) carboxy,
3) phenylaminocarbonyl optionally substituted by substituent C, and
4) sulfonylaminocarbonyl substituted by substituent C,
wherein substituent C is at least one substituent selected from a group consisting of a) to e) below:
a) lower alkyl optionally substituted (with a proviso that the substituent is halogen),
b) halogen,
c) monocyclic hydrocarbon optionally substituted (with a proviso that the substituent is lower alkyl, and/or halogen),
d) monocyclic heterocycle, and
e) aryl lower alkyl optionally substituted (with a proviso that the substituent is lower alkyl, and/or halogen).

The more preferable aspect of $R^3$ is carboxy.
The preferable aspects of this invention are exemplified below. Each symbol is the same as shown above.
In formula (I):

[Formula 43]

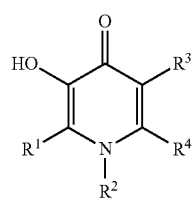

1)
A compound wherein $R^1$ is hydrogen (hereinafter, $R^1$ is R1-1)
A compound wherein $R^1$ is lower alkyl optionally substituted by substituent A (hereinafter, $R^1$ is R1-2)
wherein substituent A is at least a substituent selected from a group consisting of halogen, amino, and hydroxy;
2)
A compound wherein $R^2$ is amino optionally substituted by substituent B (hereinafter, $R^2$ is R2-1)
wherein substituent B is at least a substituent selected from a group consisting of alkyl, aryl, and aryl lower alkyl;

A compound wherein $R^2$ is a group shown below:

$$\text{—}(CX^1X^2)m\text{—}Y\text{—}(CH_2)n\text{—}P\text{—}Q\begin{smallmatrix}\diagup A^1\\ \text{—}A^2\\ \diagdown A^3\end{smallmatrix}\quad\text{[Formula 44]}$$

(hereinafter, $R^2$ is R2-2);
A compound wherein $R^2$ is a group shown below:

$$\text{—}(CX^1X^2)m\text{—}Y\text{—}(CH_2)n\text{—}P\text{—}C\equiv C\text{-}Q\text{-}A^4 \quad\text{[Formula 45]}$$

(hereinafter, $R^2$ is R2-3);
A compound wherein $R^2$ is a group shown by $-(CX^1X^2)_m-Y-(CH2)_n-P-C=C-Q-A^5$ (hereinafter, $R^2$ is R2-4);
A compound wherein $R^2$ is a group shown by $-(CX^1X^2)_m-Y-(CH_2)_n-P-(CH_2)_{r1}-Q-A^6$ (hereinafter, $R^2$ is R2-5);
A compound wherein $R^2$ is a group shown by $-(CX^1X^2)_m-Y-(CH_2)_n-P-CO-Q-A^7$ (hereinafter, $R^2$ is R2-6);
A compound wherein $R^2$ is a group shown by $-(CX^1X^2)_m-Y-(CH_2)_n-P-CO-O-(CH_2)_{r2}-Q-A^9$ (hereinafter, $R^2$ is R2-7);
A compound wherein $R^2$ is a group shown by $-(CX^1X^2)_m-Y-(CH_2)_n-P-NH-CO-O-Q-A^{10}$ (hereinafter, $R^2$ is R2-8);
A compound wherein $R^2$ is a group shown by $-(CX^1X^2)_m-Y-(CH_2)_n-P-O-Q-A^{11}$ (hereinafter, $R^2$ is R2-9);
A compound wherein $R^2$ is a group shown by $-(CX^1X^2)_m-Y-(CH_2)_n-P-S-Q-A^{12}$ (hereinafter, $R^2$ is R2-10);
A compound wherein $R^2$ is a group shown by $-(CX^1X^2)_m-Y-(CH_2)_n-P-SO_2-Q-A^{13}$ (hereinafter, $R^2$ is R2-11);
[wherein $X^1$ and $X^2$ are each independently hydrogen, hydroxy, hydroxy lower alkyl, lower alkyl, aryl, aryl lower alkyl, or monocyclic heterocycle,
Y is a single bond, S, $SO_2$, O, NH, NHCO, or CONH,
m and n are each independently an integer of 0 or more, with a proviso that m of $X^1$s may be the same or different, m of $X^2$s may be the same or different,
(with a proviso that P is a single bond, monocyclic hydrocarbon, monocyclic heterocycle, condensed polycyclic hydrocarbon, or condensed polycyclic heterocycle, wherein when P is not a single bond, P may be substituted by one or more substituent selected from a group consisting of halogen, hydroxy, nitrile, amino, lower alkylamino, aminosulfonyl, aminocarbonyl, lower alkylcarbonyl, lower alkyl, halogeno lower alkyl, lower alkyloxy, oxo, and aryl,
Q is monocyclic hydrocarbon, monocyclic heterocycle, condensed polycyclic hydrocarbon, or condensed polycyclic heterocycle,
$A^1, A^2, A^3, A^4, A^5, A^6, A^7, A^8, A^9, A^{10}, A^{11}, A^{12}, A^{13}, A^{14}$, and $A^{15}$ are each independently selected from a substituent group consisting of hydrogen, lower alkyl, halogeno lower alkyl, lower alkyloxy lower alkyl, lower alkyloxy, lower alkyloxy lower alkyloxy, halogeno lower alkyloxy, halogeno lower alkylcarbonyl, aryl, aryloxy, lower alkyloxy aryl, aryl lower alkyloxy, lower alkylcarbonyl, aminocarbonyl, lower alkyl aminocarbonyl, cycloalkylaminocarbonyl, amino, lower alkylamino, lower alkylcarbonylamino, cycloalkyl lower alkylamino, aminosulfonyl, arylsulfonyl, lower alkylsulfonyl, lower alkylsulfonylamino, morpholinylcarbonyl, pyrroridinylcarbonyl, hydroxy, hydroxy lower alkyl, nitrile, oxo, aryl aminocarbonyl and halogen;
r1, r2, and r3 are each independently an integer of 1 or more)]
A compound wherein $R^2$ is a group shown by C4-C10alkyl (hereinafter, $R^2$ is R2-12);
A compound wherein $R^2$ is a group shown by lower alkyloxy lower alkyloxy (hereinafter, $R^2$ is R2-13);
3)
A compound wherein $R^3$ is hydroxy (hereinafter, $R^3$ is R3-1);
A compound wherein $R^3$ is carboxy (hereinafter, $R^3$ is R3-2);
A compound wherein $R^3$ is phenylaminocarbonyl optionally substituted by substituent C (hereinafter, $R^3$ is R3-3);
A compound wherein $R^3$ is sulfonylaminocarbonyl optionally substituted by substituent C (hereinafter, $R^3$ is R3-4);
A compound wherein $R^3$ is monocyclic heterocycle optionally substituted by substituent C (hereinafter, $R^3$ is R3-5);
A compound wherein $R^3$ is condensed polycyclic heterocycle optionally substituted by substituent C (hereinafter, $R^3$ is R3-6);
wherein substituent C is at least one substituent selected from a group consisting of a) to e);
  a) optionally substituted lower alkyl (with a proviso that the substituent is halogen),
  b) halogen,
  c) optionally substituted monocyclic hydrocarbon (with a proviso that the substituent is lower alkyl, and/or halogen),
  d) monocyclic heterocycle, and
  e) optionally substituted aryl lower alkyl (with a proviso that the lower alkyl, and/or halogen);
4)
A compound wherein $R^4$ is hydrogen (hereinafter, $R^4$ is R4-1);
A compound wherein $R^4$ is lower alkyl optionally substituted by substituent D (hereinafter, $R^4$ is R4-2);
wherein substituent D is at least one substituent selected from a group consisting of halogen, amino, and hydroxy.
A compound wherein the combinations of $R^1$, $R^2$, $R^3$, and $R^4$ are as follows:
(R1-1, R2-1, R3-1, R4-1), (R1-1, R2-1, R3-1, R4-2), (R1-1, R2-1, R3-2, R4-1), (R1-1, R2-1, R3-2, R4-2), (R1-1, R2-1, R3-3, R4-1), (R1-1, R2-1, R3-3, R4-2), (R1-1, R2-1, R3-4, R4-1), (R1-1, R2-1, R3-4, R4-2), (R1-1, R2-1, R3-5, R4-1), (R1-1, R2-1, R3-5, R4-2), (R1-1, R2-1, R3-6, R4-1), (R1-1, R2-1, R3-6, R4-2), (R1-1, R2-2, R3-1, R4-1), (R1-1, R2-2, R3-1, R4-2), (R1-1, R2-2, R3-2, R4-1), (R1-1, R2-2, R3-2, R4-2), (R1-1, R2-2, R3-3, R4-1), (R1-1, R2-2, R3-3, R4-2), (R1-1, R2-2, R3-4, R4-1), (R1-1, R2-2, R3-4, R4-2), (R1-1, R2-2, R3-5, R4-1), (R1-1, R2-2, R3-5, R4-2), (R1-1, R2-2, R3-6, R4-1), (R1-1, R2-2, R3-6, R4-2), (R1-1, R2-3, R3-1, R4-1), (R1-1, R2-3, R3-1, R4-2), (R1-1, R2-3, R3-2, R4-1), (R1-1, R2-3, R3-2, R4-2), (R1-1, R2-3, R3-3, R4-1), (R1-1, R2-3, R3-3, R4-2), (R1-1, R2-3, R3-4, R4-1), (R1-1, R2-3, R3-4, R4-2), (R1-1, R2-3, R3-5, R4-1), (R1-1, R2-3, R3-5, R4-2), (R1-1, R2-3, R3-6, R4-1), (R1-1, R2-3, R3-6, R4-2), (R1-1, R2-4, R3-1, R4-1), (R1-1, R2-4, R3-1, R4-2), (R1-1, R2-4, R3-2, R4-1), (R1-1, R2-4, R3-2, R4-2), (R1-1, R2-4, R3-3, R4-1), (R1-1, R2-4, R3-3, R4-2), (R1-1, R2-4, R3-4, R4-1), (R1-1, R2-4, R3-4, R4-2), (R1-1, R2-4, R3-5, R4-1), (R1-1, R2-4, R3-5, R4-2), (R1-1, R2-4, R3-6, R4-1), (R1-1, R2-4, R3-6, R4-2), (R1-1, R2-5, R3-1, R4-1), (R1-1, R2-5, R3-1, R4-2), (R1-1, R2-5, R3-2, R4-1), (R1-1, R2-5, R3-2, R4-2), (R1-1, R2-5, R3-3, R4-1), (R1-1, R2-5, R3-3, R4-2), (R1-1, R2-5, R3-4, R4-1), (R1-1, R2-5, R3-4, R4-2), (R1-1, R2-5, R3-5, R4-1), (R1-1, R2-5, R3-5, R4-2), (R1-1, R2-5, R3-6, R4-1), (R1-1, R2-5, R3-6, R4-2), (R1-1, R2-6, R3-1, R4-1), (R1-1, R2-6, R3-1, R4-2), (R1-1, R2-6, R3-2, R4-1), (R1-1, R2-6, R3-2, R4-2), (R1-1, R2-6, R3-3, R4-1), (R1-1, R2-6, R3-3, R4-2), (R1-1, R2-6, R3-4, R4-1), (R1-1, R2-6, R3-4, R4-2), (R1-1, R2-6, R3-5, R4-1), (R1-1, R2-6, R3-5, R4-2), (R1-1, R2-6, R3-6, R4-1), (R1-1, R2-6, R3-6, R4-2), (R1-1, R2-7, R3-1, R4-1), (R1-1, R2-7, R3-1, R4-2), (R1-1, R2-7, R3-2, R4-1), (R1-1, R2-7, R3-2, R4-2), (R1-1, R2-7, R3-3, R4-1), (R1-1, R2-7, R3-3, R4-2), (R1-1, R2-7, R3-4, R4-1), (R1-1, R2-7, R3-4, R4-2), (R1-1, R2-7, R3-5, R4-1), (R1-1, R2-7, R3-5, R4-2), (R1-1, R2-7, R3-6, R4-1), (R1-1, R2-7, R3-6, R4-2), (R1-1, R2-8, R3-1, R4-1), (R1-1, R2-8, R3-1, R4-2), (R1-1, R2-8, R3-2, R4-1), (R1-1, R2-8, R3-2, R4-2), (R1-1, R2-8, R3-3, R4-1), (R1-1, R2-8, R3-3, R4-2), (R1-1, R2-8, R3-4, R4-1), (R1-1, R2-8, R34, R4-2), (R1-1, R2-8, R3-5, R4-1), (R1-1, R2-8, R3-5, R4-2), (R1-1, R2-8, R3-6, R4-1), (R1-1, R2-8, R3-6, R4-2), (R1-1, R2-9, R3-1, R4-1), (R1-1, R2-9, R3-1, R4-2), (R1-1, R2-9, R3-2, R4-1), (R1-1, R2-9, R3-2, R4-2), (R1-1, R2-9, R3-3, R4-1), (R1-1, R2-9, R3-3, R4-2), (R1-1, R2-9, R3-4, R4-1), (R1-1, R2-9, R3-4, R4-2), (R1-1, R2-9, R3-5, R4-1), (R1-1, R2-9, R3-5, R4-2), (R1-1, R2-9, R3-6, R4-1), (R1-1, R2-9, R3-6, R4-2), (R1-1, R2-10, R3-1, R4-1), (R1-1, R2-10, R3-1, R4-2), (R1-1, R2-10, R3-2, R4-1), (R1-1, R2-10, R3-2, R4-2), (R1-1, R2-10, R3-3, R4-1), (R1-1, R2-10, R3-3, R4-2), (R1-1, R2-10, R3-4, R4-1), (R1-1, R2-10, R3-4, R4-2), (R1-1, R2-10, R3-5, R4-1), (R1-1, R2-10, R3-5, R4-2), (R1-1, R2-10, R3-6, R4-1), (R1-1, R2-10, R3-6, R4-2), (R1-1, R2-11, R3-1, R4-1), (R1-1, R2-11, R3-1, R4-2), (R1-1, R2-11, R3-2, R4-1), (R1-1, R2-11, R3-2, R4-2), (R1-1, R2-11, R3-3, R4-1), (R1-1, R2-11, R3-3, R4-2), (R1-1, R2-11, R3-4, R4-1), (R1-1, R2-11, R3-4, R4-2), (R1-1, R2-11, R3-5, R4-1), (R1-1, R2-11, R3-5, R4-2), (R1-1, R2-11, R3-6, R4-1), (R1-1, R2-11, R3-6, R4-2), (R1-2, R2-1, R3-1, R4-1), (R1-2, R2-1, R3-1, R4-2), (R1-2, R2-1, R3-2, R4-1), (R1-2, R2-1, R3-2, R4-2), (R1-2, R2-1, R3-3, R4-1), (R1-2, R2-1, R3-3, R4-2), (R1-2, R2-1, R3-4, R4-1), (R1-2, R2-1, R3-4, R4-2), (R1-2, R2-1, R3-5, R4-1), (R1-2, R2-1, R3-5, R4-2), (R1-2, R2-1, R3-6, R4-1), (R1-2, R2-1, R3-6, R4-2), (R1-2, R2-2, R3-1, R4-1), (R1-2, R2-2, R3-1, R4-2), (R1-2, R2-2, R3-2, R4-1), (R1-2, R2-2, R3-2, R4-2), (R1-2, R2-2, R3-3, R4-1), (R1-2, R2-2, R3-3, R4-2), (R1-2, R2-2, R3-4, R4-1), (R1-2, R2-2, R3-4, R4-2), (R1-2, R2-2, R3-5, R4-1), (R1-2, R2-2, R3-5, R4-2), (R1-2, R2-2, R3-6, R4-1), (R1-2, R2-2, R3-6, R4-2), (R1-2, R2-3, R3-1, R4-1), (R1-2, R2-3, R3-1, R4-2), (R1-2, R2-3, R3-2, R4-1), (R1-2, R2-3, R3-2, R4-2), (R1-2, R2-3, R3-3, R4-1), (R1-2, R2-3, R3-3, R4-2), (R1-2, R2-3, R3-4, R4-1), (R1-2, R2-3, R3-4, R4-2), (R1-2, R2-3, R3-5, R4-1), (R1-2, R2-3, R3-5, R4-2), (R1-2, R2-3, R3-6, R4-1), (R1-2, R2-3, R3-6, R4-2), (R1-2, R2-4, R3-1, R4-1), (R1-2, R2-4, R3-1, R4-2), (R1-2, R2-4, R3-2, R4-1), (R1-2, R2-4, R3-2, R4-2), (R1-2, R2-4, R3-3, R4-1), (R1-2, R2-4, R3-3, R4-2), (R1-2, R2-4, R3-4, R4-1), (R1-2, R2-4, R3-4, R4-2), (R1-2, R2-4, R3-5, R4-1), (R1-2, R2-4, R3-5, R4-2), (R1-2, R2-4, R3-6, R4-1), (R1-2, R2-4, R3-6, R4-2), (R1-2, R2-5, R3-1, R4-1), (R1-2, R2-5, R3-1, R4-2), (R1-2, R2-5, R3-2, R4-1), (R1-2, R2-5, R3-2, R4-2), (R1-2, R2-5, R3-3, R4-1), (R1-2, R2-5, R3-3, R4-2), (R1-2, R2-5, R3-4, R4-1), (R1-2, R2-5, R3-4, R4-2), (R1-2, R2-5, R3-5, R4-1), (R1-2, R2-5, R3-5, R4-2), (R1-2, R2-5, R3-6, R4-1), (R1-2, R2-5, R3-6, R4-2), (R1-2, R2-6, R3-1, R4-1), (R1-2, R2-6, R3-1, R4-2), (R1-2, R2-6, R3-2, R4-1), (R1-2, R2-6, R3-2, R4-2), (R1-2, R2-6, R3-3, R4-1), (R1-2, R2-6, R3-3, R4-2), (R1-2, R2-6, R3-4, R4-1), (R1-2, R2-6, R3-4, R4-2), (R1-2, R2-6, R3-5, R4-1), (R1-2, R2-6, R3-5, R4-2), (R1-2, R2-6, R3-6, R4-1), (R1-2, R2-6, R3-6, R4-2), (R1-2, R2-7, R3-1, R4-1), (R1-2, R2-7, R3-1, R4-2), (R1-2, R2-7, R3-2, R4-1), (R1-2, R2-7, R3-2, R4-2), (R1-2, R2-7, R3-3, R4-1), (R1-2, R2-7, R3-3, R4-2), (R1-2, R2-7, R3-4, R4-1), (R1-2, R2-7, R3-4, R4-2), (R1-2, R2-7, R3-5, R4-1), (R1-2, R2-7, R3-5, R4-2), (R1-2, R2-7, R3-6, R4-1), (R1-2, R2-7, R3-6, R4-2), (R1-2, R2-8, R3-1, R4-1), (R1-2, R2-8, R3-1, R4-2), (R1-2, R2-8, R3-2, R4-1), (R1-2, R2-8, R3-2, R4-2), (R1-2, R2-8, R3-3, R4-1), (R1-2, R2-8, R3-3, R4-2), (R1-2, R2-8, R3-4, R4-1), (R1-2, R2-8, R3-4, R4-2), (R1-2, R2-8, R3-5, R4-1), (R1-2, R2-8, R3-5, R4-2), (R1-2, R2-8, R3-6, R4-1), (R1-2, R2-8, R3-6, R4-2), (R1-2, R2-9, R3-1, R4-1), (R1-2, R2-9, R3-1, R4-2), (R1-2, R2-9, R3-2, R4-1), (R1-2, R2-9, R3-2, R4-2), (R1-2, R2-9, R3-3, R4-1), (R1-2, R2-9, R3-3, R4-2), (R1-2, R2-9, R3-4, R4-1), (R1-2, R2-9, R3-4, R4-2), (R1-2, R2-9, R3-5, R4-1), (R1-2, R2-9, R3-5, R4-2), (R1-2, R2-9, R3-6, R4-1), (R1-2, R2-9, R3-6, R4-2), (R1-2, R2-10, R3-1, R4-1), (R1-2, R2-10, R3-1, R4-2), (R1-2, R2-10, R3-2, R4-1), (R1-2, R2-10, R3-2, R4-2), (R1-2, R2-10, R3-3, R4-1), (R1-2, R2-10, R3-3, R4-2), (R1-2, R2-10, R3-4, R4-1), (R1-2, R2-10, R3-4, R4-2), (R1-2, R2-10, R3-5, R4-1), (R1-2, R2-10, R3-5, R4-2), (R1-2, R2-10, R3-6, R4-1), (R1-2, R2-10, R3-6, R4-2), (R1-2, R2-11, R3-1, R4-1), (R1-2, R2-11, R3-1, R4-2), (R1-2, R2-11, R3-2, R4-1), (R1-2, R2-11, R3-2, R4-2), (R1-2, R2-11, R3-3, R4-1), (R1-2, R2-11, R3-3, R4-2), (R1-2, R2-11, R3-4, R4-1), (R1-2, R2-11, R3-4, R4-2), (R1-2, R2-11, R3-5, R4-1), (R1-2, R2-11, R3-5, R4-2), (R1-2, R2-11, R3-6, R4-1), (R1-2, R2-11, R3-6, R4-2).

(Manufacturing Method of the Present Invention)

A compound of the present invention can be manufactured, for example, by a general synthesis method described below. Extraction and purification can be performed by general procedures in chemical experiments.

A synthesis of compound of the present invention can be performed by referring to known methods.

As a raw material, a commercially available compound, a material described in this specification, a material referred in this specification, and other known compounds are usable.

This invention includes all isomers and mixture thereof, including tautomers.

When a salt of compound of the present invention is desired, if a salt form is obtained, the salt can be purified as it is, on the other hand, if a free form is obtained, a salt can be prepared by a general method after dissolving or suspending in a suitable solvent and by adding an acid or a base.

A compound of the present invention and a pharmaceutical acceptable salt thereof may exist as an added form with water or each solvent (hydrate or solvate), these added forms are included in the present invention.

The representative general synthetic methods of the compounds of the present invention are shown below.

In the general synthetic methods and examples, the meaning of each abbreviation is as follows.

DMF: N,N-dimethylformamide
DMA: N,N-dimethylacetamide
NMP: N-methylpyrorridone
DMI: dimethylmidazolidinone
THF: tetrahydrofuran Fmoc: 9-fluorenylmethoxycarbonyl
Boc: tert-butoxycarbonyl
Cbz: benzyloxycarbonyl
DMSO: dimethylsulfoxide
Ms: methanesulfonyl
Ts: p-toluenesulfonyl
DIBAL-H or DIBAL: diisobutylalminiumhydride
DPPA: diphenylphosphorylazide
t-BuOH: tert-butylalcohol
DIEA: diisopropylethylamine
WSC: N-ethyl-N'-(3-dimethylaminopripyl)carbodiimide
HMPA: hexamethylphosphoramide
HOBt: 1-hydroxybenzotriazol
HATU: O-(7-azabenzotriazol-1-yl)-N,N,N',N'-tetramethyl uronium hexafluorophosphate
LDA: lithium diisopropylamide
NBS: N-bromosuccinimide
IBX: 2-idoxybenzoic acid
Synthesis of Pyrone Ring Derivative I-1 or Pyridinone Ring Derivative I-2 protecting group such as arylalkyl, and the like, and other symbols are the same as described above.)

First Step

To Compound aa which is commercially available or prepared by known methods in a solvent or mixture thereof such as ethyl acetate, toluene, tetrahydrofuran, and the like, tertiary amine such as pyridine, trimethylamine, N-methylmorpholine, and 4-dimethylaminopyridine, and the like, and magnesiun chloride are added. Hereto, a reagent which has substituent corresponding to the target compound ($M^{41}O_2C$—$CH_2$—$COOP^2$, wherein $M^{41}$ is alkali metal) is added, then, the mixture is reacted at 20° C. to 80° C., preferably 40° C. to 80° C., for 2 hours~24 hours, preferably 3 hours~12 hours to obtain Compound ab.

Second Step

To Compound ab in a solvent or mixture thereof such as ethyl acetate, ether, dichloromethane, tetrahydrofuran, and the like, in the presence of tertiary amine such as pyridine, trimethylamine, and 4-dimethylaminopyridine, and the like, a reagent ag which has substituent $R^4$ corresponding to the

[Formula 46]

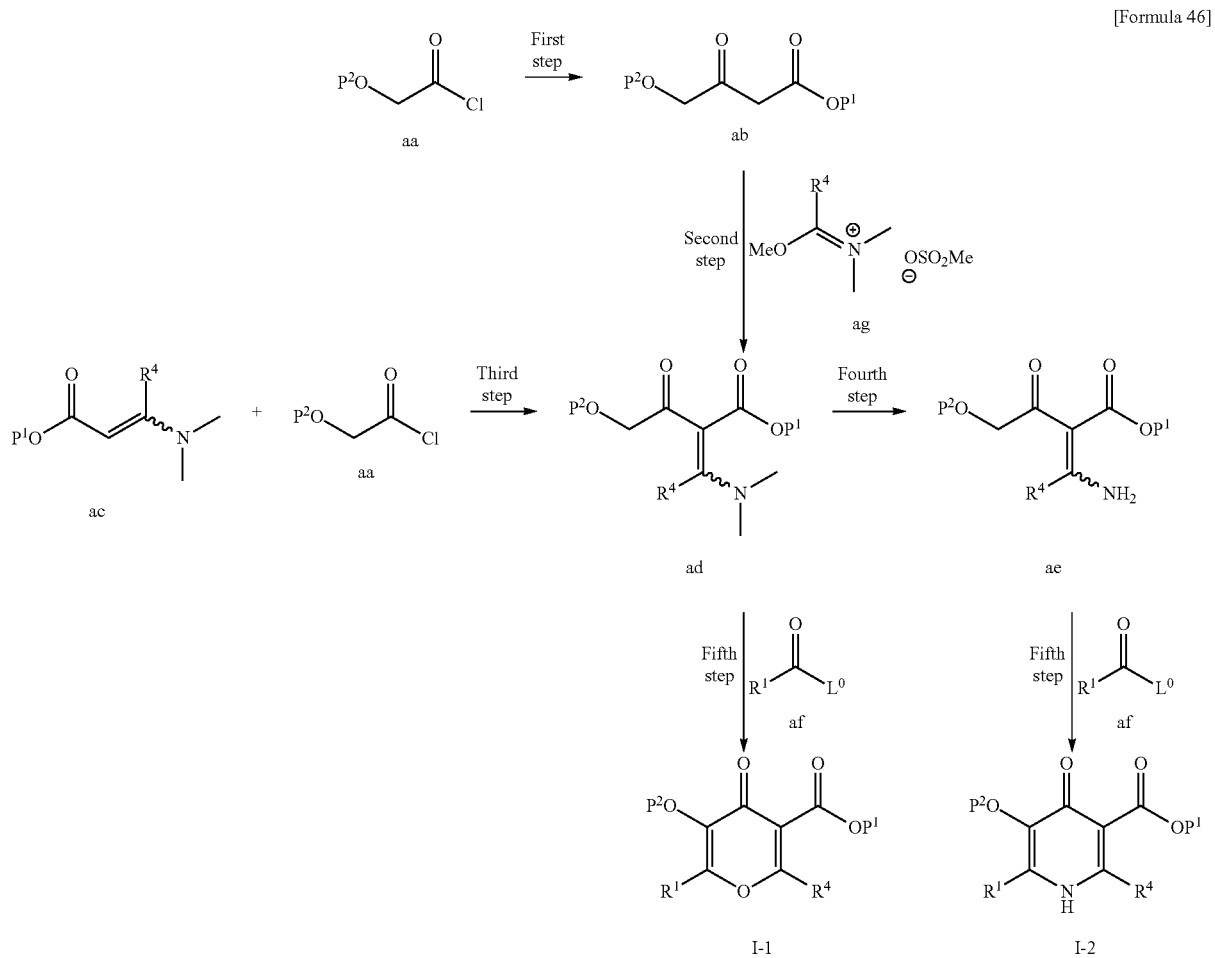

(wherein $L^0$ is a leaving group such as lower alkyloxy, and the like, $P^1$ and $P^2$ may be groups which can be protected or deprotected by methods described in Protective Groups in Organic Synthesis, Theodora W Green (John Wiley & Sons), and the like, for example, $P^1$ is a carboxy protecting group such as lower alkyl, and the like, $P^2$ is a hydroxy target compound are added, then, the mixture is reacted at 0° C. to 50° C., preferably 10° C. to 30° C., for 1 hour~24 hours, preferably 2 hours~12 hours to obtain Compound ad.

Third Step

To Compound ac which is commercially available or prepared by known methods in a solvent or mixture thereof such as ether, dichloromethane, tetrahydrofuran, and the like, in the presence of tertiaty amine such as pyridine, trimethylamine, N-methylmorpholine and 4-dimethylaminopyridine, and the like, acid halide reagent aa which have substituent corresponding to the target compound such as benzyloxyacetylchloride, and the like, is added at −40° C. to 40° C., preferably −20° C. to 20° C. Then, the mixture is reacted at −40° C. to 60° C., preferably 0° C. to 40° C. for 0.2 hours~24 hours, preferably 0.5 hours~3 hours to obtain Compound ad.

Fourth Step

To Compound ad in a solvent or mixture thereof such as ethanol, methanol, acetonitrile, and the like, ammonium salt such as ammonium acetate, ammonium chloride, and the like is added, then the mixture is reacted at reflux condition for 0.2 hours~6 hours, preferably 0.5 hours~2 hours to obtain Compound ae.

Fifth Step

To a base such as sodium hydride, potassium tert-butoxide, and the like, in a solvent or mixture thereof such as ether, dichloromethane, tetrahydrofuran, and the like, Compound ad or Compound ae is added, and the mixture is reacted at −40° C. to 20° C., preferably −40° C. to 0° C. To this reaction mixture, a reagent of which have substituent corresponding to the target compound such as methyl formate, methyl acetate is added, then the mixture is reacted at −40° C. to 40° C., preferably −40° C. to 20° C. for 0.5 hours~6 hours, preferably 1 hour~4 hours to obtain pyrone derivative I-1 or pyridinone derivative I-2.

Synthesis of Target Compound T-1 and Target Compound T-2 mixture is reacted at 0° C. to 80° C., preferably 10° C. to 50° C. for 0.2 hours~6 hours, preferably 0.5 hours~3 hours to obtain Compound I-3.

Second Step

To Compound I-3 in a solvent or mixture thereof such as ethanol, methanol, water, and the like, a base such as sodium hydroxide, potassium hydroxide, lithium hydroxide is added, then the mixture is reacted at 20° C. to 80° C., preferably 40° C. to 80° C. for 0.2 hours~6 hours, preferably 0.5 hours~3 hours to obtain Compound I-4.

Third Step

The target Compound T-1 is obtained by a known deprotecting reaction for hydroxy protecting group of Compound I-4. For example, when $P^2$ is benzyl, to Compound I-4 or Compound bb in a solvent or mixture thereof such as tetrahydrofuran, ethyl acetate, methanol, a catalyst such as Pd—C, Pd(OH)$_2$, and the like is added, then under hydrogen atmosphere, the mixture is reacted by reductive reaction at 10° C. to 50° C., preferably 20° C. to 30° C. for 0.5 hours~48 hours, preferably 1 hour~12 hours to obtain the target Compound T-1 or the target Compound T-2. Or, in a solvent such as toluene, dichloromethane, and the like, an acid reagent such as TFA and the like is added thereto, and the mixture is reacted at 0° C. to 50° C., preferably 0° C. to 30° C. for 0.5 hours~48 hours, preferably 1 hour~12 hours to obtain the target compound.

[Formula 47]

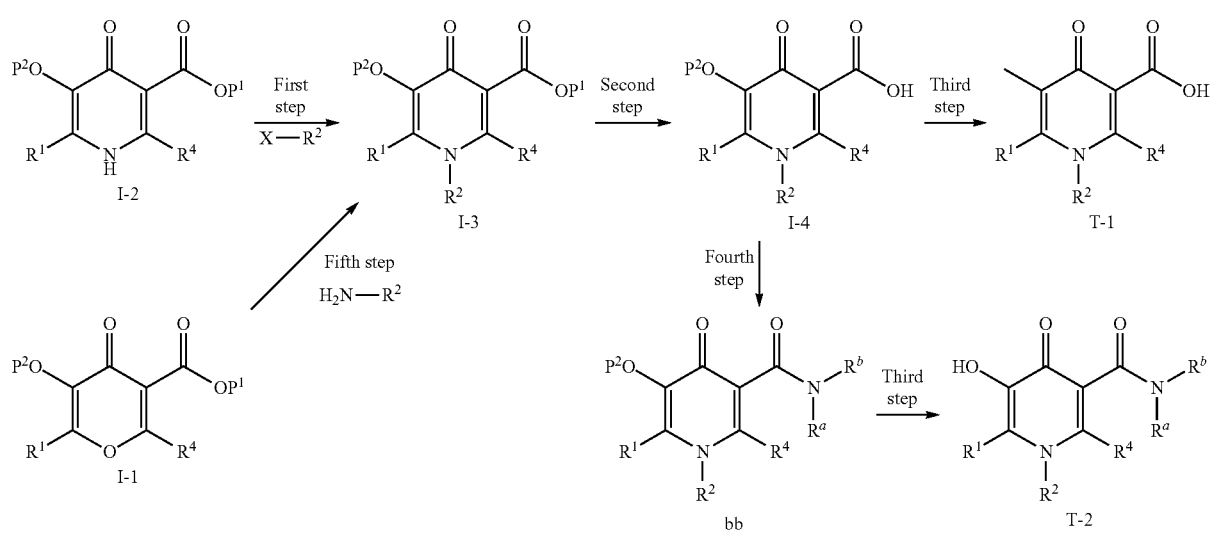

(wherein X is a leaving group such as halogen, OMs, OTs, and the like, $R^a$ is hydrogen, $R^b$ is a substituent corresponding to the target compound such as optionally substituted lower alkyl sulfonyl, optionally substituted phenylsulfonyl, optionally substituted heterocyclic sulfonyl, optionally substituted phenyl, and the like, and other symbols are the same as described above.)

First Step

To Compound I-1 in the presence of a solvent such as DMF, DMA, NMP and DMI, and the like, a base such as potassium carbonate, sodium carbonate, cesium carnobate, and the like is added, then, a reagent (X—$R^2$) which has substituent corresponding to the target compound is added thereto, and the Fourth Step To a solvent or mixture such as ether, dichloromethane, tetrahydrofuran, and the like, in the presence of pyridine, trimethylamine, tertiary amine such as diisopropylethylamine and 4-dimethylaminopyridine, and the like, an amidation reagent such as isobutyl carbonochloridate, HATU, and the like is added, then Compound I-4 is added hereto, and the mixture is reacted at −20° C. to 20° C., preferably −10° C. to 10° C. for 0.1 hours~2 hours, more preferably 0.2 hours~1 hour. To the reaction mixture, a reagent which have a substituent corresponding to the target compound such as methylsulfonic amide, and the like is added, and the mixture is reacted at 0° C. to 80° C., preferably 10° C. to 30° C. for 1 hour~48 hours, preferably 2 hours~24 hours to obtain Compound bb.

Fifth Step

To Compound I-1 in a solvent or mixture thereof such as ethanol, isopropylalcohol, DMF, DMA, tetrahydrofuran, dioxane, toluene, and the like, acetic acid and $H_2N$—$R^2$ are added if needed, then the mixture is reacted at 20° C. to 150° C., preferably 20° C. to 80° C. for 0.5 hours~12 hours, preferably 1 hour~6 hours, to obtain Compound I-3.

Synthesis of Compound cc

[Formula 48]

(wherein $L^1$ is methanesulfonyl, p-toluenesulfonyl, and the like, to form a leaving group as $L^1O$, A is carbocycle or heterocycle which is a cyclic group corresponding to the target product, $L^2$ is halogen, M is an organometal reagent such as $B(OR^L)_2$ or $SnR^L_3$, and the like, $R^L$ is hydrogen, lower alkyl, or halogeno lower alkyl, $R^c$ is a substituent corresponding to the target compound, and other symbols are the same as described above.)

First Step To Compound I-1, in the presence of a solvent such as DMF, DMA, NMP and DMI, a base such as potassium carbonate, sodium carbonate, cesium carbonate, and the like, and reagent ca or ca' which has a substituent corresponding to the target compound are added, then the mixture is reacted at 0° C. to 80° C., preferably 10° C. to 50° C. for 0.2 hours~6 hours, preferably 0.5 hours~3 hours to obtain Compound cb.

Second Step

To Compound cb in a solvent or mixture thereof such as tetrahydrofuran, dioxane, ethanol, isopropylalcohol, DMF, DMA, water, and the like, Compound M-$R^c$, 0 valent Pd catalyst such as $PdP(Ph)_4$, and the like, and a base such as sodium hydrate, sodium carbonate, potassium carbonate, sodium methoxide and sodium ethoxide, and the like are added, then the mixture is reacted at 50° C. to 120° C., preferably 60° C. to 100° C. for 1 hour~48 hours, preferably 2 hours~24 hours to obtain Compound cc.

Synthesis of Compound dd

[Formula 49]

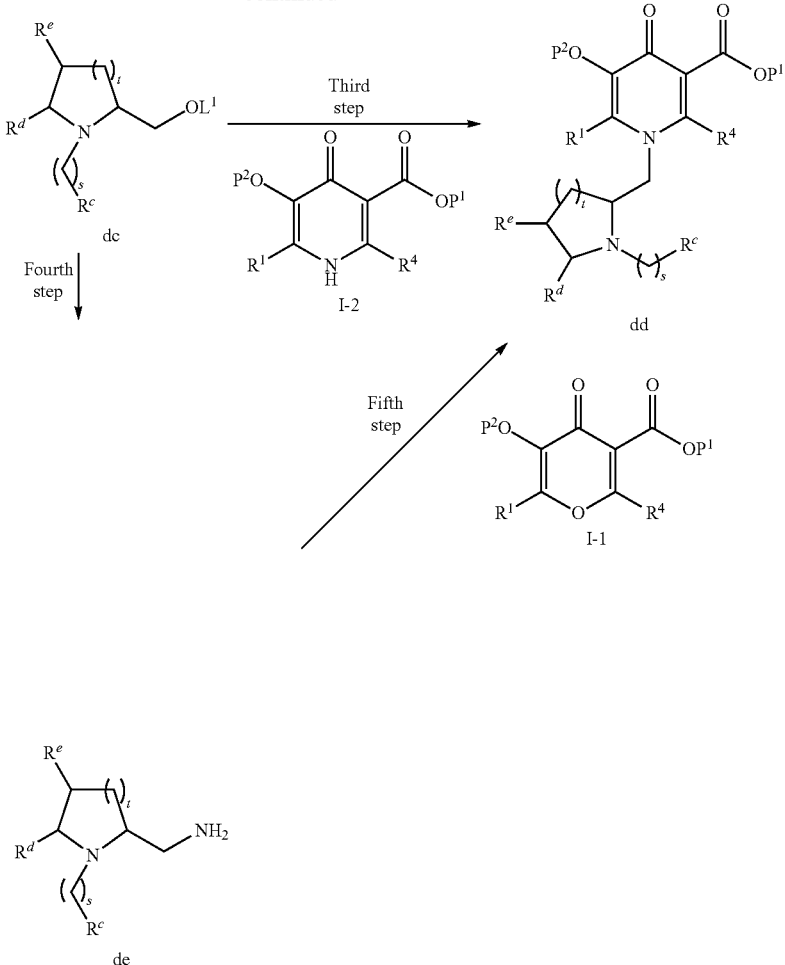

(wherein t and s are each independently an integer of 0 to 4, $R^d$ and $R^e$ are each independently lower alkyl, halogen, or hydroxy, and other symbols are the same as described above.)

First Step

To Compound da in a solvent or mixture thereof such as ether, dichloromethane, tetrahydrofuran, dioxane, and the like, $R^c$—$(CH_2)_{s-1}$—CHO is added, and reducing agent such as $NaBH(OAc)_3$, NaH, $NaBH_4$, and the like is added, then the mixture is reacted at 0° C. to 50° C., preferably 0° C. to 20° C. for 0.1 hours~12 hours, preferably 0.5 hours~4 hours to obtain Compound db.

Second Step

To Compound db in a solvent or mixture thereof such as ether, dichloromethane, tetrahydrofuran, dioxane, a base such as triethylamine, and the like and MsCl, TsCl, and the like are added, then the mixture is reacted at −20° C. to 50° C., preferably −10° C. to 30° C. for 0.5 hours~12 hours, preferably 1 hour~6 hours to obtain Compound dc.

Third Step

To Compound dc and Compound I-2 in a solvent such as DMF, DMA, NMP and DMI, and the like, a base such as potassium carbonate, sodium carbonate, cesium carbonate, and the like are added, and the mixture is reacted at 0° C. to 100° C., preferably 10° C. to 50° C. for 0.2 hours~12 hours, preferably 1 hours~6 hours to obtain Compound dd.

Fourth Step

To Compound dc in a solvent or mixture thereof such as DMF, DMA, NMP and DMI, and the like, sodium azide is added, and the mixture is reacted at 20° C. to 100° C., preferably 40° C. to 80° C. for 0.5 hours~12 hours, preferably 1 hour~6 hours to obtain intermediate compound which is azidated. To the compound, in a solvent or mixture thereof such as ether, ethyl acetate, methanol, tetrahydrofuran, and the like, Pd—C is added and the mixture is reacted by reductive reaction under hydrogen atmosphere at 10° C. to 50° C., preferably 20° C. to 30° C. for 0.5 hours~48 hours, preferably 1 hour~12 hours, to obtain Compound de.

As an another aspect, the following method can be applicable: in the synthesis of Compound de, after condensation reaction of Compound db and phthalimide, in a solvent or mixture thereof such as dichloromethane, tetrahydrofuran, dioxane, and the like, the mixture is reacted with hydradine, methylhydradine, and the like to form amino group.

Fifth Step

To Compound I-1, in a solvent or mixture thereof such as ethanol, isopropylalcohol, acetonitrile, toluene, and the like, acetic acid and Compound de are added, if needed, and the mixture is reacted at 40° C. to 150° C., preferably 50° C. to 80° C. for 0.5 hours~24 hours, preferably 1 hour~12 hours to obtain Compound dd.

Synthesis of Target Compound eg

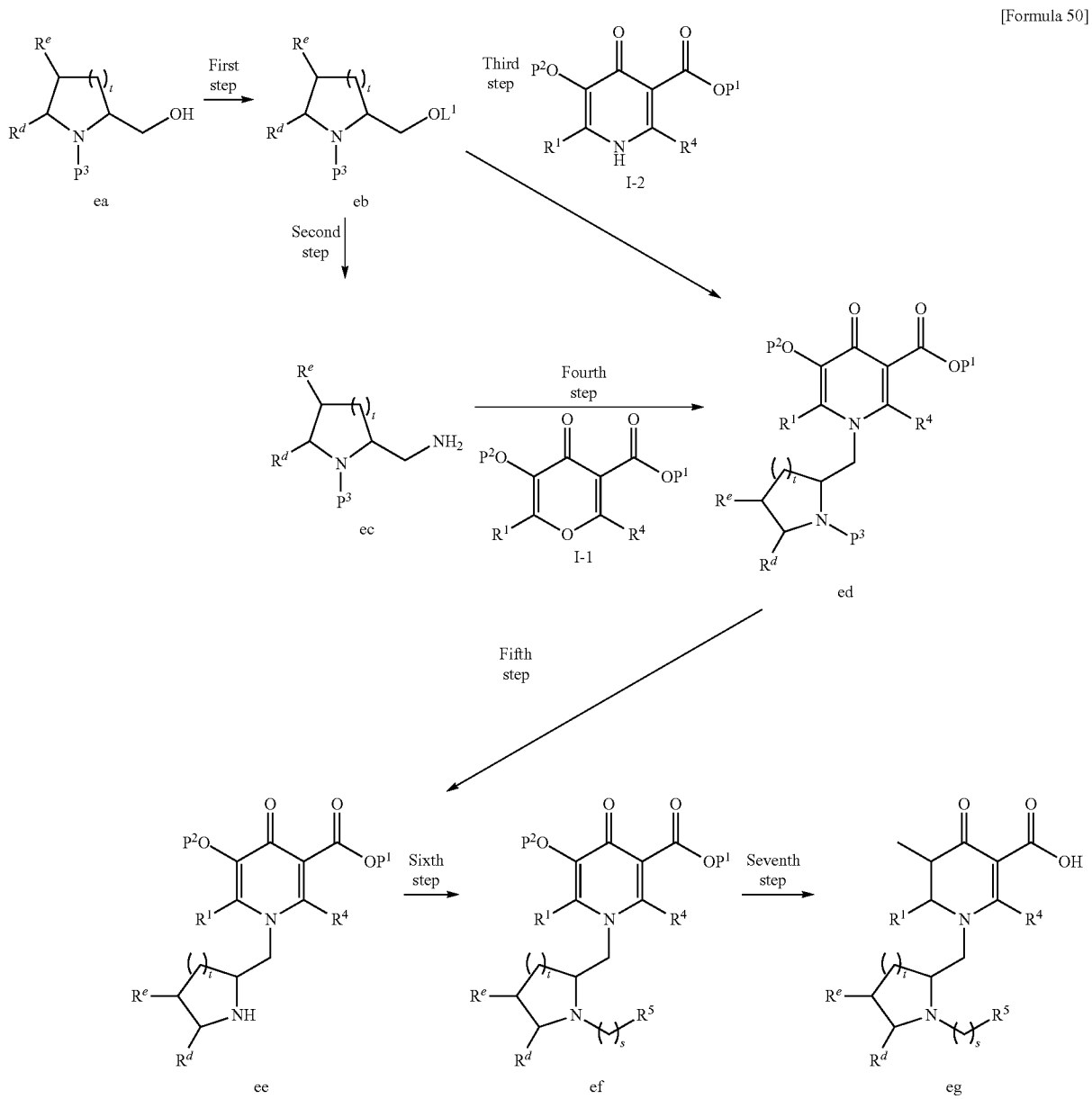

[Formula 50]

(wherein $P^3$ is a substituent which is protected and/or deprotected by a method described in Protective Groups in Organic Synthesis, Theodora W Green (John Wiley & Sons), and the like, for example, Fmoc group, Boc group, Cbz group, and the like, $R^5$ is all sorts of substituents which is corresponding to the target compound, and other symbols are the same as described above.)

First Step

To Compound ea in a solvent or mixture thereof such as ether, dichloromethane, tetrahydrofuran, dioxane, and the like, a base such as triethylamine, and the like, and MsCl, TsCl, and the like is added, and the mixture is reacted at −20° C. to 50° C., preferably 10° C. to 30° C. for 0.5 hours~12 hours, preferably 1 hour~6 hours to obtain Compound eb.

Second Step

A Compound eb in a solvent such as DMF, DMA, NMP and DMI, and the like, sodium azide is added thereto, and the mixture is reacted at 20° C. to 100° C., preferably 40° C. to 80° C. for 0.5 hours~12 hours, preferably 1 hour~6 hours to obtain an intermediate which is performed an azidation reaction. To the compound in a solvent or mixture thereof such as ether, ethyl acetate, methanol, tetrahydrofuran, and the like, a catalyst such as Pd—C, Pd(OH)$_2$, and the like is added, then under hydrogen atmosphere, the mixture is reacted by reductive reaction at 10° C. to 50° C., preferably 20° C. to 30° C. for 0.5 hours~48 hours, preferably 1 hour~12 hours to obtain Compound ec.

Or, as an another aspect, the following method can be applicable: in the synthesis of Compound ec, after condensation reaction of Compound ea and phthalimide, in a solvent or mixture thereof such as dichloromethane, tetrahydrofuran, dioxane, and the like, the mixture is reacted with hydradine, methylhydradine, and the like to form amino group.

Third Step

A Compound eb and Compound I-2 in a solvent such as DMF, DMA, NMP and DMI, and the like, a base such as potassium carbonate, sodium carbonate, cesium carbonate, and the like are mixed therewith, and the mixture is reacted at 0° C. to 100° C., preferably 10° C. to 50° C. for 0.2 hours~12 hours, preferably 1 hours~6 hours to obtain Compound ed.

Fourth Step

To Compound I-1 in a solvent or mixture thereof such as ethanol, isopropylalcohol, acetonitrile, toluene, and the like, acetic acid and Compound ec are added, if needed, then the mixture is reacted at 40° C. to 150° C., preferably 50° C. to 80° C. for 0.5 hours~24 hours, preferably 1 hours~12 hours to obtain Compound ed.

Fifth Step

To Compound ed in a protic solvent or mixture thereof such as ethanol, water, and the like, a base such as triethylamine, dicyclohexylamine, pyperidine, morpholine, and the like is added, and the mixture is reacted at 20° C. to 80° C., preferably 20° C. to 60° C. for 0.5 hours~24 hours, preferably 2 hours~12 hours to obtain Compound ee.

Sixth Step

To Compound ee in a solvent such as DMF, DMA, NMP and DMI, and the like, $R^5$—$(CH_2)_s$—X (wherein, $R^5$ and X is same above), and a base such as potassium carbonate, sodium carbonate, cesium carbonate, and the like are mixed, then the mixture is reacted at 0° C. to 100° C., preferably 10° C. to 50° C. for 0.2 hours~24 hours, preferably 1 hour~12 hours to obtain Compound ef.

Seventh Step

A Compound eg is obtained by reacting known deprotecting reaction to Compound ef.

Synthesis of Compound fe

[Formula 51]

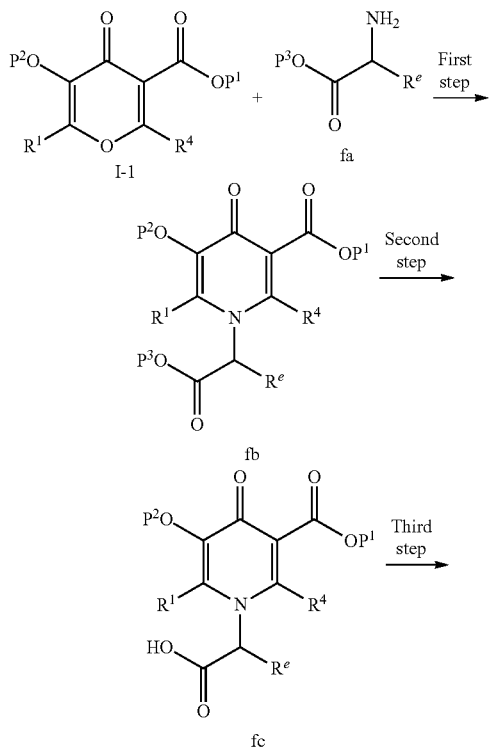

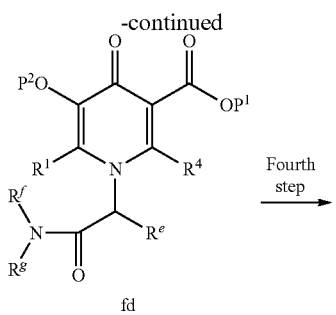

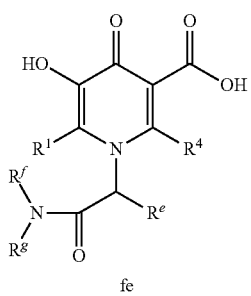

(wherein $R^g$ and $R^f$ is each independently a group corresponding to the target compound such as hydrogen, carbocycle, heterocycle, and the like, and other symbols are the same as described above.)

First Step

To Compound I-1 in the presence of solvent such as ethanol, methanol, isopropylalcohol, and the like, Compound fa and a base such as sodium hydrogencarbonate, sodium carbonate, potassium carbonate, and the like, are added, and the mixture is reacted at 0° C. to 80° C., preferably 10° C. to 50° C. for 0.5 hours~24 hours, preferably 1 hour~12 hours to obtain Compound fb.

Second Step

A Compound fc is obtained by reacting known deprotecting reaction to Compound fb.

Third Step

Alternatively, Compound fc in a solvent of DMF, tetrahydrofuran, dichloromethane, methanol, and the like, in the presence of dehydration condensing reagents such as dicyclohexylcarbodiimide, carbonyldiimidazol, dicyclohexylcarbodiimide-N-hydroxybenzotriazol, 4-(4,6-dimethoxy-1,3,5-triazine-2-yl)-4-methylmorpholinium chloride, hexafluorophosphoric-2-(7-aza-1H-benzotriazol-1-yl)-1,1,3,3-tetramethyl uronium, and the like, is reacted with Compound $R^gR^fNH$ which have substituent corresponding to the target compound at −80° C. to 100° C., preferably −20° C. to 40° C. for 0.1 hours~24 hours, preferably 1 hour~12 hours to obtain Compound fd.

Fourth Step

A Compound fe is obtained by reacting known deprotecting reaction to Compound fd.

Synthesis of Compound gp

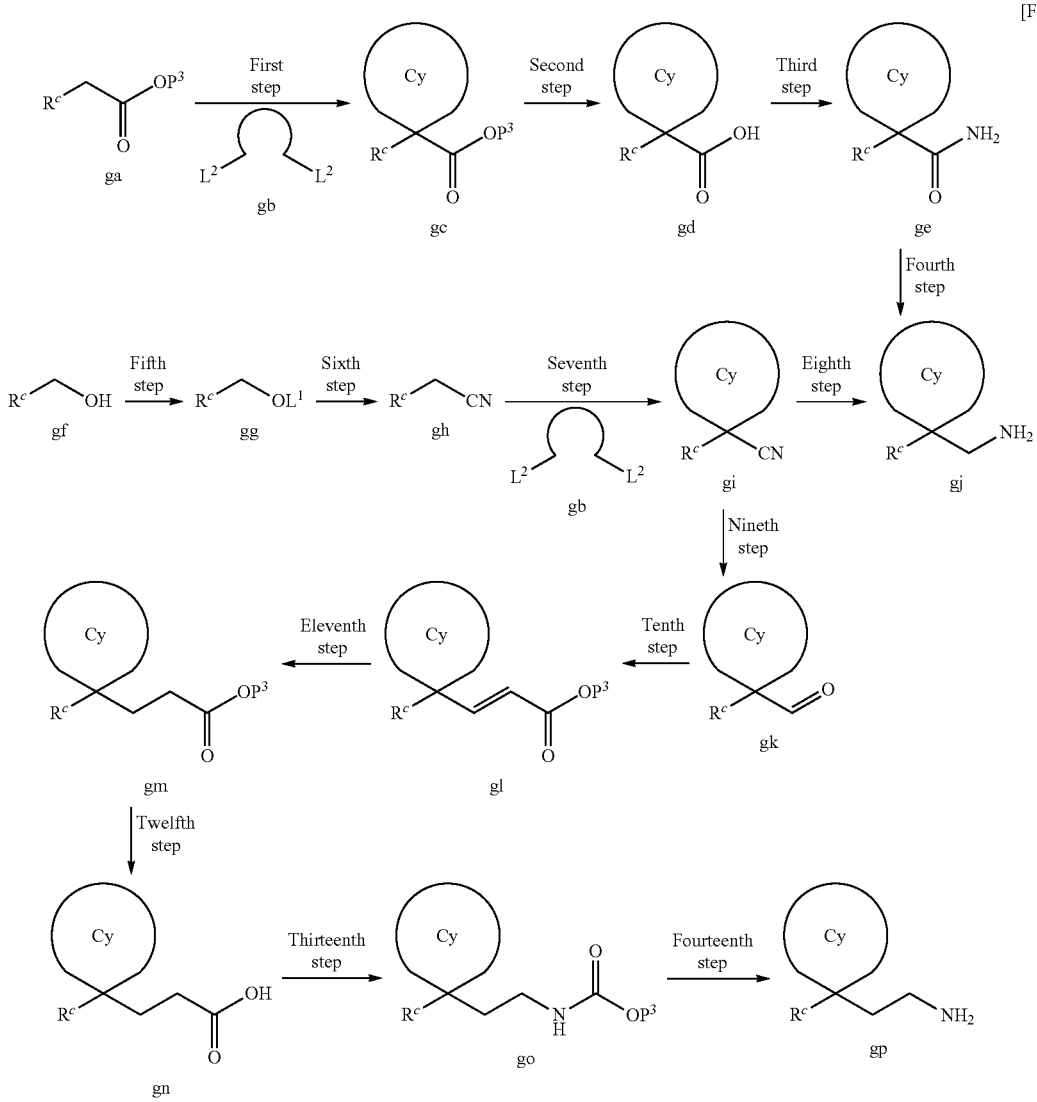

[Formula 52]

(wherein $L^2$ is a leaving group such as halogen, OMs, OTs, and the like, and Cy is a cyclic group corresponding to a target product, and other symbols are the same as described above.)

First Step

To Compound ga in a solvent or mixture thereof such as tetrahydrofuran, dichloromethane, ether, DMSO, and the like, a base such as NaH, LDA, and the like, is added, and Compound gb in a solvent or mixture thereof such as tetrahydrofuran, dichloromethane, ether, DMSO, and the like is added, then the mixture is reacted at 0° C. to 100° C., preferably 0° C. to 40° C. for 0.1 hours~24 hours, preferably 0.5 hours~6 hours to obtain Compound gc.

Second Step

A Compound gd is obtained by reacting known deprotecting reaction to Compound gc.

Third Step

To Compound gd in a solvent such as DMF, tetrahydrofuran, dichloromethane, methanol, and the like, in the presence of dehydration condensing reagents such as dicyclohexylcarbodiimide, carbonyldiimidazol, dicyclohexylcarbodiimide-N-hydroxybenzotriazol, 4-(4,6-dimethoxy-1,3,5-triazine-2-yl)-4-methylmorpholinium chloride, hexafluorophosphoric-2-(7-aza-1H-benzotriazol-1-yl)-1,1,3,3-tetramethyl uronium, and the like, ammonia water or ammonium chloride is added, and the mixture is reacted at −20° C. to 30° C., preferably 0° C. to 20° C. for 0.1 hours~6 hours, preferably 0.2 hours~2 hours to obtain Compound ge.

Fourth Step

To a reducing agent such as $LiAlH_4$, $NaBH_4$, $LiBH_4$ in a solvent or mixture thereof such as tetrahydrofuran, dioxane, toluene, and the like, Compound ge is added and the mixture is reacted at −20° C. to 100° C., preferably 0° C. to 80° C. for 0.2 hours~24 hours, preferably 1 hour~6 hours. Subsequently, potassium fluoride is added thereto and the mixture is reacted at −20° C. to 40° C., preferably 0° C. to 20° C. for 0.5 hours~24 hours, preferably 1 hour~12 hours to obtain Compound gj.

Fifth Step

To Compound gf in a solvent or mixture thereof such as ether, dichloromethane, tetrahydrofuran, dioxane, and the like, a base such as triethylamine, and the like, and MsCl, TsCl, and the like are added, then the mixture is reacted at −20° C. to 50° C., preferably −10° C. to 30° C. for 0.5 hours~12 hours, preferably 1 hour~6 hours to obtain Compound gg.

Sixth Step

To Compound gg in a solvent such as DMF, DMA, NMP, DMI and DMSO, and the like, NaCN or KCN is added, and the mixture is reacted at 0° C. to 80° C., preferably 0° C. to 40° C. for 0.2 hours~6 hours, preferably 0.5 hours~3 hours to obtain Compound gh.

Seventh Step

A Compound gi is obtained by the same method as described in First step.

Eighth Step

To Compound gi in a solvent such as methanol, ethanol, isopropylalcohol, and the like, ammonia and Raney Nickel are added, under hydrogen atmosphere, then the mixture is reacted at 0° C. to 40° C., preferably 10° C. to 30° C. for 0.5 hours~24 hours, preferably 1 hour~12 hours to obtain Compound gj.

Ninth Step

To Compound gi in a solvent or mixture thereof such as n-hexane, n-heptane, toluene, dichloromethane, and the like, DIBAL-H is added thereto, and the mixture is reacted at −80° C. to 0° C., preferably −80° C. to −40° C. for 0.2 hours~4 hours, preferably 0.2 hours~1 hour to obtain Compound gk.

Tenth Step

To Compound $(R^pO)_2P(=O)CH_2COOP^3$ (wherein $R^p$ is lower alkyl, halogeno lower alkyl, and the like, and $P^3$ is the same as described above) in a solvent such as tetrahydrofuran, dioxane, ether, and the like, a base such as NaH, LDA is added, and the mixture is reacted at −20° C. to 60° C., preferably 0° C. to 30° C. for 0.1 hours~2 hours, preferably 0.1 hours~1 hour. Subsequently, a solution in Compound gk is added thereto, and the mixture is reacted at 0° C. to 60° C., preferably 0° C. to 30° C. for 0.5 hours~48 hours, preferably 1 hour~24 hours to obtain Compound gl.

Eleventh Step

To Compound gl in a solvent or mixture thereof such as methanol, ethanol, ethyl acetate, tetrahydrofuran, and the like, a catalyst such as $PtO_2$, Pd—C, $Pd(OH)_2$, and the like are added, and the mixture is reacted by reductive reaction under hydrogen atmosphere, at 0° C. to 60° C., preferably 0° C. to 30° C. for 0.5 hours~24 hours, preferably 1 hour~12 hours, to obtain Compound gm.

Twelfth Step

A Compound gn is obtained by reacting known deprotecting reaction to Compound gm.

Thirteenth Step

A Compound gn in a solvent or mixture thereof such as toluene, tetrahydrofuran, dioxane, and the like, triethylamine and DPPA is added, then the mixture is reacted at 0° C. to 60° C., preferably 0° C. to 30° C. for 0.5 hours~24 hours, preferably 1 hour~6 hours. Subsequently, an alcohol such as t-BuOH is added thereto, and the mixture is reacted at 40° C. to 100° C., preferably 60° C. to 100° C. for 1 hour~48 hours, preferably 2 hours~24 hours to obtain Compound go.

Fourteenth Step

To Compound go in a solvent or mixture thereof such as toluene, tetrahydrofuran, dioxane, and the like, trifluoroacetic acid is added, and the mixture is reacted at 0° C. to 80° C., preferably 0° C. to 30° C. for 1 hour~24 hours, preferably 1 hour~6 hours to obtain Compound gp.

Synthesis of Compound hf

[Formula 53]

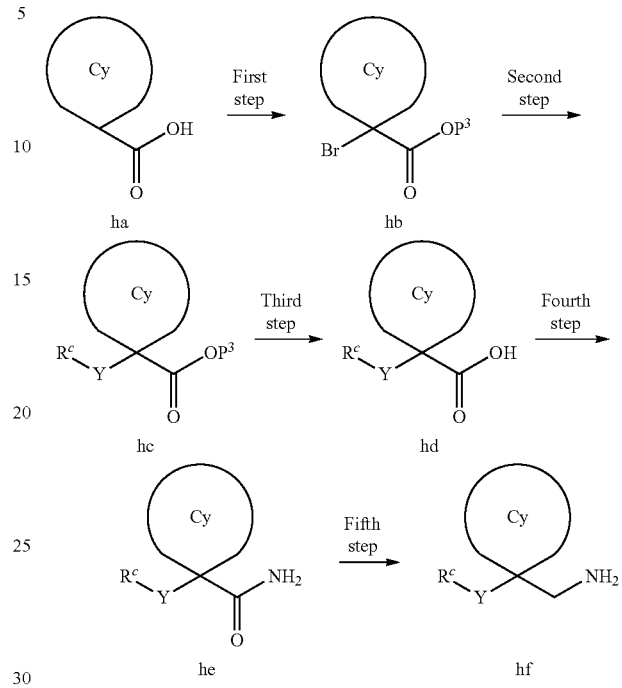

(wherein Y is O or S, and other symbols are the same as described above.)

First Step

To Compound ha in a solvent such as dichloroethane, carbon tetrachloride, and the like, bromine and $ClSO_3H$ are added, and the mixture is reacted under reflux condition for 1 hour~24 hours, preferably 1 hour~16 hours. In addition, Compound hb is obtained by reacting known general carboxy protecting reaction.

Second Step

To Compound hb in a solvent such as acetonitrile, tetrahydrofuran, toluene, and the like, $R^c$—YH, and a base such as sodium carbonate, potassium carbonate, cesium carbonate, and the like are added, and the mixture is reacted at 40° C. to 100° C., preferably 40° C. to 80° C. for 1 hour~24 hours, preferably 1 hour~12 hours to obtain Compound hc.

Third Step

A Compound hd is obtained by reacting known general deprotecting reaction to carboxylate ester hc.

Fourth Step

To Compound hd in the presence or absence of base such as DIEA, triethylamine, and the like, in a solvent such as DMF, tetrahydrofuran, dichloromethane, methanol, and the like, in the presence of dehydration condensing reagents such as dicyclohexylcarbodiimide, carbonyldiimidazol, dicyclohexylcarbodiimide-N-hydroxybenzotriazol, 4-(4,6-dimethoxy-1,3,5-triazine-2-yl)-4-methylmorpholinium chloride, hexafluorophosphoric-2-(7-aza-1H-benzotriazol-1-yl)-1,1,3,3-etramethyl uronium, and the like, ammonia water or ammonium chloride is added, and the mixture is reacted at 0° C. to 60° C., preferably 10° C. to 40° C. for 1 hour~48 hours, preferably 1 hour~24 hours to obtain Compound he.

Fifth Step

To Compound he in a solvent or mixture thereof such as tetrahydrofuran, dioxane, toluene, and the like, a reducing agent such as $LiAlH_4$, $NaBH_4$, $LiBH_4$, and the like is added, and the mixture is reacted at −20° C. to 100° C., preferably 0° C. to 80° C. for 0.2 hours~24 hours, preferably 1 hour~6 hours to obtain Compound hf.

Synthesis of Target Compound T-3

[Formula 54]

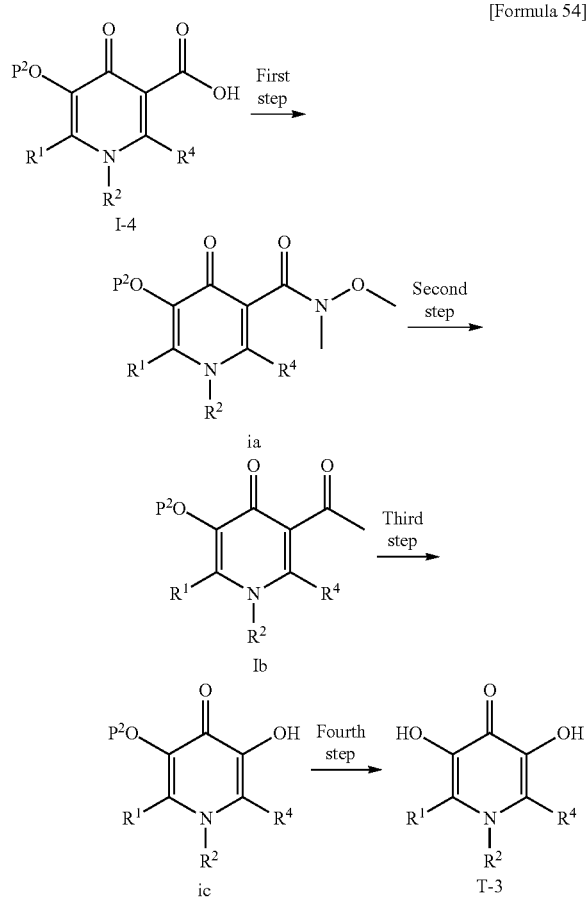

(wherein each symbol is the same as described above.)

First Step

To Compound I-4 in a solvent or mixture thereof such as HMPA, MeCN, DMF, DMA, NMP and DMI, and the like, thionylchloride, chlorine gas, and the like is added, and the mixture is reacted at −20° C. to 20° C., preferably −10° C. to 10° C. for 0.1 hours~4 hours, preferably 0.2 hours~2 hours to obtain an acid-chloride intermediate. Hereto, N,O-dimethylhydroxylamine hydrochloric acid salt is added, and the mixture is reacted at −20° C. to 60° C., preferably −10° C. to 30° C. for 0.5 hours~6 hours, preferably 0.5 hours~3 hours to obtain Compound ia.

Second Step

To Compound ia in a solvent or mixture thereof such as tetrahydrofuran, dichloromethane, ether, toluene, n-heptane, and the like, an aforementioned solution of methylmagnesium bromide is added, and the mixture is reacted at −80° C. to 0° C., preferably −60° C. to −10° C. for 0.1 hours~6 hours, preferably 0.2 hours~2 hours to form Compound ib.

Third Step

To Compound ib in a solvent or mixture thereof such as tetrahydrofuran, dichloromethane, ether, toluene, chloroform, and the like, m-chloroperbenzoic acid is added, and the mixture is reacted at 0° C. to 60° C., preferably 0° C. to 30° C. for 0.5 hours~12 hours, preferably 1 hour~6 hours to obtain Compound ic.

Fourth Step

A Compound T-3 is obtained by reacting known alcohol deprotecting reaction to Compound ic.

Synthesis of Compound T-3

[Formula 55]

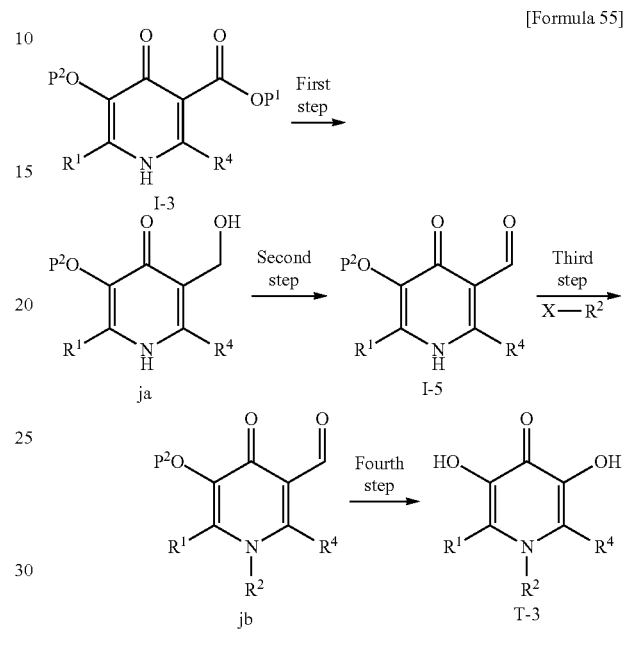

(wherein each symbol is the same as described above.)

First Step

To Compound I-3 in a solvent or mixture thereof such as tetrahydrofuran, ether, dioxane, toluene, and the like, a reducing agent such as $LiAlH_4$, $LiBH_4$, and the like is added, and the mixture is reacted at 0° C. to 60° C., preferably 0° C. to 40° C. for 0.5 hours~12 hours, preferably 0.5 hours~4 hours to obtain Compound ja.

Second Step

To Compound ja in a solvent such as tetrahydrofuran, DMF, DMA, and the like, an oxidizing reagent such as $MnO_2$, pyridinium dichromate, and the like is added, and the mixture is reacted at 20° C. to 90° C., preferably 40° C. to 70° C. for 0.5 hours~24 hours, preferably 1 hour~12 hours to obtain Compound I-5.

Third Step

To Compound I-5 in a solvent such as DMF, DMA, NMP, and DMI, and the like, a base such as potassium carbonate, sodium carbonate, cesium carbonate, and the like, and a reagent (X—$R^2$) which have a substituent corresponding to the target compound are added, and the mixture is reacted at 0° C. to 80° C., preferably 10° C. to 50° C. for 0.5 hours~24 hours, preferably 1 hour~6 hours to obtain Compound jb.

Fourth Step

To Compound jb in a solvent or mixture thereof such as tetrahydrofuran, dichloromethane, ether, toluene, chloroform, and the like, m-chloroperbenzoic acid is added, and the mixture is reacted at 0° C. to 60° C., preferably 0° C. to 30° C. for 0.5 hours~12 hours, preferably 1 hour~6 hours to obtain an intermediate compound. A Compound T-3 is obtained by reacting known alcohol deprotecting reaction to the intermediate compound.

Synthesis of Compound Ke

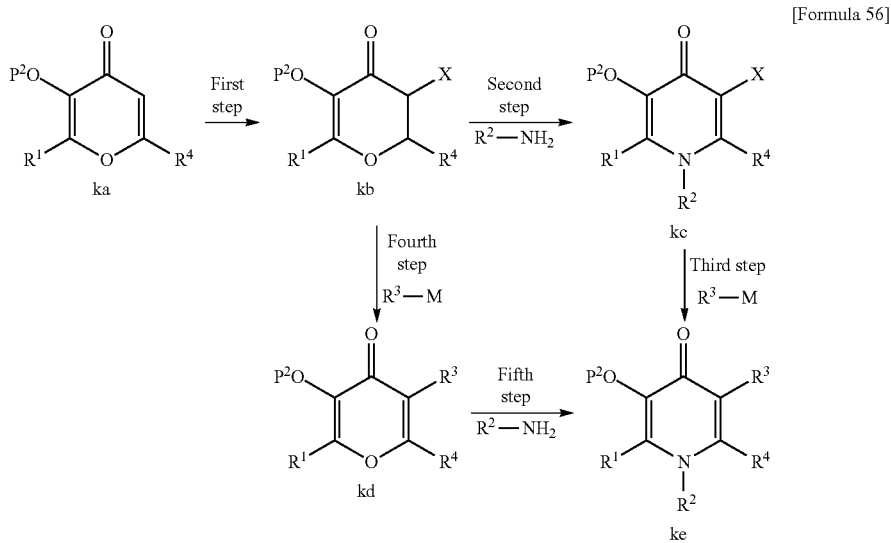

[Formula 56]

(wherein each symbol is the same as described above.)

First Step

To Compound ka in a solvent or mixture thereof such as tetrahydrofuran, ether, dioxane, dichloromethane, and the like, halogenating agent such as bromine or NBS, and the like is added, and the mixture is reacted at −20° C. to 40° C., preferably 10° C. to 20° C. for 0.5 hours~12 hours, preferably 1 hour~6 hours to obtain Compound kb.

Second Step

To Compound kb in a solvent or mixture thereof such as ethanol, isopropylalcohol, DMF, DMA, tetrahydrofuran, dioxane, toluene, and the like, acetic acid and $R^2$—$H_2N$ are added if needed, the mixture is reacted at 20° C. to 150° C., preferably 20° C. to 80° C. for 0.5 hours~12 hours, preferably 1 hour~6 hours to obtain Compound kc.

Third Step

To Compound kc in a solvent such as dichloromethane, ether, tetrahydrofuran, dioxane, and the like, $R^3$-M (wherein M is an organometal reagent such as $B(OR^L)_2$ or $SnR^L_3$, and the like) is added, and the mixture is reacted at 20° C. to 100° C., preferably 20° C. to 80° C. for 0.5 hours~12 hours, preferably 1 hour~6 hours to obtain Compound ke.

Fourth Step

A Compound kd is obtained according to a same method as described in Third step.

Fifth Step

A Compound ke is obtained according to a same method as described in Second step.

The compound of the present invention is useful for symptom and/or disorder induced by infection with influenza virus. It is useful for medical treatment, prevention, and/or symptom relief for example, cold symptom involved with fever, chills, headache, muscle pain, and feeling of generalized worthlessness, airway inflammation such as sore throat, snivel, congested nose, cough, phlegm, gastrointestinal symptom such as stomachache, emesis, diarrehea, in addition, concomitant disease involved with secondary infection such as accute encephalopathy, pneumonia.

The compounds of the present invention can be a medicament of which side effect is reduced because the compounds have effects of high inhibitory activities and high selectivities against virus, especially cap-dependent endonuclease that is influenza specific enzyme.

In addition, the compounds can be a medicament for virus other than influenza because the compounds probably have inhibitory activities to virus dependent enzyme similar to cap-dependent endonuclease such as HIV (human immunodeficient virus) integrase and HIV ribonuclease H, and HBV (B type hepatitis virus) ribonuclease H, and the like.

In addition, the compounds of the present invention can be a good medicament because the compounds have advantages of high metabolic stability, high solubility, high oral absorbability, favorable bioavailability, favorable clearance, high transition to lung, long half-period, high metabolic stability in a liver, high non-binding rate for protein, low inhibition for hERG channel, low inhibition for CYP, and/or indicate negative in Ames test, and genetic toxicity test.

The compounds of the present invention can be administered by oral or parenteral route. For oral administration, the compounds of the present invention can be used in any form of usual formulations, for example, formulations in a solid form such as tablets, powders, granules, capsules; formulations in a liquid form such as aqueous formulation; oily suspension; syrup or elixir. For parenteral administration, the compounds of the present invention can be used in a form of aqueous or oily suspending injection, or nose drops. In the preparation of such formulation, conventional excipients, binding agents, lubricants, aqueous solvents, oleaginous solvents, emulsifying agents, suspending agents, preservatives, stabilizers, and the like can be optionally used. The formulation of the present invention may be prepared by combining (for example, blending) a therapeutically effective amount of a compound of the present invention with a pharmaceutically acceptable carrier or diluent.

For oral administration, daily dosage of the compound of the present invention can be approximately 0.05-3000 mg, preferably approximately 0.1-1000 mg per day for an adult, while such dosage varies depending on the administration route therefor, age, body weight, conditions of the patient, and disease in the patient. The dosage may be divided for administration, if necessary. In case of parenteral administration, the daily dosage for an adult can be between approximately 0.01-1000 mg, preferably approximately 0.05-500 mg.

The present invention is further explained by the following Examples and Experiments, which are not intended to limit the scope of the present invention in any way.

EXAMPLE 1

[Formula 57]

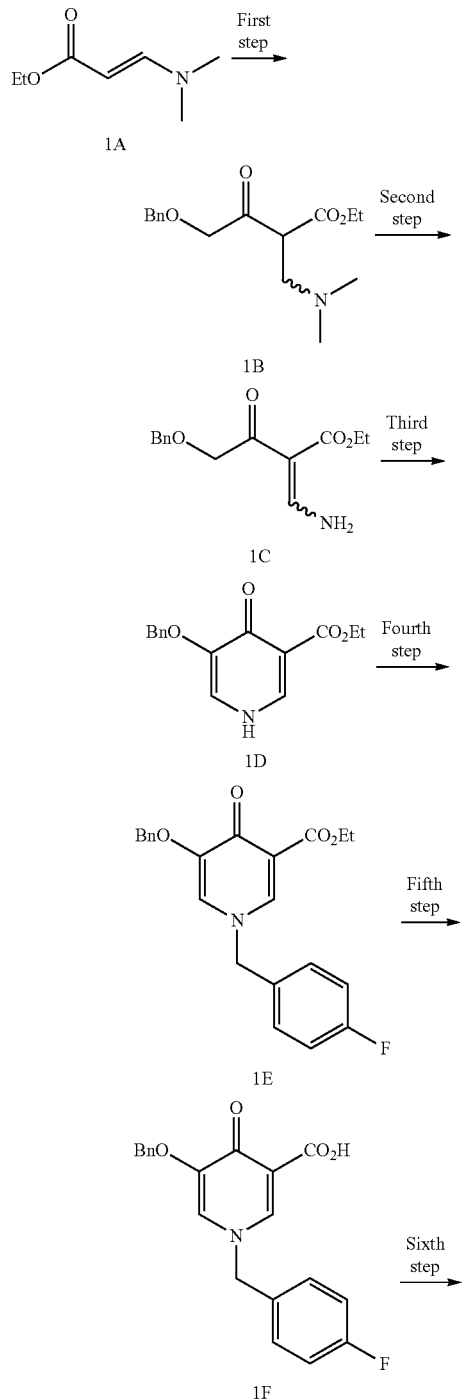

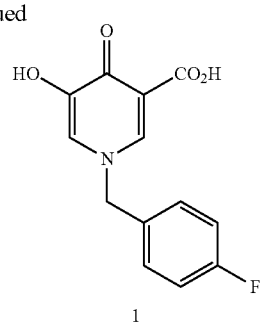

First Step

A solution of Compound 1A (12.8 g, 89.4 mmol) and pyridine (8.50 g, 107 mmol) in dichloromethane (90 mL) was cooled to 1 to 3° C., then keeping the temperature, a solution of benzyloxyacetyl chloride (19.8 g, 107 mmol) in dichloromethane (90 mL) was added dropwise thereto for 50 minutes. After the reaction mixture was stirred at the temperature for 30 minutes, the temperature was gradually raised to 15° C. for 60 minutes, then ice water was added thereto. The dichloromethane layer was separated and the water layer was once extracted with dichloromethane. The combined extracted solution was washed three times with sat. NaCl aq. then was dried. The solvent was evaporated, then the obtained oily substance was purified by silica gel column chromatography. Elution was conducted with n-hexane, then, with n-hexane-ethyl acetate (1:1, v/v). The target fraction was condensed to obtain Compound 1B (22.2 g) as oily substance.

$^1$HNMR (CDCl$_3$) δ: 1.25 (3H, t, J=7.2 Hz), 2.90 (3H, brs), 3.24 (3H, brs), 4.15 (2H, q, J=7.2 Hz), 4.45 (2H, s), 4.58 (2H, s), 7.25-7.38 (5H, m), 7.72 (1H, s).

Second Step

Compound 1B (29.7 g, 102 mmol) was dissolved in EtOH (340 mL), and ammonium acetate (23.6 g, 310 mmol) was added thereto, then the mixture was refluxed for 45 minutes. The reaction mixture was condensed in vacuo, and the residue was extracted with ethyl acetate-water. The ethyl acetate layer was separated, then water layer was extracted with ethyl acetate once. The combined extracted solution was washed with water, NaHCO$_3$ aq., water, and sat. NaCl aq. in order, and dried. The solvent was evaporated and n-hexane-ether was added to the obtained oily substance, then the precipitated solid was filtered to obtain Compound 1C (24.7 g).

MS: m/z=264 [M+H]$^+$.

Third Step

Sodium hydride (60%, 5.79 g, 145 mmol) was suspended in THF (170 mL) and cooled to −20° C. A solution of Compound 1C (12.7 g, 48.2 mmol) in THF (130 mL) was added dropwise for 1.5 hours while keeping the temperature at −15 to −10° C. The reaction mixture was stirred at −12 to −10° C. for 1 hour, then cooled to −20° C. again. Then, ethyl formate (85 mL) was added dropwise at −16° C. or below. The reaction mixture was gradually warmed to room temperature and stirred for 2 hours, then cooled to 0° C., and 2N HCl (85 mL) was added thereto. The mixture was condensed and the obtained residue was suspended in ethyl acetate (300 mL)-water (300 mL), and stirred. The precipitated solid was filtered, then washed with ethyl acetate, and dried to obtain Compound 1D (6.61 g).

$^1$HNMR (DMSO-d$_6$) δ: 1.25 (3H, t, J=7.2 Hz), 4.17 (2H, q, J=7.2 Hz), 4.98 (2H, s), 7.34-7.40 (6H, m), 8.11 (1H, d, J=1.6 Hz), 11.6 (1H, brs).

MS: m/z=274 [M+H]$^+$.

Fourth Step

To a suspension of Compound 1D (310 mg, 1.13 mmol) in DMF (8 mL), potassium carbonate (235 mg, 1.70 mmol) was added at room temperature, followed by stirring for 15 minutes. 4-Fluorobenzyl amine (330 mg, 1.75 mmol) was added thereto and the mixture was stirred for 1 hour. The reaction mixture was added to ice water, and the precipitated solid was filtered and washed with water, then dissolved in ethyl acetate. The organic layer was washed with sat. NaCl aq., and dried. The solvent was evaporated and ethyl acetate-n-hexane was added to precipitate Compound 1E (410 mg) as a solid.

$^1$HNMR (CDCl$_3$) δ: 1.38 (3H, t, J=6.9 Hz), 4.36 (2H, q, J=6.9 Hz), 4.84 (2H, s), 5.14 (2H, s), 6.78 (1H, d, J=2.4 Hz), 7.03 (4H, d, J=6.9 Hz), 7.26-7.29 (5H, m), 8.10 (1H, d, J=2.4 Hz).

MS: m/z=382 [M+H]$^+$.

Fifth Step

To a solution of Compound 1E (382 mg, 1.0 mmol) in EtOH (8 mL) solution, 2N NaOH (2 mL) was added and stirred for 1.5 hours with heating. The reaction mixture was condensed in vacuo, then the obtained residue was dissolved in water (10 mL), and 2N HCl was added thereto to adjust pH3. The precipitate was filtered, washed with water, then dried to obtain Compound 1F (340 mg).

$^1$HNMR (DMSO-d$_6$) δ: 5.08 (2H, s), 5.35 (2H, s), 7.22 (2H, t, J=9.0 Hz), 7.35-7.50 (7H, m), 8.11 (1H, d, J=1.8 Hz), 8.76 (1H, d, J=1.8 Hz).

MS: m/z=354 [M+H]$^+$.

Sixth Step

Compound 1F (340 mg, 0.96 mmol) was dissolved in THF (20 mL)-MeOH (20 mL), then 10% Pd—C (100 mg) was added thereto and subjected to a catalytic reductive reaction under hydrogen atmosphere. The catalyst was removed by filtration, then the filtrate was condensed. The obtained residue was dissolved in MeOH—CHCl$_3$, then insoluble productes were removed by filtration. The filtrate was condensed, then MeOH was added to precipitated solid to obtain Compound 1 (135 mg) as a solid.

$^1$HNMR (DMSO-d$_6$) δ: 5.33 (2H, s), 7.49 (1H, d, J=8.4 Hz), 7.51 (1H, d, J=8.4 Hz), 7.84 (1H, d, J=2.1 Hz), 8.68 (1H, d, J=2.1 Hz), 10.0 (1H, brs).

MS: m/z=264 [M+H]$^+$.

EXAMPLE 2

[Formula 58]

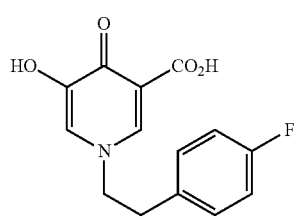

2

Compound 2 was synthesized according to Example 1.

$^1$HNMR (DMSO-d$_6$) δ: 3.08 (2H, t, J=7.5 Hz), 4.34 (2H, t, J=7.5 Hz), 7.13 (2H, t, J=9.0 Hz), 7.26 (1H, d, J=8.1 Hz), 7.28 (1H, d, J=8.1 Hz), 7.84 (1H, d, J=2.1 Hz), 8.37 (1H, d, J=2.1 Hz), 10.0 (1H, brs), 16.0 (1H, brs).

MS: m/z=278 [M+H]$^+$.

EXAMPLE 3

[Formula 59]

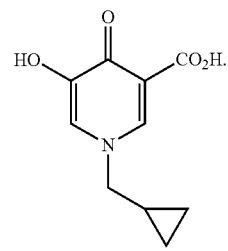

3

Compound 3 was synthesized according to Example 1.

MS: m/z=465 [M+H]$^+$.

EXAMPLE 4

[Formula 60]

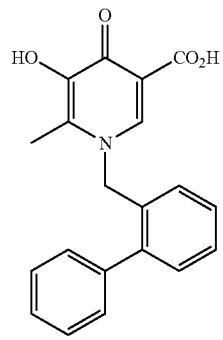

4

Compound 4 was synthesized by the similar method using ethyl 5-(benzyloxy)-6-methyl-4-oxo-1,4-dihydropyridine-3-carboxylate (International Publication No. 2006/088173 pamphlet) according to Example 1.

$^1$HNMR (DMSO-d$_6$) δ: 1.95 (3H, s), 5.45 (2H, s), 6.80 (1H, d, J=8.1 Hz), 7.30-7.50 (10H, m), 8.49 (1H, s).

EXAMPLE 5

[Formula 61]

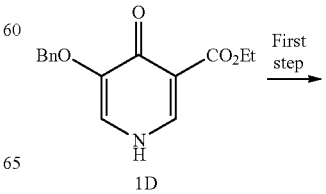

First step →

1D

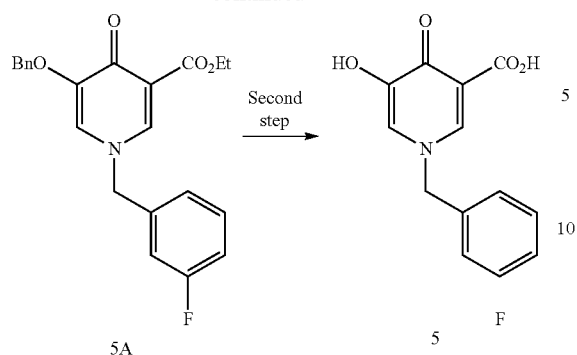

First Step

Compound 1D (27 mg) was dissolved in DMF (1 mL), then m-fruorobenzylbromide (22 mg) and cesium carbonate (98 mg) were added thereto and the mixture was stirred at room temperature for 8 hours. The reaction mixture was filtered and the filtrate was purified by preparative isolation using LCMS. Compound 5A obtained by condensation was used in the next step.

MS: m/z=382 [M+H]$^+$.

Second Step

To a solution of Compound 5A in DMF (0.5 mL) solution, 2N sodium hydroxide aq. (0.2 mL) was added and the mixture was stirred at room temperature for 2 hours. To the reaction mixture was added ion-exchange resin DOWEX(50W-X8), then which was filtered and washed with DMF. The filtrate was condensed, then trifluoroacetic acid (0.5 mL) was added thereto and stirred at 80° C. for 4 hours. The reaction mixture was condensed, and water and chloroform were added thereto, then the organic layer was separated. The organic layer was condensed, then purified by preparative isolation using LCMS to obtain Compound 5 (18.5 mg).

MS: m/z=264 [M+H]$^+$.

Compound 6-18 were synthesized according to the Example 5.

TABLE 1

| Example | Structure | MS(M + 1) |
|---|---|---|
| 6 | 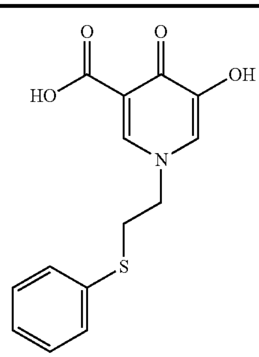 | 292 |

TABLE 2

| Example | Structure | MS(M + 1) |
|---|---|---|
| 7 | 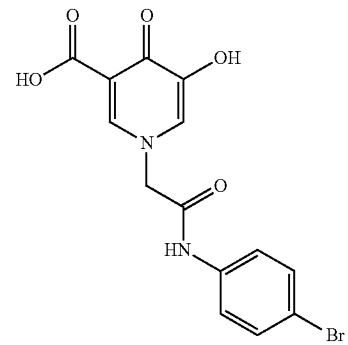 [SMILES: O=C(Cn1cc(O)c(=O)c(C(=O)O)c1)Nc1ccc(Br)cc1] | 367 |
| 8 | 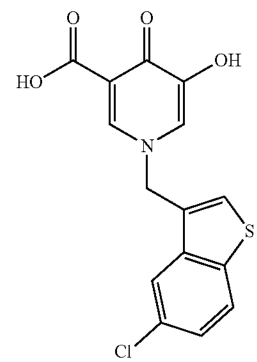 [SMILES: O=C(O)c1cn(Cc2csc3ccc(Cl)cc23)cc(O)c1=O] | 336 |
| 9 | 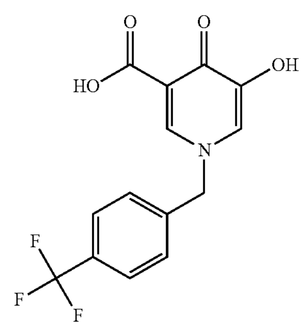 [SMILES: O=C(O)c1cn(Cc2ccc(C(F)(F)F)cc2)cc(O)c1=O] | 314 |
| 10 | 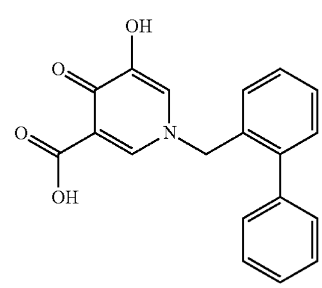 [SMILES: O=C(O)c1cn(Cc2ccccc2-c2ccccc2)cc(O)c1=O] | 322 |

TABLE 3
| Example | Structure | MS(M + 1) |
|---|---|---|
| 11 | 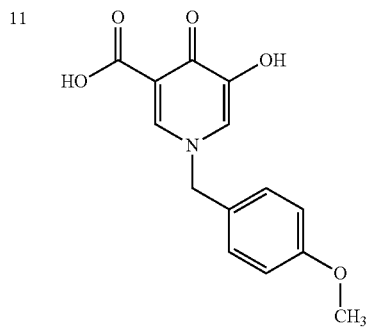 | 276 |
| 12 | 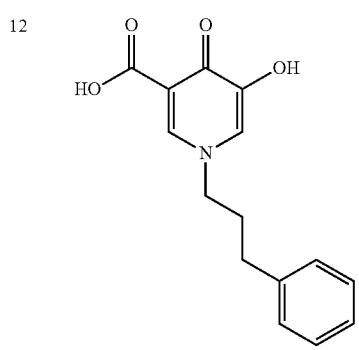 | 274 |
| 13 | 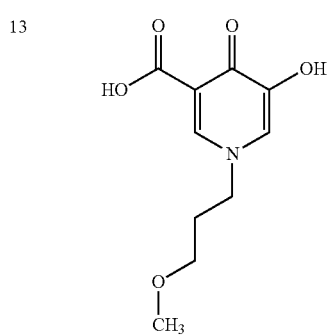 | 228 |
| 14 | 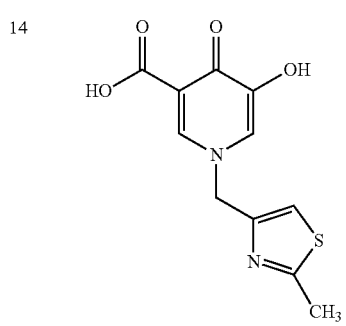 | 267 |
TABLE 4
| Example | Structure | MS(M + 1) |
|---|---|---|
| 15 | 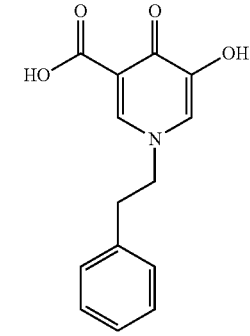 [SMILES: O=C(O)c1cn(CCc2ccccc2)cc(O)c1=O] | 260 |
| 16 | 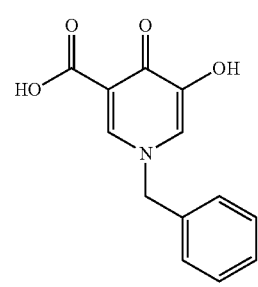 [SMILES: O=C(O)c1cn(Cc2ccccc2)cc(O)c1=O] | 246 |
| 17 | 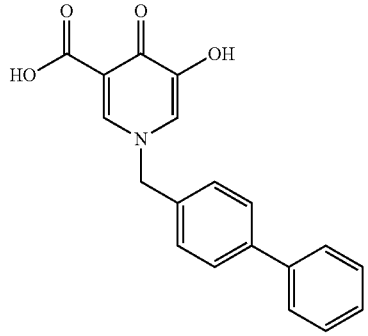 [SMILES: O=C(O)c1cn(Cc2ccc(-c3ccccc3)cc2)cc(O)c1=O] | 322 |
| 18 | 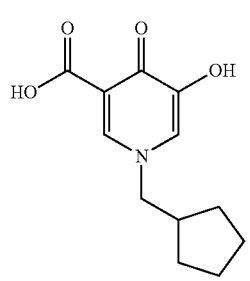 [SMILES: O=C(O)c1cn(CC2CCCC2)cc(O)c1=O] | 238 |

EXAMPLE 19

[Formula 62]

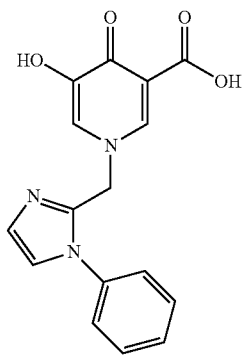

Compound 19 was synthesized by the similar method using 2-chloromethyl-1-phenyl-imidazole (International Publication No. 2004/056481 pamphlet) according to Example 1.

MS: m/z=311 [M+H]$^+$.

$^1$HNMR (DMSO-d$_6$) δ: 5.50 (2H, s), 7.06 (1H, d, J=2.0 Hz), 7.45-7.58 (7H, m), 8.32 (1H, d, J=2.0 Hz), 10.05 (1H, s), 15.95 (1H, s).

EXAMPLE 20

[Formula 63]

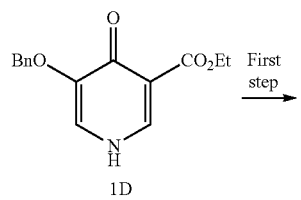

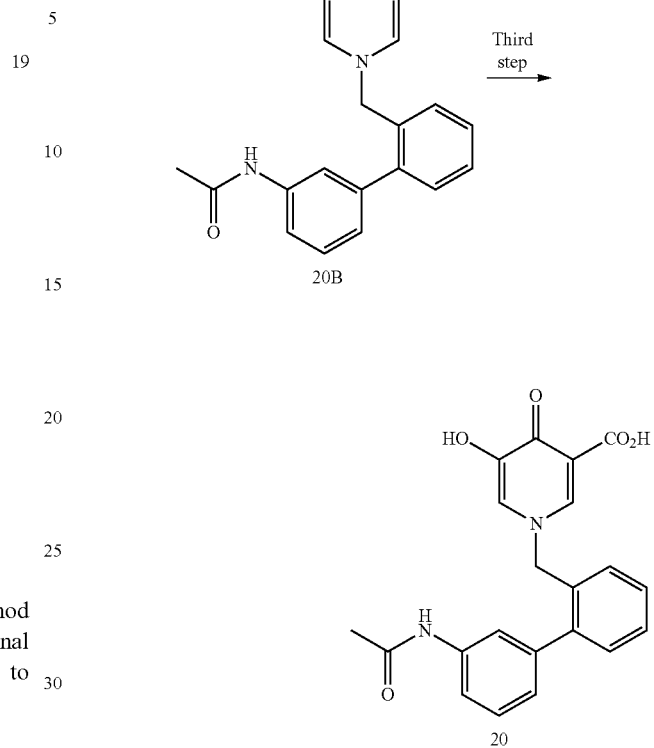

First Step

Compound 20A (156 mg) was synthesized from Compound 1D (100 mg) by the synthetic method according to Compound 1F.

$^1$HNMR (DMSO-d$_6$) δ: 1.22 (3H, t, J=7.2 Hz), 4.16 (2H, q, J=7.2 Hz), 4.95 (2H, s), 5.22 (2H, s), 6.90 (1H, d, J=7.6 Hz), 7.12 (1H, t, J=8.0 Hz), 7.30-7.45 (6H, m), 7.59 (1H, s) 7.93 (1H, d, J=8.0 Hz), 8.30 (1H, s).

Second Step

To a solution of Compound 20A (20 mg) in dioxane (1 mL), 3-acetylaminophenylboronic acid (10.7 mg), tetrakis triphenylphosphine (6.9 mg), and 2N potassium carbonate aq. (0.2 mL) were added and the mixture was stirred at 100° C. for 5 hours. To the reaction mixture, 2N sodium hydroxide aq. (1 mL) was added and the mixture was stirred at room temperature for 1 hour, then the reaction mixture was filtered with celite. The filtrate was extracted with chloroform, then the organic layer was condensed and purified by preparative isolation using LCMS to obtain Compound 20B which was used in the next step.

MS: m/z=469 [M+H]$^+$.

Third Step

To Compound 20B, trifluoroacetic acid (0.5 mL) was added and the mixture was stirred at 80° C. for 5 hours. The mixture was purified by preparative isolation using LCMS to obtain Compound 20 (4.39 mg).

MS: m/z=379 [M+H]$^+$.

Compound 21-54 were synthesized by the similar method according to Example 20.

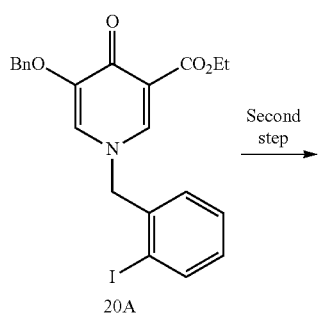

TABLE 5

| Example | Structure | MS(M + 1) |
|---|---|---|
| 21 | (structure) | 364 |
| 22 | (structure) | 364 |

TABLE 6

| Example | Structure | MS(M + 1) |
|---|---|---|
| 23 | (structure) | 378 |
| 24 | (structure) | 356 |

TABLE 6-continued

| Example | Structure | MS(M + 1) |
|---|---|---|
| 25 | (structure) | 366 |
| 26 | (structure) | 352 |

TABLE 7

| Example | Structure | MS(M + 1) |
|---|---|---|
| 27 | (structure) | 366 |
| 28 | (structure) | 371 |

TABLE 7-continued
| Example | Structure | MS(M + 1) |
|---|---|---|
| 29 | 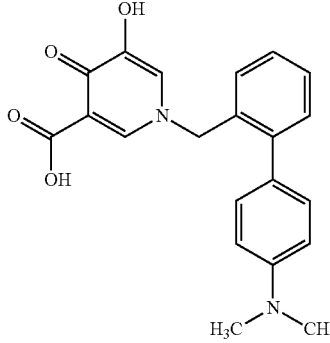 | 365 |
| 30 | 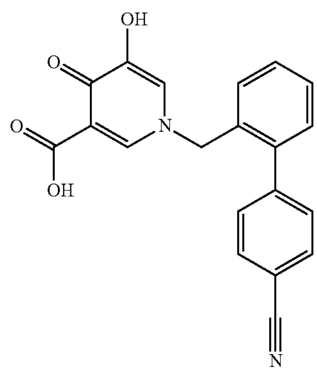 [SMILES: N#Cc1ccc(-c2ccccc2Cn2cc(O)c(=O)c(C(=O)O)c2)cc1] | 347 |
TABLE 8
| Example | Structure | MS (M + 1) |
|---|---|---|
| 31 | 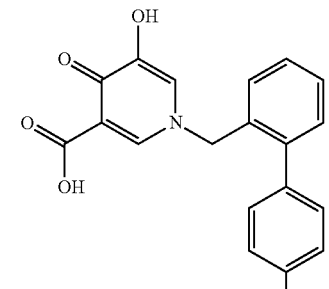 | 380 |
| 32 | 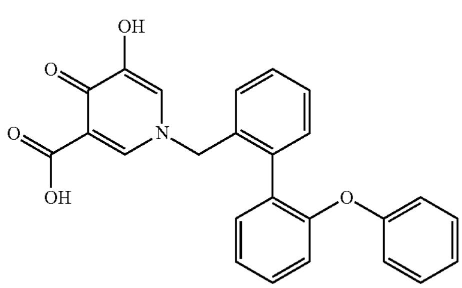 [SMILES: O=C(O)c1cn(Cc2ccccc2-c2ccccc2Oc2ccccc2)cc(O)c1=O] | 414 |
TABLE 8-continued
| Example | Structure | MS (M + 1) |
|---|---|---|
| 33 | 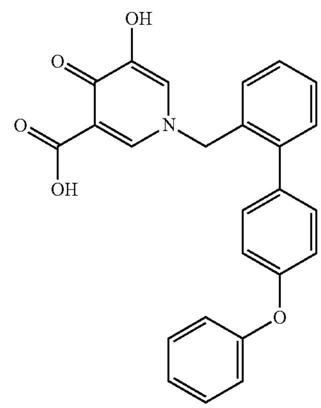 [SMILES: O=C(O)c1cn(Cc2ccccc2-c2ccc(Oc3ccccc3)cc2)cc(O)c1=O] | 414 |
TABLE 9
| Example | Structure | MS (M + 1) |
|---|---|---|
| 34 | 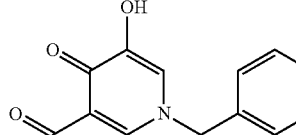 | 407 |
| 35 | 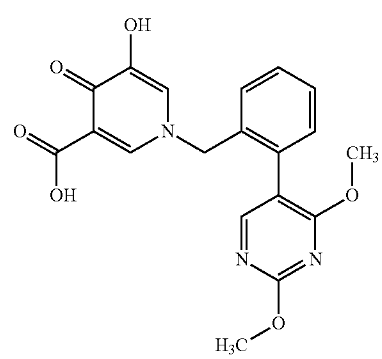 [SMILES: COc1ncc(-c2ccccc2Cn2cc(O)c(=O)c(C(=O)O)c2)c(OC)n1] | 384 |
| 36 | 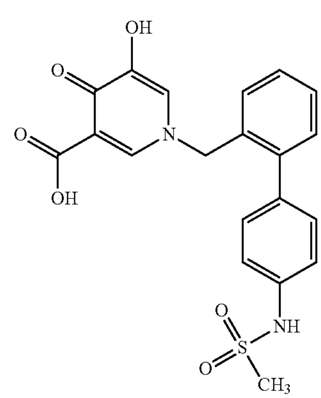 [SMILES: CS(=O)(=O)Nc1ccc(-c2ccccc2Cn2cc(O)c(=O)c(C(=O)O)c2)cc1] | 415 |

TABLE 9-continued

| Example | Structure | MS (M + 1) |
|---|---|---|
| 37 | (structure) | 373 |

TABLE 10

| Example | Structure | MS (M + 1) |
|---|---|---|
| 38 | (structure) | 415 |
| 39 | (structure) | 393 |
| 40 | (structure) | 400 |

TABLE 10-continued

| Example | Structure | MS (M + 1) |
|---|---|---|
| 41 | (structure) | 365 |

TABLE 11

| Example | Structure | MS (M + 1) |
|---|---|---|
| 42 | (structure) | 419 |
| 43 | (structure) | 435 |

TABLE 11-continued
| Example | Structure | MS(M + 1) |
|---|---|---|
| 44 | 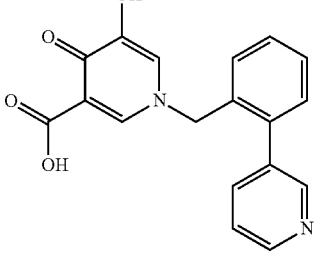 | 405 |
TABLE 12
| Example | Structure | MS(M + 1) |
|---|---|---|
| 45 | 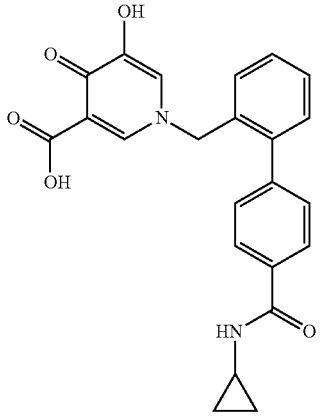 [SMILES: O=C(NC1CC1)c1ccc(-c2ccccc2Cn2cc(O)c(=O)c(C(=O)O)c2)cc1] | 323 |
| 46 | 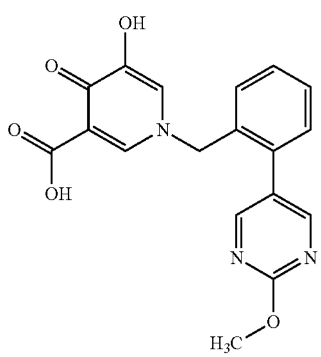 [SMILES: COc1ncc(-c2ccccc2Cn2cc(O)c(=O)c(C(=O)O)c2)cn1] | 354 |
| 47 | 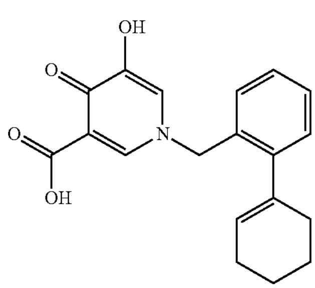 [SMILES: O=C(O)c1cn(Cc2ccccc2C2=CCCCC2)cc(O)c1=O] | 326 |
TABLE 12-continued
| Example | Structure | MS(M + 1) |
|---|---|---|
| 48 | 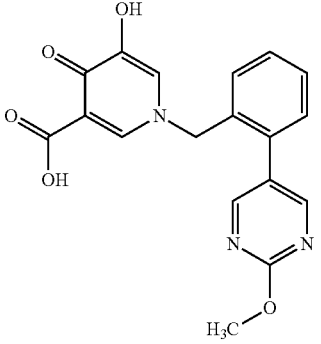 | 378 |
TABLE 13
| Example | Structure | MS (M + 1) |
|---|---|---|
| 49 | 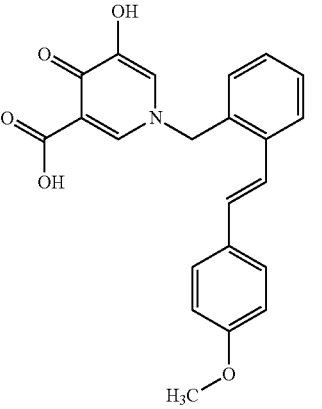 [SMILES: COc1ccc(/C=C/c2ccccc2Cn2cc(O)c(=O)c(C(=O)O)c2)cc1] | 338 |
| 50 | 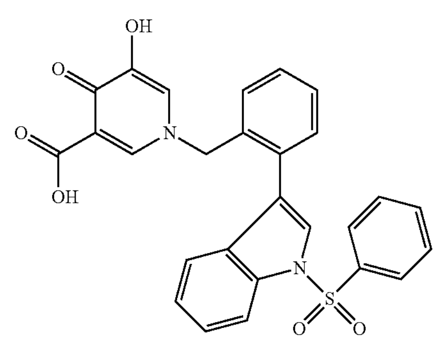 [SMILES: O=C(O)c1cn(Cc2ccccc2-c2cn(S(=O)(=O)c3ccccc3)c3ccccc23)cc(O)c1=O] | 501 |

TABLE 13-continued

| Example | Structure | MS (M + 1) |
|---------|-----------|------------|
| 51 | 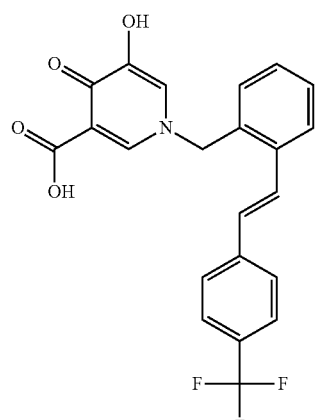 | 416 |

TABLE 14

| Example | Structure | MS(M + 1) |
|---------|-----------|-----------|
| 52 | 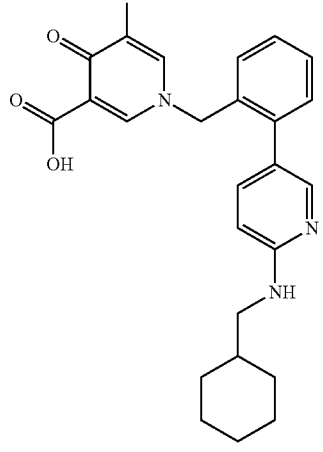 | 434 |
| 53 | 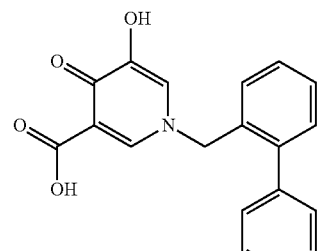 | 374 |
| 54 | | 348 |

EXAMPLE 52

Synthetic Method of Boronic Acid 52C Used in Second Step

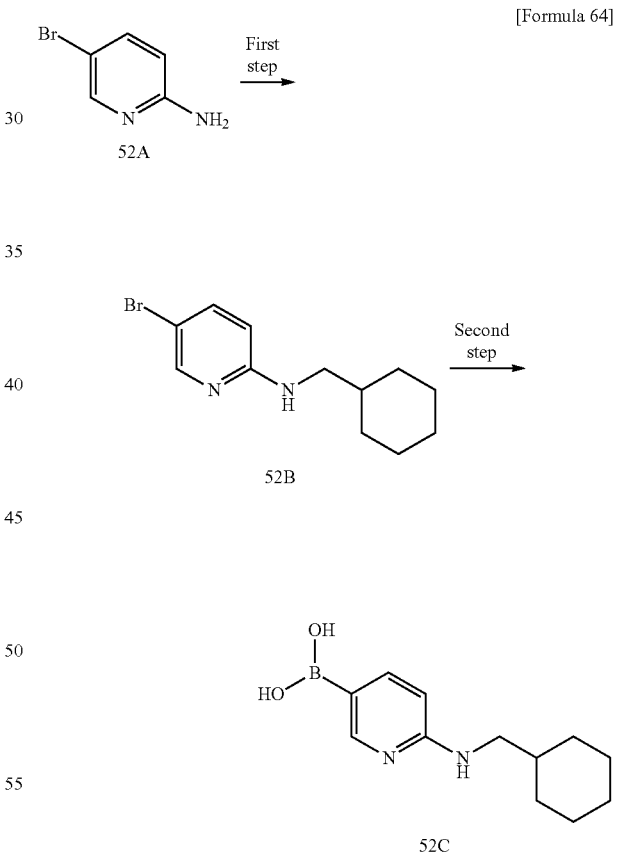

[Formula 64]

First Step

To a solution of Compound 52A (5.0 g) in dichloromethane (25 mL), cyclohexylaldehyde (3.85 mL), sodium triacetoxyborohydride (9.12 g), and acetic acid (1.82 mL) were added, the mixture was stirred at room temperature for 5 hours. To the reaction mixture, 2N sodium hydroxide aq. was added, the mixture was extracted with chloroform, then organic layer was washed with water, and dried over anhydrous $Na_2SO_4$.

The solvent was evaporated in vacuo, the residue was purified by silica gel column chromatography (ethyl acetate:hexane=1:20~1:4) to obtain Compound 52B (3.45 g).

¹HNMR (CDCl3) δ: 0.91-1.10 (2H, m), 1.15-1.30 (3H, m), 1.50-1.55 (1H, m), 1.60-1.83 (5H, m), 3.07 (2H, t, J=6.3 Hz), 4.57 (1H, brs), 6.28 (1H, dd, J=0.6, 9.3 Hz), 7.45 (1H, dd, J=2.4, 8.4 Hz) 8.08 (1H, dd, J=1.8, 2.4 Hz).

Second Step

To a solution of Compound 52B (2.97 g) in THF (60 mL), sodium hydride (60%, 485 mg) was added and stirred at room temperature for 5 minutes, then the mixture was stirred at 60° C. for 1 hour. The reaction mixture was cooled to −78° C., 1.58M n-butyl lithium in hexane solution (14.0 mL) was added dropwise thereto, then stirred at −78° C. for 1.5 hours. To the reaction mixture, triisopropyloxy boran (8.4 mL) was added, the mixture was stirred for 5 minutes, then warmed to room temperature and stirred for 2 hours. To the reaction mixture, ammonium chloride aq. was added and the mixture was extracted with ethyl acetate. The organic layer was washed with ammonium chloride aq., NaHCO₃ aq., and water, then dried over anhydrous Na₂SO₄. The solvent was evaporated in vacuo to obtain residue. The residue was washed with diisopropylether to obtain Compound 52C (1.69 g).

¹HNMR (CDCl₃) δ: 0.85-1.68 (11H, m), 3.06 (2H, brs), 4.79 (1H, brs), 6.20-6.55 (1H, m), 7.76-8.08 (1H, m) 8.33-8.77 (1H, m).

EXAMPLE 55

[Formula 65]

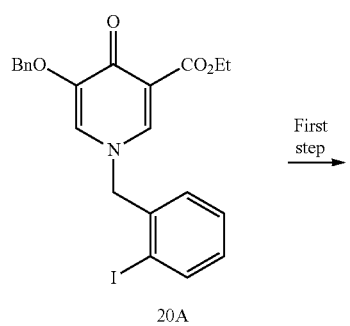

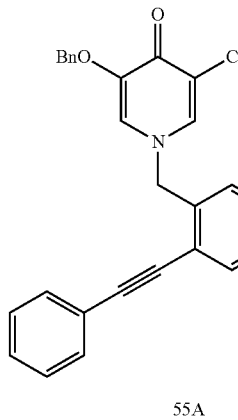

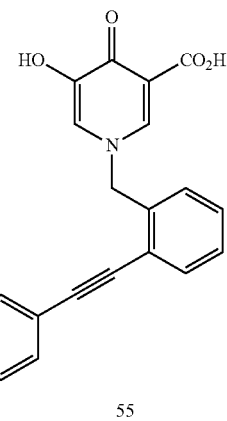

First Step

To a solution of Compound 20A (20 mg) in dioxane (1 mL), phenylacetylene (4.2 mg), dichlorobistriphenylphosphine palladium (2.9 mg), Copper (I) iodide (3.9 mg), and triethylamine (11 μl) were added, then the mixture was stirred at 110° C. for 5 hours. The reaction mixture was filtered with celite, water was added thereto, then extracted with chloroform. The solvent was evaporated in vacuo, then the mixture was purified by preparative isolation with LCMS to obtain Compound 55A.

MS: m/z=464 [M+H]⁺.

Second Step

Compound 55 (6.22 mg) was synthesized from Compound 55A by the synthetic method according to Compound 20.

MS: m/z=346 [M+H]⁺.

EXAMPLE 56

[Formula 66]

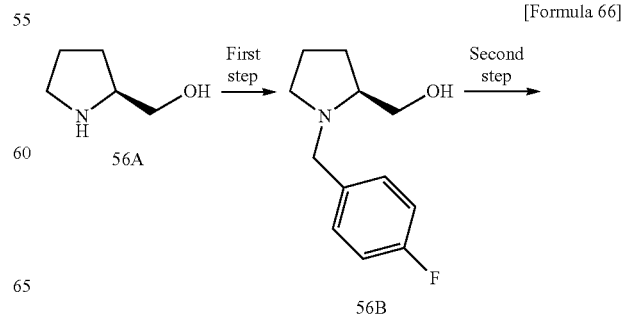

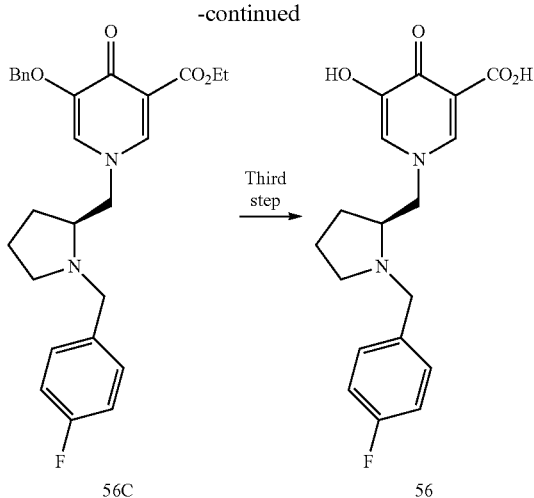

First Step

To a solution of 4-fluorobenzaldehyde (1.24 g, 10 mmol) in dichloromethane (30 mL), a solution of Compound 56A (1.01 g, 10 mmol) in dichloromethane (20 mL) was added dropwise at room temperature, then sodium triacetoxyhydroborate (4.70 g, 22 mmol) was added thereto, and the reaction mixture was stirred for 1.5 hours. After the reaction mixture was condensed, the residue was extracted with ethyl acetate-water, then NaHCO$_3$ (6.0 g, 71 mmol) was added thereto. The ethyl acetate layer was isolated, then additionally, extracted with water-ethyl acetate. The combined extracted solution was washed three times, then washed with sat. NaCl aq., and dried. The solvent was evaporated, then obtained oily substance was purified by silica gel column chromatography. Elution was conducted with ethyl acetate to obtain Compound 56B (1.30 g) as oily substance after evaporation of the target fraction.

$^1$HNMR (CDCl$_3$) δ: 1.60-1.95 (4H, m), 2.22-2.30 (1H, m), 2.70-2.75 (1H, m), 2.92-2.98 (1H, m), 3.33 (1H, d, J=13.2 Hz), 3.43 (1H, dd, J=10.8, 2.0 Hz), 3.64 (1H, dd, J=10.8, 3.6 Hz), 3.93 (1H, d, J=13.2 Hz), 6.97-7.05 (2H, m), 7.24-7.28 (2H, m).

Second Step

Compound 56B (1.3 g, 6.2 mmol) and triethylamine (0.76 g, 7.5 mmol) were dissolved in dichloromethane (6 mL), then the mixture was cooled to 0° C., a solution of methanesulfonyl chloride (0.86 g, 7.5 mmol) in dichloromethane (3 mL) was added dropwise thereto. The reaction mixture was stirred at 0° C. for 2 hours, then evaporated. The residue was extracted with ethyl acetate-sat. NaHCO$_3$ aq., then ethyl acetate layer was washed with water, and sat. NaCl aq., and dried. The solvent was concentrated at low temperature in vacuo, then the obtained residue was dissolved in DMF (2 mL). The solution was added to a suspension of Compound 1D (270 mg, 0.99 mmol) and cesium carbonate (980 mg, 3.01 mmol) in DMF (8 mL) at room temperature, then stirred for 1 hour. The reaction mixture was diluted with water, and washed with ethyl acetate twice. The extracted solution was washed with water three times, and sat. NaCl aq., then dried. The solvent was evaporated, and the obtained oily substance was purified by silica gel column chromatography. Elution was conducted with ethyl acetate-methanol (10:1, v/v), then Compound 56C (0.43 g) as oily substance was obtained after evaporation of the target fraction.

$^1$HNMR (CDCl$_3$) δ: 1.41 (3H, t, J=7.2 Hz), 1.60-1.80 (4H, m), 2.20-2.35 (1H, m), 2.80-2.90 (2H, m), 3.35-3.65 (4H, m), 4.40 (2H, q, J=7.2 Hz), 5.18 (1H, d, J=12 Hz), 5.24 (1H, d, J=12 Hz), 6.95-7.09 (3H, m), 7.20-7.42 (7H, m), 8.10 (1H, d, J=2.4 Hz).

MS: m/z=465 [M+H]$^+$.

Third Step

Compound 56 (70 mg) was synthesized as a solid from Compound 56C according to Example 1.

$^1$HNMR (DMSO-d$_6$) δ: 1.40-1.95 (4H, m), 2.22 (1H, q, J=6.8 Hz), 2.70-2.75 (1H, m), 2.95-3.05 (1H, m), 3.78 (1H, d, J=13.2 Hz), 4.07 (1H, dd, J=13.2, 5.6 Hz), 4.18 (1H, dd, J=13.2, 4.8 Hz), 7.06 (2H, t, J=8.8 Hz), 7.26-7.30 (2H, m), 7.83 (1H, d, J=1.6 Hz), 8.50 (1H, d, J=1.6 Hz).

MS: m/z=347 [M+H]$^+$.

EXAMPLE 57

[Formula 67]

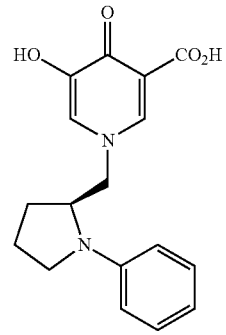

57

Compound 57 was synthesized by the similar method according to Example 56.

$^1$HNMR (DMSO-d$_6$) δ: 1.61-1.78 (2H, m), 1.84-2.00 (1H, m), 3.01-3.08 (1H, m), 3.33-3.40 (1H, m), 4.18-4.26 (3H, m), 6.60 (2H, d, J=8.1 Hz), 6.61 (1H, d, J=6.9 Hz), 7.12 (1H, dd, J=6.9, 8.1 Hz), 7.76 (1H, d, J=1.8 Hz), 8.37 (1H, d, J=1.8 Hz), 9.94 (1H, s).

EXAMPLE 58

[Formula 68]

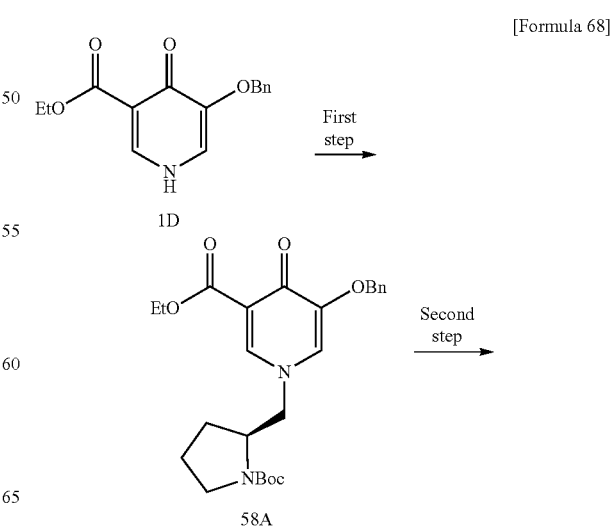

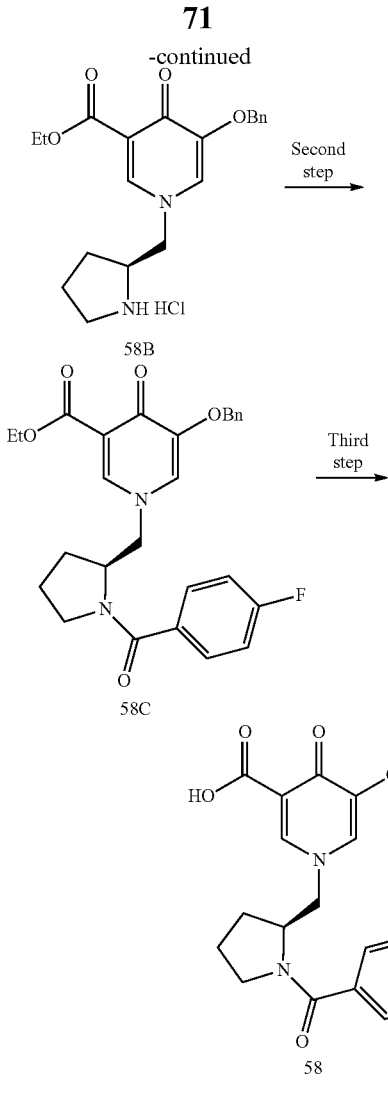

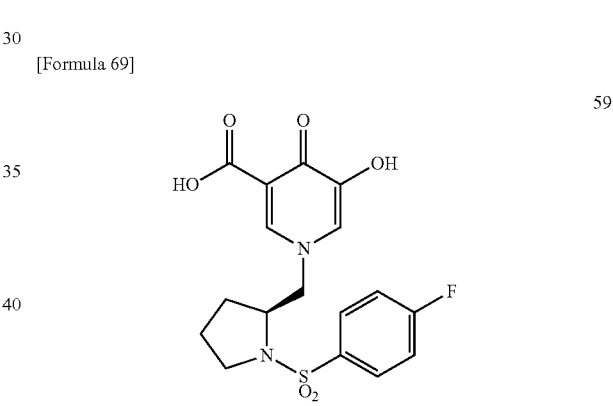

Compound 58B (641 mg, 1.80 mmol) and pyridine (153 mg, 1.94 mmol) in dichloromethane was stirred at ice water bath, then 4-fluorobenzoyl chloride (246 mg, 1.55 mmol) was added thereto, subsequently, the mixture was warmed to room temperature. The reaction mixture was diluted with water, then extraced with dichloromethane three times. The extracted solution was dried over $Na_2SO_4$, then the solvent was evaporated. The obtained oily substance was purified by silica gel column chromatography with ethyl acetate-methanol (10:1, v/v). The target fraction was evaporated to obtain Compound 58C (601 mg) as oily substance.

$^1$HNMR (DMSO-d6) δ: 1.19 (3H, t, J=7.2 Hz), 1.58-1.70 (3H, m), 1.90-1.99 (1H, m), 3.20-3.33 (1H, m), 3.72-3.45 (1H, m), 3.99-4.26 (2H, m), 4.14 (2H, q, J=7.2 Hz), 4.54 (1H, brs), 4.93 (2H, s), 7.25 (2H, t, J=8.7 Hz), 7.33-7.39 (5H, m), 7.52 (2H, t, J=5.7 Hz), 7.65 (1H, s), 8.19 (1H, s).

Third Step

Compound 58 (106 mg) as a solid was synthesized from Compound 58C (601 mg) according to Example 1.

$^1$HNMR (DMSO-$d_6$) δ: 1.66-1.91 (3H, m), 1.97-2.03 (1H, m), 3.19-3.23 (1H, m), 3.49-3.55 (1H, m), 4.14-4.21 (1H, m), 4.33-4.39 (1H, m), 4.62-4.64 (1H, m), 7.25 (2H, t, J=8.7 Hz) 7.47 (2H, t, J=5.7 Hz), 7.88 (1H, s), 8.53 (1H, s), 9.92 (1H, brs).

EXAMPLE 59

[Formula 69]

59

Compound 59 as a solid was synthesized according to Example 58.

$^1$HNMR (DMSO-$d_6$) δ: 1.41-1.57 (3H, m), 1.68-1.80 (1H, m), 3.12-3.20 (1H, m), 3.29-3.41 (1H, m), 4.12-4.22 (3H, m), 7.45 (2H, t, J=8.7 Hz), 7.83-7.89 (3H, m), 8.50 (1H, d, J=8.7.8 Hz) 9.97 (1H, brs).

First Step

To a suspension of Compound 1D (500 mg, 1.83 mmol) and cesium carbonate (2.98 g, 9.15 mmol) in DMF (3 mL), (S)-tert-butyl 2-((methylsulfonyloxy)methyl)pyrrolidine-1-carboxylate (Journal of the American Chemical Society; 115; 15; 1993; 7045, 2.08 g, 7.45 mmol) was added, then the mixture was stirred at 80° C. for 3 hours. The reaction mixture was diluted with water and extracted with ethyl acetate three times. The extracted solution was washed with water three times, then organic layer was dried over $Na_2SO_4$. The solvent was evaporated, then the obtained oily substance was purified by silica gel column chromatography with ethyl acetate-methanol (10:1, v/v). The target fraction was condensed to obtain Compound 58A (532 mg) as oily substance.

$^1$HNMR ($CDCl_3$) δ: 1.35-1.69 (3H, m), 1.38 (3H, t, J=7.2 Hz), 1.48 (9H, s), 3.09-3.45 (2H, m), 3.85-3.97 (3H, m), 4.36 (2H, q, J=7.2 Hz), 5.15-5.25 (2H, m), 6.81 (0.32H, s), 6.93 (0.68H, s), 7.27-7.40 (5H, m), 7.96 (1H, d. J=1.8 Hz).

Second Step

Compound 58A (532 mg, 1.17 mmol) was dissolved in 4N HCl in ethyl acetate solution (3 mL), the mixture was stirred at room temperature for 3 hours. The reaction mixture was neutralized with sat. $NaHCO_3$ aq., then extracted with ethyl acetate three times. The extracted solution was dried over $Na_2SO_4$, the solvent was evaporated to obtain crude purified Compound 58B (364 mg). A solution of the crude purified

EXAMPLE 60

[Formula 70]

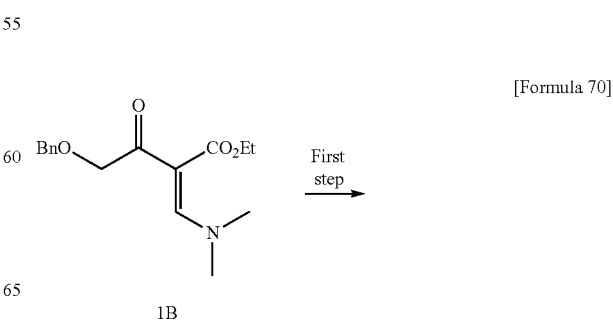

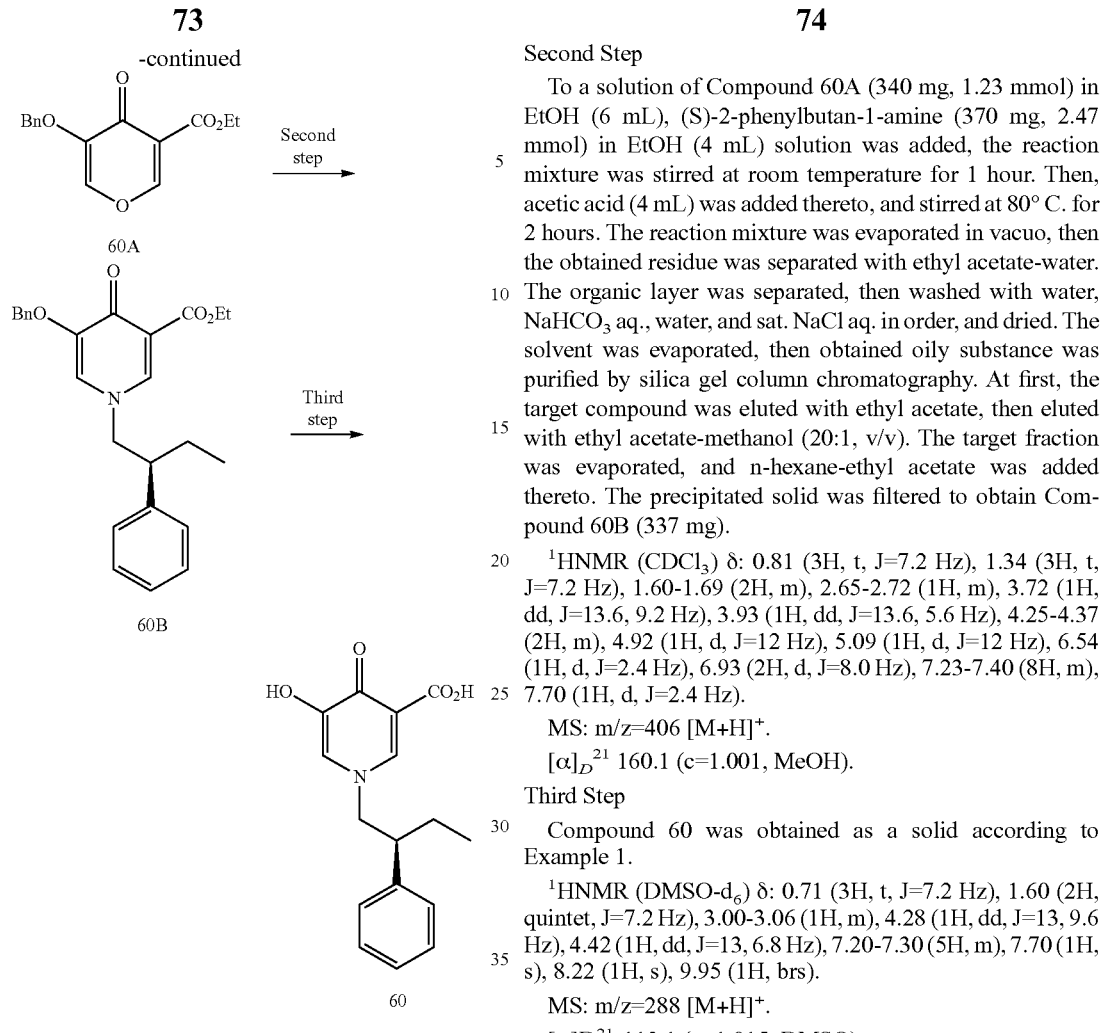

First Step

To a solution of potassium tert-butoxide (1.98 g, 17.6 mmol) in THF (25 mL), ethyl formate (30 mL) was added dropwise at room temperature. The mixture was stirred for 30 minutes at room temperature, Compound 1B (2.57 g, 8.82 mmol) in THF (15 mL) solution was added dropwise for 10 minutes. The reaction mixture was stirred for 3.5 hours and left to stand over night. To the reaction mixture, 2N HCl (12 mL) was added, then the mixture was evaporated in vacuo. The residue was extracted with ethyl acetate-water. After the ethyl acetate was separated, the water layer was extracted with ethyl acetate twice. The combined extracted solution was washed with NaHCO$_3$ aq., water, and sat. NaCl aq. in order, and dried. The solvent was evaporated, then the obtained residue was purified by silica gel column chromatography. At first, the target compound was eluted with n-hexane-ethyl acetate (2:1, v/v), then with n-hexane-ethyl acetate (1:1, v/v). The target fraction was evaporated and n-hexane was added thereto. The precipitated solid was filtered to obtain Compound 60A (1.77 g).

$^1$HNMR (CDCl$_3$) δ: 1.37 (3H, t, J=7.2 Hz), 4.37 (2H, q, J=7.2 Hz), 5.11 (2H, s), 7.30-7.40 (5H, m), 7.55 (1H, s), 8.40 (1H, s).

MS: m/z=275 [M+H]$^+$.

Second Step

To a solution of Compound 60A (340 mg, 1.23 mmol) in EtOH (6 mL), (S)-2-phenylbutan-1-amine (370 mg, 2.47 mmol) in EtOH (4 mL) solution was added, the reaction mixture was stirred at room temperature for 1 hour. Then, acetic acid (4 mL) was added thereto, and stirred at 80° C. for 2 hours. The reaction mixture was evaporated in vacuo, then the obtained residue was separated with ethyl acetate-water. The organic layer was separated, then washed with water, NaHCO$_3$ aq., water, and sat. NaCl aq. in order, and dried. The solvent was evaporated, then obtained oily substance was purified by silica gel column chromatography. At first, the target compound was eluted with ethyl acetate, then eluted with ethyl acetate-methanol (20:1, v/v). The target fraction was evaporated, and n-hexane-ethyl acetate was added thereto. The precipitated solid was filtered to obtain Compound 60B (337 mg).

$^1$HNMR (CDCl$_3$) δ: 0.81 (3H, t, J=7.2 Hz), 1.34 (3H, t, J=7.2 Hz), 1.60-1.69 (2H, m), 2.65-2.72 (1H, m), 3.72 (1H, dd, J=13.6, 9.2 Hz), 3.93 (1H, dd, J=13.6, 5.6 Hz), 4.25-4.37 (2H, m), 4.92 (1H, d, J=12 Hz), 5.09 (1H, d, J=12 Hz), 6.54 (1H, d, J=2.4 Hz), 6.93 (2H, d, J=8.0 Hz), 7.23-7.40 (8H, m), 7.70 (1H, d, J=2.4 Hz).

MS: m/z=406 [M+H]$^+$.

$[α]_D^{21}$ 160.1 (c=1.001, MeOH).

Third Step

Compound 60 was obtained as a solid according to Example 1.

$^1$HNMR (DMSO-d$_6$) δ: 0.71 (3H, t, J=7.2 Hz), 1.60 (2H, quintet, J=7.2 Hz), 3.00-3.06 (1H, m), 4.28 (1H, dd, J=13, 9.6 Hz), 4.42 (1H, dd, J=13, 6.8 Hz), 7.20-7.30 (5H, m), 7.70 (1H, s), 8.22 (1H, s), 9.95 (1H, brs).

MS: m/z=288 [M+H]$^+$.

$[α]D^{21}$ -112.1 (c=1.015, DMSO).

EXAMPLE 61

[Formula 71]

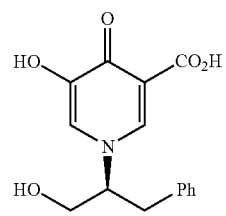

Compound 61 was obtained as a solid according to Example 60.

$^1$HNMR (DMSO-d$_6$) δ: 3.05-3.20 (2H, m), 3.70-3.80 (2H, m), 4.55-4.65 (1H, m), 5.20 (1H, s), 7.16-7.30 (5H, m), 7.94 (1H, d, J=1.6 Hz), 8.32 (1H, d, J=1.6 Hz).

MS: m/z=290 [M+H]$^+$.

EXAMPLE 62

[Formula 72]

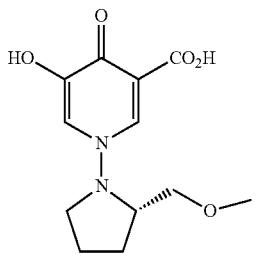

62

Compound 62 was obtained as a solid according to Example 60.

$^1$HNMR (DMSO-$d_6$) δ: 1.45-1.60 (1H, m), 1.75-1.85 (1H, m), 1.85-1.95 (1H, m), 2.00-2.10 (1H, m), 3.10 (3H, s), 3.25-3.40 (4H, m), 3.50-3.60 (1H, m), 8.14 (1H, d, J=2.4 Hz), 8.43 (1H, d, J=2.4 Hz), 10.1 (1H, brs).

MS: m/z=269 [M+H]$^+$.

EXAMPLE 63

[Formula 73]

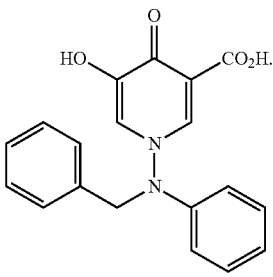

63

Compound 63 was obtained as a solid according to Example 60.

$^1$HNMR (DMSO-$d_6$) δ: 4.98 (2H, s), 6.92 (2H, d, J=8.1 Hz), 7.07 (1H, t, J=7.2 Hz), 7.27-7.39 (7H, m), 7.89 (1H, d, J=2.4 Hz), 8.31 (1H, d, J=2.4 Hz), 10.4 (1H, brs), 15.5 (1H, brs).

MS: m/z=337 [M+H]$^+$.

EXAMPLE 64

[Formula 74]

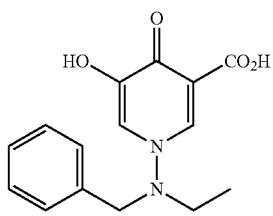

64

Compound 64 was obtained as a solid according to Example 60.

$^1$HNMR (DMSO-$d_6$) δ: 0.91 (3H, t, J=7.2 Hz), 3.21 (2H, q, J=7.2 Hz), 4.28 (2H, s), 7.24-7.32 (5H, m), 8.13 (1H, d, J=2.0 Hz), 8.18 (1H, d, J=2.0 Hz), 10.1 (1H, brs).

MS: m/z=289 [M+H]$^+$.

EXAMPLE 65

[Formula 75]

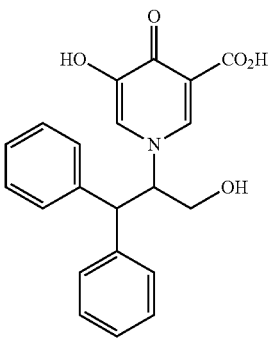

65

Compound 65 was obtained using [6,7,8,9-tetrahydro-5H-benzo[7]annulen-5-yl]methylamine (EP 179667) according to Example 60.

$^1$HNMR (DMSO-$d_6$) δ: 1.35-1.80 (6H, m), 2.75-2.85 (1H, m), 3.00-3.15 (1H, m), 3.42 (1H, brm), 4.44-4.58 (2H, m), 6.88 (1H, d, J=7.2 Hz), 7.02 (1H, t, J=7.2 Hz), 7.09 (1H, t, J=7.2 Hz), 7.14 (1H, d, J=7.2 Hz), 7.79 (1H, s), 8.32 (1H, s), 9.95 (1H, brs).

MS: m/z=314 [M+H]$^+$.

EXAMPLE 66

[Formula 76]

66

Compound 66 was obtained as a solid according to Example 60.

¹HNMR (DMSO-d₆) δ: 3.10-3.59 (2H, m), 4.55 (1H, d, J=12.4 Hz), 4.95-5.03 (1H, m), 5.23-5.33 (1H, m), 6.80-7.18 (6H, m), 7.26 (1H, d, J=7.4 Hz), 7.40 (1H, d, J=7.4 Hz), 7.85 (1H, s), 8.43 (1H, s).

EXAMPLE 67

[Formula 77]

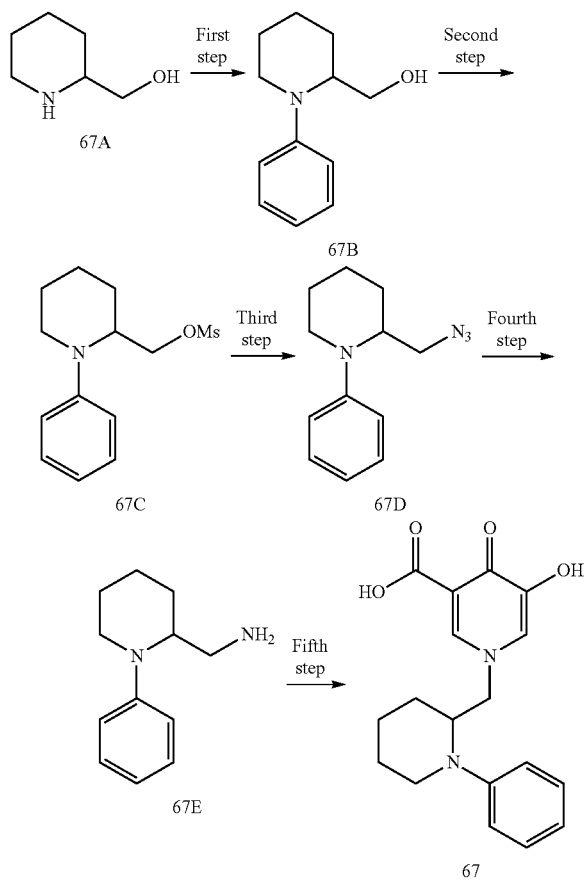

First Step

Compound 67A (500 mg), iodobenzene (1.06 g), copper iodide (50 mg), sodium hydroxide (347 mg) were dissolved in 2-propanol (5 mL) under nitrogen atmosphere, then the mixture was stirred at 90° C. for 6 hours. The dichloromethane (10 mL)-water (10 mL) were added thereto, the mixture was extracted, and additionally, water layer was extracted with dichloromethane (10 mL). The oil layers were combined, then washed with 0.1M NaCl (20 mL), and sat. NaCl aq., and dried over MgSO₄. The MgSO₄ was filtered and the filtrate was evaporated in vacuo and the residue was purified by silica gel chromatography to obtain Compound 67B (366 mg).

MS: 192.00 m/z [M+H]⁺.

Second Step

Compound 67B (254 mg) was dissolved in dichloromethane (3 mL) under nitrogen atmosphere, then cooled to 0° C., methanesulfonylchloride (0.114 mL) and triethylamine (0.552 mL) were added thereto, then stirred under nitrogen atmosphere at 0° C. for 4 hours and 30 minutes. To the reaction mixture, a solution of sat. sodium hydrogencarbonate was added, the mixture was extracted with ethyl acetate. The extracted solution was dried over MgSO₄. The MgSO₄ was filtered and the filtrate was evaporated in vacuo to obtain Compound 67C (345 mg).

¹HNMR (CDCl₃): δ 1.60-1.90 (6H, m), 2.81 (3H, s), 2.96-3.05 (1H, m), 3.33-3.39 (1H, m), 4.08-4.15 (1H, m), 4.26 (2H, d, J=6.0 Hz), 6.83 (1H, t, J=9.0 Hz), 6.94 (2H, d, J=6.0 Hz), 7.22-7.27 (2H, m).

Third Step

Compound 67C (435 mg) was dissolved in DMF (3 mL), sodium azide was added thereto at room temperature (142 mg) and stirred at 60° C. for 3 hours. Water (10 mL) was added thereto, and extracted with ethyl acetate, then the oil layer was combined. The solution was washed with sat. NaCl aq., and dried over MgSO₄. The MgSO₄ was filtered and the filtrate was evaporated in vacuo. The obtained residue was purified by silica gel chromatography to obtain Compound 67D (288 mg).

¹HNMR (CDCl₃) δ: 1.40-1.49 (1H, m), 1.63-1.83 (3H, m), 1.92-1.99 (2H, m), 3.15-3.32 (2H, m), 3.59-3.67 (1H, m), 3.73-3.79 (1H, m), 3.88 (1H, dd, J=15.0, 3.0 Hz), 6.66-6.73 (3H, m), 7.19-7.25 (2H, m).

Fourth Step

Compound 67D (133 mg) was dissolved in THF (2 mL), Pd—C (10% dry) (18 mg) was added thereto and stirred at room temperature under hydrogen atmosphere for 6 hours. The Pd—C was filtered, the solvent was evaporated in vacuo to obtain residue of Compound 67E (126 mg).

MS: 191.20 m/z [M+H]⁺.

Fifth Step

Compound 67 was synthesized from Compound 67E according to Example 60.

MS: 329.05 m/z [M+H]⁺.

EXAMPLE 68

[Formula 78]

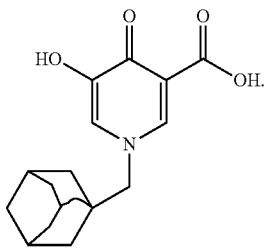

Compound 68 was synthesized according to Example 60.

MS: m/z=304 [M+H]⁺.

¹HNMR (DMSO-d₆) δ: 1.32 (6H, s), 1.42 (3H, d, J=12.2 Hz), 1.52 (3H, d, J=12.2 Hz), 1.83 (3H, s), 3.76 (2H, s), 7.54 (1H, d, J=2.0 Hz), 8.16 (1H, d, J=2.0 Hz), 9.88 (1H, s), 16.00 (1H, s).

EXAMPLE 69

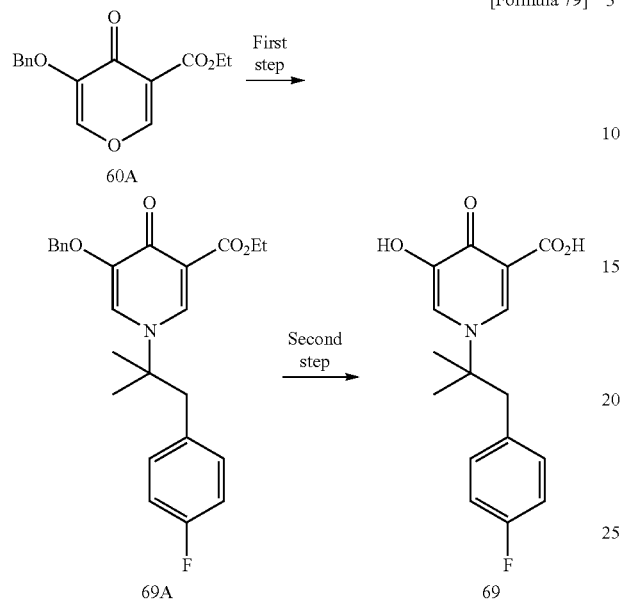

[Formula 79]

First Step

To a solution of Compound 60A (14 mg) in ethanol (1 mL), 1-(4-fluorophenyl)-2-methylpropane-2-amine (8.54 mg) was added, the solution was stirred at 80° C. for 5 hours. The reaction mixture was evaporated and obtained residue was purified by preparative isolation using LCMS to obtain Compound 69A.

MS: m/z=424 [M+H]$^+$.

Second Step

Compound 69 (2.4 mg) was obtained from Compound 69A according to the synthetic method of Example 5.

MS: m/z=306 [M+H]$^+$.

EXAMPLE 70~114

The following compounds were obtained according to Example 69.

TABLE 15

| Example | Structure | MS(M + 1) |
|---|---|---|
| 70 | (structure) | 374 |

TABLE 16

| Example | Structure | MS(M + 1) |
|---|---|---|
| 71 | (structure) | 358 |
| 72 | (structure) | 336 |
| 73 | (structure) | 336 |
| 74 | (structure) | 294 |

TABLE 17

| Example | Structure | MS(M + 1) |
|---|---|---|
| 75 | (structure) | 288 |

TABLE 17-continued

| Example | Structure | MS(M + 1) |
| --- | --- | --- |
| 76 | 3-chlorophenethyl N-substituted 5-hydroxy-4-oxo-1,4-dihydropyridine-3-carboxylic acid | 294 |
| 77 | 3-fluorophenethyl N-substituted 5-hydroxy-4-oxo-1,4-dihydropyridine-3-carboxylic acid | 278 |
| 78 | 2-[2,2-dimethyl-4-(2-methoxyphenyl)tetrahydropyran-4-yl]ethyl N-substituted 5-hydroxy-4-oxo-1,4-dihydropyridine-3-carboxylic acid | 402 |

TABLE 18

| Example | Structure | MS(M + 1) |
| --- | --- | --- |
| 79 | 2-pyrrolidin-1-yl-2-[4-(trifluoromethyl)phenyl]ethyl N-substituted 5-hydroxy-4-oxo-1,4-dihydropyridine-3-carboxylic acid | 397 |
| 80 | 2-(4-methoxyphenoxy)propyl N-substituted 5-hydroxy-4-oxo-1,4-dihydropyridine-3-carboxylic acid | 320 |
| 81 | 2-(4-fluorophenoxy)propyl N-substituted 5-hydroxy-4-oxo-1,4-dihydropyridine-3-carboxylic acid | 308 |
| 82 | 2-(2-chlorophenoxy)propyl N-substituted 5-hydroxy-4-oxo-1,4-dihydropyridine-3-carboxylic acid | 324 |
| 83 | 2-[(4-chlorophenyl)thio]ethyl N-substituted 5-hydroxy-4-oxo-1,4-dihydropyridine-3-carboxylic acid | 326 |

TABLE 19

| Example | Structure | MS(M + 1) |
| --- | --- | --- |
| 84 | (5-methyl-3-phenylisoxazol-4-yl)methyl N-substituted 5-hydroxy-4-oxo-1,4-dihydropyridine-3-carboxylic acid | 327 |
| 85 | (2,3-dihydro-1,4-benzodioxin-2-yl)methyl N-substituted 5-hydroxy-4-oxo-1,4-dihydropyridine-3-carboxylic acid | 304 |

TABLE 19-continued

| Example | Structure | MS(M + 1) |
|---------|-----------|-----------|
| 86 | 5-hydroxy-4-oxo-1-(4-hydroxyphenethyl)-1,4-dihydropyridine-3-carboxylic acid | 276 |
| 87 | 5-hydroxy-4-oxo-1-(chroman-2-ylmethyl)-1,4-dihydropyridine-3-carboxylic acid | 302 |
| 88 | 5-hydroxy-4-oxo-1-(3,3-diphenylpropyl)-1,4-dihydropyridine-3-carboxylic acid | 350 |

TABLE 20

| Example | Structure | MS(M + 1) |
|---------|-----------|-----------|
| 89 | 5-hydroxy-4-oxo-1-((1S,2R)-2-hydroxy-1,2-diphenylethyl)-1,4-dihydropyridine-3-carboxylic acid (Chiral) | 352 |
| 90 | 5-hydroxy-4-oxo-1-((R)-1-cyclohexylethyl)-1,4-dihydropyridine-3-carboxylic acid (Chiral) | 266 |
| 91 | 5-hydroxy-4-oxo-1-neopentyl-1,4-dihydropyridine-3-carboxylic acid | 226 |

TABLE 20-continued

| Example | Structure | MS(M + 1) |
|---------|-----------|-----------|
| 92 | 5-hydroxy-4-oxo-1-cyclopentyl-1,4-dihydropyridine-3-carboxylic acid | 224 |

TABLE 21

| Example | Structure | MS(M + 1) |
|---------|-----------|-----------|
| 93 | 5-hydroxy-4-oxo-1-(cyclohexylmethyl)-1,4-dihydropyridine-3-carboxylic acid | 252 |
| 94 | 5-hydroxy-4-oxo-1-((S)-tetrahydrofuran-2-ylmethyl)-1,4-dihydropyridine-3-carboxylic acid (Chiral) | 240 |
| 95 | 5-hydroxy-4-oxo-1-(4-chlorophenethyl)-1,4-dihydropyridine-3-carboxylic acid | 294 |
| 96 | 5-hydroxy-4-oxo-1-(2-(1H-indol-3-yl)ethyl)-1,4-dihydropyridine-3-carboxylic acid | 299 |

TABLE 22

| Example | Structure | MS(M + 1) |
| --- | --- | --- |
| 97 | Chiral | 336 |
| 98 | 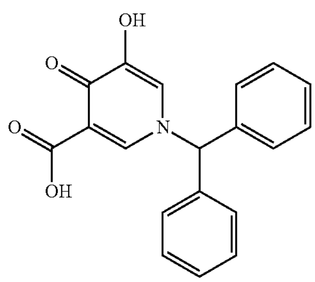 [SMILES: O=C(O)c1cn(C(c2ccccc2)c2ccccc2)cc(O)c1=O] | 322 |
| 99 | 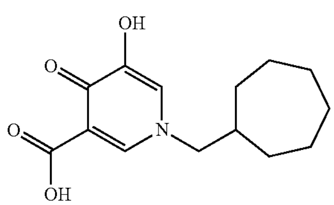 [SMILES: O=C(O)c1cn(CC2CCCCCC2)cc(O)c1=O] | 266 |
| 100 | 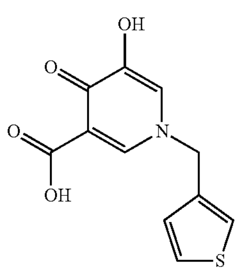 [SMILES: O=C(O)c1cn(Cc2ccsc2)cc(O)c1=O] | 252 |

TABLE 23

| Example | Structure | MS(M + 1) |
| --- | --- | --- |
| 101 | | 352 |
| 102 | 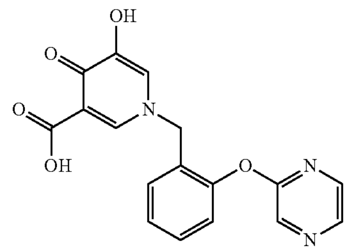 [SMILES: O=C(O)c1cn(Cc2ccccc2Oc2cnccn2)cc(O)c1=O] | 340 |
| 103 | 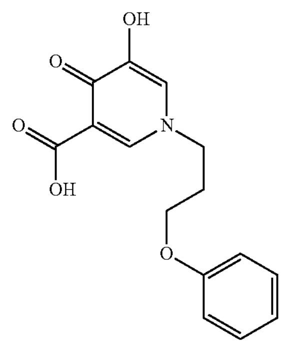 [SMILES: O=C(O)c1cn(CCCOc2ccccc2)cc(O)c1=O] | 290 |
| 104 | 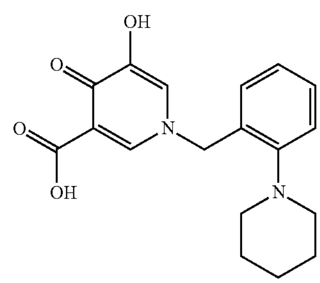 [SMILES: O=C(O)c1cn(Cc2ccccc2N2CCCCC2)cc(O)c1=O] | 329 |

TABLE 24

| Example | Structure | MS(M + 1) |
| --- | --- | --- |
| 105 | 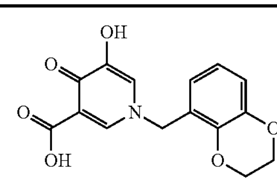 | 304 |
| 106 | Chiral | 344 |

TABLE 24-continued

| Example | Structure | MS(M + 1) |
|---|---|---|
| 107 | (5-hydroxy-4-oxo-1-(2-(3,5-dimethylisoxazol-4-yl)ethyl)-1,4-dihydropyridine-3-carboxylic acid) | 279 |
| 108 | Chiral; (1-((1S,2S)-2-(benzyloxy)cyclohexyl)-5-hydroxy-4-oxo-1,4-dihydropyridine-3-carboxylic acid) | 344 |
| 109 | 1-(1-(hydroxymethyl)cyclopentyl)-5-hydroxy-4-oxo-1,4-dihydropyridine-3-carboxylic acid | 254 |

TABLE 25

| Example | Structure | MS(M + 1) |
|---|---|---|
| 110 | 5-hydroxy-4-oxo-1-(3-(phenylsulfonyl)propyl)-1,4-dihydropyridine-3-carboxylic acid | 338 |
| 111 | 1-(2-((2-(hydroxymethyl)phenyl)thio)benzyl)-5-hydroxy-4-oxo-1,4-dihydropyridine-3-carboxylic acid | 384 |
| 112 | 5-hydroxy-4-oxo-1-((1-phenylcyclopentyl)methyl)-1,4-dihydropyridine-3-carboxylic acid | 314 |
| 113 | 5-hydroxy-1-((1-hydroxycyclopentyl)methyl)-4-oxo-1,4-dihydropyridine-3-carboxylic acid | 254 |

TABLE 25-continued

| Example | Structure | MS(M + 1) |
|---|---|---|
| 114 | Chiral; 1-((1S,2S)-2-hydroxycyclopentyl)-5-hydroxy-4-oxo-1,4-dihydropyridine-3-carboxylic acid | 240 |

EXAMPLE 115

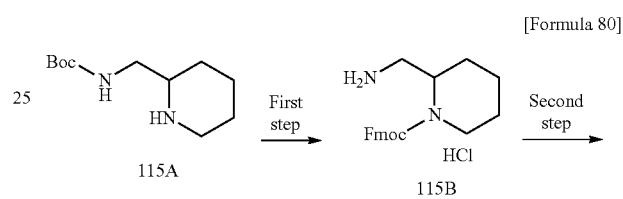

[Formula 80]

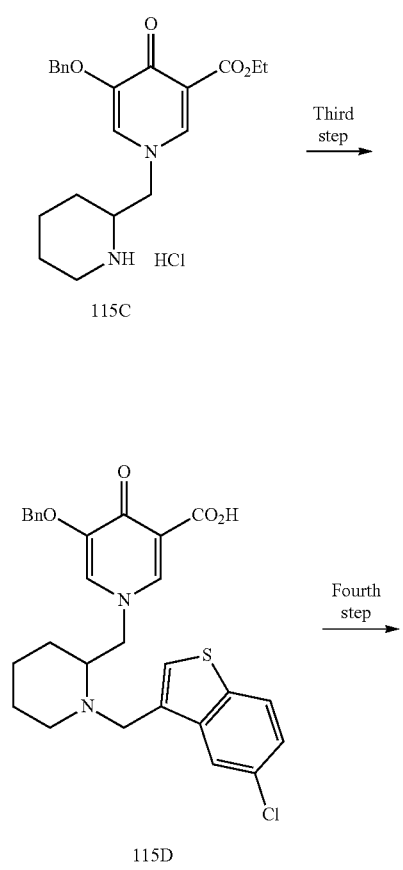

89
-continued

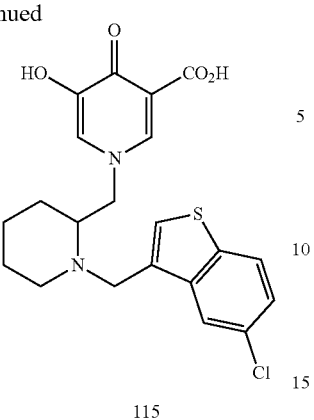

115

First Step

To a solution of Compound 115A (1.0 g) in dioxane (20 mL), sodium bicarbonate (588 mg), water (2 mL), and Fmoc chloride (1.2 g) were added, then the mixture was stirred at room temperature for 3 hours. To the reaction mixture, water was added, then the mixture was extracted with ethyl acetate. The organic layer was dried over anhydrous $Na_2SO_4$. The solvent was evaporated in vacuo to obtain residue, then a solution of 4N HCl-ethyl acetate (5 mL) was added thereto. The mixture was stirred at room temperature for 2 hours, then the precipitated solid was filtered to obtain Compound 115B (1.05 g).

$^1$HNMR (DMSO-$d_6$) δ: 0.98-1.64 (6H, m), 2.75-3.16 (3H, m), 3.59-3.73 (1H, m), 4.13-4.46 (4H, m), 7.35 (2H, t, J=7.2 Hz), 7.42 (2H, t, J=7.2 Hz), 7.63 (2H, d, J=5.6 Hz), 7.89 (2H, d, J=7.6 Hz), 7.95 (3H, brs).

Second Step

To Compound 115B (1.05 g) in toluene (30 mL), Compound 60A (0.77 g) and triethylamine (0.58 mL) were added, then stirred at 100° C. for 6 hours. To the reaction mixture, water was added, then extracted with ethyl acetate. The organic layer was dried over anhydrous $Na_2SO_4$, then solvent was evaporated in vacuo. DMF (5 mL) and triethylamine (5 mL) were added to the residue, then it left standing at room temperature over night. The reaction mixture was evaporated, then 4N HCl-ethyl acetate solution (5 mL) was added thereto and stirred at room temperature for 2 hours. The reaction mixture was evaporated and ethyl acetate was added thereto. The mixture was stirred for a while, and supernatant liquid was removed. The residue of Compound 115C was obtained as a crude product.

MS: m/z=371 [M+H]$^+$.

Third Step

To a solution of Compound 115C (20 mg) in DMF (1 mL), cesium carbonate (49 mg) and 2-bromomethyl-5-chlorobenzothiophene (18 mg) were added, then the mixture was stirred at room temperature for 5 hours. To the reaction mixture, 2N sodium hydroxide solution was added and stirred at room temperature for 1 hour, then 2N HCl and chloroform were added thereto and the mixture was extracted. The obtained residue after condensation of the organic layer was purified by preparative separation using LCMS to obtain Compound 115D which was used in the next step.

MS: m/z=523 [M+H]$^+$.

Fourth Step

Compound 115 (4.9 mg) was obtained from Compound 115D according to the synthetic method of Example 5.

MS: m/z=433 [M+H]$^+$.

90

The following compounds were obtained using Compound 115C or Compound 58B according to Example 115.

TABLE 26

| Example | Structure | MS(M + 1) |
|---|---|---|
| 116 | 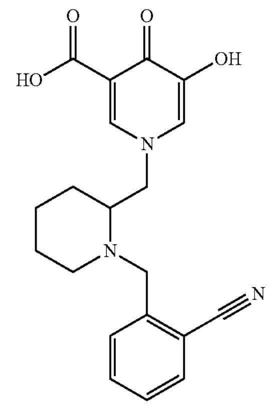 [SMILES: N#Cc1ccccc1CN1CCCCC1Cn1cc(O)c(=O)c(C(=O)O)c1] | 368 |

TABLE 227

| Example | Structure | MS(M + 1) |
|---|---|---|
| 117 | 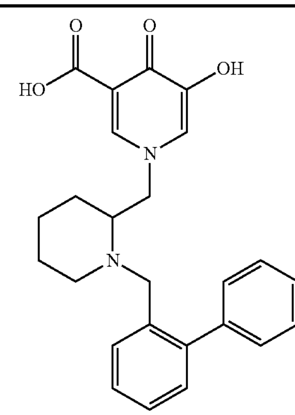 | 419 |
| 118 | 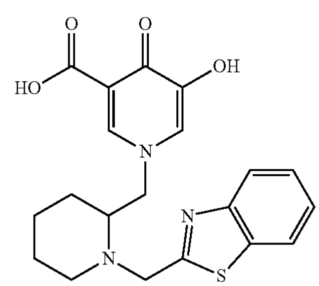 [SMILES: O=C(O)c1cn(CC2CCCCN2Cc2nc3ccccc3s2)cc(O)c1=O] | 400 |
| 119 | 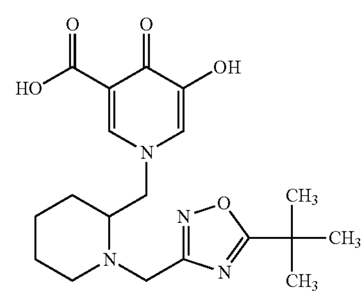 [SMILES: CC(C)(C)c1nc(CN2CCCCC2Cn2cc(O)c(=O)c(C(=O)O)c2)no1] | 391 |

TABLE 227-continued
| Example | Structure | | MS(M + 1) |
|---|---|---|---|
| 120 | | Chiral | 419 |
| 121 | 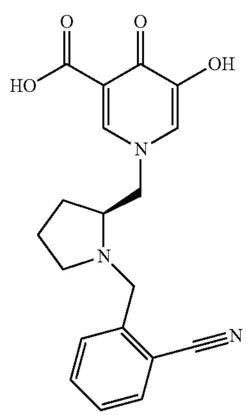 | Chiral | 354 |
| 122 | 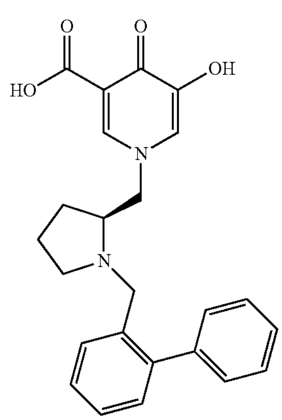 | Chiral | 405 |
TABLE 28
| Example | Structure | | MS(M + 1) |
|---|---|---|---|
| 123 | 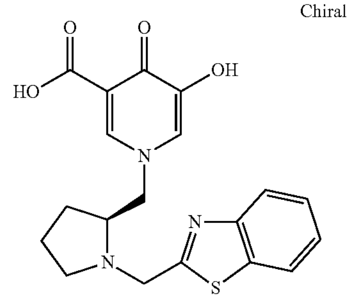 [SMILES: O=C(O)c1cn(C[C@@H]2CCCN2Cc2nc3ccccc3s2)cc(O)c1=O] | Chiral | 386 |
TABLE 29
| Example | Structure | | MS(M + 1) |
|---|---|---|---|
| 124 | 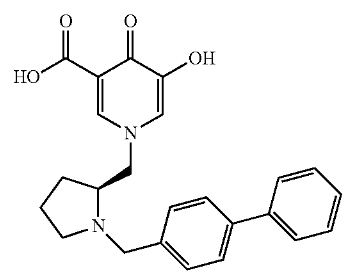 | Chiral | 405 |
EXAMPLE 125
[Formula 81]
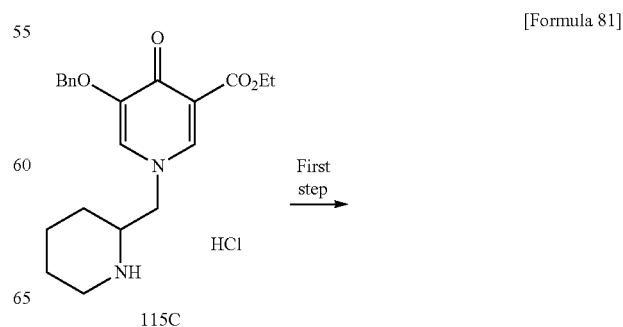
First step
115C

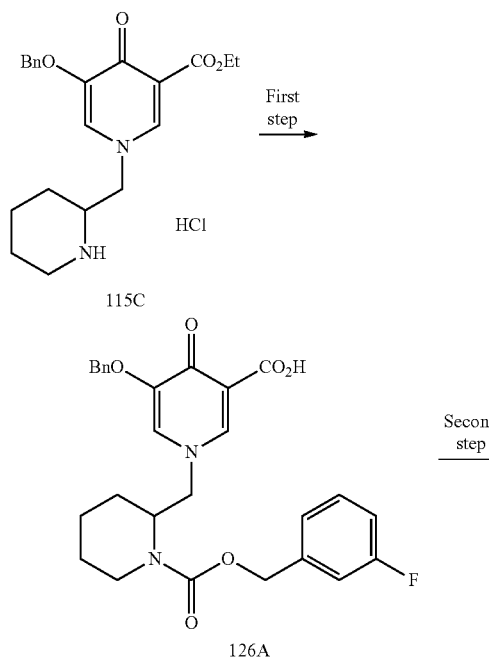

First Step

To a solution of Compound 115C (20 mg) in dichloromethane (1 mL), sodium triacetoxyborohydride (32 mg), acetic acid (11 µl), and triethylamine (7 µl) were added, then the mixture was stirred at room temperature for 4 hours. Water was added to the reaction mixture, then stirred at room temperature for a while. To the reaction mixture 2N HCl aq. and chloroform were added, then the mixture was extracted. The obtained residue after evaporation of organic layer was purified by preparative separation using LCMS to obtain Compound 125A which was used in the next step.

MS: m/z=523 [M+H]$^+$.

Second Step

Compound 125 (4.9 mg) was obtained from Compound 125A according to Example 5.

MS: m/z=433 [M+H]$^+$.

EXAMPLE 126

[Formula 82]

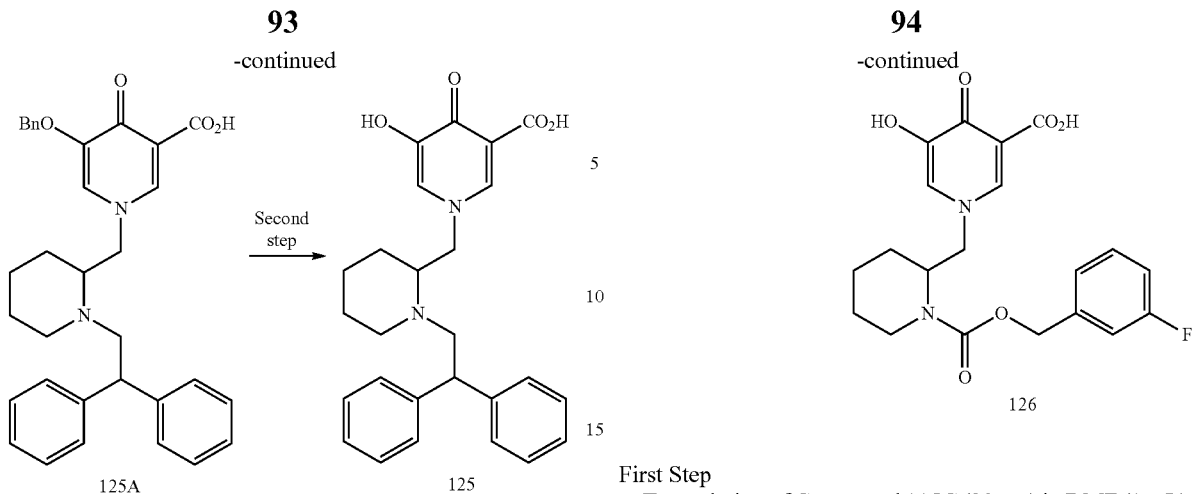

First Step

To a solution of Compound 115C (20 mg) in DMF (1 mL), cesium carbonate (49 mg) and 3-fluorobenzylchloride (5.5 mg) were added, then the mixture was stirred at room temperature for 5 hours. 2N sodium hydroxide aq. was added to the reaction mixture, the mixture was stirred at room temperature for 1 hour. Then, 2N HCl, and chloroform were added thereto and the mixture was extracted. The obtained residue after evaporation of organic layer was purified by preparative separation using LCMS to obtain Compound 126A which was used in the next step.

MS: m/z=495 [M+H]$^+$.

Second Step

Compound 126 (0.51 mg) was obtained from Compound 126A according to Example 5.

MS: m/z=405 [M+H]$^+$.

The following compounds were obtained using Compound 115C or Compound 58B according to Example 126.

TABLE 30

| Example | Structure | MS(M + 1) |
|---------|-----------|-----------|
| 127 | 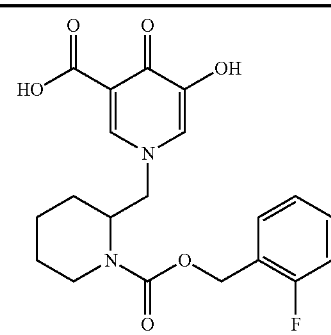 | 405 |
| 128 | 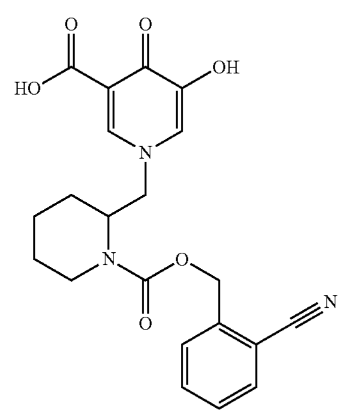 [SMILES: N#Cc1ccccc1COC(=O)N1CCCCC1Cn1cc(O)c(=O)c(C(=O)O)c1] | 412 |

TABLE 30-continued
| Example | Structure | MS(M + 1) |
|---|---|---|
| 129 | 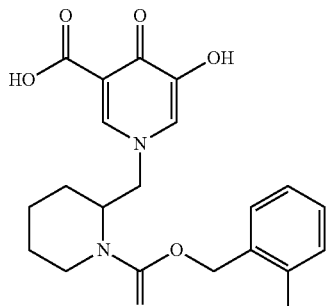 | 455 |
TABLE 31
| Example | Structure | MS(M − 1) |
|---|---|---|
| 130 | 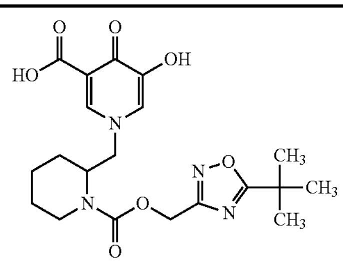 | 435 |
| 131 | Chiral | 471 |
| 132 | Chiral | 398 |
TABLE 32
| Example | Structure | MS(M − 1) |
|---|---|---|
| 133 | Chiral | 441 |
| 134 | Chiral | 430 |
| 135 | Chiral | 387 |

TABLE 33

| Example | Structure | MS(M + 1) |
|---|---|---|
| 136 | Chiral | 401 |

EXAMPLE 137

[Formula 83]

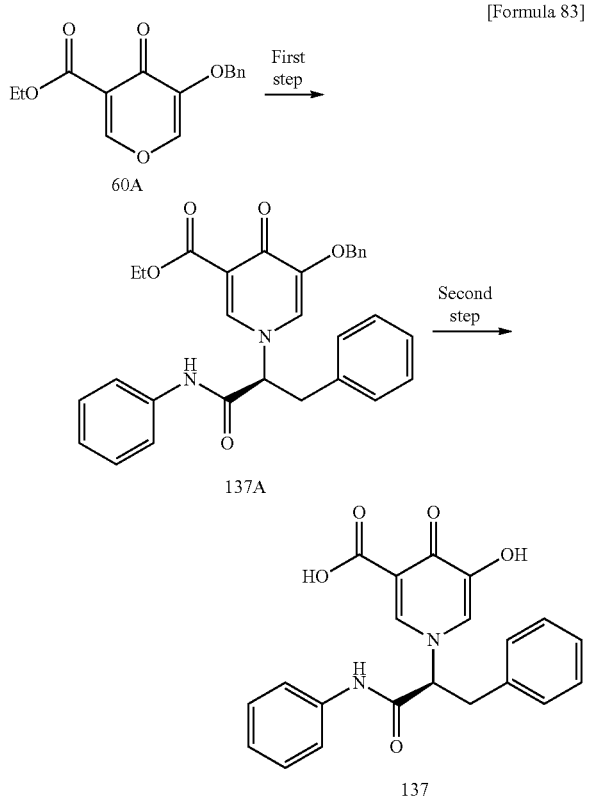

First Step

To a solution of Compound 60A (1 g, 3.65 mmol) and tert-butyl (S)-2-amino-3-phenylpropanoate hydrochloride (1.41 g, 5.47 mmol) in EtOH (10 mL), NaHCO$_3$ (460 mg, 5.47 mmol) was added, then the mixture was stirred at room temperature for 1 hour. Then, acetic acid (10 mL) was added thereto, and stirred at room temperature for 2 hours. The reaction mixture was diluted with 2N HCl aq. and extracted with ethyl acetate three times. The extracted solution was washed with sat. NaHCO$_3$ aq., and dried over Na$_2$SO$_4$, then the solvent was evaporated. The residue was dissolved in 4N HCl-dioxane solution at room temperature for 3 hours. The reaction mixture was evaporated in vacuo. The solution composed of the residue (117 mg), WSC (80 mg, 0.417 mmol), and HOBt (45 mg, 0.334 mmol) in DMF (3 mL) was stirred at room temperature for 30 minutes, then aniline (38.8 mg, 0.416 mmol) was added thereto and the mixture was stirred for 3 hours. The reaction mixture was diluted with water and extracted with ethyl acetate three times. The extracted solution was washed with water three times, and dried over Na$_2$SO$_4$. Then the solvent was evaporated, and the obtained oily substance was purified by silica gel column chromatography. The target compound was eluted with ethyl acetate-methanol (10:1, v/v), then the target fraction was evaporated to obtain Compound 137A (117 mg) as oily substance.

$^1$HNMR (CDCl$_3$) δ: 0.96-1.02 (3H, m), 3.01-3.09 (1H, m), 3.37-3.41 (1H, m), 3.86-3.98 (1H, m), 4.69-4.83 (1H, m), 4.77 (2H, s), 5.35-5.41 (1H, m), 6.90 (2H, s), 7.05 (3H, s), 7.14-7.23 (6H, m), 7.47 (1H, d, J=19.2 Hz), 7.58 (2H, d, J=7.5 Hz), 8.16 (1H, d, J=15.6 Hz), 10.61 (1H, d, J=9.0 Hz).

Second Step

Compound 137 (25 mg) as a solid was obtained from Compound 137A (117 mg) according to Example 1.

$^1$HNMR (DMSO-d$_6$) δ: 3.45 (1H, dd, J=9.9 Hz, 12.3 Hz), 3.61 (1H, dd. J=6.6, 12.3 Hz), 5.37 (1H, dd, J=6.6, 9.9 Hz), 7.11 (1H, t, J=7.5 Hz), 7.15-7.23 (1H, m), 7.25-7.27 (4H, m), 7.34 (2H, t, J=7.8 Hz), 7.54-7.56 (2H, m), 7.91 (1H, d, J=1.8 Hz), 8.39 (1H, d, J=1.8 Hz), 10.15 (1H, brs), 10.46 (1H, s).

EXAMPLE 138

[Formula 84]

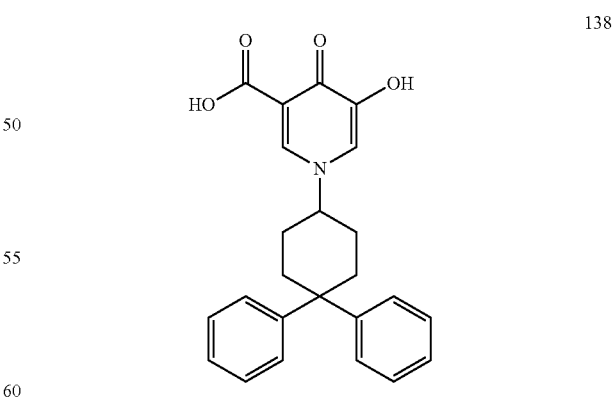

Compound 138 was obtained using 4,4-diphenylcyclohexanamine (Patent No. DE1793611) according to Example 60.

MS: 390.05 m/z [M+H]$^+$.

EXAMPLE 139

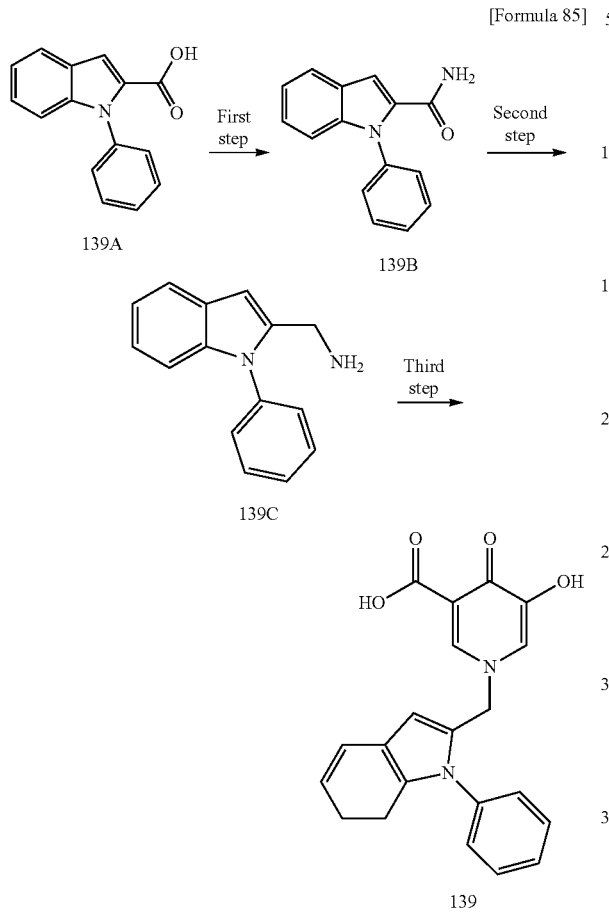

EXAMPLE 140

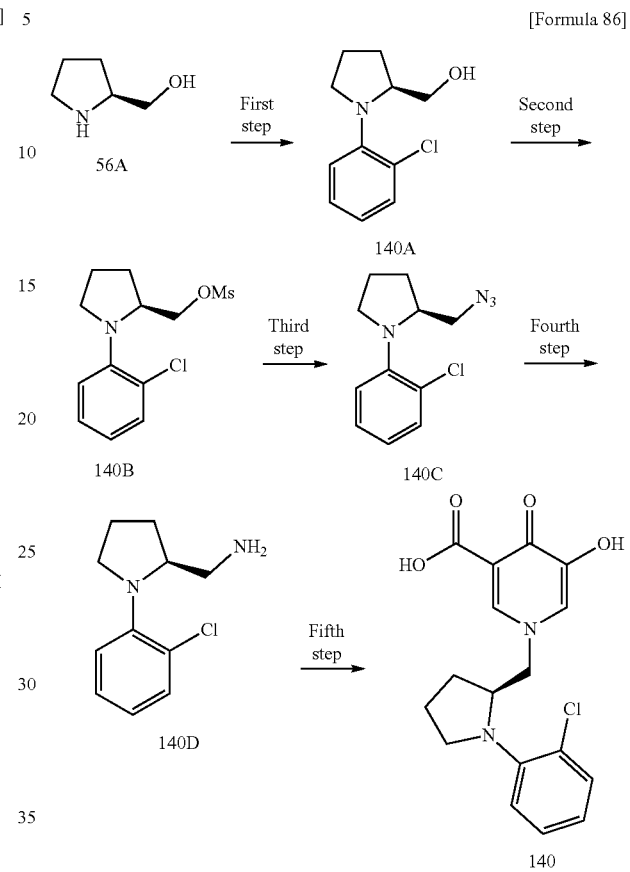

First Step

Compound 139A (365 mg) was dissolved in DMF (3 mL), carbonyldiimidazol (299 mg) was added thereto and the mixture was stirred at room temperature for 25 minutes. Then, 28% ammonia aq. (1.0 mL) was added thereto, and the mixture was stirred at room temperature for 30 minutes. Water was added thereto, then precipitated solid was filtered, and obtained solid was purified by silica gel chromatography to obtain Compound 139B (279 mg).

MS: 237.10 m/z $[M+H]^+$.

Second Step

Lithium alminium hydride (58 mg) was dissolved in THF (3 mL), the mixture was cooled in ice water bath under nitrogen atmosphere, then a solution of Compound 139B (279 mg) in THF (8 mL) was added dropwise thereto. The mixture was stirred at 0° C. for 1 hour, then stirred at 60° C. for 2 hours. The reaction mixture was cooled in ice water bath, $Na_2SO_4$.10hydrate (600 mg), and potassium fluoride (86 mg) were added thereto, then stirred for 4 hours. The reaction mixture was filtered with celite, then filtrate was evaporated in vacuo. The residue was purified by amino silica gel chromatography to obtain Compound 139C (211 mg).

$^1$HNMR ($CDCl_3$) δ: 3.89 (2H, s), 6.56 (1H, s), 7.11-7.14 (3H, m), 7.26-7.60 (6H, m).

Third Step

Compound 139 was obtained using Compound 139C according to Example 60

MS: 361.05 m/z $[M+H]^+$.

First Step

Compound 56A (500 mg), 1-chloro-2-iodobenzene (1.41 g), copper iodide (47 mg), and sodium hydroxide (395 mg) were dissolved in 2-propanol (5 mL), then the mixture was stirred under nitrogen atmosphere at 90° C. for 3 hours. The dichloromethane (10 mL) and water (10 mL) were added thereto, then the mixture was extracted, additionally, water layer was extracted with dichloromethane (10 mL). The oil layer was combined and washed with 0.1M NaCl (20 mL) and sat. NaCl aq., then dried over $MgSO_4$. The $MgSO_4$ was filtered, then filtrate was evaporated in vacuo to obtain Compound 140A (1.13 g).

MS: 212.00 m/z $[M+H]^+$.

Second Step

Compound 140A (1.04 g) was dissolved in dichloromethane (5 mL), then after the solution was cooled to 0° C. under nitrogen atmosphere, methanesulfonyl chloride (0.423 mL) and triethylamine (2.05 mL) were added thereto, and the mixture was stirred at 0° C. under nitrogen atmosphere for 3 hours. In addition, methanesulfonylchloride (0.423 mL), and triethylamine (2.05 mL) were added thereto, the mixture was stirred at 0° C. for 1 hour. After sat. sodium bicarbonate aq. was added to the reaction mixture, the mixture was extracted with ethyl acetate, and dried over $MgSO_4$. The $MgSO_4$ was filtered, then filtrate was evaporated in vacuo to obtain crude Compound 140B (1.45 g).

Third Step

Compound 140B (1.45 g) was dissolved in DMF (7 mL), sodium azide (533 mg) was added thereto at the room temperature, then the mixture was stirred at 60° C. for 6 hours. After water (20 mL) was added thereto, the mixture was extracted with ethyl acetate. The combined oil layer was washed with sat. NaCl aq., and dried over MgSO$_4$. The MgSO$_4$ was filtered and evaporated in vacuo. The residue was purified by silica gel chromatography to obtain crude Compound 140C (488 mg).

MS: 236.90 m/z [M+H]$^+$.

Fourth Step

Compound 140C (488 mg) was dissolved in THF (5 mL), water (0.341 mL) and triphenylphosphine (496 mg) were added thereto, and the mixture was stirred at room temperature for 30 minutes, then stirred at 50° C. for 2 hours. The reaction mixture was evaporated and the residue was purified by amino silica gel chromatography to obtain crude Compound 140D (200 mg).

MS: 211.06 m/z [M+H]$^+$.

Fifth Step

Compound 140 was obtained using Compound 140D according to Example 60.

MS: 349.05 m/z [M+H]$^+$.

EXAMPLE 141

[Formula 87]

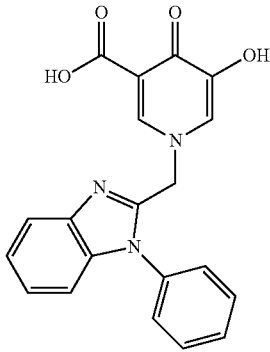

141

Compound 141 was obtained using (1-phenyl-1H-benzo[d]imidazol-2-yl)methanamine (International Publication No. 2006/062224 pamphlet) according to Example 60.

MS: 362.25 m/z [M+H]$^+$.

EXAMPLE 142

[Formula 88]

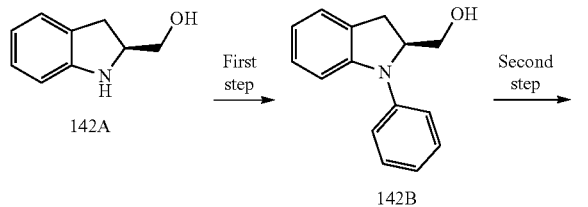

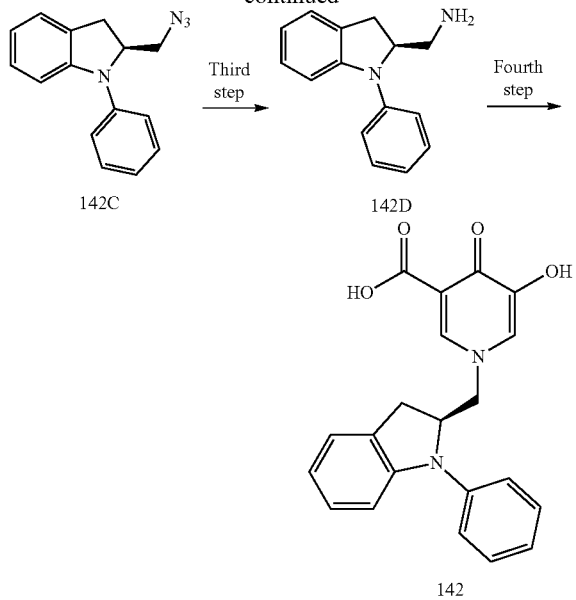

First Step

Compound 142A (500 mg), 1-chloro-2-iodobenzene (820 mg), copper iodide (32 mg) and sodium hydroxide (268 mg) were dissolved in 2-propanol (3 mL), then the mixture was stirred under nitrogen atmosphere at 90° C. for 5 hours. Dichloromethane (10 mL) and water (10 mL) were added thereto, then the mixture was extracted, in addition water layer was extracted with dichloromethane (10 mL). The oil layer was combined and washed with 0.1M NaCl (20 mL) and sat. NaCl aq., and dried over MgSO$_4$. MgSO$_4$ was filtered, and filtrate was evaporated in vacuo, then the mixture was purified by silica gel chromatography to obtain Compound 142B (385 mg).

MS: 225.90 m/z [M+H]$^+$.

Second Step

Compound 142B (385 mg) was dissolved in DMF (6 mL), the mixture was stirred at 0° C., then under nitrogen atmosphere, DBU (0.309 mL), and DPPA (564 mg) were added thereto, the mixture was stirred at room temperature for 1 hour and 30 minutes. After the reaction mixture was stirred at 50° C. for 3 hours, additionally stirred at 80° C. for 5 hours, then sodium azide (222 mg) was added thereto, the mixture was stirred at 60° C. for 12 hours. Water (20 mL) was added thereto, then the mixture was extracted with ethyl acetate, and dried over MgSO$_4$. MgSO$_4$ was filtered and filtrate was evaporated in vacuo, then silica gel chromatography was conducted to obtain Compound 142C (164 mg).

MS: 251.00 m/z [M+H]$^+$.

Third Step

Compound 142C (160 mg) was dissolved in THF (2 mL), Pd—C (10% dry) (20 mg) was added thereto and the mixture was stirred at room temperature under hydrogen atmosphere for 4 hours. Pd—C was filtered and solvent was evaporated in vacuo to obtain residue of Compound 142D (144 mg).

MS: 225.20 m/z [M+H]$^+$.

Fourth Step

Compound 142 was obtained using Compound 142D according to Example 60.

MS: 363.00 m/z [M+H]$^+$.

EXAMPLE 143

[Formula 89]

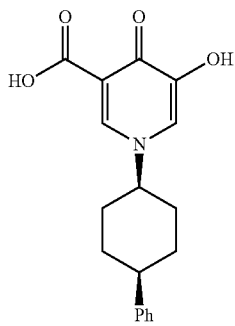

143

Compound 143 was obtained using cis-4-phenylcyclohexanamine (Bioorganic & Medicinal Chemistry Letters, 18(3), 1146-1150, 2008) according to Example 60.

MS: 314.20 m/z [M+H]$^+$.

EXAMPLE 144

[Formula 90]

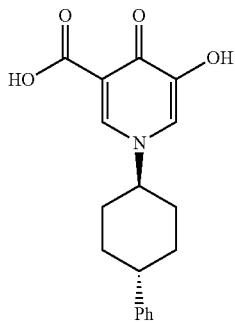

144

Compound 144 was obtained using trans-4-phenylcyclohexanamine (Bioorganic & Medicinal Chemistry Letters, 18(3), 1146-1150, 2008) according to Example 60.

MS: 313.95 m/z [M+H]$^+$.

EXAMPLE 145

[Formula 91]

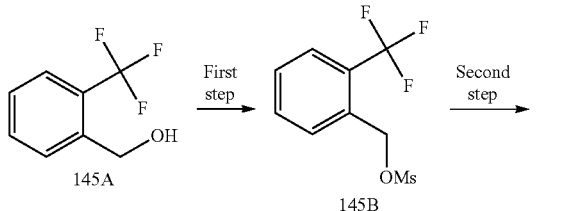

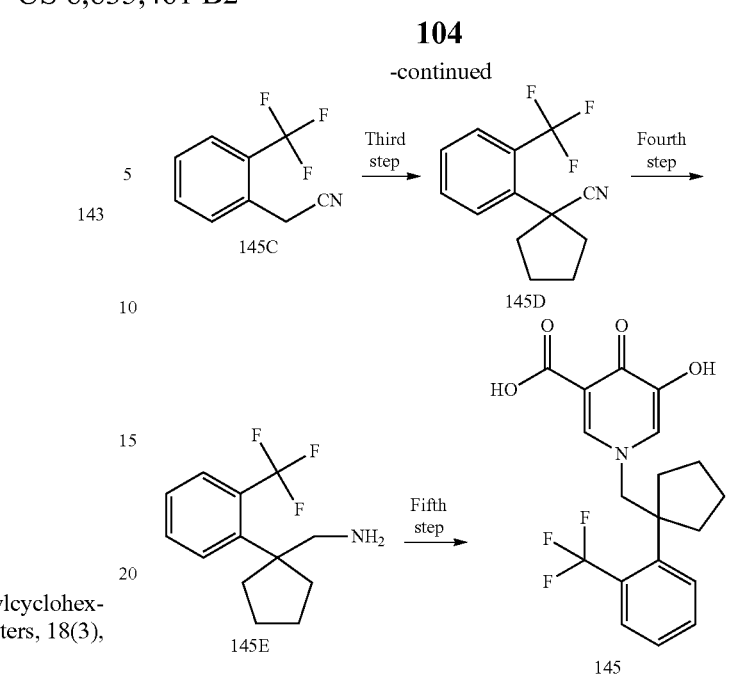

First Step

Compound 145A (2.64 g, 15 mmol) was dissolved in dichloromethane (80 mL), then trimethylamine (3.033 g, 30 mmol) and MsCl (2.222 g, 19.5 mmol) were added thereto at 0° C. The mixture was stirred at room temperature for 1 hour, then water (20 mL) was added thereto. The mixture was extracted with dichloromethane (50 mL×3), then organic layer was washed with sat. NaCl aq., and dried over Na$_2$SO$_4$. After evaporation in vauo, Compound 145B (3.97 g) was obtained.

MS: m/z=277 [M+Na]$^+$.

$^1$HNMR (CDCl$_3$) δ: 3.03 (3H, s), 5.41 (2H, s), 7.51-7.73 (4H, m).

Second Step

Compound 145B (3.68 g, 14 mmol) was dissolved in DMSO (15 mL), then NaCN (1.029 g, 21 mmol) was added thereto. The mixture was stirred at room temperature for 1 hour, then water (20 mL) was added thereto. The mixture was extracted with dichloromethane (50 mL×3), the organic layer was washed with sat. NaCl aq., and dried over Na$_2$SO$_4$. After evaporation in vauo, Compound 145C (3.89 g) was obtained.

MS: m/z=208 [M+Na]$^+$.

$^1$HNMR (CDCl$_3$) δ: 3.96 (2H, s), 7.46-7.70 (4H, m).

Third Step

To a suspension of NaH (1.003 g, 25.08 mmol) in DMSO (7 mL), a solution of Compound 145C (2.109 g, 11.4 mmol) and 1,4-dibromobutane (2.44 g, 11.4 mmol) in DMSO-Et$_2$O (1:1, 14 mL) was added dropwise at 0° C. The mixture was stirred at room temperature for 1 hour, then water and 10% HCl aq. were added thereto. The mixture was extracted with ethyl acetate (50 mL×3), organic layer was washed with sat. NaCl aq., and dried over Na$_2$SO$_4$. After evaporation in vauo, residue was purified by silica gel column chromatography (ethyl acetate-petroleum ether=1:9) to obtain Compound 145D (1.3 g, 48%).

MS: m/z=262 [M+Na]$^+$.

Fourth Step

Compound 145D (717 mg, 3 mmol) was dissolved in MeOH—NH$_3$ (20 mL), then Raney nickel was added thereto. The mixture was stirred under hydrogen atmosphere at room temperature. After filtration, the filtrate was evaporated in vacuo to obtain Compound 145E (630 mg).

MS: m/z=244 [M+H]⁺.

Fifth Step

Compound 145 was obtained as a solid using Compound 145E according to Example 60.

MS: m/z=382 [M+H]⁺.

$^1$HNMR (DMSO-$d_6$) δ: 1.75 (2H, m), 1.90 (4H, m), 2.25 (2H, m), 4.31 (2H, s), 7.02 (1H, s), 7.21 (1H, s), 7.49 (2H, m), 7.59 (1H, s), 7.84 (1H, s), 9.92 (1H, s), 15.91 (1H, s).

Compound 146~184 were synthesized using commercially available or known raw material according to Example 145.

EXAMPLE 146

[Formula 92]

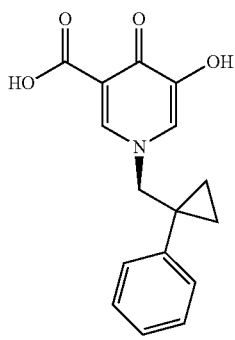

146

MS: m/z=286 [M+H]⁺.

$^1$HNMR (DMSO-$d_6$) δ: 0.92 (2H, t, J=5.2 Hz), 1.15 (2H, t, J=5.2 Hz), 4.34 (2H, s), 7.57 (1H, d, J=2.0 Hz), 7.15-7.27 (5H, m), 8.04 (1H, d, J=2.0 Hz), 9.90 (1H, s), 15.87 (1H, s).

EXAMPLE 147

[Formula 93]

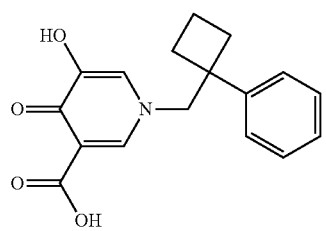

147

MS: m/z=300 [M+H]⁺.

$^1$HNMR (DMSO-$d_6$) δ: 1.77-1.80 (1H, m), 2.11-2.14 (1H, m), 2.31-2.34 (4H, m), 4.48 (2H, s), 6.99-7.01 (2H, m), 7.19-7.31 (4H, m), 7.84 (1H, d, J=2.0 Hz), 9.86 (1H, s), 15.93 (1H, s).

EXAMPLE 148

[Formula 94]

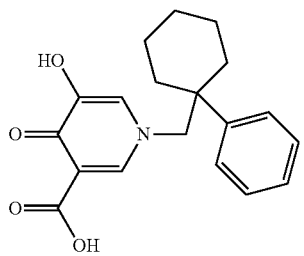

148

MS: m/z=328 [M+H]⁺.

$^1$HNMR (DMSO-$d_6$) δ: 1.15-1.26 (3H, m), 1.48-1.59 (5H, m), 2.20-2.23 (2H, m), 4.19 (2H, s), 7.08 (1H, d, J=2.0 Hz), 7.22-7.36 (5H, m), 7.69 (1H, d, J=2.0 Hz), 9.84 (1H, s), 15.93 (1H, s).

EXAMPLE 149

[Formula 95]

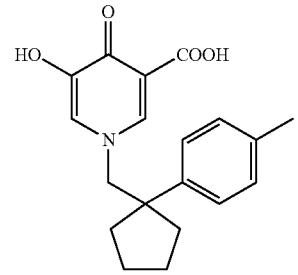

149

MS: m/z=328 [M+H]⁺.

$^1$H-NMR (DMSO): 1.56 (2H, s), 1.88-1.92 (6H, m), 2.26 (3H, s), 4.30 (2H, s), 7.09 (5H, m), 7.73 (1H, d, J=2.0 Hz), 9.99 (1H, s), 15.99 (1H, s).

EXAMPLE 150

[Formula 96]

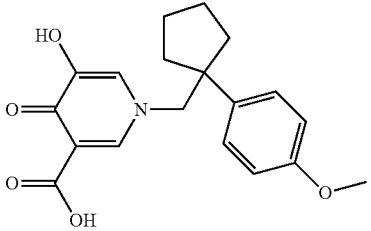

150

MS: m/z=344 [M+H]⁺.

$^1$HNMR (DMSO-$d_6$) δ: 1.56 (2H, m), 1.79-1.89 (6H, m), 3.72 (3H, s), 4.28 (2H, s), 6.84 (2H, d, J=8.8 Hz), 7.10 (2H, d, J=8.8 Hz), 7.10 (1H, s), 7.73 (1H, d, J=1.2 Hz), 9.86 (1H, s), 15.95 (1H, s).

EXAMPLE 151

[Formula 97]

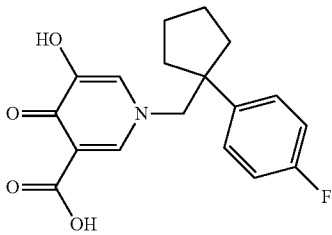

151

MS: m/z=332 [M+H]+.
$^1$HNMR (DMSO-$d_6$) δ: 1.58-1.59 (2H, m), 1.81 (2H, m), 1.91-1.92 (4H, m), 4.31 (2H, s), 7.10-7.25 (5H, m), 7.70 (1H, d, J=2.0 Hz), 9.89 (1H, s), 15.92 (1H, s).

EXAMPLE 152

[Formula 98]

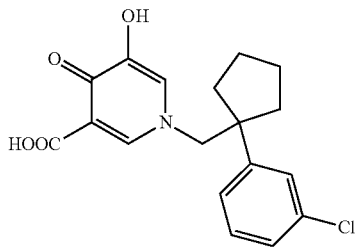

152

MS: m/z=348 [M+H]+.
$^1$HNMR (DMSO-$d_6$) δ: 1.58-1.59 (2H, m), 1.80 (2H, m), 1.92-1.93 (4H, m), 4.34 (2H, s), 7.16 (2H, d, J=2.0 Hz), 7.31-7.34 (3H, m), 7.75 (1H, d, J=2.0 Hz), 9.93 (1H, s), 15.92 (1H, s).

EXAMPLE 153

[Formula 99]

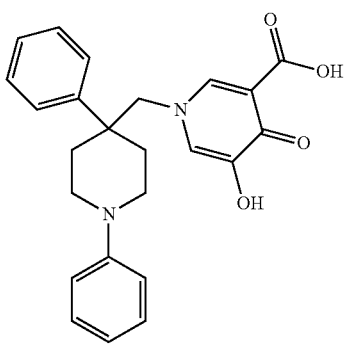

153

MS: m/z=405 [M+H]+.
$^1$HNMR (DMSO-$d_6$) δ: 1.96-1.98 (2H, m), 2.33-2.36 (2H, m), 2.67-2.69 (2H, m), 3.54-3.56 (2H, m), 4.26 (2H, s), 6.71 (1H, s), 6.89 (3H, m), 7.16 (2H, m), 7.25 (1H, s), 7.32-7.33 (2H, m), 7.71 (1H, s).

EXAMPLE 154

[Formula 100]

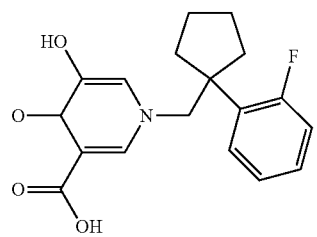

154

MS: m/z=332 [M+H]+.
$^1$HNMR (DMSO-$d_6$) δ: 1.66 (2H, m), 1.85-1.93 (4H, m), 2.02 (2H, m), 4.33 (2H, s), 7.09-7.21 (5H, m), 7.73 (1H, d, J=1.2 Hz), 9.90 (1H, s), 15.88 (1H, s).

EXAMPLE 155

[Formula 101]

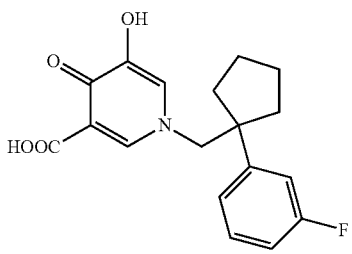

155

MS: m/z=332 [M+H]+.
$^1$HNMR (DMSO-$d_6$) δ: 1.57 (2H, m), 1.81 (2H, m), 1.93 (4H, m), 4.34 (2H, s), 7.01-7.15 (4H, m), 7.33 (1H, d, J=7.2 Hz), 7.73 (1H, s), 9.93 (1H, s), 15.92 (1H, s).

EXAMPLE 156

[Formula 102]

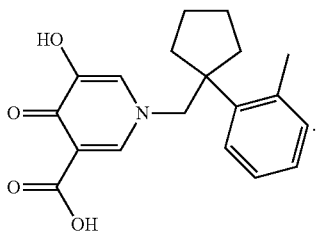

156

MS: m/z=328 [M+H]+.
$^1$HNMR (DMSO-$d_6$) δ: 1.71 (2H, m), 1.88 (4H, m), 2.11-2.13 (2H, m), 2.40 (3H, s), 4.31 (2H, s), 6.85 (1H, d, J=8.0

Hz), 6.97-7.01 (2H, m), 7.13-7.20 (2H, m), 7.59 (1H, d, J=2.0 Hz), 9.86 (1H, s), 15.94 (1H, s).

EXAMPLE 157

[Formula 103]

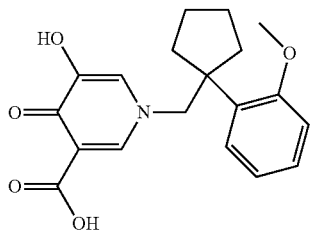

157

MS: m/z=344 [M+H]⁺.
¹HNMR (DMSO-d₆) δ: 1.61 (2H, m), 1.81 (2H, m), 1.92-1.97 (4H, m), 3.84 (3H, s), 4.38 (2H, s), 6.79 (1H, m), 6.88 (1H, m), 7.04-7.06 (2H, m), 7.25 (1H, m), 7.72 (1H, d, J=2.0 Hz), 9.84 (1H, s), 15.92 (1H, s).

EXAMPLE 158

[Formula 104]

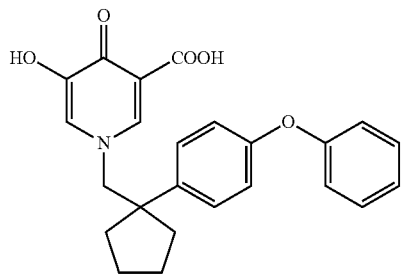

158

MS: m/z=406 [M+H]⁺.
¹HNMR (DMSO-d₆) δ: 1.61-1.63 (2H, m), 1.83 (2H, t, J=2.8 Hz), 1.93-1.94 (4H, m), 4.32 (2H, s), 6.93-6.9 7 (4H, m), 7.10 (1H, t, J=7.6 Hz), 7.20-7.24 (3H, m), 7.35-7.38 (2H, m), 7.64 (1H, d, J=2.0 Hz), 9.95 (1H, s), 15.95 (1H, s).

EXAMPLE 159

[Formula 105]

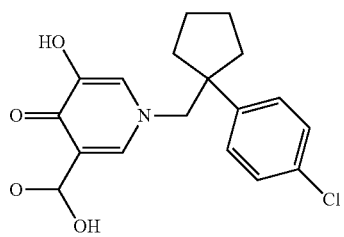

159

MS: m/z=348 [M+H]⁺.
¹HNMR (DMSO-d₆) δ: 1.57 (2H, m), 1.80 (2H, m), 1.90-1.91 (4H, m), 4.33 (2H, s), 7.12 (1H, d, J=1.6 Hz), 7.22 (2H, d, J=8.4 Hz), 7.34 (2H, d, J=8.4 Hz), 7.70 (1H, d, J=1.6 Hz), 9.90 (1H, s), 15.92 (1H, s).

EXAMPLE 160

[Formula 106]

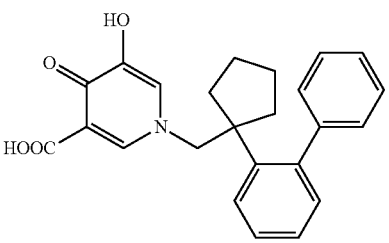

160

MS: m/z=390 [M+H]⁺.
¹HNMR (DMSO-d₆) δ: 1.52-1.58 (8H, s), 4.19 (2H, s), 7.03 (3H, m), 7.22-7.37 (7H, s), 7.75 (1H, s), 9.89 (1H, s), 16.01 (1H, s).

EXAMPLE 161

[Formula 107]

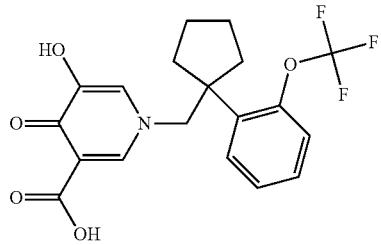

161

MS: m/z=398 [M+H]⁺.
¹HNMR (DMSO-d₆) δ: 1.72 (2H, m), 1.87-1.90 (4H, m), 2.10-2.12 (2H, m), 4.29 (2H, s), 7.03 (1H, d, J=1.8 Hz), 7.26 (4H, m), 7.65 (1H, d, J=1.8 Hz), 9.90 (1H, s), 15.88 (1H, s).

EXAMPLE 162

[Formula 108]

162

MS: m/z=348 [M+H]⁺.
¹HNMR (DMSO-d₆) δ: 1.65-1.68 (2H, m), 1.87-2.00 (4H, m), 2.13-2.16 (2H, m), 4.48 (2H, s), 7.05 (1H, s), 7.11 (1H, d, J=7.6 Hz), 7.20 (1H, t, J=7.6 Hz), 7.30 (1H, t, J=7.6 Hz), 7.51 (1H, d, J=7.6 Hz), 7.67 (1H, s), 9.93 (1H, s), 15.88 (1H, s).

EXAMPLE 163

[Formula 109]

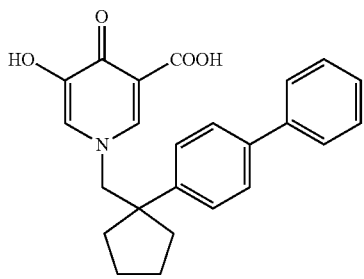

MS: m/z=390 [M+H]⁺.
¹HNMR (DMSO-d$_6$) δ: 1.55-1.61 (2H, m), 1.81 (2H, t, J=8.4 Hz), 1.86-1.95 (4H, m), 4.22 (2H, s), 6.65 (1H, s), 7.29-7.37 (3H, m), 7.41-7.47 (2H, m), 7.55-7.60 (4H, m), 7.65 (1H, d, J=9.2 Hz).

EXAMPLE 164

[Formula 110]

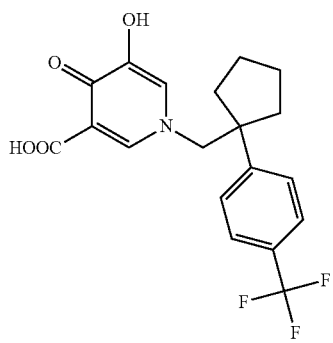

MS: m/z=382 [M+H]⁺.
¹HNMR (DMSO-d$_6$) δ: 1.59-1.60 (2H, m), 1.81-1.84 (2H, m), 1.92-1.98 (4H, m), 4.38 (2H, s), 7.16 (1H, d, J=1.4 Hz), 7.45 (2H, d, J=8.0 Hz), 7.65 (2H, d, J=8.0 Hz), 7.72 (1H, d, J=1.4 Hz), 9.91 (1H, s), 15.86 (1H, s).

EXAMPLE 165

[Formula 111]

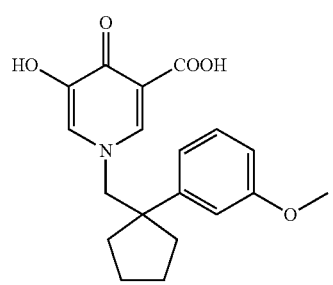

MS: m/z=344 [M+H]⁺.
¹HNMR (DMSO-d$_6$) δ: 1.58-1.60 (2H, s), 1.80-1.92 (6H, m), 3.71 (3H, s), 4.31 (2H, s), 6.73-6.75 (2H, m), 6.80-6.82 (1H, m), 7.13 (1H, d, J=2.0 Hz), 7.20 (1H, t, J=8.4 Hz), 7.74 (1H, d, J=2.0 Hz), 9.95 (1H, s), 15.94 (1H, s).

EXAMPLE 166

[Formula 112]

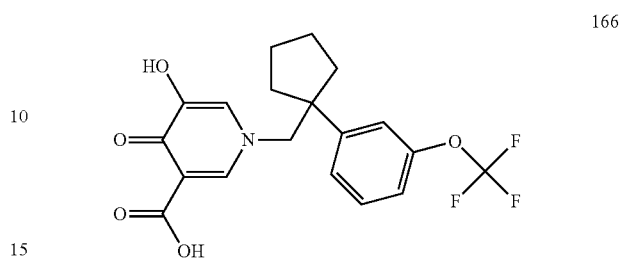

MS: m/z=398 [M+H]⁺.
¹HNMR (DMSO-d$_6$) δ: 1.58 (2H, m), 1.82 (2H, m), 1.95 (2H, m), 4.35 (2H, s), 7.12 (1H, s), 7.18-7.47 (5H, m), 7.68 (1H, d, J=1.2 Hz), 9.90 (1H, s), 15.86 (1H, s).

EXAMPLE 167

[Formula 113]

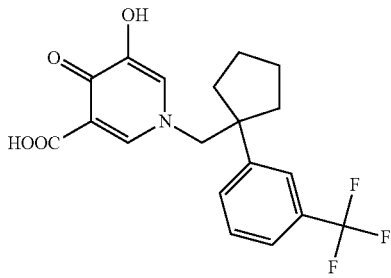

MS: m/z=382 [M+H]⁺.
¹HNMR (DMSO-d$_6$) δ: 1.59 (2H, m), 1.82 (2H, m), 1.98 (4H, m), 4.35 (2H, s), 7.19 (1H, s), 7.42 (1H, s), 7.55-7.65 (4H, m), 9.93 (1H, s), 15.88 (1H, s).

EXAMPLE 168

[Formula 114]

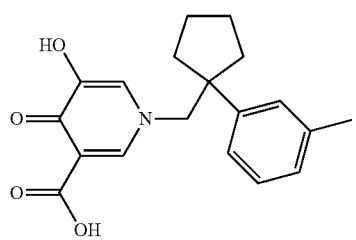

MS: m/z=328 [M+H]⁺.
¹HNMR (DMSO-d$_6$) δ: 1.58 (2H, m), 1.79 (2H, m), 1.91-1.93 (4H, m), 2.25 (3H, s), 4.29 (2H, s), 7.11 (1H, d, J=7.6 Hz), 7.01-7.19 (4H, m), 7.70 (1H, d, J=2.0 Hz), 9.88 (1H, s), 15.93 (1H, s).

EXAMPLE 169

[Formula 115]

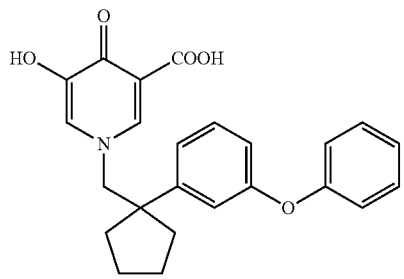

MS: m/z=406 [M+H]$^+$.

$^1$HNMR (DMSO-d$_6$) δ: 1.53-1.63 (2H, m), 1.75-1.76 (2H, m), 1.82-1.90 (4H, m), 4.34 (2H, s), 6.78 (1H, s), 6.85-6.88 (3H, m), 7.09 (2H, t, J=7.2 Hz), 7.21 (1H, d, J=2.0 Hz), 7.32-7.37 (3H, m), 7.69 (1H, d, J=2.0 Hz), 9.99 (1H, s), 15.99 (1H, s).

EXAMPLE 170

[Formula 116]

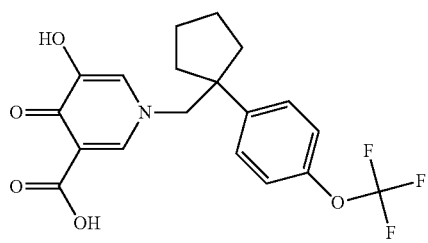

MS: m/z=398 [M+H]$^+$.

$^1$HNMR (DMSO-d$_6$) δ: 1.58-1.60 (2H, m), 1.76-1.81 (2H, m), 1.93-1.94 (4H, m), 4.37 (2H, s), 7.16 (1H, d, J=2.0 Hz), 7.27 (2H, d, J=8.8 Hz), 7.34 (2H, d, J=8.8 Hz), 7.70 (1H, d, J=2.0 Hz), 9.90 (1H, s), 15.87 (1H, s).

EXAMPLE 171

[Formula 117]

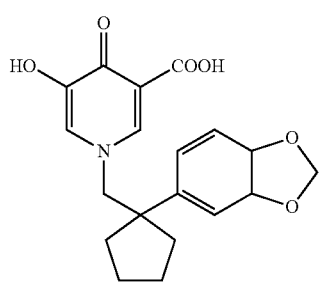

MS: m/z=358 [M+H]$^+$.

$^1$HNMR (DMSO-d$_6$) δ: 1.58 (2H, m), 1.78-1.86 (6H, m), 4.27 (2H, s), 5.97 (2H, s), 6.56-6.58 (1H, m), 6.79-6.88 (2H, m), 7.15 (1H, d, J=1.6 Hz), 7.73 (1H, d, J=1.6 Hz), 9.99 (1H, s), 15.97 (1H, s).

EXAMPLE 172

[Formula 118]

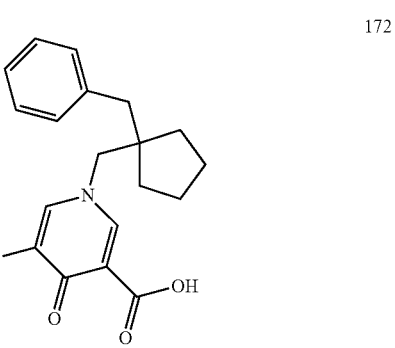

MS: m/z=343 [M+H]$^+$.

$^1$HNMR (DMSO-d$_6$) δ: 1.38-1.51 (8H, m), 2.65 (2H, s), 4.16 (2H, s), 7.16-7.31 (5H, m), 7.73 (1H, d, J=2.0 Hz), 8.37 (1H, d, J=2.0 Hz), 9.92 (1H, s), 16.01 (1H, s).

EXAMPLE 173

[Formula 119]

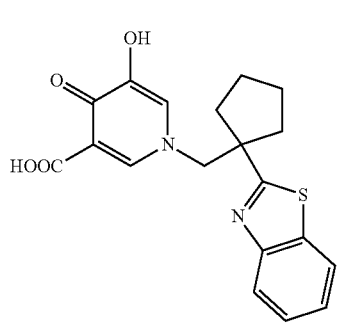

MS: m/z=371 [M+H]$^+$.

$^1$HNMR (DMSO-d$_6$) δ: 1.62-1.64 (2H, m), 1.82-1.86 (2H, m), 2.00-2.04 (2H, m), 2.25-2.28 (2H, m), 4.64 (2H, s), 7.37 (1H, d, J=1.6 Hz), 7.44 (1H, d, J=7.6 Hz), 7.49 (1H, t, J=7.6 Hz), 7.96 (1H, d, J=8.0 Hz), 8.10 (2H, m), 9.94 (1H, s), 15.83 (1H, s).

EXAMPLE 174

[Formula 120]

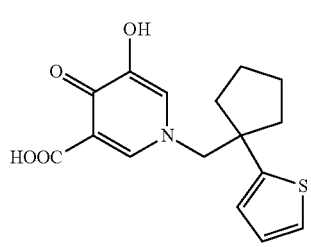

MS: m/z=320 [M+H]+.
¹HNMR (DMSO-d₆) δ: 1.56-1.59 (2H, m), 1.76-1.78 (2H, m), 1.87-1.91 (2H, m), 1.99-2.01 (2H, m), 4.29 (2H, s), 6.84 (1H, d, J=2.8 Hz), 6.93-6.95 (1H, m), 7.09 (1H, s), 7.39 (1H, d, J=4.0 Hz), 7.77 (1H, s), 9.99 (1H, s), 15.93 (1H, s).

EXAMPLE 175

[Formula 121]

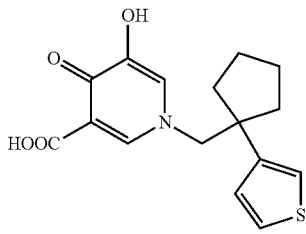

175

MS: m/z=320 [M+H]+.
¹HNMR (DMSO-d₆) δ: 1.52-1.54 (2H, m), 1.74-1.82 (4H, m), 1.93-1.95 (2H, m), 4.29 (2H, s), 7.10-7.13 (3H, m), 7.53-7.55 (1H, m), 7.73 (1H, s), 10.12 (1H, s), 16.16 (1H, s).

EXAMPLE 176

[Formula 122]

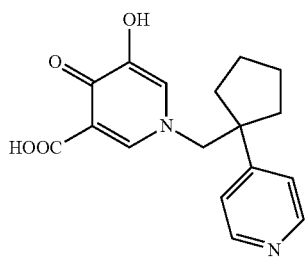

176

MS: m/z=315 [M+H]+.
¹HNMR (DMSO-d₆) δ: 1.53 (2H, s), 1.89-1.92 (6H, m), 4.40 (2H, s), 7.22 (d, 3H), 7.83 (s, 1H), 8.49 (s, 2H), 9.95 (s, 1H), 15.90 (s, 1H).

EXAMPLE 177

[Formula 123]

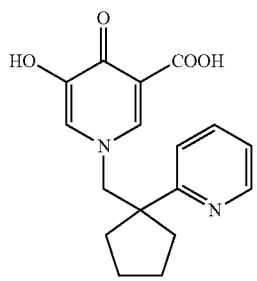

177

MS: m/z=315 [M+H]+.
¹HNMR (DMSO-d₆) δ: 1.49-1.53 (2H, m), 1.77-1.86 (4H, m), 2.15-2.19 (2H, m), 4.46 (2H, s), 7.11 (1H, d, J=2.0 Hz), 7.24-7.27 (1H, m), 7.33 (1H, d, J=7.6 Hz), 7.70-7.74 (2H, m), 8.55-8.56 (1H, m), 9.88 (1H, s), 15.91 (1H, s).

EXAMPLE 178

[Formula 124]

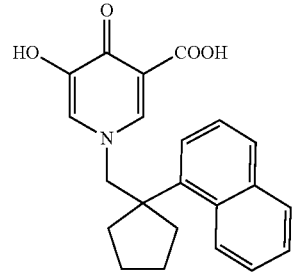

178

MS: m/z=364 [M+H]+.
¹HNMR (DMSO-d₆) δ: 1.69 (2H, s), 1.91-1.92 (2H, m), 2.11-2.14 (2H, m), 2.29 (2H, s), 4.64 (2H, s), 6.79 (1H, d, J=1.8 Hz), 7.16 (1H, d, J=7. Hz), 7.32 (1H, t, J=7.6 Hz), 7.49 (1H, d, J=1.8 Hz), 7.55-7.62 (2H, m), 7.85 (1H, d, J=8.4 Hz), 8.02 (1H, d, J=7.6 Hz), 8.30 (1H, d, J=8.4 Hz), 9.88 (1H, s), 15.91 (1H, s).

EXAMPLE 179

[Formula 125]

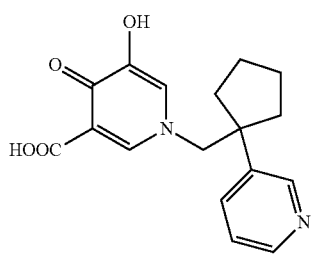

179

MS: m/z=315 [M+H]+.
¹HNMR (DMSO-d₆) δ: 1.57 (2H, s), 1.82 (2H, s), 1.98-2.03 (4H, m), 4.38 (2H, s), 7.18 (1H, s), 7.32 (1H, s), 7.63 (1H, d, J=2.0 Hz), 7.77 (1H, s,), 8.44 (2H, s), 9.95 (1H, s), 15.95 (1H, s).

EXAMPLE 180

[Formula 126]

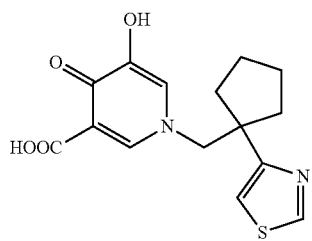

180

MS: m/z=321 [M+H]$^+$.

$^1$HNMR (DMSO-d$_6$) δ: 1.53 (2H, s), 1.76-1.85 (4H, m), 2.10-2.12 (2H, m), 4.43 (2H, s), 7.14 (1H, s), 7.40 (1H, s), 7.71 (1H, s), 9.14 (1H, s), 9.84 (1H, s), 15.91 (1H, s).

EXAMPLE 181

[Formula 127]

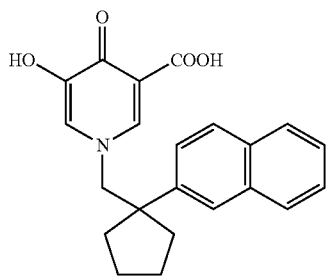

MS: m/z=364 [M+H]$^+$.

$^1$HNMR (DMSO-d$_6$) δ: 1.61 (2H, s), 1.83 (2H, s), 2.02-2.07 (4H, m), 4.31 (2H, s), 6.56 (1H, d, J=2.0 Hz), 7.46-7.51 (4H, m), 7.66 (1H, s), 7.82-7.88 (3H, m), 9.89 (1H, s), 15.91 (1H, s).

EXAMPLE 182

[Formula 128]

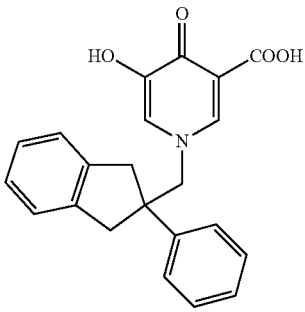

MS: m/z=362 [M+H]$^+$.

$^1$HNMR (DMSO-d$_6$) δ: 3.04-3.63 (4H, m), 4.32 (2H, s), 7.06-7.11 (2H, m), 7.14-7.19 (3H, m), 7.20 (1H, d, J=2.0 Hz), 7.23-7.80 (4H, m), 7.81 (1H, d, J=2.0 Hz), 9.89 (1H, s), 15.97 (1H, s).

EXAMPLE 183

[Formula 129]

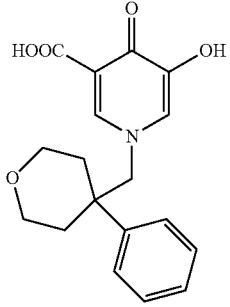

MS: m/z=330 [M+H]$^+$.

$^1$HNMR (DMSO-d$_6$) δ: 1.84-1.91 (2H, m), 2.15-2.18 (2H, m), 3.25-3.32 (2H, m), 3.70-3.74 (2H, m), 4.23 (2H, s), 7.02 (1H, s), 7.19-7.29 (3H, m), 7.35-7.37 (2H, m), 7.66 (1H, s), 9.88 (1H, s), 15.96 (1H, s).

EXAMPLE 184

[Formula 130]

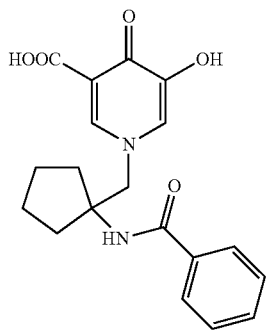

MS: m/z=356 [M+H]$^+$.

$^1$HNMR (DMSO-d$_6$) δ: 1.71 (6H, m), 2.09-2.11 (2H, m), 4.58 (2H, s), 7.42-7.56 (4H, m), 7.67 (1H, d, J=2.0 Hz), 7.93 (1H, s), 8.20 (1H, d, J=2.0 Hz), 9.99 (1H, s), 16.00 (1H, s).

EXAMPLE 185

[Formula 131]

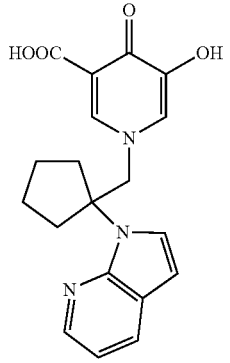

MS: m/z=354 [M+H]⁺.

¹HNMR (DMSO-d$_6$) δ: 1.60-1.61 (2H, m), 1.81-1.86 (2H, m), 2.22-2.28 (2H, m,), 2.57-2.60 (2H, m), 4.81 (2H, s), 6.42 (1H, d, J=3.8 Hz), 6.74 (1H, d, J=2.2 Hz), 7.13-7.16 (1H, m), 7.36 (1H, d, J=3.8 Hz), 7.42 (1H, d, J=2.2 Hz), 8.00 (1H, dd, J=1.4 Hz, J=7.6 Hz), 8.26 (1H, dd, J=1.4, 4.4 Hz), 9.84 (1H, s), 15.82 (1H, s).

EXAMPLE 186

[Formula 132]

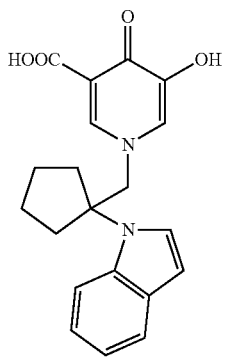

186

MS: m/z=353 [M+H]⁺.

¹HNMR (DMSO-d$_6$) δ: 1.70-1.77 (2H, m), 1.88-1.90 (2H, m), 2.30-2.33 (4H, m), 4.63 (2H, s), 6.38 (1H, d, J=3.2 Hz), 6.50 (1H, d, J=1.6 Hz), 7.08-7.19 (2H, m), 7.52 (1H, d, J=1.6 Hz), 7.59-7.67 (2H, m), 9.83 (1H, s), 15.81 (1H, s).

EXAMPLE 187

[Formula 133]

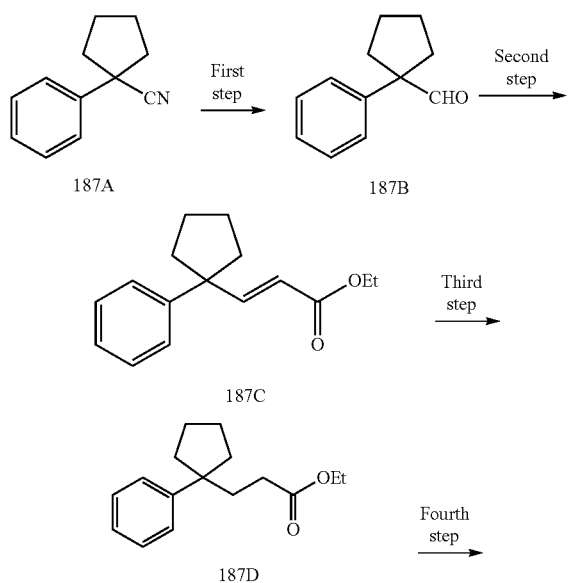

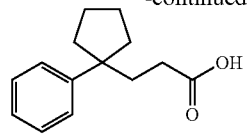 Fifth step →

187E

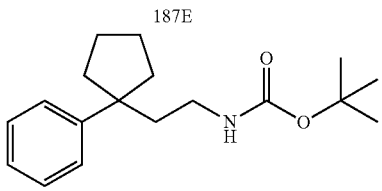 Sixth step →

187F

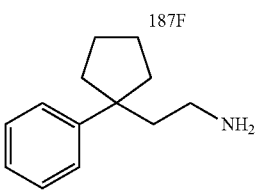 Seventh step →

187G

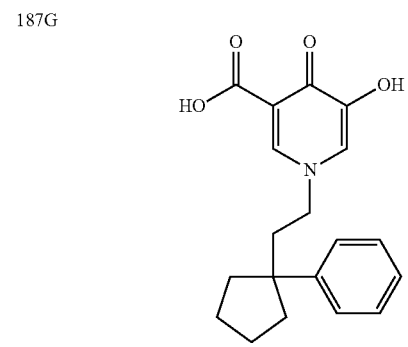

187

First Step

Compound 187A (6.2 g, 36.2 mmol) was dissolved in n-heptane, then the mixture was cooled to −60° C. A solution of DIBAL-H (1M, 45.3 mL, 45.3 mmol) was added dropwise thereto and the mixture was stirred at −60° C. for 30 minutes. 4N NaOH aq. was added slowly thereto, then the mixture was stirred for 1 hour. The organic layer was separated, and dried over Na$_2$SO$_4$, the solvent was evaporated in vacuo to obtain Compound 187B (4.37 g, 69%) as a oil.

MS: m/z=175 [M+H]⁺.

Second Step

Triethylphosphonoacetate (450 mg, 2 mmol) was added to a solution of NaH (80 mg, 2 mmol, 60%) in THF, and the mixture was stirred at room temperature for 10 minutes. A solution of Compound 187B (177 mg, 1 mmol) in THF was stirred at room temperature for 16 hour. Then ice water was added thereto, and the mixture was extracted with ethyl acetate (50 mL×2). The organic layer was washed with sat. NaCl aq., then dried over Na$_2$SO$_4$. The solvent was evaporated in vacuo, the residue was purified by silica gel column chromatography (ethyl acetate:petroleum ether=1:9) to obtain Compound 187C (167 mg, 68%) as a oil.

MS: m/z=245 [M+H]⁺.

¹HNMR (DMSO-d$_6$) δ: 1.26 (3H, t, J=7.3 Hz), 1.68-1.81 (4H, m), 1.90-2.15 (4H, q, J=7.3 Hz), 4.14-4.18 (2H, m), 5.60 (1H, d, J=15.8 Hz), 7.06 (1H, d, J=15.8 Hz), 7.18-7.35 (5H, m).

Third Step

Compound 187C (590 mg, 2.42 mmol) was dissolved in methanol (50 mL), PtO$_2$ (60 mg) was added thereto. The mixture was stirred under hydrogen atmosphere at room temperature for 3 hours. After the catalyst was removed, filtrate was evaporated in vacuo to obtain Compound 187D (480 mg, 81%) as a oil.

MS: m/z=247 [M+H]$^+$.

Fourth Step

Compound 187D (480 mg, 1.95 mmol) was disslved in THF (15 mL) and methanol (15 mL), then aquerous LiOH (245 mg, 5.85 mmol) (15 mL) was added thereto at room temperature for 3 hours. 10% HCl aq. was added thereto, then the mixture was extracted with dichloromethane (50 mL×2). The organic layer was washed with sat. NaCl aq., and dried over Na$_2$SO$_4$. The solvent was evaporated to obtain Compound 187E as a yellow solid (400 mg, 94%).

MS: m/z=241 [M+Na]$^+$.

Fifth Step

Compound 187E was dissolved in toluene (20 mL), then triethylamine (334 mg, 3.30 mmol) and DPPA (910 mg, 3.30 mmol) were added thereto at room temperature for 4 hours. In addition, t-BuOH (10 mL) was added thereto and the mixture was refluxed for 16 hours. The mixture was evaporated in vacuo, the residue was purified by silica gel column chromatography (ethyl acetate:petroleum ether=1:24) to obtain Compound 187F as a solid (320 mg, 40%).

MS: m/z=290 [M+H]$^+$.

Sixth Step

Compound 187F (320 mg, 1.10 mmol) was dissolved in dichloromethane (25 mL), trifluoroacetic acid (1 mL) was added thereto, and the mixture was stirred at room temperature for 3 hours. Then Compound 187G was obtained after evaporation in vacuo.

MS: m/z=190 [M+H]$^+$.

Seventh Step

Compound 187 was obtained using Compound 187G according to Example 60.

MS: m/z=328 [M+H]$^+$.

$^1$HNMR (DMSO-d$_6$) δ: 1.61-1.63 (2H, m), 1.68-1.70 (2H, m), 1.76-1.79 (4H, m), 2.14 (2H, t, J=7.7 Hz), 3.80 (2H, t, J=7.7 Hz), 7.13-7.16 (1H, m), 7.25-7.30 (4H, m), 7.55 (1H, d, J=2.0 Hz), 8.19 (1H, d, J=2.0 Hz), 9.91 (1H, s), 16.05 (1H, s).

EXAMPLE 188~190

[Formula 134]

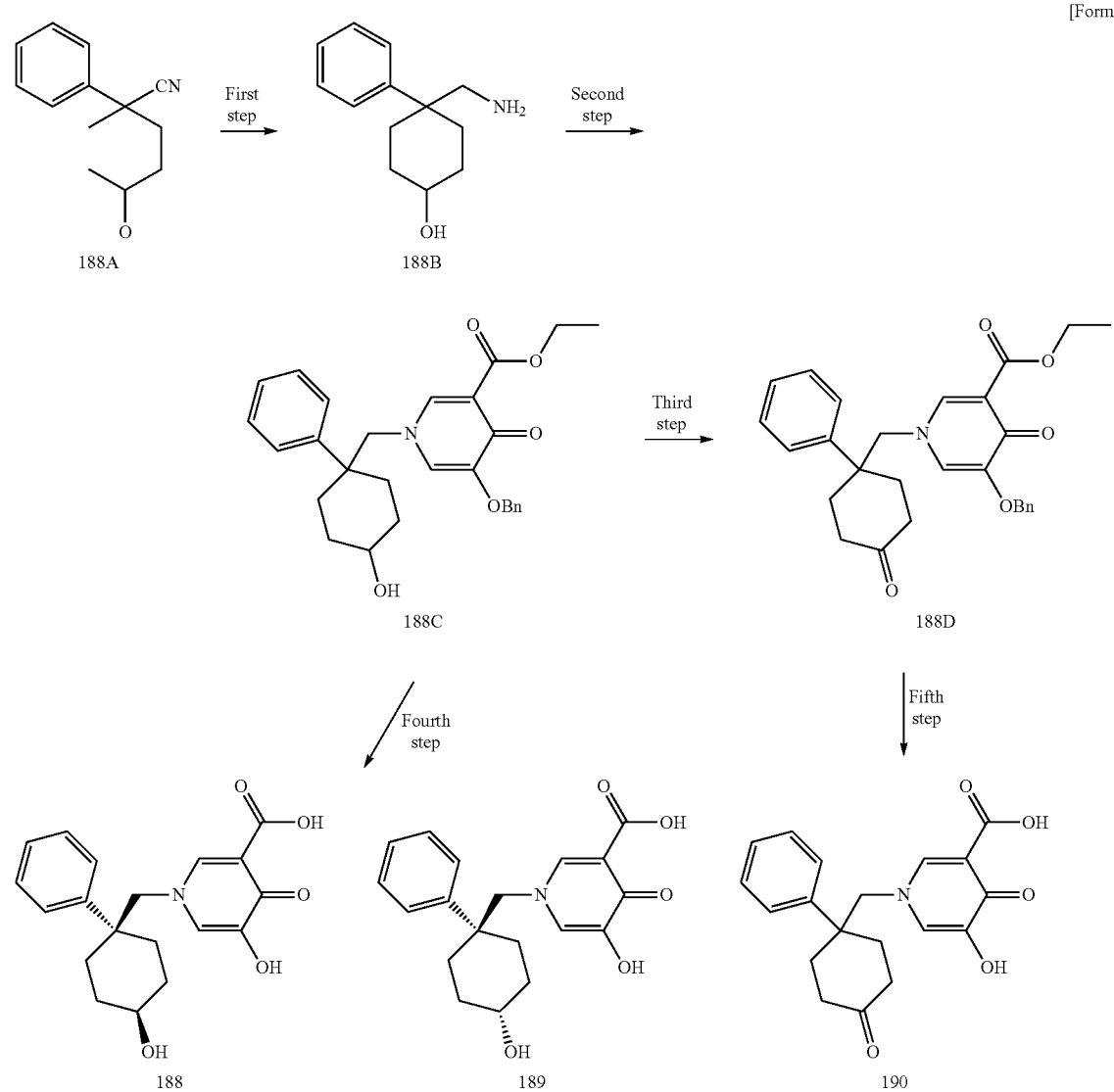

First Step

Compound 188B was obtained using Compound 188A according to Fourth step in Example 145.

MS: m/z=206 [M+H]+.

Second Step

Compound 188C was obtained using Compound 188B according to Second step in Example 60.

Third Step

Compound 188C (150 mg, 0.325 mmol) was dissolved in ethyl acetate (20 mL), and 2-iodoxybenzoic acid (132 mg, 0.470 mmol) was added thereto. The mixture was refluxed for 3 hours, then insoluble material was filtered. The filtrate was evaporated in vacuo to obtain Compound 188D (176 mg).

MS: m/z=460 [M+H]+.

Fourth Step

Compound 188 and Compound 189 were obtained using Compound 188B according to Example 1 and purification with HPLC.

EXAMPLE 188

MS: m/z=344 [M+H]+.

$^1$HNMR (DMSO-$d_6$) δ: 1.34-1.36 (2H, m), 1.57-1.60 (2H, m), 1.93-2.05 (4H, m), 3.64 (1H, s), 4.22 (2H, s), 4.51 (1H, d, J=2.0 Hz), 7.14 (1H, d, J=2.0 Hz), 7.31-7.40 (5H, m), 7.70 (1H, d, J=2.0 Hz), 9.86 (1H, s), 15.95 (1H, s).

EXAMPLE 189

MS: m/z=344 [M+H]+.

$^1$HNMR (DMSO-$d_6$) δ: 1.34-1.36 (2H, m), 1.57-1.60 (2H, m), 1.93-2.06 (4H, m), 3.64 (1H, s), 4.22 (2H, s), 4.50 (1H, d, J=2.0 Hz), 7.13 (1H, d, J=2.0 Hz), 7.31-7.41 (5H, m), 7.70 (1H, d, J=2.0 Hz), 9.86 (1H, s), 15.94 (1H, s).

Fifth Step

Compound 190 was obtained using Compound 188C according to Example 1.

MS: m/z=342 [M+H]+.

$^1$HNMR (DMSO-$d_6$) δ: 2.12-2.13 (6H, m), 2.22-2.24 (2H, m), 4.31 (2H, s), 7.12 (1H, d, J=2.0 Hz), 7.42-7.46 (5H, m), 7.74 (1H, d, J=2.0 Hz), 9.89 (1H, s), 15.90 (1H, s).

EXAMPLE 191

[Formula 135]

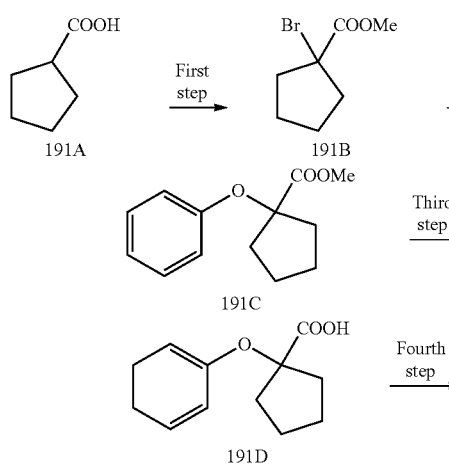

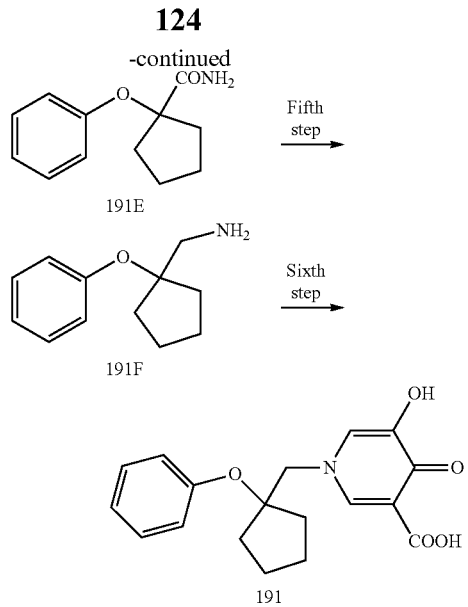

First Step

Compound 191A (1.14 g, 10 mmol) was dissolved in DCE (50 mL), then Br$_2$ (1.6 g, 10 mmol) and ClSO$_3$H (1.17 g, 10 mmol) were added thereto, then the mixture was refluxed for 2 hours. After evaporation in vacuo, methanol (50 mL) was added thereto and the mixture was refluxed over night. After evaporation in vacuo, the residue was purified by silica gel column chromatography (ethyl acetate:petroleum ether=1:19) to obtain Compound 191B (1.105 g, 53%) as a oil.

MS: m/z=207 [M+H]−.

$^1$HNMR (CDCl$_3$) δ: 1.76-1.81 (2H, m), 1.96-2.02 (2H, m), 2.29-2.32 (4H, m), 3.80 (3H, s).

Second Step

A solution including Compound 191B (1.105 mg, 5.34 mmol), phenol (477 mg, 5.07 mol), and cesium carbonate (3.83 g, 11.75 mmol) in acetonitrile (20 mL) was stirred at 70° C. for 4 hours. After evaporation in vacuo, the mixture was diluted with ethyl acetate (50 mL)-water (50 mL), then water layer was extracted with ethyl acetate (50 mL×3). The organic layer was washed with sat. NaCl aq., dried over Na$_2$SO$_4$, and evaporated in vacuo. The residue was purified by silica gel column chromatography (ethyl acetate:petroleum ether=1:19) to obtain Compound 191C (360 mg, 32%) as a oil.

MS: m/z=221 [M+H]+.

Third Step

Compound 191C (360 mg, 1.64 mmol) was dissolved in methanol (10 mL), then aqueous NaOH (131 mg, 3.27 mmol) (3 mL) was added thereto and the mixture was refluxed for 1 hour. After evaporation in vacuo, 10% HCl aq. was added to the residue to be pH 2, then precipitated solid was filtered to obtain Compound 191D (300 mg, 89%).

MS: m/z=207 [M+H]+.

$^1$HNMR (CDCl$_3$) δ: 1.71-1.73 (4H, m), 2.01-2.06 (2H, m), 2.18-2.23 (2H, m), 6.72 (2H, d, J=8.0 Hz), 6.91 (1H, t, J=7.6 Hz), 7.25 (2H, t, J=8.0 Hz), 12.98 (1H, s).

Fourth Step

Compound 191D (300 mg, 1.456 mmol) was dissolved in DMF (15 mL), DIEA (355 mg, 2.91 mmol), HOBt (393 mg, 2.91 mmol), WSC (559 mg, 2.91 mmol), and NH$_4$Cl (234 mg, 4.37 mmol) were added thereto, then the mixture was stirred overnight. The mixture was diluted with ethyl acetate (50 mL)-water (50 mL), water layer was extracted with ethyl acetate (50 mL×3). The organic layer was washed with sat.

NaCl aq., dried over Na$_2$SO$_4$, and evaporated in vacuo, to obtain Compound 191E (360 mg).

MS: m/z=206 [M+H]$^+$.

Fifth Step

Compound 191E (320 mg, 1.756 mmol) was dissolved in THF (10 mL), then LiAlH$_4$ (111 mg, 2.634 mmol) was added slowly at 0° C., and the mixture was refluxed for 30 minutes. Na$_2$SO$_4$.10H$_2$O was added thereto and the mixture was stirred at room temperature for 2 hours. After filtration, the filtrate was evaporated in vacuo to obtain Compound 191F.

MS: m/z=192 [M+H]$^+$.

Sixth Step

Compound 191 was obtained using Compound 191F according to Example 60.

MS: m/z=330 [M+H]$^+$.

$^1$HNMR (DMSO-d$_6$) δ: 1.58-1.82 (8H, m), 4.63 (2H, s), 7.01-7.10 (3H, m), 7.33 (2H, t, J=8.0 Hz), 87.69 (1H, s), 8.44 (1H, s), 10.09 (1H, s), 16.05 (1H, s).

EXAMPLE 192

[Formula 136]

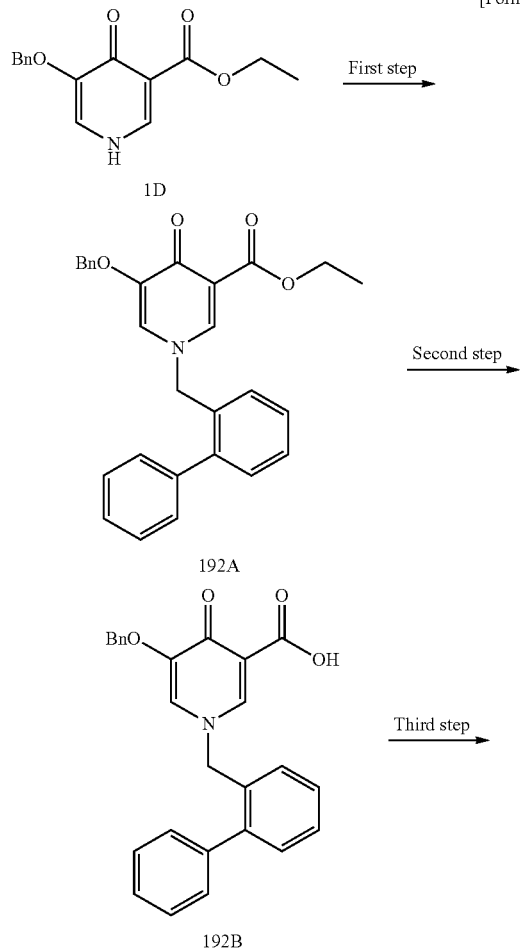

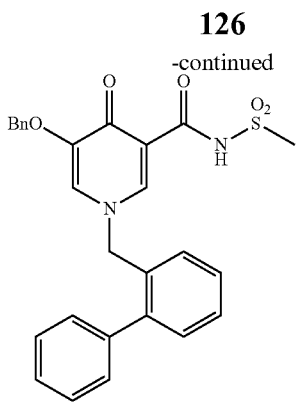

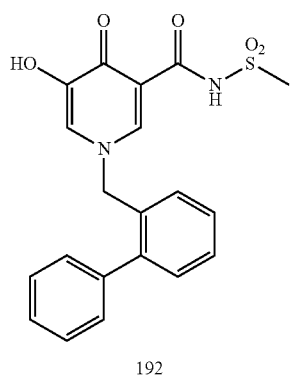

First Step

Compound 192A was synthesized according to Fourth step in Example 1.

MS: m/z=440 [M+H]$^+$.

Second Step

Compound 192B was synthesized using Compound 192A according to Fifth step in Example 1.

Third Step

To a solution of triethylamine (148 mg, 1.45 mmol) and isobutyl carbonochloridate (80.0 mg, 0.583 mmol) in dichloromethane (50 mL), Compound 192B (200 mg, 0.486 mmol) in dichloromethane (10 mL) solution was added dropwise, and the mixture was stirred under nitrogen atmosphere at 0 to 5° C. for 30 minutes. Methylsulfonamide (55.5 mg, 0.583 mmol) and dimethylaminopyridine (30.0 mg, 0.243 mmol) were added thereto and the mixture was stirred at room temperature for 18 hours. After evaporation, the residue was purified by silica gel column chromatography (methanol:dichloromethane=1:19) to obtain Compound 192C as a white solid (76.5 mg, 32%).

MS: m/z=489 [M+H]$^+$.

Fourth Step

Compound 192 was synthesized using Compound 192C according to Sixth step in Example 1.

MS: m/z=399 [M+H]$^+$.

$^1$HNMR (DMSO): 3.34 (3H, s), 5.33 (2H, s), 7.24-7.30 (5H, m), 7.41-7.45 (5H, m), 8.04 (1H, s), 9.64 (1H, s), 13.7 (1H, s).

Compound 193~215 were synthesized using commercially available or known raw material according to Example 192.

EXAMPLE 193
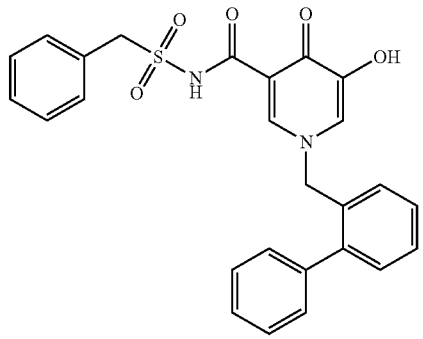
[Formula 137]
MS: m/z=475[M+H]+.
1HNMR (DMSO): 4.80 (2H, s), 5.37 (2H, s), 7.23-7.49 (15H, m), 8.06 (1H, s), 9.64 (1H, s), 13.60 (1H, s).
EXAMPLE 194
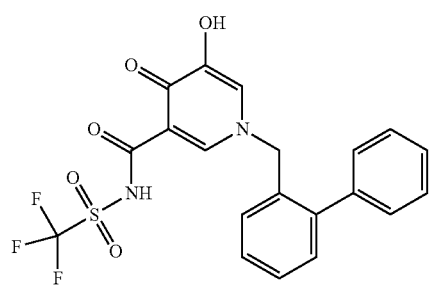
[Formula 138]
MS: m/z=453[M+H]+.
1HNMR (DMSO): 5.61 (2H, s), 7.25-7.47 (7H, m), 7.49-7.53 (2H, m), 7.74 (1H, d, J=2.0 Hz), 8.25 (1H, d, J=2.0 Hz), 11.16 (1H, s).
EXAMPLE 195
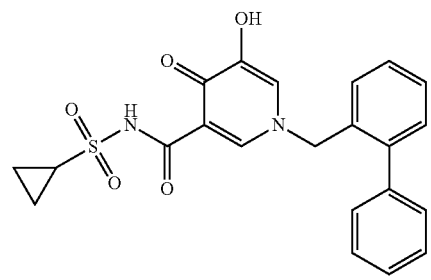
[Formula 139]
MS: m/z=425[M+H]+.
1HNMR (DMSO-d6) δ: 1.10-1.15 (4H, m), 3.03 (1H, q, J=8.4 Hz), 5.33 (2H, s), 7.24-7.29 (5H, m), 7.29-7.47 (5H, m), 8.06 (1H, d, J=2.0 Hz), 9.64 (1H, s), 13.74 (1H, s).
EXAMPLE 196
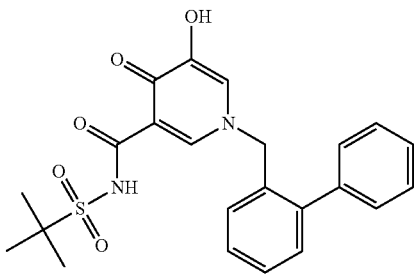
[Formula 140]
MS: m/z=441[M+H]+.
1HNMR (DMSO-d6) δ: 1.37 (9H, s), 5.33 (2H, s), 7.23-7.46 (10H, m), 8.00 (1H, d, J=2.0 Hz), 9.63 (1H, s), 13.68 (1H, s).
EXAMPLE 197
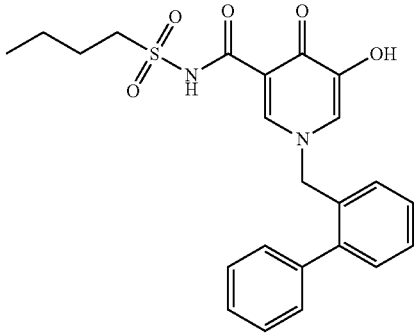
[Formula 141]
MS: m/z=441 [M+H]+.
1HNMR (DMSO-d6) δ: 0.86-0.90 (3H, m), 1.38-1.43 (2H, m), 1.62-1.68 (2H, m), 3.47 (2H, t, J=7.2 Hz), 5.34 (2H, s), 7.23-7.47 (10H, m), 8.01 (1H, d, J=2.0 Hz), 9.65 (1H, s), 13.7 (1H, s).
EXAMPLE 198
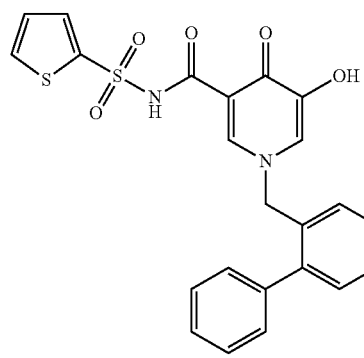
[Formula 142]

MS: m/z=467[M+H]⁺.

¹HNMR (DMSO-d₆) δ: 5.31 (2H, s), 7.22-7.47 (11H, m), 7.87 (1H, d, J=2.0 Hz), 7.94 (1H, s), 8.08 (1H, d, J=2.0 Hz), 9.73 (1H, s), 14.47 (1H, s).

EXAMPLE 199

[Formula 143]

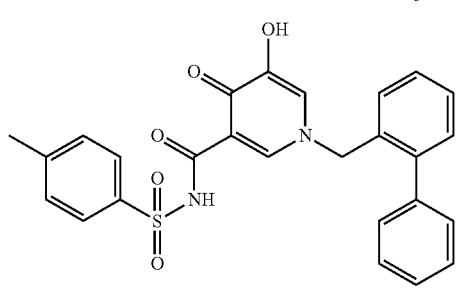

MS: m/z=475[M+H]⁺.

¹HNMR (DMSO-d₆) δ: 2.40 (3H, s), 5.26 (2H, s), 7.18-7.46 (12H, m), 7.87-7.88 (3H, m), 9.64 (1H, s), 14.12 (1H, s).

EXAMPLE 200

[Formula 144]

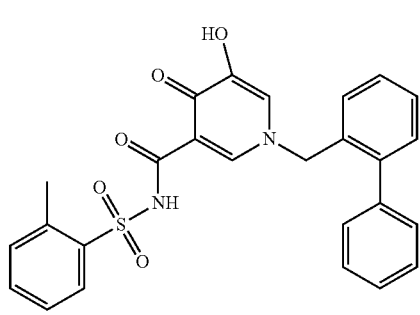

MS: m/z=475 [M+H]⁺.

¹HNMR (DMSO-d₆) δ: 2.56 (3H, s), 5.27 (2H, s), 7.19-7.31 (8H, m), 7.41-7.48 (4H, m), 7.62 (1H, s), 7.81 (1H, s), 8.02 (1H, d, J=8.0 Hz), 9.73 (1H, s), 14.37 (1H, s).

EXAMPLE 201

[Formula 145]

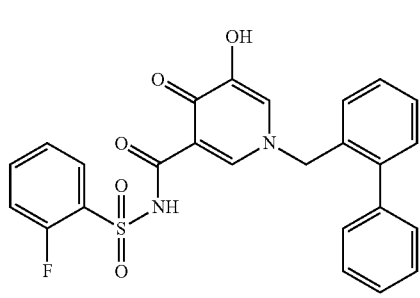

MS: m/z=479[M+H]⁺.

¹HNMR (DMSO-d₆) δ: 5.27 (2H, s), 7.14-7.33 (8H, m), 7.41-7.52 (4H, m), 7.80-7.82 (2H, m), 7.99 (1H, s), 9.75 (1H, s), 14.62 (1H, s).

EXAMPLE 202

[Formula 146]

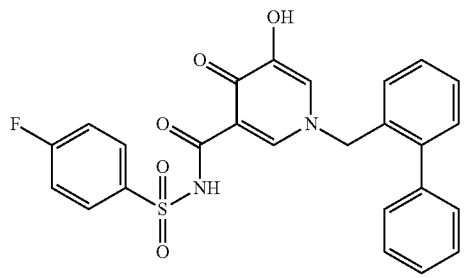

MS: m/z=479[M+H]⁺.

¹HNMR (DMSO-d₆) δ: 5.27 (2H, s), 7.18-7.35 (8H, m), 7.39-7.52 (4H, m), 7.88 (1H, s), 8.07-8.10 (2H, m), 9.69 (1H, s), 14.32 (1H, s).

EXAMPLE 203

[Formula 147]

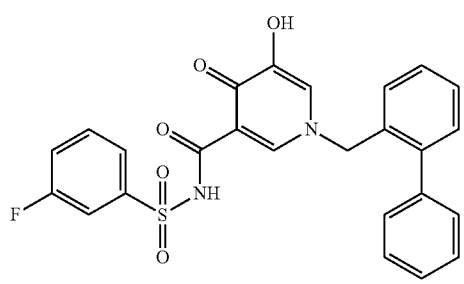

MS: m/z=479[M+H]⁺.

¹HNMR (DMSO-d₆) δ: 5.28 (2H, s), 7.17-7.31 (8H, m), 7.34-7.47 (2H, m), 7.61-7.90 (5H, m), 9.21 (1H, s), 14.48 (1H, s).

EXAMPLE 204

[Formula 148]

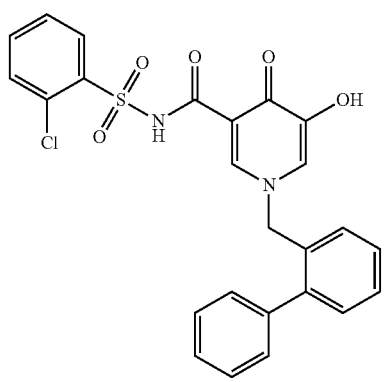

MS: m/z=495[M+H]⁺.

¹HNMR (DMSO-d₆) δ: 5.28 (2H, s), 7.09-7.45 (10H, m), 7.62-7.80 (4H, m), 8.18-8.20 (1H, m), 9.79 (1H, s), 14.67 (1H, s).

EXAMPLE 205
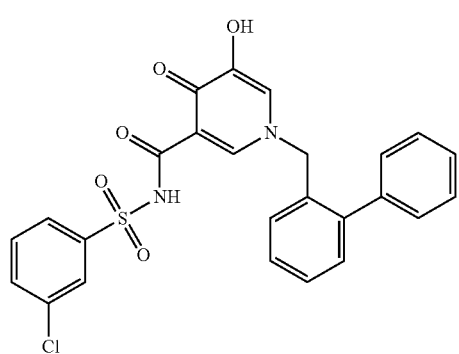
MS: m/z=495[M+H]+.
1HNMR (DMSO-d6) δ: 5.29 (2H, s), 7.18-7.32 (8H, m), 7.40-7.47 (2H, m), 7.68-7.84 (1H, m), 7.84-8.03 (4H, m), 9.75 (1H, s), 14.53 (1H, s).
EXAMPLE 206
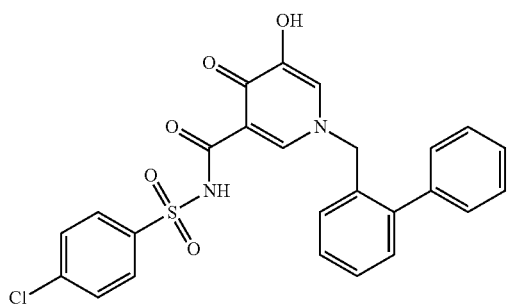
MS: m/z=495[M+H]+.
1HNMR (DMSO-d6) δ: 5.28 (2H, s), 7.17-7.24 (8H, m), 7.26-7.34 (2H, m), 7.73 (2H, d, J=8.4 Hz), 7.87 (1H, s), 8.01 (2H, d, J=8.4 Hz), 9.73 (1H, s), 14.42 (1H, s).
EXAMPLE 207
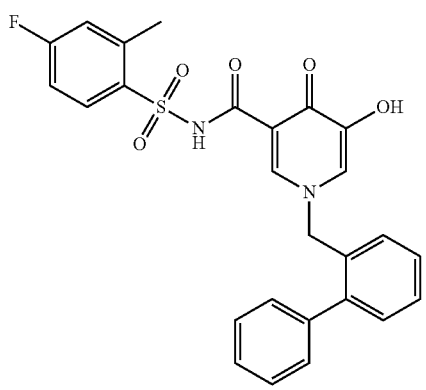
MS: m/z=493[M+H]+.
1HNMR (DMSO-d6) δ: 2.56 (3H, s), 5.27 (2H, s), 7.36-7.39 (12H, m), 7.82 (1H, d, J=2.0 Hz), 8.08-8.11 (1H, m), 9.74 (1H, s), 14.5 (1H, s).
EXAMPLE 208
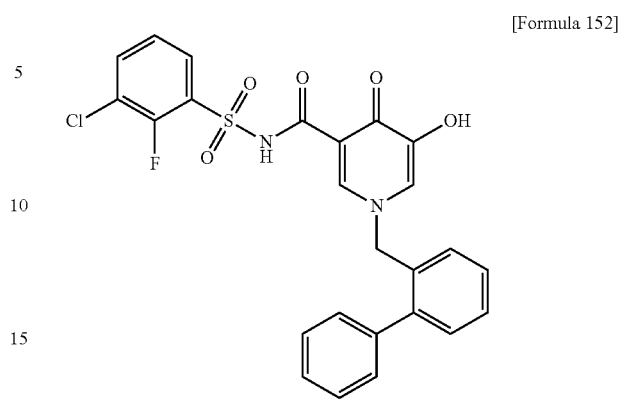
MS: m/z=513[M+H]+.
1HNMR (DMSO-d6) δ: 5.31 (2H, s), 7.10-7.13 (1H, m), 7.20-7.33 (7H, m), 7.40-7.54 (3H, m), 7.84-7.87 (1H, m), 7.97-8.00 (2H, m), 9.88 (1H, s), 15.01 (1H, s).
EXAMPLE 209
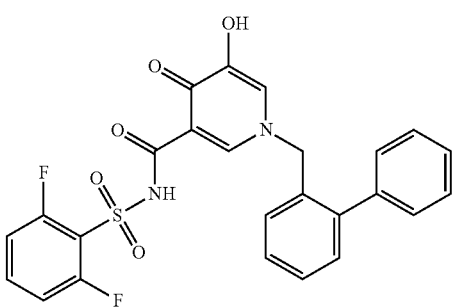
MS: m/z=497[M+H]+.
1HNMR (DMSO-d6) δ: 5.29 (2H, s), 7.15-7.30 (10H, m), 7.34-7.48 (2H, m), 7.79-7.86 (1H, m), 7.87 (1H, s), 9.83 (1H, s), 14.89 (1H, s).
EXAMPLE 210
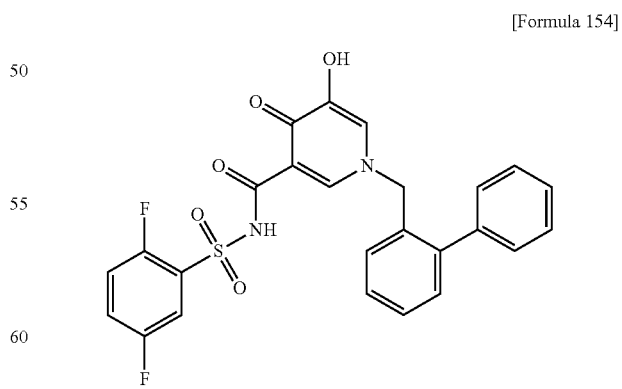
MS: m/z=497[M+H]+.
1HNMR (DMSO-d6) δ: 5.29 (2H, s), 7.16-7.35 (8H, m), 7.40-7.46 (2H, m), 7.59-7.79 (3H, m), 7.87 (1H, d, J=2.0 Hz), 9.85 (1H, s), 14.94 (1H, s).

EXAMPLE 211
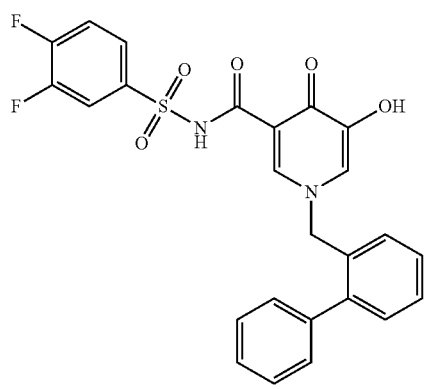
[Formula 155]
MS: m/z=497[M+H]⁺.
¹HNMR (DMSO-d₆) δ: 5.30 (2H, s), 7.22-7.47 (10H, m), 7.71-7.78 (1H, m), 7.91-8.09 (2H, m), 8.10-8.13 (1H, m), 9.77 (1H, s), 14.57 (1H, s).
EXAMPLE 212
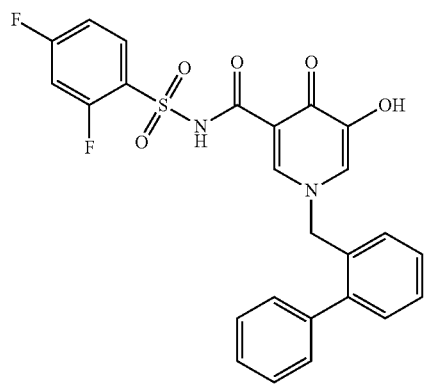
[Formula 156]
MS: m/z=497[M+H]⁺.
¹HNMR (DMSO-d₆) δ: 5.30 (2H, s), 7.17-7.47 (11H, m), 7.60-7.86 (1H, m), 7.87 (1H, d, J=2.0 Hz), 8.07-8.11 (1H, m), 9.82 (1H, s), 14.76 (1H, s).
EXAMPLE 213
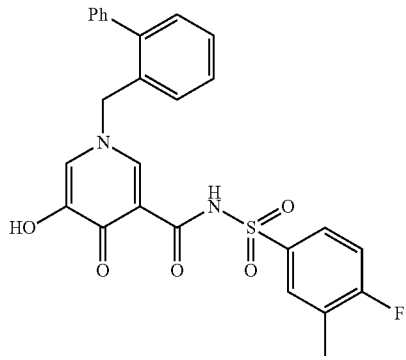
[Formula 157]
MS: m/z=493 [M+H]⁺.
¹HNMR (DMSO-d₆) δ: 2.33 (3H, s), 5.28 (2H, s), 7.20-7.58 (11H, m), 7.74 (2H, d, J=8.0 Hz), 7.91 (1H, d, J=2.0 Hz), 9.68 (1H, s), 14.36 (1H, s).
EXAMPLE 214
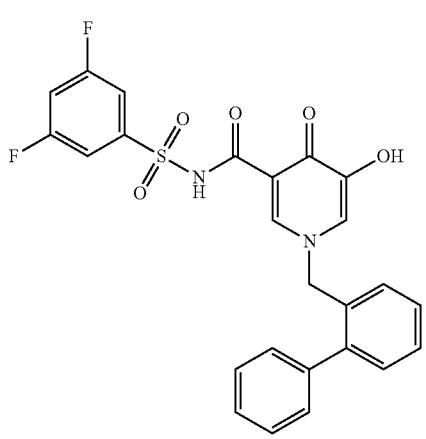
[Formula 158]
MS: m/z=497[M+H]⁺.
¹HNMR (DMSO-d₆) δ: 5.31 (2H, s), 7.22-7.48 (10H, m), 7.72-7.76 (3H, m), 7.95 (1H, d, J=2.0 Hz), 9.82 (1H, s), 14.77 (1H, s).
EXAMPLE 215
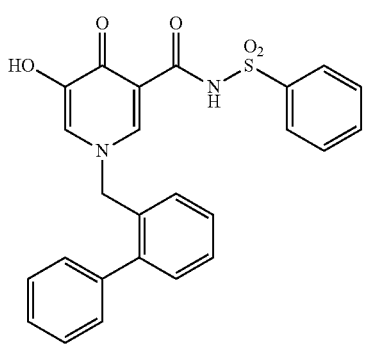
[Formula 159]
¹HNMR (DMSO-d₆) δ: 5.26 (2H, s), 7.11-7.32 (8H, m), 7.38-7.44 (2H, m), 7.60-7.75 (3H, m), 7.83-7.86 (1H, m), 7.95-8.00 (2H, m), 9.67 (1H, brs), 14.2 (1H, brs).

EXAMPLE 216

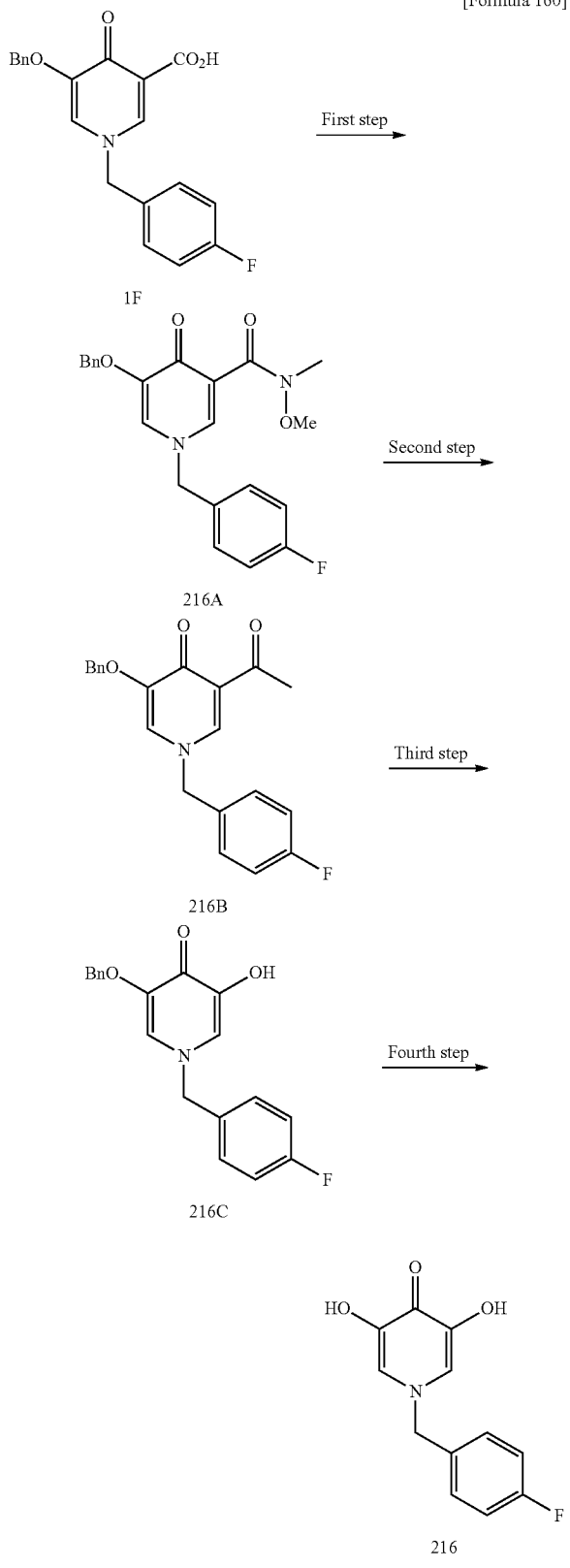

First Step

Compound 1F (1.03 g, 2.92 mmol) was dissolved in HMPA (12 mL)-MeCN (1.2 mL), then the mixture was cooled to −5° C. Then, thionyl chloride (440 mg, 3.70 mmol) was added dropwise thereto and the mixture was stirred keeping at −5 to 5° C. for 1 hour. N,O-dimethylhydroxylamine hydrochloride salt (600 mg, 6.15 mmol) was added thereto, then the reaction temperature was gradually warmed to 15° C. and stirred for 2 hours. To the reaction mixture excess sat. NaHCO$_3$ aq. was added and the mixture was extracted with ethyl acetate three times. The extracted solution was washed with water and sat. NaCl aq., then dried. The solvent was evaporated and obtained oily substance was purified by silica gel column chromatography with ethyl acetate-methanol (20:3, v/v). The target fraction was evaporated to obtain Compound 216A (1.00 g) as an oily substance.

$^1$HNMR (CDCl$_3$) δ: 3.30 (3H, s), 3.80 (3H, s), 4.82 (2H, s), 5.15 (2H, s), 6.84 (1H, d, J=2.4 Hz), 7.04 (4H, d, J=6.9 Hz), 7.27-7.60 (6H, m).

Second Step

A solution of Compound 216A (1.00 g, 2.52 mmol) in THF (10 mL) was cooled to −60° C. A solution of methylmagnesium bromide in THF (0.97M, 4 mL, 3.88 mmol) was added thereto, the mixture was stirred at −50° C. for 30 minutes. The reaction mixture was gradually warmed to −10° C., and aqueous ammonium chloride was added thereto, then the mixture was extracted with ethyl acetate twice. The extracted solution was washed with water, and sat. NaCl aq., and dried. The solvent was evaporated and obtained oily substance was purified with silica gel column chromatography with ethyl acetate. The target fraction of eluate was evaporated and obtained solid was washed with n-hexane to obtain Compound 216B (840 mg).

$^1$HNMR (CDCl$_3$) δ: 2.77 (3H, s), 4.87 (2H, s), 5.09 (2H, s), 6.77 (1H, d, J=2.4 Hz), 7.05 (4H, d, J=6.9 Hz), 7.30-7.40 (5H, m), 8.14 (1H, d, J=2.4 Hz).

Third Step

To a solution of Compound 216B (750 mg, 2.13 mmol) in chloroform (40 mL), m-chloroperbenzoic acid (70%, 960 mg, 3.89 mmol) was added and the mixture was stirred at room temperature for 3 hours. To the reaction mixture, excess 10% sodium bisulfite aq. was added. The chloroform layer was separated and washed with NaHCO$_3$ aq., water, and sat. NaCl aq., and dried. The solvent was evaporated and obtained residue was suspended in EtOH (30 mL) and refluxed to be a solution. The solution was evaporated to be half volume, then cooled to room temperature. The precipitated solid was filtered to obtain Compound 216C.

$^1$HNMR (DMSO-d$_6$) δ: 5.01 (2H, s), 5.05 (2H, s), 7.18 (2H, t, J=9.0 Hz), 7.28-7.42 (7H, m), 7.51 (1H, d, J=2.1 Hz), 7.69 (1H, d, J=2.1 Hz).

MS: m/z=326 [M+H]$^+$

Fourth Step

Compound 216C (210 mg, 0.65 mmol) was dissolved in trifluoroacetic acid (8 mL) and the mixture was refluxed for 3 hours. The reaction mixture was evaporated in vacuo, then residue was diluted with water, and neutralized with NaHCO$_3$ aq. The obtained precipitates was filtered and washed with water and ether, then methanol was added to the precipitate solid to obtain Compound 216 (100 mg) after filtration.

$^1$HNMR (DMSO-d$_6$) δ: 5.02 (2H, s), 7.20 (2H, t, J=9.0 Hz), 7.39 (1H, d, J=8.4 Hz), 7.41 (1H, d, J=8.7 Hz), 7.50 (2H, s).

MS: m/z=236 [M+H]$^+$

EXAMPLE 217

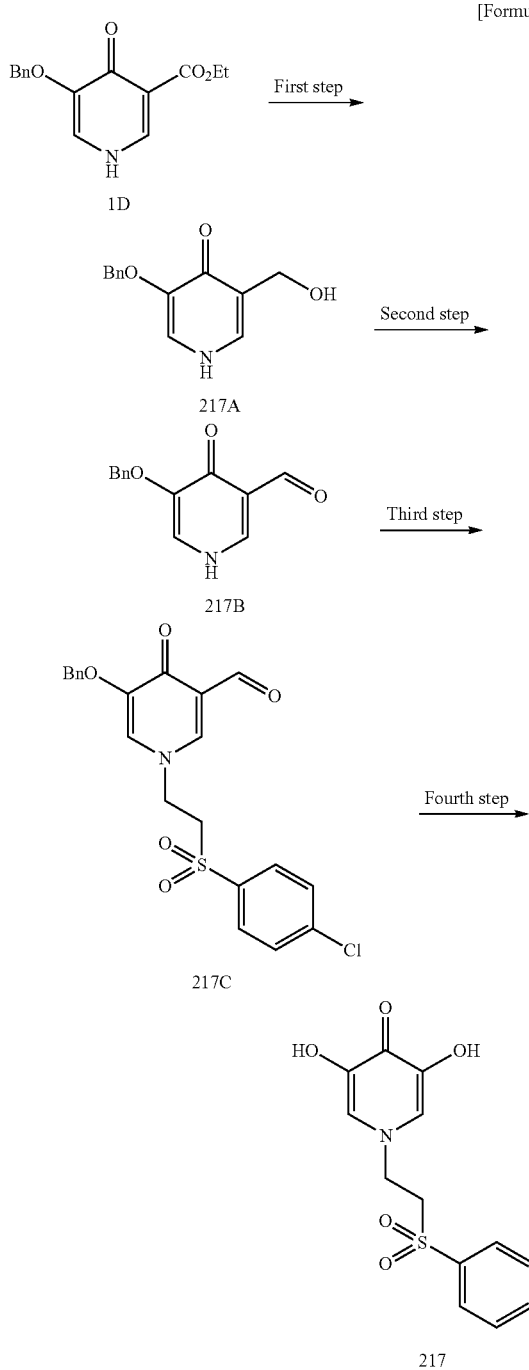

First Step

To a solution of Compound 1D (1.0 g) in THF (30 mL), lithium aluminum hydride (278 mg) was added, then the mixture was stirred at room temperature for 2 hours. To the reaction mixture, water (0.3 mL), 2N sodium hydroxide aq. (0.3 mL), and water (0.9 mL) were added, the mixture was filtered with celite and washed with DMF. After the solvent was evaporated in vacuo, the residue of Compound 217A as a crude product was obtained, which was used in the next step.

Second Step

To a solution of Compound 217A crude product in THF (30 mL) and DMF (30 mL), manganese dioxide (3.0 g) was added, and the mixture was stirred at 65° C. for 5 hours. The reaction mixture was filtered with celite, then filtrate was evaporated in vacuo to obtain Compound 217B.

$^1$HNMR (DMSO-$d_6$) δ: 5.01 (2H, s), 6.87 (1H, brs), 7.30-7.41 (5H, m), 7.53 (1H, s), 8.00 (1H, s), 9.93 (1H, s).

Third Step

To a solution of Compound 217B (20 mg) in DMF (1 mL), potassium carbonate (21 mg), 1-chloro-4-(2-chloroethane-sulfonyl)benzene (28.4 mg) were added, and the mixture was stirred at room temperature for 3 hours. After filtration, the reaction mixture was purified by preparative separation using LCMS to obtain Compound 217C which was used in the next step.

MS: m/z=432 [M+H]$^+$.

Fourth Step

To a solution of Compound 217C in dichloromethane (1.5 mL), metachloroperbenzoic acid (15.1 mg) was added, then the mixture was stirred at room temperature for 4 hours. To the reaction mixture, sat. NaHCO$_3$ aq. was added, and the mixture was extracted with chloroform. The organic layer was evaporated in vacuo and trifluoroacetic acid (0.8 mL) was added to the residue, then the mixture was stirred at 80° C. for 4 hours. The reaction mixture was purified by preparative separation using LCMS to obtain Compound 217 (3.6 mg).

MS: m/z=330 [M+H]$^+$.

Following Compounds were obtained according to Example 217.

TABLE 34

| Example | Structure | MS(M + 1) |
|---|---|---|
| 218 | (HO-pyridinone-OH with N-CH2-biphenyl) | 294 |
| 219 | (HO-pyridinone-OH with N-CH2-cyclopentyl) | 210 |

EXAMPLE 220

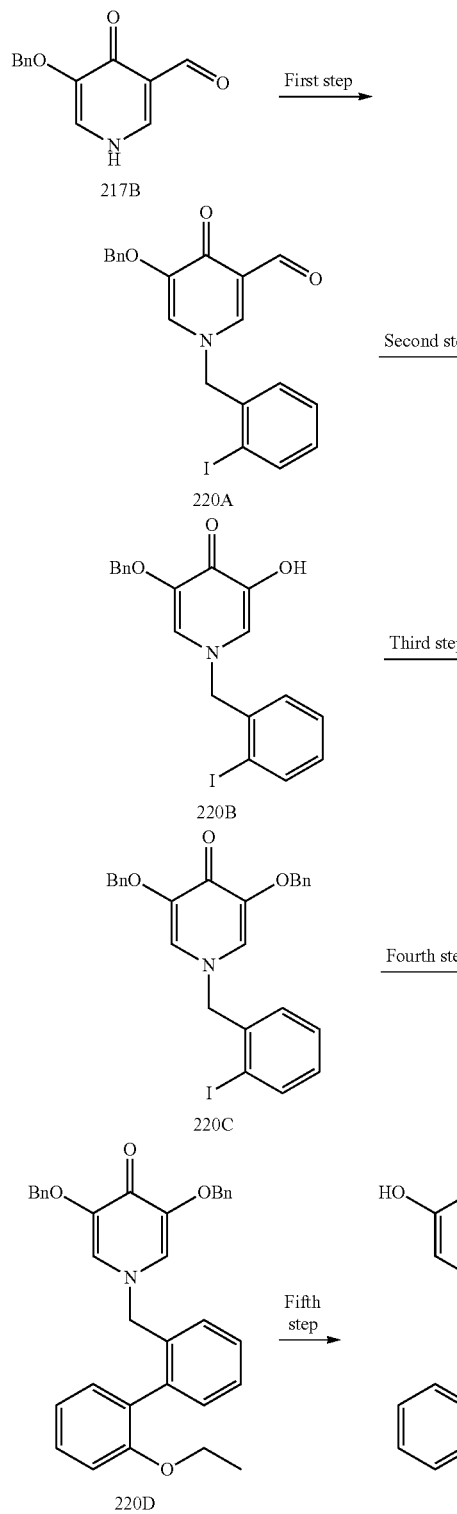

First Step

A crude product of Compound 220A was synthesizaed from Compound 217B (500 mg) according to Compound 1E.

$^1$HNMR (DMSO-d$_6$) δ: 4.99 (2H, s), 5.23 (2H, s), 7.02 (1H, d, J=7.2), 7.14 (1H, t, J=7.2), 7.35-7.42 (6H, m), 7.64 (1H, s), 7.94 (1H, d, J=7.2), 8.19 (1H, s), 10.13 (1H, s).

Second Step

To a solution of Compound 220A (500 mg) in dichloromethane (15 mL), metaperchloroperbenzoic acid (194 mg) was added, then the mixture was stirred at room temperature for 4 hours. To the reaction mixture, sat. NaHCO$_3$ aq. was added, then the mixture was extracted with chloroform. The organic layer was dried over anhydrous Na$_2$SO$_4$ and the solvent was evaporated in vacuo to obtain crude product Compound 220B which was used in the next step.

Third Step

To a solution of Crude product of Compound 220B (200 mg) in acetone (10 mL), potassium carbonate (96 mg) and benzylbromide (95 mg) were added, then the mixture was stirred at 60° C. for 1 hour. The reaction mixture was filtered and purified by preparative separation using LCMS to obtain Compound 220C (51 mg).

MS: m/z=524 [M+H]$^+$.

Fourth Step

Compound 220D was synthesized from Compound 220C (13 mg) according to the second step of Example 20.

MS: m/z=518 [M+H]$^+$.

Fifth Step

Compound 220 (3.7 mg) was obtained from Compound 220D according to the third step of Example 20.

MS: m/z=338 [M+H]$^+$.

The following Compounds were synthesized according to Example 220.

TABLE 35

| Example | Structure | MS(M + 1) |
|---|---|---|
| 221 | ![structure] | 344 |
| 222 | ![structure] | 346 |

EXAMPLE 223

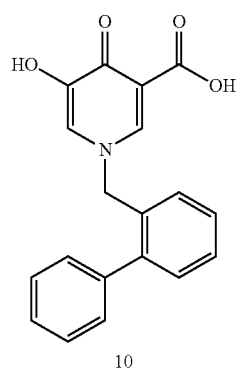

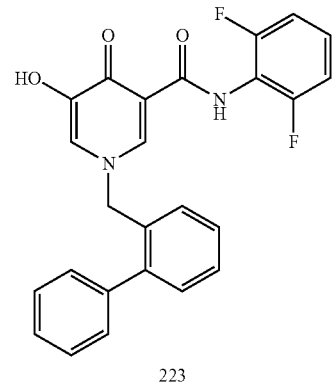

First Step

Compound 10 (20 mg, 0.062 mmol) was dissolved in DMF (1 mL), then HATU (36 mg, 0.093 mmol) and DIEA (16 μL, 0.093 mmol) were added thereto, and the mixture was stirred over night. The reaction mixture was purified by LCMS to obtain Compound 223 (6.7 mg).

MS: m/z=433 [M+H]$^+$.

The following compounds were synthesized using known amines according to Compound 60.

EXAMPLE 224

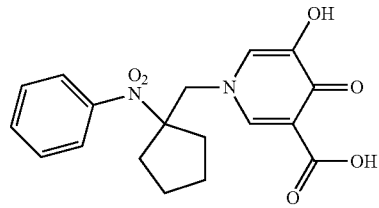

LC-MS: m/z=378 [M+H]$^+$.

$^1$HNMR (DMSO-d$_6$): 1.33-1.38 (2H, m), 1.40-1.45 (2H, m), 1.76-1.83 (2H, m), 2.14-2.21 (2H, m), 4.62 (2H, s), 7.70-7.72 (2H, m), 7.81-7.86 (2H, m), 7.92-7.95 (2H, m), 8.53 (1H, d, J=2.0 Hz), 10.09 (1H, s), 15.86 (1H, s).

EXAMPLE 225

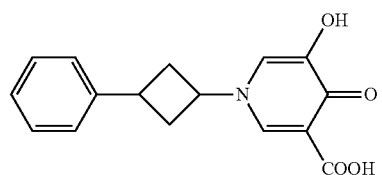

LC-MS: m/z=286[M+H]$^+$.

$^1$HNMR (DMSO-d$_6$): 2.64-2.66 (1H, m), 2.85-2.88 (1H, m), 2.89-2.97 (1H, m), 3.20-3.33 (1H, m), 3.59-3.61 (1H, m), 5.15-5.20 (1H, m), 7.20-7.26 (1H, m), 7.30-7.38 (2H, m), 7.38 (1H, s), 7.39 (1H, s), 7.92 (1H, s), 8.05 (1H, s), 10.07 (1H, s), 16.09 (1H, s).

EXAMPLE 226

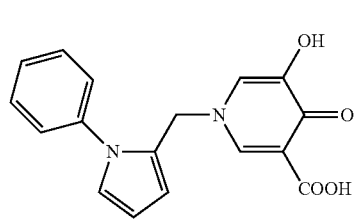

LC-MS: m/z=311[M+H]$^+$.

$^1$HNMR (DMSO-d$_6$): 5.36 (2H, s), 6.248 (1H, t, J=4.0 Hz), 6.45 (1H, s), 7.04 (1H, t, J=4.0 Hz), 7.25 (2H, d, J=8.8 Hz), 7.31 (1H, d, J=8.8 Hz), 7.41-7.43 (3H, m), 7.92 (1H, d, J=8.8 Hz), 9.97 (1H, s), 15.87 (1H, s).

EXAMPLE 227

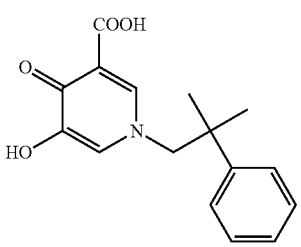

LC-MS: m/z=288 [M+H]$^+$.

$^1$HNMR (DMSO-d$_6$): 1.32 (6H, s), 4.33 (2H, s), 7.24-7.41 (6H, m), 8.04 (1H, d, J=2.0 Hz), 9.92 (1H, s), 15.97 (1H, s).

The following compounds were synthesized using known alcohol according to Compound 56.

EXAMPLE 228

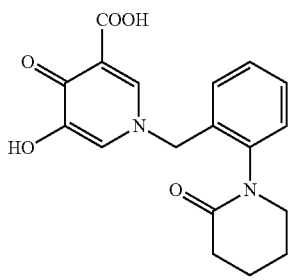

[Formula 168]

LC-MS: m/z=343 [M+H]$^+$.
$^1$HNMR (DMSO-d$_6$): 1.86 (4H, s), 2.36 (2H, t, J=6.0 Hz), 3.23 (1H, d, J=11.3 Hz), 3.60 (1H, t, J=6.0 Hz), 5.18-5.26 (2H, m), 7.33-7.40 (3H, m), 7.45-7.49 (1H, m), 7.64 (1H, d, J=2.0 Hz), 8.48 (1H, d, J=2.0 Hz), 10.08 (1H, s), 16.02 (1H, s).

EXAMPLE 229

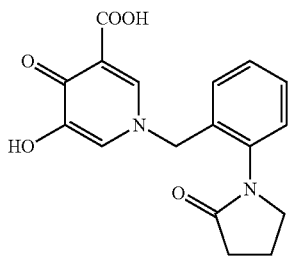

[Formula 169]

LC-MS: m/z=329 [M+H]$^+$.
$^1$HNMR (DMSO-d$_6$): 2.06-2.13 (2H, m), 2.42 (2H, t, J=8.0 Hz), 3.66 (2H, t, J=7.0 Hz), 5.26 (2H, s), 7.32 (1H, d, J=7.0 Hz), 7.38 (2H, t, J=7.2 Hz), 7.45-7.49 (1H, m), 7.65 (1H, d, J=2.0 Hz), 8.46 (1H, d, J=2.0 Hz), 10.11 (1H, s), 15.97 (1H, s).

EXAMPLE 230

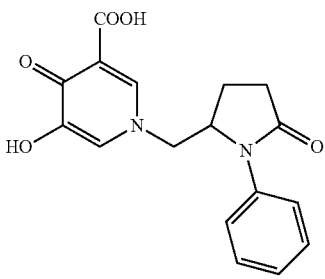

[Formula 170]

LC-MS: m/z=329 [M+H]$^+$.
$^1$HNMR (DMSO-d$_6$): 2.24-2.37 (2H, m), 2.53-2.60 (2H, m), 4.22-4.26 (1H, m), 6.98 (1H, t, J=7.2 Hz), 7.18 (2H, t, J=7.6 Hz), 7.32 (2H, d, J=7.6 Hz), 7.66 (1H, s), 8.26 (1H, d, J=1.6 Hz), 9.79 (1H, s), 15.76 (1H, s).

EXAMPLE 231

[Formula 171]

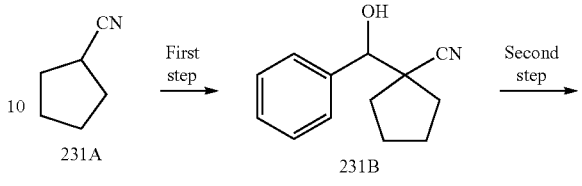

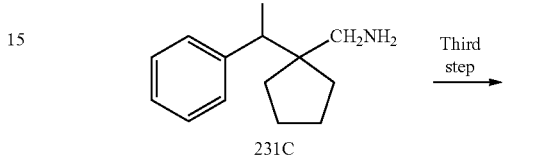

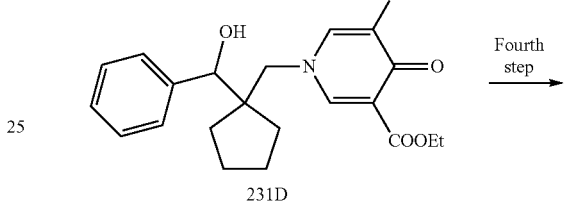

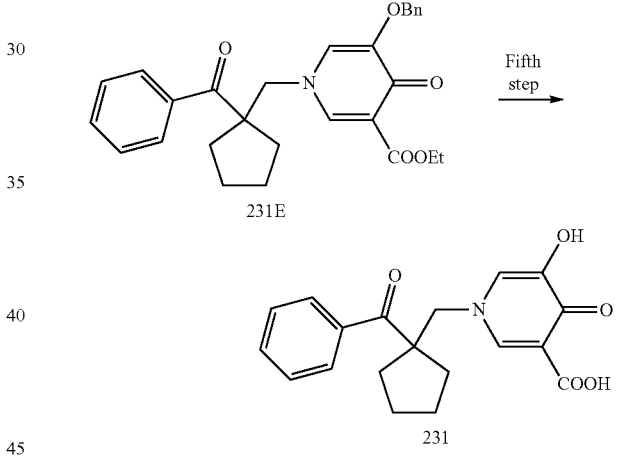

First Step

Compound 231A (950 mg, 10 mmol) was dissolved in anhydrous THF (50 mL), and the mixture was cooled to −78° C., then LDA (2M, 11 mmol) was added dropwise thereto. 30 minutes later, benzaldehyde (1.06 g, 10 mmol) was added thereto and the mixture was stirred at room temperature for 2 hours. To the reaction mixture, sat NH$_4$Cl aq. was added, and the mixture was extracted with ethyl acetate (50 mL×3). The organic layer was washed with sat. NaCl aq., and dried over Na$_2$SO$_4$, then the solvent was evaporated. The obtained residue was purified by silica gel column chromatography (a solution of 5% to 30% ethyl acetate-petroleum ether) to obtain Compound 231B (1.75 g, 85%).

LC-MS: m/z=202 [M+H]$^+$.

Second Step

Compound 231B was slowly added and dissolved in anhydrous THF (50 mL), then LiAlH$_4$ (210 mg, 5 mmol) was slowly added thereto. After 20 minutes reflux, the mixture was cooled to room temperature, then THF (200 mL) was added thereto. Na$_2$SO$_4$.10H2O (5 g) was slowly added thereto, then the mixture was filtered and the filtrate was evaporated in vacuo to obtain Compound 231C (896 mg, 87.4%).

LC-MS: m/z=206 [M+H]$^+$.

Third Step

Compound 231D was obtained using Compound 231C according to second step in Example 60.

LC-MS: m/z=463 [M+H]$^+$.

Fourth Step

Compound 231D (795 mg, 1.72 mmol) was dissolved in ethyl acetate (30 mL), IBX (1.45 g, 5.16 mmol) was added thereto and the mixture was refluxed for 3 days. After filtration, the filtrate was evaporated in vacuo to obtain Compound 231E (763 mg, 96.4%).

LC-MS: m/z=461 [M+H]$^+$.

Fifth Step

Compound 231 was synthesized according to Example 1.

LC-MS: m/z=342 [M+H]$^+$.

$^1$HNMR (DMSO-d$_6$): 1.54 (2H, s), 1.73 (2H, s), 1.85 (2H, s), 2.12 (2H, s), 4.70 (2H, s), 7.36 (1H, s), 7.54-7.56 (2H, m), 7.63 (1H, d, J=2.0 Hz), 7.85-7.87 (2H, m), 8.19 (1H, s), 10.10 (1H, s), 15.87 (1H, s).

EXAMPLE 232 mmol), EDC-HCl (768 mg, 4 mmol) and aniline (186 mg, 2 mmol) were added thereto and the mixture was stirred at room temperature over night. To the reaction mixture, ethyl acetate (50 mL)-water (50 mL) was added, then the mixture was extracted by ethyl acetate (50 mL×3). The organic layer was washed with water and sat. NaCl aq., and dried over Na$_2$SO$_4$, then solvent was evaporated to obtain Compound 232B (1.34 g).

LC-MS: m/z=319 [M+H]$^+$.

Second Step

Compound 232B (1.34 g) was dissolved in 1,2-dichloromethane (30 mL), then TFA (5 mL) was added thereto and the mixture was stirred at room temperature for 1 hour. After the evaporation in vacuo, the residue was purified by silica gel chromatography (dichloromethane:methanol:Et$_3$N=40:1: 0.05) to obtain Compound 232C (412 mg).

LC-MS: m/z=219 [M+H]$^+$.

Third Step

Compound 232 was synthesized according to Example 60.

LC-MS: m/z=357 [M+H]$^+$.

$^1$HNMR (DMSO-d$_6$): 1.58-1.67 (6H, m), 2.14 (2H, s), 4.48 (2H, s), 7.09-7.80 (1H, m), 7.30-7.31 (2H, m), 7.48-7.50 (2H, m), 7.57 (1H, d, J=2.0 Hz), 8.35 (1H, d, J=2.0 Hz), 9.58 (1H, s), 10.07 (1H, s), 15.94 (1H, s).

EXAMPLE 233

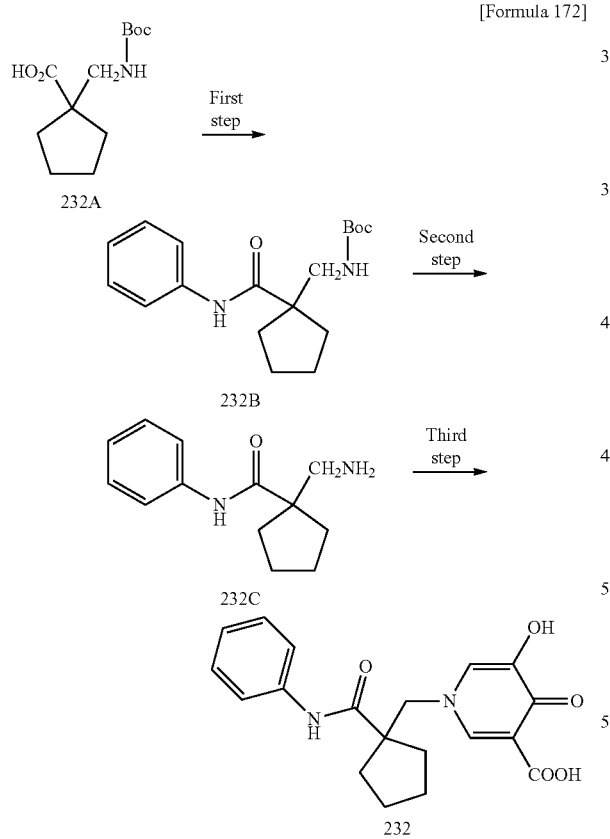

[Formula 172]

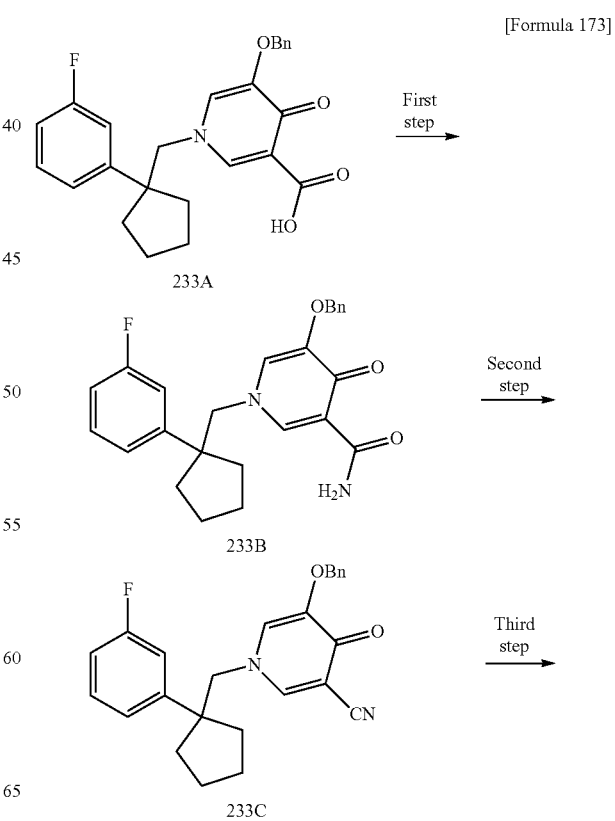

[Formula 173]

First Step

Compound 232A (586 mg, 2 mmol, Bioorganic & Medicinal Chemistry Letters (1999), 9(3), 369-374) was dissolved in DMF (10 mL), DIEA (488 mg, 4 mmol), HOBt (540 mg, 4

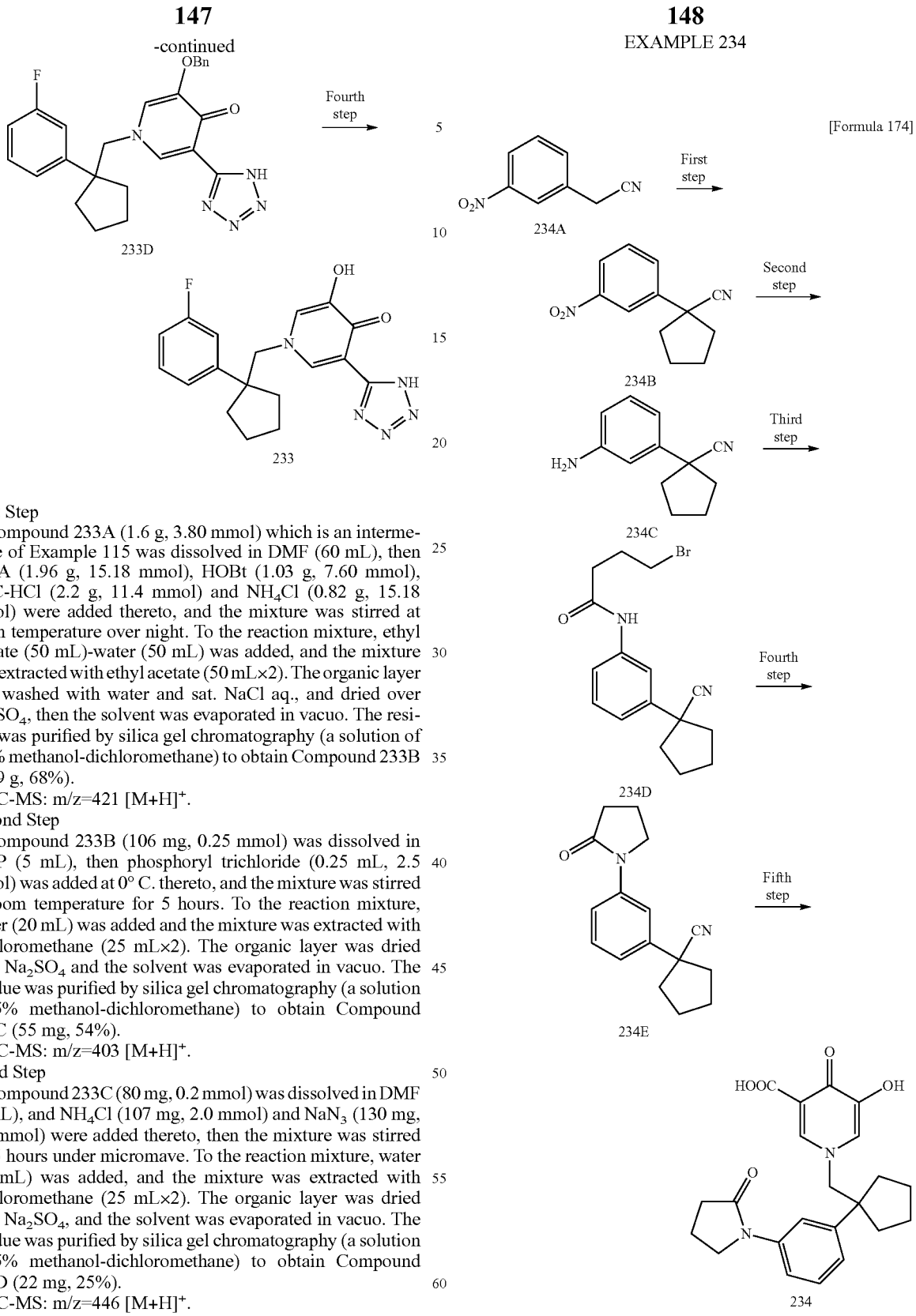

EXAMPLE 234

First Step
Compound 233A (1.6 g, 3.80 mmol) which is an intermediate of Example 115 was dissolved in DMF (60 mL), then DIEA (1.96 g, 15.18 mmol), HOBt (1.03 g, 7.60 mmol), EDC-HCl (2.2 g, 11.4 mmol) and $NH_4Cl$ (0.82 g, 15.18 mmol) were added thereto, and the mixture was stirred at room temperature over night. To the reaction mixture, ethyl acetate (50 mL)-water (50 mL) was added, and the mixture was extracted with ethyl acetate (50 mL×2). The organic layer was washed with water and sat. NaCl aq., and dried over $Na_2SO_4$, then the solvent was evaporated in vacuo. The residue was purified by silica gel chromatography (a solution of 2.5% methanol-dichloromethane) to obtain Compound 233B (1.09 g, 68%).

LC-MS: m/z=421 $[M+H]^+$.

Second Step
Compound 233B (106 mg, 0.25 mmol) was dissolved in NMP (5 mL), then phosphoryl trichloride (0.25 mL, 2.5 mmol) was added at 0° C. thereto, and the mixture was stirred at room temperature for 5 hours. To the reaction mixture, water (20 mL) was added and the mixture was extracted with dichloromethane (25 mL×2). The organic layer was dried over $Na_2SO_4$ and the solvent was evaporated in vacuo. The residue was purified by silica gel chromatography (a solution of 5% methanol-dichloromethane) to obtain Compound 233C (55 mg, 54%).

LC-MS: m/z=403 $[M+H]^+$.

Third Step
Compound 233C (80 mg, 0.2 mmol) was dissolved in DMF (2 mL), and $NH_4Cl$ (107 mg, 2.0 mmol) and $NaN_3$ (130 mg, 2.0 mmol) were added thereto, then the mixture was stirred for 5 hours under micromave. To the reaction mixture, water (20 mL) was added, and the mixture was extracted with dichloromethane (25 mL×2). The organic layer was dried over $Na_2SO_4$, and the solvent was evaporated in vacuo. The residue was purified by silica gel chromatography (a solution of 5% methanol-dichloromethane) to obtain Compound 233D (22 mg, 25%).

LC-MS: m/z=446 $[M+H]^+$.

Fourth Step
Compound 233 was synthesized according to Example 1.

$^1$HNMR (DMSO-$d_6$): 1.58-1.59 (2H, m), 1.81-1.82 (2H, m), 1.94-1.96 (4H, m), 4.29 (2H, s), 6.98-7.10 (4H, m), 7.30-7.32 (1H, m), 7.92 (1H, d, J=2.0 Hz), 9.25 (1H, s), 15.97 (1H, s).

First Step
Compound 234B was synthesized according to Third step in Example 145.

LC-MS: m/z=217 $[M+H]^+$.

Second Step

Compound 234B (0.75 g, 3.5 mmol) was dissolved in ethyl acetate (100 mL), and $SnCl_2 \cdot 2H_2O$ (4.7 g, 20.8 mmol) was added thereto, then the mixture was refluxed for 2 hours. To the reaction mixture, ammonia water was added thereto to be pH 7~8, then after filtration, the filtrate was evaporated in vacuo to obtain Compound 234C (0.6 g, 93.4%).

LC-MS: m/z=187 [M+H]$^+$.

Third Step

Compound 234C (400 mg, 2.2 mmol) was dissolved in dichloromethane (30 mL), DIPEA (555 mg, 4.3 mmol) and 4-bromobutanoyl chloride (600 mg, 3.2 mmol) were added dropwise at 0° C. thereto, and the mixture was stirred at room temperature for 2 hours. To the reaction mixture, $NH_4Cl$ aq. (2 M, 5 mL) was added, the mixture was extracted with dichloromethane (25 mL×2). The organic layer was washed with sat. NaCl aq., and dried over $Na_2SO_4$. The solvent was evaporated in vacuo to obtain Compound 234D (800 mg).

LC-MS: m/z=336 [M+H]$^+$.

Fourth Step

Compound 234D (800 mg, 2.4 mmol) was dissolved in THF (50 mL), and t-BuOK (400 mg, 3.6 mmol) was added thereto at 0° C., then the mixture was stirred at room temperature for 2 hours. To the reaction mixture, water was added and the mixture was extracted with ethyl acetate (50 mL×2). The organic layer was washed with sat. NaCl aq., and dried over $Na_2SO_4$, then the solvent was evaporated in vacuo. The residue was purified by silica gel chromatography (a solution of 20% ethyl acetate-petroleum ether) to obtain Compound 11E (350 mg, 58%).

LC-MS: m/z=255 [M+H]$^+$

EXAMPLE 235

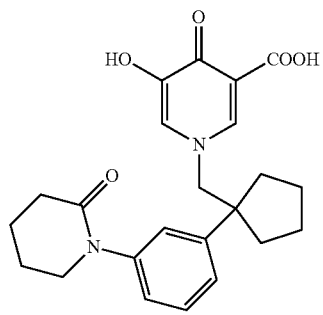

[Formula 175]

Compound 235 was synthesized according to Example 234.

LC-MS: m/z=411 [M+H]$^+$.

$^1$HNMR (DMSO-d$_6$): 1.60-1.62 (2H, m), 1.82-1.84 (6H, m), 1.92-1.94 (4H, m), 2.35 (2H, t, J=5.6 Hz), 3.49 (2H, t, J=5.2 Hz), 4.30 (2H, s), 7.04-7.15 (4H, m), 7.30 (1H, t, J=7.6 Hz), 7.71 (1H, d, J=2.0 Hz), 9.86 (1H, s), 15.91 (1H, s).

EXAMPLE 236

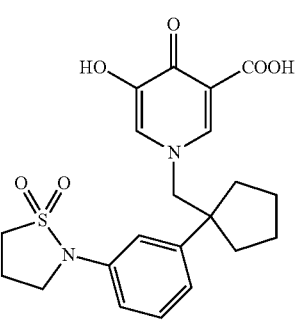

[Formula 176]

Compound 236 was synthesized according to Example 234.

LC-MS: m/z=433 [M+H]$^+$.

$^1$HNMR (DMSO-d$_6$): 1.58 (2H, s), 1.80-1.82 (2H, m), 1.90-1.92 (4H, m), 2.35-2.40 (2H, m), 3.48 (2H, t, J=8.0 Hz), 3.70 (2H, t, J=6.4 Hz), 4.32 (s, 2H), 6.97 (t, J=8.4 Hz, 2H), 7.08-7.12 (m, J=1.6 Hz, 2H), 7.29 (t, J=8.4 Hz, 1H), 7.80 (d, J=1.6 Hz, 1H), 9.85 (s, 1H), 15.93 (s, 1H).

EXAMPLE 237

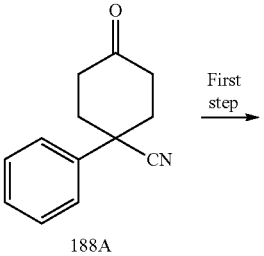

[Formula 177]

First step →

188A

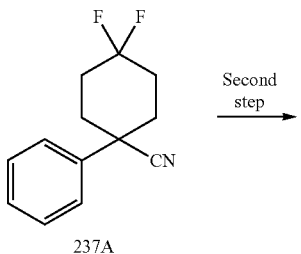

Second step →

237A

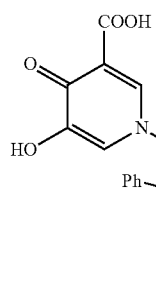

237

First Step

Compound 188A (3.24 g, 26.3 mmol) was dissolved in dichloromethane (40 mL), then a solution of (diethylamino)

sulfur trifluoride (46.7 g, 28.9 mmol) in dichloromethane (20 mL) was added dropwise thereto at 0° C., then the mixture was stirred for 2 hours. To the reaction mixture, water (100 mL) was added, then organic layer was dried over MgSO$_4$ and the solvent was evaporated in vacuo to the volume of 10 mL. A solution of MCPBA (4.5 g, 20.0 mmol) in chloroform (60 mL) was stirred for 30 minutes, and dried over MgSO$_4$. The solvent was evaporated in vacuo to the volume of 10 mL. The dichloromethane solution after processing was added thereto and stirred at room temperature for 18 hours. The mixture was washed with aqueous sodium hydroxide (1.5 M, 30 mL×3) and the organic layer was dried over MgSO$_4$ and evaporated in vacuo to obtain Compound 237A (2 g).

LC-MS: m/z=222 [M+H]$^+$.

Second Step

Compound 237 was obtained according to Compound 145.

LC-MS: m/z=364 [M+H]$^+$.

$^1$HNMR (DMSO-d$_6$): 1.47-1.62 (2H, m), 1.84 (2H, t, J=13.2 Hz,), 2.03-2.05 (2H, m), 2.37 (2H, d, J=13.2 Hz), 4.28 (2H, s), 7.10 (1H, d, J=2.0 Hz), 7.29-7.40 (5H, m), 7.68 (1H, d, J=2.0 Hz), 9.89 (1H, s), 15.88 (1H, s).

EXAMPLE 238

[Formula 178]

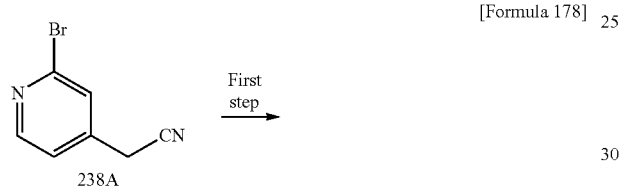

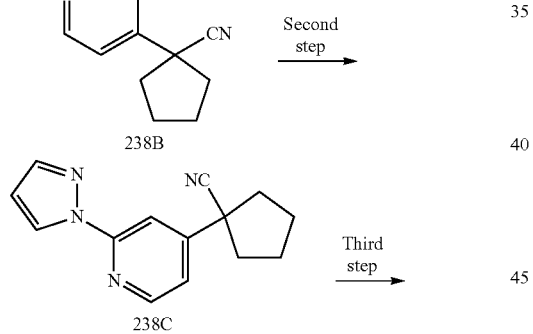

First Step

Compound 238B was synthesized using Compound 238A (Synlett (2000), (10), 1488-1490) according to third step of Example 145.

LC-MS: m/z=253 [M+H]$^+$.

Second Step

A solution of Compound 238B (0.5 g, 2.0 mmol), 1H-pyrazole (0.15 g, 2.2 mmol), CuI (40 mg, 0.2 mmol), L-proline (46 mg, 0.4 mmol) and K$_2$CO$_3$ (0.55 g, 4.0 mmol) in DMSO (50 mL) was stirred at 120° C. for 7 days. To the reaction mixture, ethyl acetate-water was added and the mixture was extracted by ethyl acetate (50 mL×2). The organic layer was washed with sat. NaCl aq., and dried over Na$_2$SO$_4$, then evaporated in vacuo. The residue was purified by silica gel chromatography (a solution of 10% ethyl acetate-petroleum ether) to obtain Compound 238C (250 mg, 52%).

LC-MS: m/z=239 [M+H]$^+$.

Third Step

Compound 238 was synthesized according to Compound 145.

LC-MS: m/z=381 [M+H]$^+$.

$^1$HNMR (DMSO-d$_6$): 1.58 (2H, s), 1.83 (2H, s), 1.99-2.02 (4H, m), 4.45 (2H, s), 6.57-6.58 (1H, m), 7.18-7.20 (1H, m), 7.28 (1H, d, J=2.0 Hz), 7.81 (2H, t, J=0.8 Hz), 7.91 (1H, d, J=1.6 Hz), 8.37 (1H, d, J=5.2 Hz), 8.61 (1H, d, J=2.4 Hz), 9.96 (1H, s), 15.97 (1H, s).

EXAMPLE 239

[Formula 179]

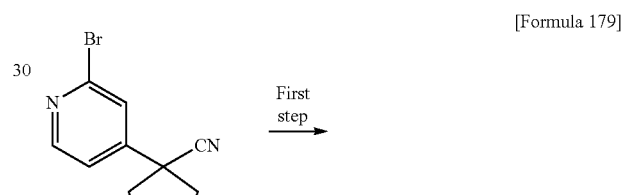

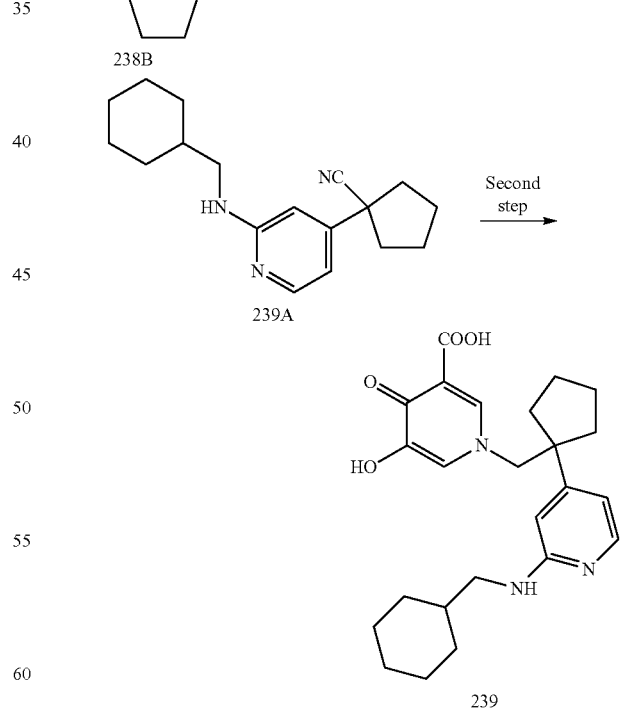

First Step

Compound 238B (0.55 g, 2.2 mmol) was dissolved in NMP (50 mL), cyclohexylmethanamine (2.5 g, 21.9 mmol) was added thereto and the mixture was stirred at 200° C. for 2 hours under microwave. The reaction mixture was diluted with dichloromethane-water and extracted with dichloromethane (100 mL×2). The residue was purified by silica gel chromatography (a solution of 25% ethyl acetate-petroleum ether) to obtain Compound 239A (0.47 g, 86%).

LC-MS: m/z=284 [M+H]⁺.

Second Step

Compound 239 was obtained according to Compound 145.

LC-MS: m/z=426 [M+H]⁺.

¹HNMR (DMSO-d₆): 0.81-0.84 (2H, m), 1.13-1.19 (2H, m), 1.56-1.58 (4H, m), 1.66 (5H, m), 1.81-1.83 (6H, m), 3.01 (2H, d, J=6.4 Hz), 4.30 (2H, s), 6.14 (1H, s), 6.37-6.39 (2H, m), 7.23 (1H, d, J=1.2 Hz), 7.86 (2H, d, J=5.2 Hz), 9.89 (1H, s), 15.97 (1H, s).

EXAMPLE 240

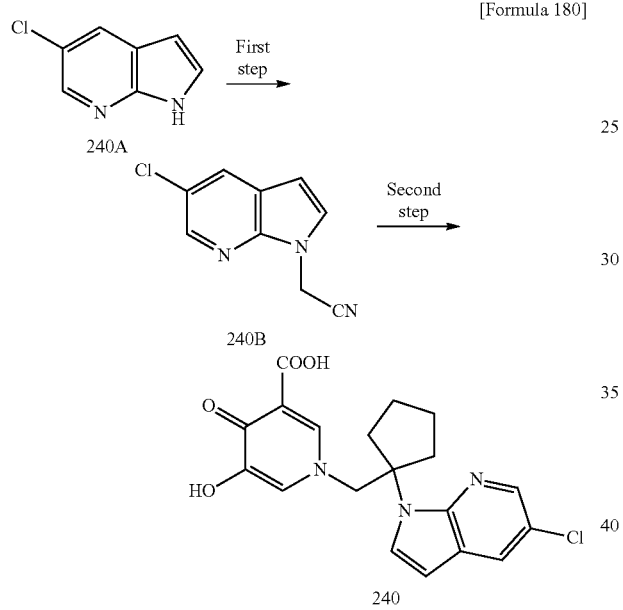

[Formula 180]

First Step

NaH (1.35 g, 33.75 mmol) was suspended in DMF (100 mL), then a solution of Compound 240A (2.58 g, 16.9 mmol) and bromoacetonitrile (3.05 g, 14.1 mmol) in DMF (30 mL) was added thereto under ice water bath. Then the mixture was stirred at room temperature over night. To the reaction mixture, water was added and the mixture was extracted with ethyl acetate (100 mL×2). The organic layer was washed with sat. NaCl aq., dried over Na₂SO₄, and evaporated in vacuo. The residue was purified by silica gel chromatography (a solution of 3% ethyl acetate petroleum ether) to obtain Compound 240B (1.28 g, 44.5%).

LC-MS: m/z=192 [M+H]⁺.

Second Step

Compound 240 was synthesized according to Example 145.

LC-MS: m/z=388 [M+H]⁺.

¹HNMR (DMSO-d₆): 1.61 (2H, d, J=4.0 Hz), 1.87 (2H, d, J=7.6 Hz), 2.23-2.29 (2H, m), 2.56 (2H, t, J=6.8 Hz), 4.76 (2H, s), 6.44 (1H, d, J=3.6 Hz), 6.79 (1H, d, J=2.4 Hz), 7.42 (1H, d, J=2.4 Hz), 7.47 (1H, d, J=3.6), 8.13 (1H, d, J=2.0 Hz), 8.26 (1H, d, J=2.0 Hz), 9.84 (1H, s), 15.77 (1H, s).

EXAMPLE 241

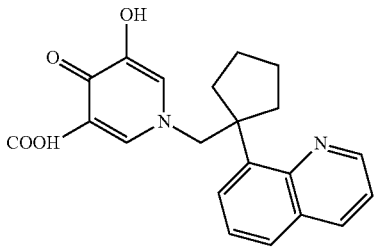

[Formula 181]

Compound 241 was synthesized using commercially available 8-Bromomethylquinoline according to Example 145.

LC-MS: m/z=365 [M+H]⁺.

¹HNMR (DMSO-d₆): 1.65 (2H, s), 1.89 (2H, d, J=4.0 Hz), 2.17 (2H, d, J=6.4 Hz), 2.30 (2H, s), 4.90 (2H, s), 6.83 (1H, d, J=2.0 Hz), 7.14-7.44 (3H, m), 7.60-7.62 (1H, m), 7.90-7.92 (1H, m), 8.42-8.45 (1H, m), 8.99-9.01 (1H, m), 9.87 (1H, s), 15.86 (1H, s).

EXAMPLE 242

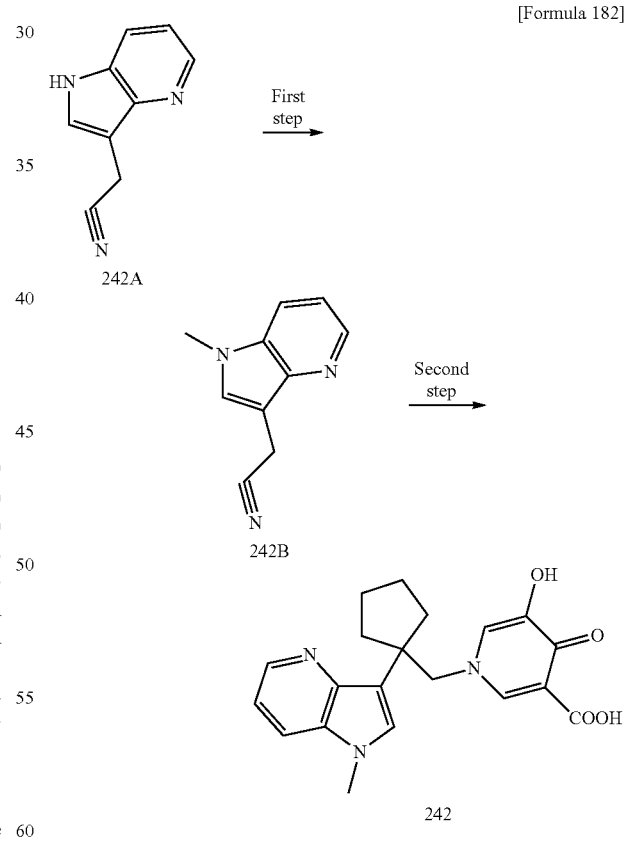

[Formula 182]

First Step

Compound 242A (900 mg, 5.73 mmol, WO2003/05397) was dissolved in DMF, then cesium carbonate (2.156 g, 6.3 mmol) and CH₃I (980 mg, 6.88 mmol) were added thereto, and the mixture was stirred at room temperature for 1 hour. The solvent was evaporated in vacuo, the residue was purified by silica gel chromatography (a solution of 40% ethyl acetate-petroleum ether) to obtain Compound 242B (475 mg, 48.5%).

LC-MS: m/z=172 [M+H]+.

Second Step

Compound 242 was synthesized according to Example 145.

LC-MS: m/z=368 [M+H]+.

$^1$HNMR (DMSO-d$_6$): 1.57-1.59 (2H, m), 1.78 (2H, s), 1.92-1.96 (2H, m), 2.12-2.14 (2H, m), 3.82 (3H, s), 4.49 (2H, s), 7.23 (1H, s), 7.53 (1H, s), 7.68-7.70 (2H, m), 8.41 (1H, s), 8.56 (1H, s), 9.98 (1H, s).

EXAMPLE 243

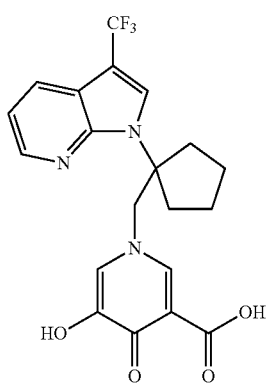

[Formula 183]

Compound 243 was synthesized using 3-(Trifluoromethyl)-1H-pyrrolo[2,3-b]pyridine as a known compound (Synthesis, (2), 251-258; 2007) according to Example 240.

$^1$HNMR (DMSO-d$_6$): 1.62-1.63 (2H, m), 1.87-1.88 (2H, m), 2.31-2.35 (2H, m), 2.61-2.64 (2H, m), 4.78 (2H, s), 6.87 (1H, d, J=2.0 Hz), 7.33-7.36 (2H, m), 8.01 (1H, s), 8.08 (1H, d, J=6.0 Hz), 8.43 (1H, dd, J=1.6 Hz, J=4.8 Hz), 9.85 (1H, s), 15.69 (1H, s).

EXAMPLE 244

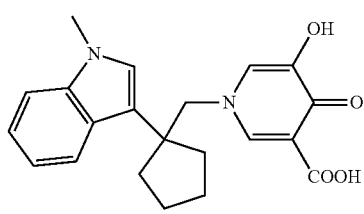

[Formula 184]

Compound 244 was synthesized using 1-(1-methyl-1H-indol-3-yl)-cyclopentanemethanamine as a known compound (Journal of Medicinal Chemistry (1996), 31(2), 123-32) according to Example 60.

LC-MS: m/z=367 [M+H]+.

$^1$HNMR (DMSO-d$_6$): 1.62 (2H, d, J=4.0 Hz), 1.79 (2H, d, J=2.4 Hz), 1.88-1.95 (4H, m), 3.66 (3H, s), 4.42 (2H, s), 6.97 (1H, s), 7.04-7.08 (2H, m), 7.19 (1H, t, J=7.2 Hz), 7.44 (1H, d, J=8.0 Hz), 7.58 (1H, d, J=1.6 Hz), 7.68 (1H, d, J=8.0 Hz), 9.89 (1H, s), 15.97 (1H, s).

EXAMPLE 245

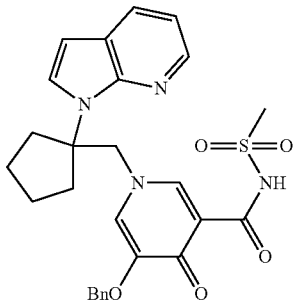

[Formula 185]

Compound 245 was synthesized using synthetic intermediate of Example 185 according to Example 192.

LC-MS: m/z=431 [M+H]+.

$^1$HNMR (DMSO-d$_6$): 1.61-1.62 (2H, br), 1.82-1.86 (2H, br), 2.24-2.27 (2H, br), 2.56-2.60 (2H, br), 3.29 (3H, s), 4.79 (2H, s), 6.43 (1H, s), 6.64 (1H, s), 7.13-7.16 (1H, m), 7.37 (1H, d, J=4.0 Hz), 7.45 (1H, d, J=2.0 Hz), 8.00 (1H, dd, J=1.6 Hz, J=8.0 Hz), 8.27 (1H, dd, J=1.2 Hz, J=4.4 Hz), 9.52 (1H, s), 13.75 (1H, s).

EXAMPLE 246

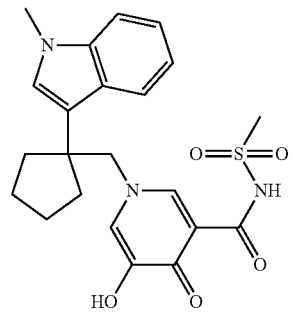

[Formula 186]

Compound 246 was synthesized using synthetic intermediate of Example 244 according to Example 192.

LC-MS: m/z=444 [M+H]+.

$^1$HNMR (DMSO-d$_6$): 1.61-1.63 (2H, br), 1.79-1.80 (2H, br), 1.92-1.93 (2H, br), 2.00-2.01 (2H, br), 3.29 (3H, s), 3.66 (3H, s), 4.38 (2H, s), 6.96-7.08 (3H, m), 7.18-7.19 (1H, m), 7.43 (1H, d, J=7.6 Hz), 7.52 (1H, d, J=1.6 Hz), 7.68 (1H, d, J=8.0 Hz), 9.47 (1H, s), 13.77 (1H, s).

EXAMPLE 247

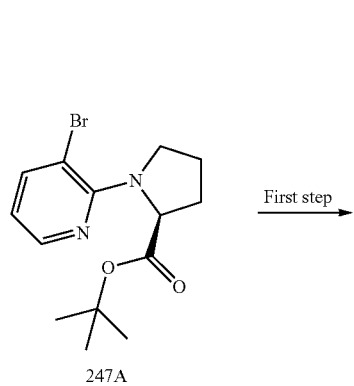

247A

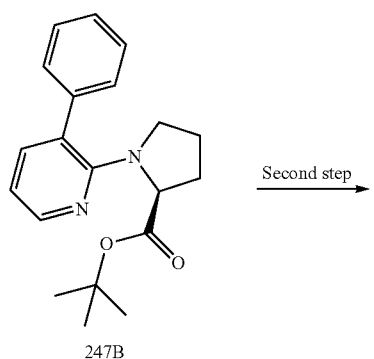

247B

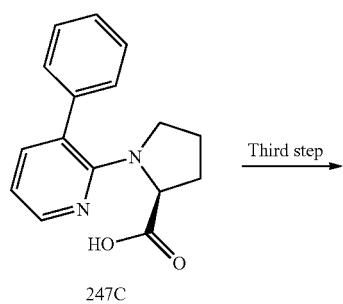

247C

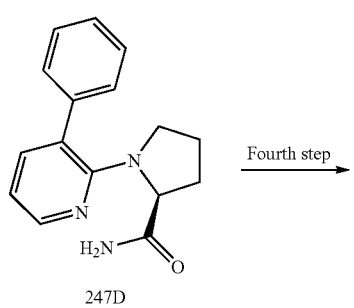

247D

[Formula 187]

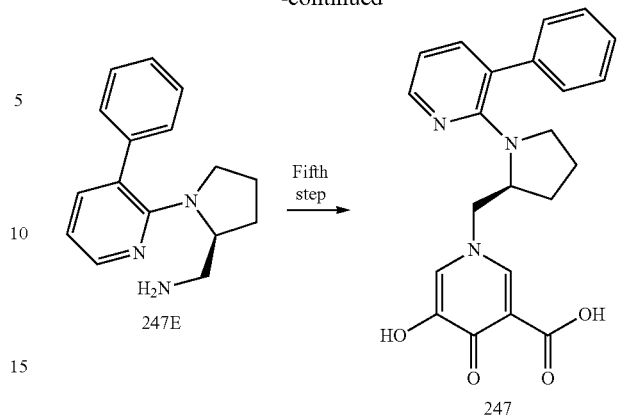

247E

247

First Step

Compound 247A (1.92 g, 5.87 mmol, WO2006/025783A1) in DME (50 mL) was stirred with phenylboronic acid (860 mg, 7.04 mmol), Pd(PPh$_3$)$_4$ (348 mg, 0.30 mmol), and NaHCO$_3$ aq. (11.7 mL, 11.74 mmol) at 80° C. The reaction mixture was cooled to room temperature and the reaction mixture was purified by silica gel chromatography (a solution of 5% ethyl acetate-petroleum ether) to obtain Compound 247B (1.22 g, 64%).

LC-MS: m/z=325 [M+H]$^+$.

Second Step

A solution of Compound 247B (790 mg, 2.44 mmol) in trifluoroacetic acid (10 mL) was stirred at room temperature for 3 hours. The mixture was evaporated, then the residue was crystallized with ethanol (10 mL) to obtain Compound 247C (570 mg, 87%).

LC-MS: m/z=269 [M+H]$^+$.

Third Step

Compound 247C (985 mg, 3.68 mmol) was dissolved in DMF (25 mL), then NH$_4$Cl (390 mg, 7.36 mmol), HOBt (497 mg, 3.68 mmol), EDCI (1.41 g, 7.36 mmol) and DIEA (952 mg, 7.36 mmol) were added thereto, and the mixture was stirred at room temperature over night. To the reaction mixture, water (50 mL) was added, and the mixture was extracted with ethyl acetate (50 mL×2). The organic layer was washed with sat. NaCl aq., and dried over Na$_2$SO$_4$, then the mixture was filtered and the solvent was evaporated in vacuo. The residue was purified by silica gel chromatography (a solution of 3% ethyl acetate-petroleum ether) to obtain Compound 247D (740 mg, 75%).

LC-MS: m/z=268 [M+H]$^+$.

Fourth Step

Compound 247D (430 mg, 1.70 mmol) was dissolved in THF (50 mL), then LiAlH$_4$ (130 mg, 3.4 mol) was slowly added thereto at room temperature, and refluxed and stirred overnight. After cooling the mixture, Na$_2$SO$_4$.10H2O was added thereto and the mixture was filtered. The filtrate was evaporated in vacuo to obtain Compound 247E which was used in the next step without purification.

LC-MS: m/z=254 [M+H]$^+$.

Fifth Step

Compound 247 was synthesized using Compound 247E according to Example 60.

LC-MS: m/z=392 [M+H]$^+$.

$^1$HNMR (DMSO-d$_6$): 1.48-1.52 (3H, m), 2.08-2.09 (1H, m), 2.56-2.71 (2H, m), 4.30-4.40 (2H, m), 4.81 (1H, m), 6.81 (1H, dd, J=4.8 Hz, J=7.2 Hz), 7.32-7.44 (5H, m), 7.78 (1H, d,

J=1.6 Hz), 7.99 (1H, dd, J=2.0 Hz, J=4.8 Hz), 8.40 (1H, d, J=2.0 Hz), 9.96 (1H, s), 16.08 (1H, s).

Test Example

Measurement of Cap-Dependant Endonuclease (CEN) Inhibitory Activity

1) Preparation of Substrate

30merRNA(5'-pp-[m2'-O]GAA UAU(-Cy3) GCA UCA CUA GUA AGC UUU GCU CUA-BHQ2-3':manufactured by Japan Bioservice) in which G at a 5' end is diphosphate-modified, a hydroxy group at 2' position is methoxylation-modified, U sixth from a 5' end is labelled with Cy3, and a 3' end is labelled with BHQ2 was purchased, and a cap structure was added using ScriptCap system manufactured by EPI-CENTRE (a product was m7G [5']-ppp-[5'] [m2'-O]GAA UAU(-Cy3) GCA UCA CUA GUA AGC UUU GCU CUA(-BHQ2)-3'). This was separated and purified by denatured polyacrylamide gel electrophoresis, and used as a substrate.

2) Preparation of Enzyme

RNP was prepared from a virus particle using standard method (Reference Document: VIROLOGY(1976) 73, p327-338 OLGA M. ROCHOVANSKY). Specifically, A/WSN/33 virus ($1\times10^3$ PFU/mL, 200 µL) was inoculated in a 10 days old embryonated chicken egg. After incubation at 37° C. for 2 days, the allantoic fluid of the chicken egg was recovered. A virus particle was purified by ultracentrifugation using 20% sucrose, solubilized using TritonX-100 and lysolecithin, and an RNP fraction (50-70% glycerol fraction) was collected by ultracentrifugation using a 30-70% glycerol density gradient, and was used as an enzyme solution (containing approximately 1 nM PB1•PB2•PA complex).

3) Enzymatic Reaction

An enzymatic reaction solution (2.5 µL) (composition: 53 mM Tris-hydrochloride (pH 7.8), 1 mM $MgCl_2$, 1.25 mM dithiothreitol, 80 mM NaCl, 12.5% glycerol, enzyme solution 0.15 µL) was dispensed into a 384-well plate made of polypropylene. Then, 0.5 µL of a test substance solution which had been serially diluted with dimethyl sulfoxide (DMSO) was added to the plate. As a positive control (PC) or a negative control (NC), 0.5 µL of DMSO was added to the plate respectively. Each plate was mixed well. Then, 2 µL of a substrate solution (1.4 nM substrate RNA, 0.05% Tween20) was added to initiate a reaction. After room temperature incubation for 60 minutes, 1 µL of the reaction solution was collected and added to 10 µL of a Hi-Di formamide solution (containing GeneScan 120 Liz Size Standard as a sizing marker: manufactured by Applied Biosystem (ABI)) in order to stop the reaction. For NC, the reaction was stopped in advance by adding EDTA (4.5 mM) before initiation of the reaction (all concentrations described above are final concentrations).

3) Measurement of Inhibition Ratio ($IC_{50}$ Value)

The stopped solution was heated at 85° C. for 5 minutes, rapidly cooled on ice for 2 minutes, and analyzed with ABI PRIZM 3730 genetic analyzer. A peak of the cap-dependent endonuclease product was quantitated by an analysis software ABI Genemapper, the CEN reaction inhibition ratio (%) of a test compound was obtained by setting the fluorescent intensity of PC and NC as 0% inhibition and 100% inhibition, respectively, then, the $IC_{50}$ value was obtained using a curve fitting software (XLfit2.0:Model 205 (manufactured by IDBS etc.)). The $IC_{50}$ values of test substances are shown in Table 36.

TABLE 36

| Example No | CEN $IC_{50}$ (µM) |
|---|---|
| 10 | 0.219 |
| 18 | 0.845 |
| 22 | 0.217 |
| 46 | 0.325 |
| 52 | 0.459 |
| 57 | 0.426 |
| 112 | 0.061 |
| 116 | 0.221 |
| 127 | 0.313 |
| 167 | 0.012 |
| 171 | 0.016 |
| 173 | 0.047 |
| 177 | 0.110 |
| 178 | 0.028 |
| 182 | 0.278 |
| 183 | 0.177 |
| 185 | 0.005 |
| 186 | 0.035 |
| 195 | 0.677 |
| 197 | 0.531 |
| 222 | 0.513 |

Example 226, 227, 231, 232, 233, 234, 235, 236, 236, 238, 239, 240, 242, 243, 244, 245, 246 also exhibited the $IC_{50}$ of 1.0 µM or less.

Preparation Example 1

A granule containing the following ingredients is manufactured.

| Ingredient | A compound shown by formula (I) | 10 mg |
|---|---|---|
| | lactose | 700 mg |
| | cornstarch | 274 mg |
| | HPC-L | 16 mg |
| | | 1000 mg |

A compound shown by formula (I) and lactose are passed through a 60 mesh sieve. Corn starch is passed through a 120 mesh sieve. These are mixed with V-type blendor. To the mixture, aqueous HPC-L (low viscosity of hydroxypropylcellulose) is added, then the mixture is kneaded together, granulated (extrusive granulation pore diameter 0.5~1 mm), and dried. The obtained dried granule is passed through vibrating sieve (12/60 mesh) to obtain a granule.

Preparation Example 2

A granule for encapsulation containing the following ingredients is manufactured.

| Ingredient | A compound shown by formula (I) | 15 mg |
|---|---|---|
| | lactose | 90 mg |
| | cornstarch | 42 mg |
| | HPC-L | 3 mg |
| | | 150 mg |

A compound shown by formula (I) and lactose are passed through a 60 mesh sieve. Corn starch is passed through a 120 mesh sieve. These are mixed and aqueous HPC-L (low viscosity of hydroxypropylcellulose) is added thereto, then the mixture is kneaded together, granulated, and dried. The obtained dried granule is trimmed and 150 mg thereof is filled into a No. 4 hard gelatin capsule.

Preparation Example 3

A tablet containing the following ingredients is manufactured.

| Ingredient | | |
|---|---|---|
| A compound shown by formula (I) | 10 mg |
| lactose | 90 mg |
| microcrystal cellulose | 30 mg |
| CMC-Na | 15 mg |
| Magnesium stearate | 5 mg |
| | 150 mg |

A compound shown by formula (I), lactose, and microcrystal cellulose, CMC-Na (carboxymethylcellulose sodium salt) are passed through a 60 mesh sieve and mixed. Magnesium stearate is added to the mixed powder to obtain a mixture for tablet. The mixture is tabletted directly to obtain a 150 mg tablet.

Preparation Example 4

An injectable solution is manufactured by mixing the following ingredients under warming, followed by sterilization.

| Ingredient | | |
|---|---|---|
| A compound shown by formula (I) | 3 mg |
| non-ion surfactant | 15 mg |
| Water for injection | 1 ml |

[Industrial Applicability]

The compound of the present invention has cap-dependent endonuclease (CEN) inhibitory activity. The compound of the present invention can be a useful agent for treatment and/or prevention of symptom and/or disease induced by infection with influenza virus.

The invention claimed is:

1. A compound shown by formula (I), or a pharmaceutically acceptable salt thereof or a solvate thereof:

(I)

[wherein $R^1$ is chosen from
hydrogen and
lower alkyl optionally substituted by substituent A,
wherein substituent A is at least one group chosen from halogen, amino, and hydroxy;
$R^2$ is chosen from
a group represented by —$(CX^1X^2)_m$—Y—$(CH_2)_n$—Z,
wherein $X^1$ and $X^2$ are each independently hydrogen, hydroxy, hydroxy lower alkyl, lower alkyl, aryl, aryl lower alkyl, or monocyclic heterocycle,
Y is a single bond, S, $SO_2$, O, NH, NHCO, or CONH,
m and n are each independently an integer of 0 or 1, and each
$X^1$ may be the same or different and each $X^2$ may be the same or different, Z is chosen from a) to l) below:

a) $A^2 \overset{A^1}{\underset{A^3}{\diagdown}} Q - P -$ b) $A^4\text{-Q-C} \equiv \text{C—P—}$ c) $A^5$-Q-C=C—P—,
d) $A^6$-Q-$(CH_2)_{r1}$—P—,
e) $A^7$-Q-CO—P—,
f) $A^8$-Q-$(CH_2)_{r2}$—O—CO—P—,
g) $A^9$-Q-CO—$(CH_2)_{r3}$—O—CO—P—,
h) $A^{10}$-Q-CO—NH—P—,
i) $A^{11}$-Q-O—P—,
j) $A^{12}$-Q-S—P—,
k) $A^{13}$-Q-$SO_2$—P—, and l) $A^{14}\diagdown \atop A^{15}\diagup T-Q-P-$, wherein P is a single bond or a group chosen from monocyclic hydrocarbon, monocyclic heterocycle, condensed polycyclic hydrocarbon, and condensed polycyclic heterocycle,
each may optionally be substituted by at least one substituent chosen from halogen, hydroxy, nitrile, amino, lower alkylamino, aminosulfonyl, aminocarbonyl, lower alkylcarbonyl, lower alkyl, halogeno lower alkyl, lower alkyloxy, oxo and aryl,
Q is monocyclic hydrocarbon, condensed polycyclic hydrocarbon, monocyclic heterocycle, or condensed polycyclic heterocycle,
T is monocyclic heterocycle,
$A^1, A^2, A^3, A^4, A^5, A^6, A^7, A^8, A^9, A^{10}, A^{11}, A^{12}, A^{13}, A^{14}$ and $A^{15}$ are each independently chosen from hydrogen, lower alkyl, halogeno lower alkyl, lower alkyloxy lower alkyl, lower alkyloxy, lower alkyloxy lower alkyloxy, halogeno lower alkyloxy, halogeno lower alkylcarbonyl, aryl, aryloxy, lower alkyloxy aryl, aryl lower alkyloxy, lower alkylcarbonyl, aminocarbonyl, lower alkyl aminocarbonyl, cycloalkylaminocarbonyl, amino, lower alkylamino, lower alkylcarbonylamino, cycloalkyl lower alkylamino, aminosulfonyl, arylsulfonyl, lower alkylsulfonyl, lower alkylsulfonylamino, morpholinylcarbonyl, pyrroridinylcarbonyl, hydroxy, hydroxy lower alkyl, nitrile, oxo, arylaminocarbonyl and halogen;
r1, r2, and r3 are each independently an integer of 1 or 2]
$R^3$ is chosen from:
hydroxy,
carboxy,
phenylaminocarbonyl optionally substituted by substituent C,
sulfonylaminocarbonyl optionally substituted by substituent C, and
monocyclic heterocycle optionally substituted by substituent C,
wherein substituent C is at least one substituent chosen from a) to e)
a) lower alkyl optionally substituted with halogen,
b) halogen, c) monocyclic hydrocarbon optionally substituted with lower alkyl and/or halogen,
d) monocyclic heterocycle, and
e) aryl lower alkyl optionally substituted with lower alkyl and/or halogen;

$R^4$ is:
hydrogen or
lower alkyl.

2. The compound according to claim 1, or the pharmaceutically acceptable salt thereof or the solvate thereof, wherein $R^1$ is hydrogen.

3. The compound according to claim 1 or 2, or the pharmaceutically acceptable salt thereof or the solvate thereof, wherein $R^4$ is hydrogen.

4. The compound according to claim 1, or the pharmaceutically acceptable salt thereof or the solvate thereof, wherein $R^3$ is chosen from:
hydroxy,
carboxy,
phenylaminocarbonyl optionally substituted by substituent C, and
sulfonylaminocarbonyl substituted by substituent C.

5. The compound according to claim 4, or the pharmaceutically acceptable salt thereof or the solvate thereof, wherein $R^3$ is carboxy.

6. The compound according to claim 1 or the pharmaceutically acceptable salt thereof or the solvate thereof, wherein $R^3$ is chosen from;
monocyclic heterocycle optionally substituted by substituent C,
wherein the substituent C is chosen from a)and b):
  a) lower alkyl optionally substituted with halogen, and
  b) halogen.

7. The compound according claim 1, or the pharmaceutically acceptable salt thereof or the solvate thereof, wherein
$X^1$ and $X^2$ are each independently hydrogen, or lower alkyl,
Z is chosen from a) to l):

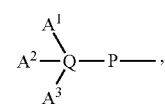  a)

($A^1$, $A^2$ and $A^3$ are each independently hydrogen, lower alkyl, halogeno lower alkyl, lower alkyloxy lower alkyl, lower alkyloxy, halogeno lower alkyloxy, halogeno lower alkylcarbonyl, aryl, aryloxy, aryl lower alkyloxy, lower alkylcarbonyl, aminocarbonyl, lower alkyl aminocarbonyl, cycloalkylaminocarbonyl, lower alkylamino, cycloalkyl lower alkylamino, arylsulfonyl, lower alkylsulfonyl, lower alkylsulfonylamino, morphollinylcarbonyl, pyrrolidinylcarbonyl, hydroxy , hydroxy lower alkyl, nitrite, oxo, arylaminocarbonyl and halogen),

  b)

($A^4$ is hydrogen),
c) $A^5$-Q-C≡C—P— ($A^5$ is hydrogen, halogeno lower alkyl, or lower alkyloxy),
d) $A^6$-Q-(CH$_2$)$_{r1}$—P— ($A^6$ is hydrogen, lower alkyl, aryl , nitrile, or halogen),
e) $A^7$-Q-CO—P— ($A^7$ is hydrogen, or halogen), f) $A^8$-Q-(CH$_2$)$_{r2}$—O—CO—P— ($A^8$ ishydrogen, lower alkyl, halogeno lower alkyl, lower alkyloxy aryl, nitrile, or halogen),
g) $A^9$-Q-CO—(CH$_2$)$_{r3}$—O—CO—P— ($A^9$ is hydrogen),
h) $A^{10}$-Q-CO—NH—P— ($A^{10}$ is hydrogen),
i) $A^{11}$-Q-O—P— ($A^{11}$ is hydrogen, or lower alkyl),
j) $A^{12}$-Q-S—P— ($A^{12}$ is hydrogen, or hydroxy lower alkyl),
k) $A^{13}$-Q-SO$_2$—P— ($A^{13}$ is hydrogen, or halogen), and

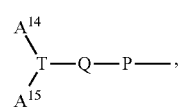  l)

($A^{14}$ and $A^{15}$ are each independently hydrogen, or oxo).

8. The compound according to claim 1, or the pharmaceutically acceptable salt thereof or the solvate thereof, wherein
$X^1$ and $X^2$ are each independently hydrogen, or lower alkyl,
Y is a single bond, S, SO$_2$, O, or CONH,
m and n are each independently an integer of 0 or more, with a proviso that m of $X^1$ may be same or different, m of $X^2$ may be same or different,
Z is chosen from a), d), and f) to j):

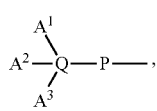  a)

(wherein $A^1$, $A^2$ and $A^3$ are each chosen from hydrogen, lower alkyl, halogeno lower alkyl, lower alkyloxy, halogeno lower alkyloxy , halogeno lower alkylcarbonyl, aryl, aryloxy, lower alkylcarbonyl, aminocarbonyl, cycloalkyl aminocarbonyl, lower alkylcarbonylamino, lower alkylamino, cycloalkyl lower alkylamino, arylsulfonyl, lower alkylsulfonyl, lower alkylsulfonylamino, hydroxy, nitrile, aryl aminocarbonyl, halogen, and groups shown below:

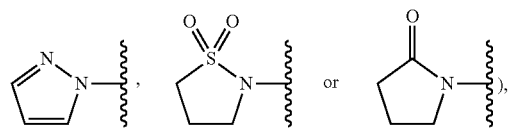

d) $A^6$-Q-(CH$_2$)$_{r1}$—P— ($A^6$ is hydrogen, nitrile, or halogen),
f) $A^8$-Q-(CH$_2$)$_{r2}$—O—CO—P— ($A^8$ is hydrogen, lower alkyl, halogeno lower alkyl, lower alkyloxy aryl, nitrile, or halogen),
h) $A^{10}$-Q-CO—NH—P— ($A^{10}$ is hydrogen),
i) $A^{11}$-Q-O—P— ($A^{11}$ is hydrogen), and
j) $A^{12}$-Q-S—P— ($A^{12}$ is hydroxy lower alkyl).

9. The compound according to claim 1 or the pharmaceutically acceptable salt thereof or the solvate thereof, wherein
$X^1$ and $X^2$ are each independently hydrogen, hydroxymethyl, methyl, ethyl, or phenyl,
Y is a single bond, or S, Z is chosen from a), d), and f) to j):

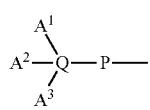

(A$^1$, A$^2$ and A$^3$ are each chosen from hydrogen, methyl, trifluoromethyl, methoxy, ethoxy, trifluoromethoxy, trifluoromethylcarbonyl, phenyl, phenoxy, methylcarbonyl, aminocarbonyl, cyclopropylaminocarbonyl, methylcarbonylamino, dimethylamino, cyclohexylmethylamino, phenylsulfonyl, methylsulfonyl, methylsulfonylamino, hydroxy, nitrile, phenylaminocarbonyl, fluoro, chloro, and groups shown below:

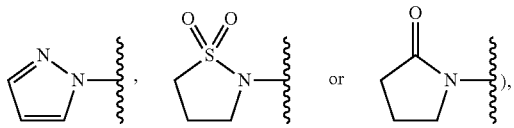

d) A$^6$-Q-(CH$_2$)$_{r1}$—P— (A$^6$ is hydrogen, nitrile, or chloro),
f) A$^8$-Q-(CH$_2$)$_{r2}$—O—CO—P— (A$^8$ is hydrogen, tert-buthyl, trifluoromethyl, methoxyphenyl, nitrile, or fluoro),
h) A$^{10}$-Q-CO—NH—P— (A$^{10}$ is hydrogen),
i) A$^{11}$-Q-O—P— (A$^{11}$ is hydrogen), and
j) A$^{12}$-Q-S—P— (A$^{12}$ is hydroxy methyl),
wherein P is a single bond or a group shown below:

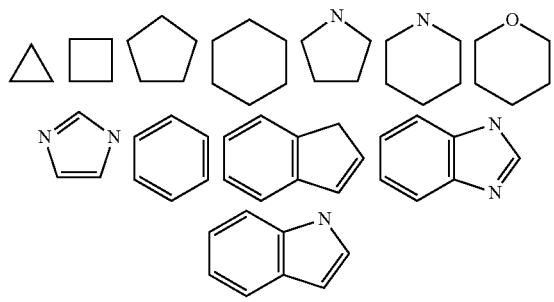

each may be optionally substituted by hydroxy, lower alkyl, oxo, or phenyl (provided when the substituent is oxo, P is saturated monocyclic hydrocarbon, or saturated monocyclic heterocycle), Q is a group shown below:

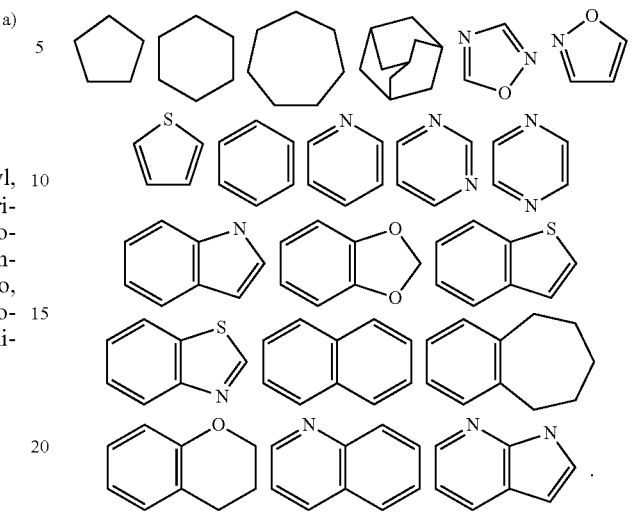

10. The compound according to claim 1, or the pharmaceutically acceptable salt thereof or the solvate thereof, wherein R$^2$ is chosen from:

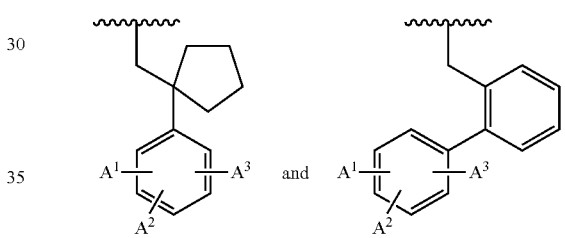

(wherein A$^1$, A$^2$ and A$^3$ are chosen from hydrogen, methyl, trifluoromethyl, methoxy, ethoxy, trifluoromethoxy, trifluoromethylcarbonyl, phenyl, phenoxy, methylcarbonyl, aminocarbonyl, cyclopropylaminocarbonyl, methylcarbonylamino, dimethylamino, methylsulfonyl, methylsulfonylamino, hydroxy, nitrile, fluoro, and chloro).

11. A pharmaceutical composition comprising a compound according to any one of claims 1 to 2 and 4 to 10, or a pharmaceutically acceptable salt thereof or a solvate thereof.

12. A pharmaceutical composition according to claim 11 which exhibits cap-dependent endonuclease inhibitory activity.

* * * * *